(12) United States Patent
Poirier et al.

(10) Patent No.: US 11,174,282 B2
(45) Date of Patent: Nov. 16, 2021

(54) AMINOSTEROID DERIVATIVES AND PROCESS FOR PRODUCING SAME

(71) Applicant: UNIVERSITÉ LAVAL, Quebec (CA)

(72) Inventors: Donald Poirier, L'Ancienne-Lorette (CA); René Maltais, Quebec (CA); Martin Perreault, Quebec (CA)

(73) Assignee: UNIVERSITÉ LAVAL, Quebec (CA)

( * ) Notice: Subject to any disclaimer, the term of this patent is extended or adjusted under 35 U.S.C. 154(b) by 0 days.

(21) Appl. No.: 16/302,237

(22) PCT Filed: Jun. 2, 2017

(86) PCT No.: PCT/CA2017/000140
§ 371 (c)(1),
(2) Date: Nov. 16, 2018

(87) PCT Pub. No.: WO2017/205964
PCT Pub. Date: Dec. 7, 2017

(65) Prior Publication Data
US 2020/0002372 A1 Jan. 2, 2020

Related U.S. Application Data

(60) Provisional application No. 62/344,812, filed on Jun. 2, 2016.

(51) Int. Cl.
*A61K 31/58* (2006.01)
*A61P 35/00* (2006.01)
*C07J 41/00* (2006.01)
*C07J 43/00* (2006.01)
*C07J 73/00* (2006.01)

(52) U.S. Cl.
CPC .............. *C07J 43/003* (2013.01); *A61P 35/00* (2018.01); *C07J 73/005* (2013.01)

(58) Field of Classification Search
CPC . A61K 31/58; A61P 35/00; C07J 41/00; C07J 43/003; C07J 73/003; C07J 73/005; C07J 73/006
See application file for complete search history.

(56) References Cited

FOREIGN PATENT DOCUMENTS

| CA | 2744369 | 6/2010 |
| WO | WO 03/073985 | 9/2003 |

OTHER PUBLICATIONS

Arpicco, et al., "Anticancer Prodrugs: An Overview of Major Strategies and Recent Developments," *Current Topics in Medicinal Chemistry*, 11; 2346-2381. 2011.
Ayan, et al., "Chemical Synthesis, Cytotoxicity, Selectivity and Bioavailability of 5α-androstane-3α,17β-diol Derivatives," *Bioorganic & Medicinal Chemistry*, 22; 5847-5859. 2014.
Bell & Wang, "Probe ADME and Test Hypotheses: a PATH Beyond Clearance in Vitro-In Vivo Correlations in Early Drug Discovery," *Expert Opinion on Drug Metabolism & Toxicology*, 8(9); 1131-1155. 2012.
International Search Report and Written Opinion Issued in Corresponding PCT Application PCT/CA2017/000140, dated Aug. 16, 2017.

(Continued)

*Primary Examiner* — Brenda L Coleman
(74) *Attorney, Agent, or Firm* — Norton Rose Fulbright US LLP

(57) ABSTRACT

Estrane-based and androstane-based aminosteroid derivatives are described herein. More specifically, the following piperazinyl-steroid compounds of Formula I, Formula II, Formula III, and Formula IV are described. The compounds display cytotoxicity on a variety of cancer cell lines. A process for producing the compounds and their use in the manufacture of pharmaceutical formulations and/or combinations is also disclosed.

Formula I

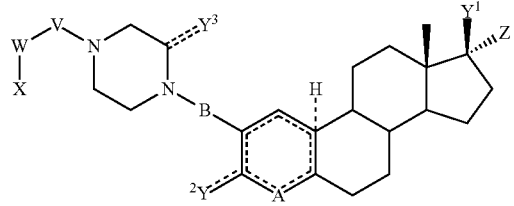

Formula II

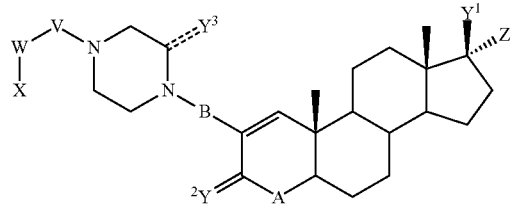

Formula III

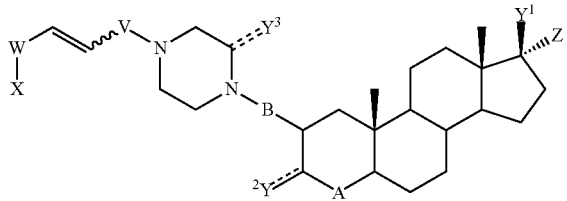

Formula IV

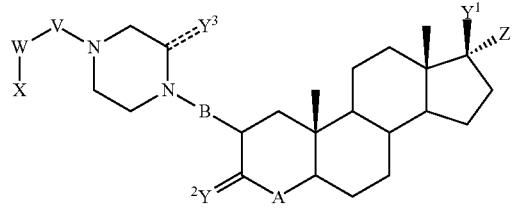

23 Claims, 10 Drawing Sheets

(56) References Cited

OTHER PUBLICATIONS

Jegham, et al., "Biological Evaluation of a New Family of Aminosteroids that Display a Selective Toxicity for Various Malignant Cell Lines," *Anticancer Drugs*, 23; 803-814. 2012.
Konigs, et al., "Cytotoxicity, Metabolism and Cellular Uptake of the Mycotoxin Deoxynivalenol in Human Proximal Tubule Cells and Lung Fibroblasts in Primary Culture," *Toxicology*, 240; 48-59. .
Nagelkerke, et al., "The Unfolded Protein Response as a Target for Cancer Therapy," *Biochum Biophys Acta*, 1846; 277-284. 2014.
Perrault, et al., "Explorative Study on the Anticancer Activity, Selectivity and Metabolic Stability of Related Analogs of Aminosteroid RM-133," *Steroids*, 115; 105-113. 2016.
Perreault, et al., "Design of a Mestranol 2-N-Piperazino-Substituted Derivative Showing Potent and Selective in Vitro and In Vivo Activities in MCF-7 Breast Cancer Models," *ChemMedChem*, 12; 177-182. 2017.
Talbot, et al., "Solid-Phase Synthesis of Libraries of Ethynylated Aminosteroid Derivatives as Potential Antileukemic Agents," *Steroids*, 107; 55-64. 2016.
Wang, et al., "The Impact of the Endoplasmic Reticulum Protein-Folding Environment on Cancer Development," *Nat Rev Cancer*, 14; 581-597. 2014.
Cushman et al., "Synthesis, Antitubulin and Antimitotic Activity, and Cytotoxicity of Analogs of 2-Methoxyestradiol, an Endogenous Mammalian Metabolite of Estradiol That Inhibits Tubulin Polymerization by Binding to the Colchicine Binding Site" *J. Med. Chem.* 1995, 38(12), 2041-2049.
Extended European Search Report issued in Corresponding European Application No. 17805435.9, dated Jan. 22, 2020.

AMINOSTEROID DERIVATIVES AND PROCESS FOR PRODUCING SAME

CROSS-REFERENCE TO RELATED APPLICATIONS

This application is a national phase under 35 U.S.C. § 371 of International Application No. PCT/CA2017/000140, filed Jun. 2, 2017, which claims the benefit of priority to U.S. Provisional Patent Application Ser. No. 62/344,812, filed Jun. 2, 2016, the contents of each of which are hereby incorporated by reference.

FIELD

The present disclosure broadly relates to aminosteroid derivatives and a process for producing same. More specifically, but not exclusively, the present disclosure relates to estrane-based and androstane-based aminosteroid derivatives. The present disclosure also relates to a process for producing the estrane-based and androstane-based aminosteroid derivatives and their use in the manufacture of pharmaceutical formulations.

BACKGROUND

Notwithstanding the many advances, cancer remains one of the leading causes of disease-related mortality. Moreover, the quality of life of cancer patients is often compromised because many patients present severe side-effects, mostly resulting from poor selectivity of the cancer drugs resulting in adverse side effects to normal healthy cells [1].

Cancer cells present higher endoplasmic reticulum (ER) stress, mainly due to more pronounced protein synthesis. Consequently, they are more prone to surpass the ER stress threshold leading to apoptosis when exposed to an endoplasmic reticulum stress aggravator (ERSA) [2, 3]. It is thus surmised that ERSA agents should be more selective for cancer cells as compared to normal cells and as a result should result in less side effects.

The present disclosure refers to a number of documents, the contents of which are herein incorporated by reference in their entirety.

SUMMARY

In an aspect, the present disclosure broadly relates to aminosteroid derivatives and a process for producing same. More specifically, but not exclusively, the present disclosure relates to estrane-based and androstane-based aminosteroid derivatives. The present disclosure also relates to a process for producing the estrane-based and androstane-based aminosteroid derivatives and their use in the manufacture of pharmaceutical formulations.

The present disclosure, in an aspect relates to an aminosteroid derivative of Formula I:

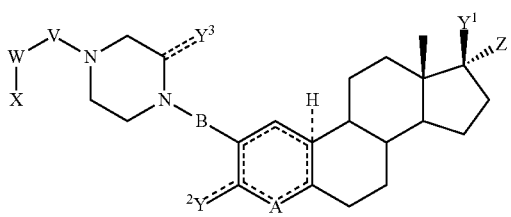

Formula I wherein:
═══ represents a single or a double bond, provided that two double bonds are not adjacent each other;
A is C, N or NR$^1$;
B is CO, SO, SO$_2$, CH$_2$, C(X$^1$)$_2$, or absent;
Y$^1$ is chosen from OH, halogen, OR$^2$, OCOR$^3$, OCONR$^4$R$^5$ and OSO$_2$NR$^4$R$^5$;
Y$^2$ is chosen from H, halogen, OH, OR$_2$, OMOM (O-methoxymethyl ether), OCOR$^3$, OCONR$^4$R$^5$, OSO$_2$NH$_2$, OPO(OH)$_2$, when Y$^2$═══C is Y$^2$—C and Y$^2$ is O or S when Y$^2$═══C is Y$^2$═C;
Y$^3$ is H$_2$ or O;
Z is H, halogen or C≡CR$_6$;

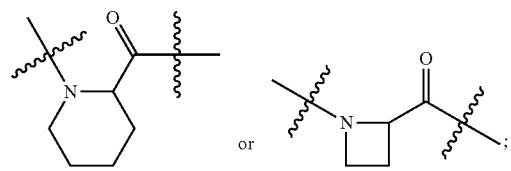 [SMILES: *C(=O)C1CCCCN1* ; *C(=O)C1CCN1*]

or

W is CO, SO$_2$, CH$_2$, CONH, CSNH, or

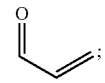

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
X$^1$ is halogen;
R$^1$ is H or alkyl;
R$^2$ is alkyl;
R$^3$ is H, alkyl or heterocyclyl;
R$^4$ and R$^5$ are independently chosen from H and alkyl; and
R$^6$ is H or alkyl;
or a pharmaceutically acceptable salt, a prodrug, an N-oxide or a solvate thereof.

The present disclosure, in an aspect relates to an aminosteroid derivative having the structure:

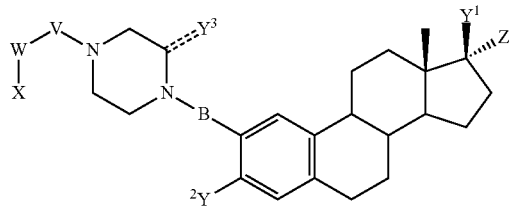

wherein:
B is CO, SO, SO$_2$, CH$_2$, C(X$^1$)$_2$, or absent;
Y$^1$ is chosen from OH, halogen, OR$^2$, OCOR$^3$, OCONR$^4$R$^5$; and OSO$_2$NR$^4$R$^5$;
Y$^2$ is chosen from H, halogen, OH, OR$_2$, OMOM (O-methoxymethyl ether), OCOR$^3$, OCONR$^4$R$^5$, OSO$_2$NH$_2$ and OPO(OH)$_2$;
Y$^3$ is H$_2$ or O;
Z is H, halogen or C≡CR$_6$;
V is an amino acid,

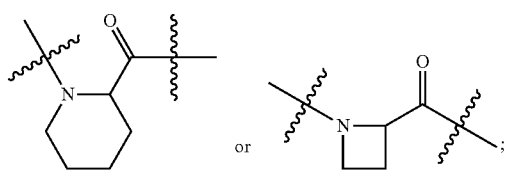 [SMILES: *C(=O)C1CCCCN1* ; *C(=O)C1CCN1*]

W is CO, SO₂, CH₂, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;

$X^1$ is halogen;

$R^2$ is alkyl;

$R^3$ is H, alkyl or heterocyclyl;

$R^4$ and $R^5$ are independently chosen from H and alkyl; and $R^6$ is H or alkyl;

or a pharmaceutically acceptable salt, a prodrug, an N-oxide or a solvate thereof.

In an embodiment the aminosteroid derivative of Formula I has a structure wherein V is proline and wherein the variables W and X are linked to form the linkage W-X, wherein W-X is chosen from

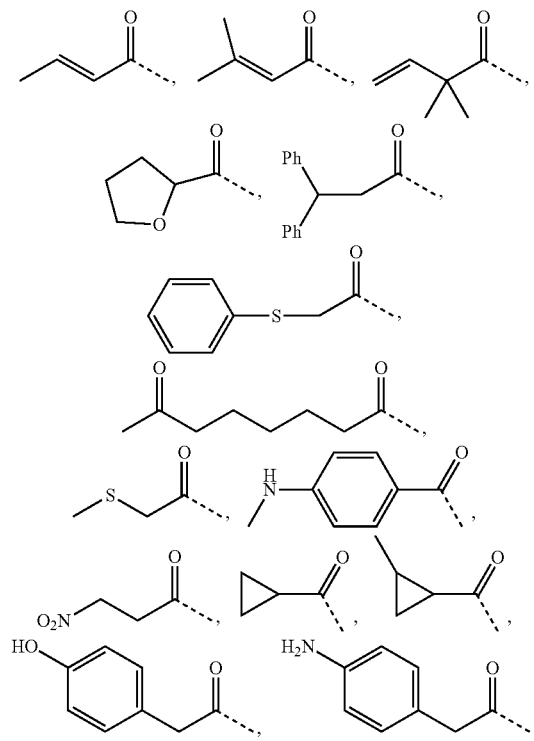

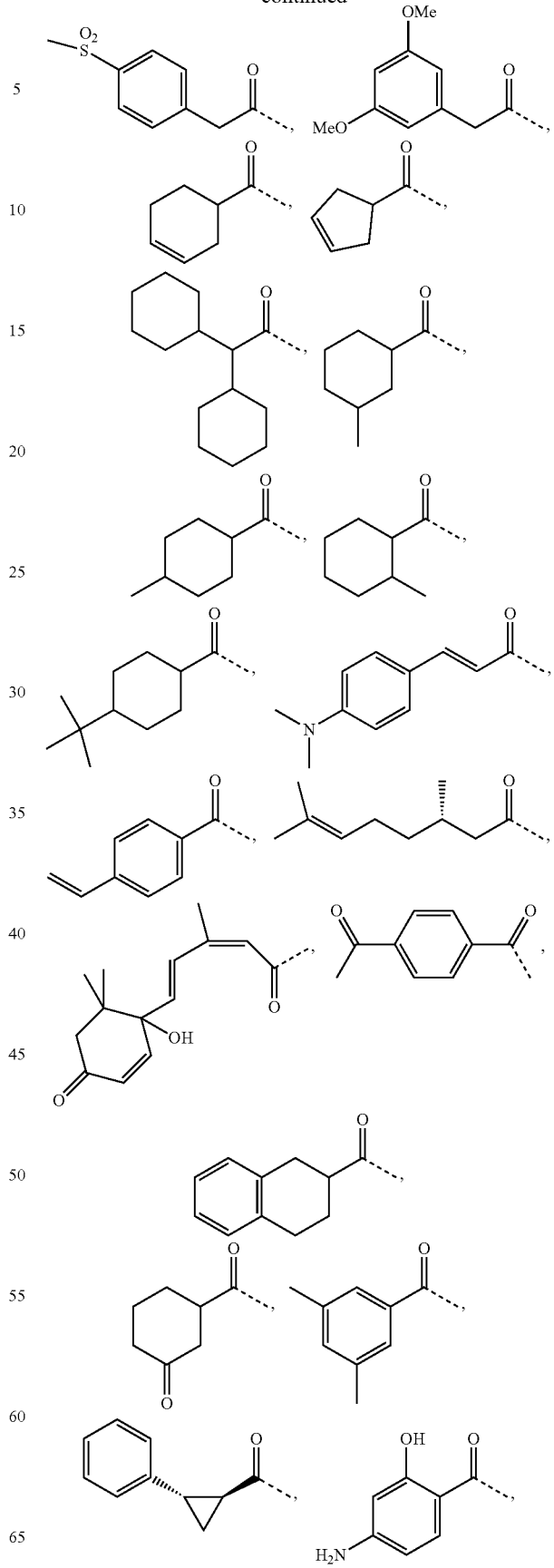

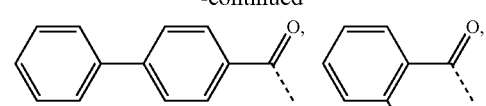
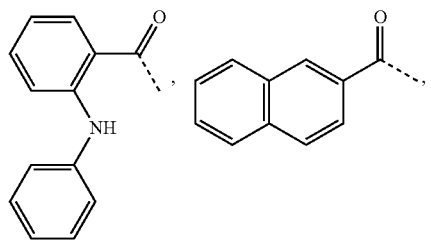
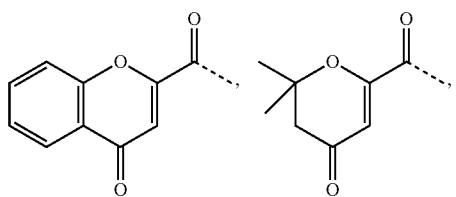
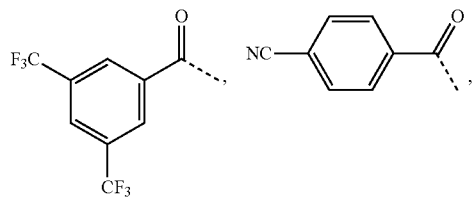
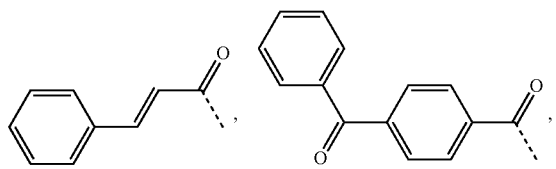
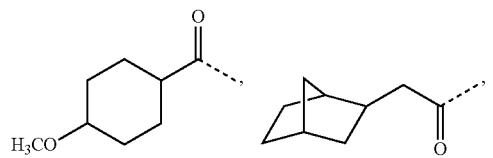
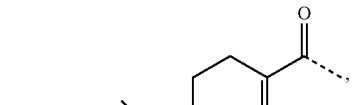
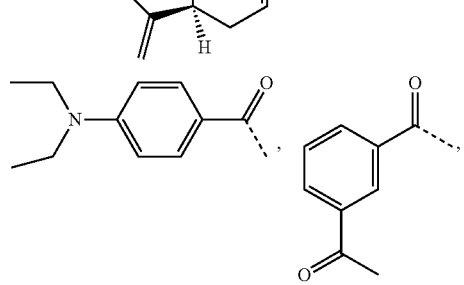
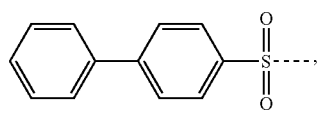
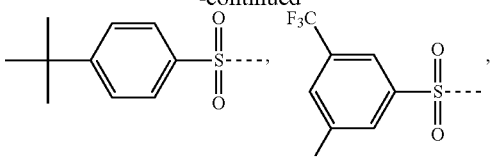
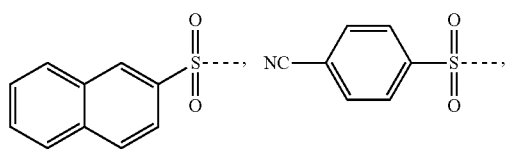
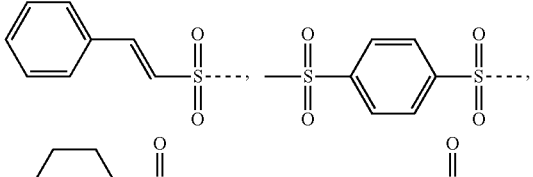
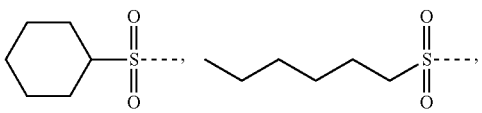
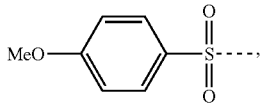
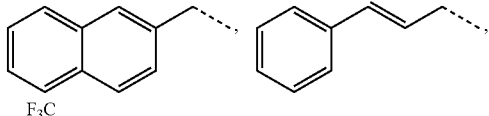
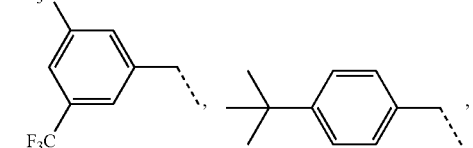
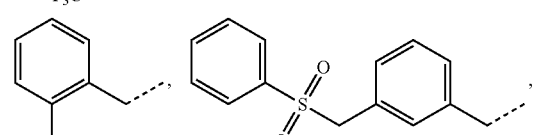
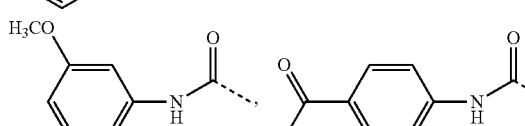
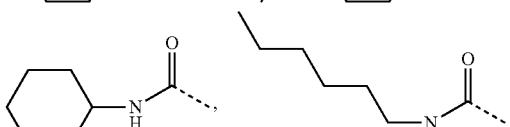
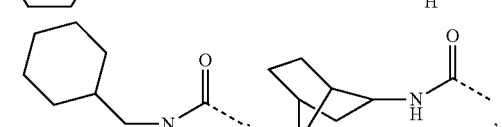
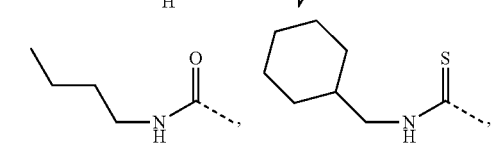

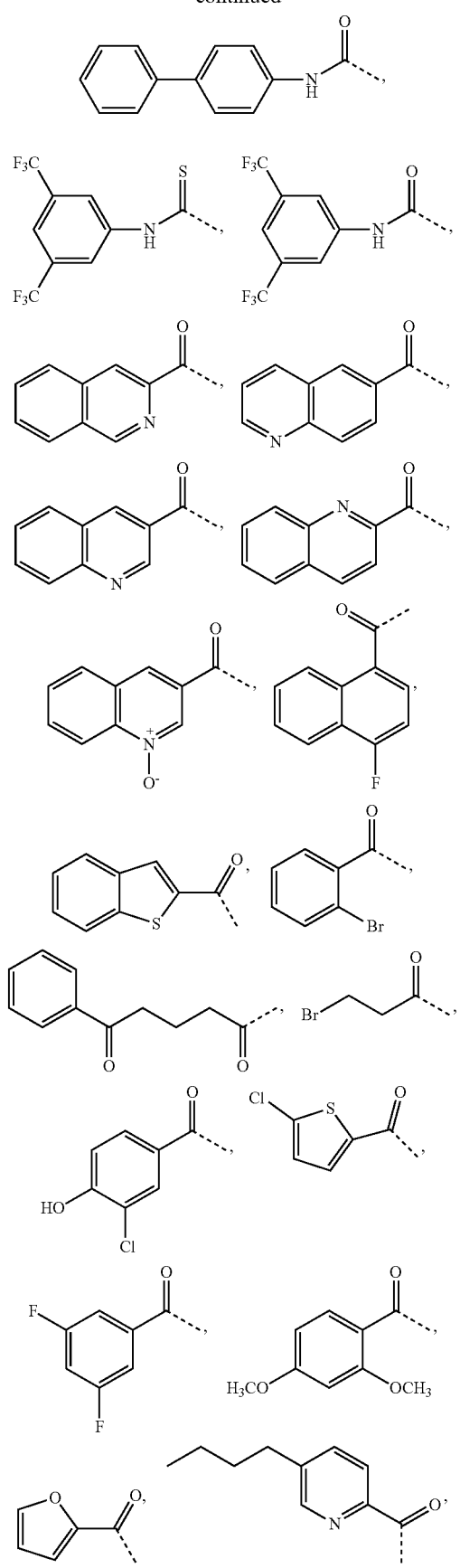
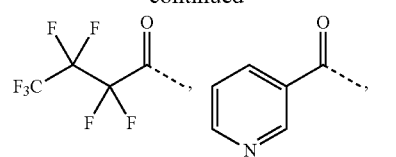
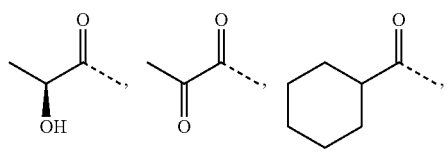
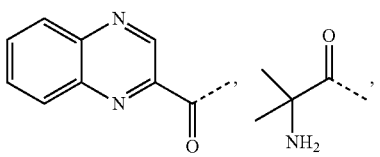
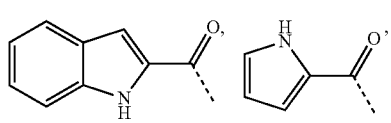
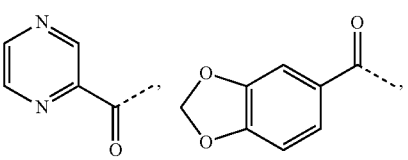
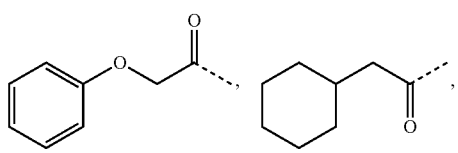
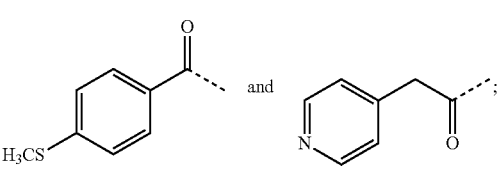
or a pharmaceutically acceptable salt, an N-oxide or a solvate thereof.

In an embodiment the aminosteroid derivative of Formula I has the structure:

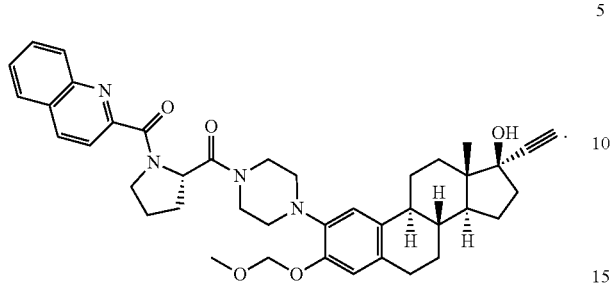

In an embodiment the aminosteroid derivative of Formula I has the structure:

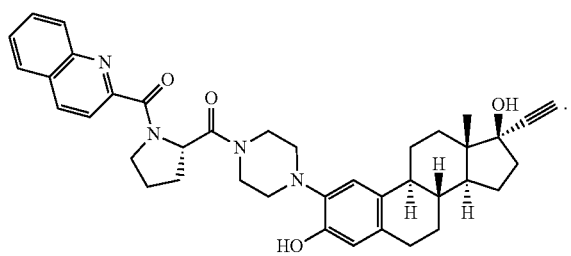

In an embodiment the aminosteroid derivative of Formula I has the structure:

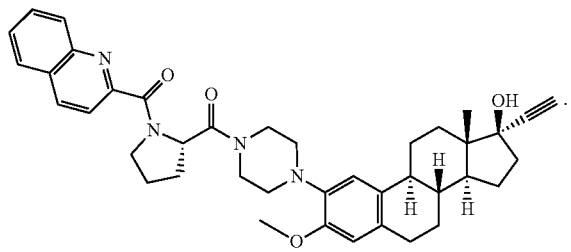

In an embodiment the aminosteroid derivative of Formula I has the structure:

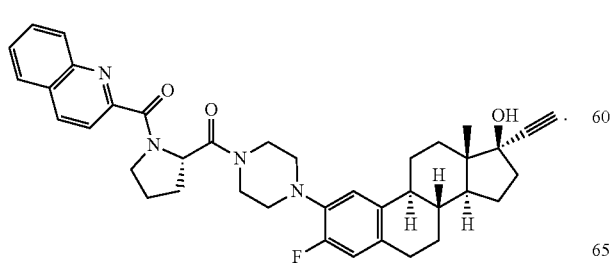

In an embodiment the aminosteroid derivative of Formula I has the structure:

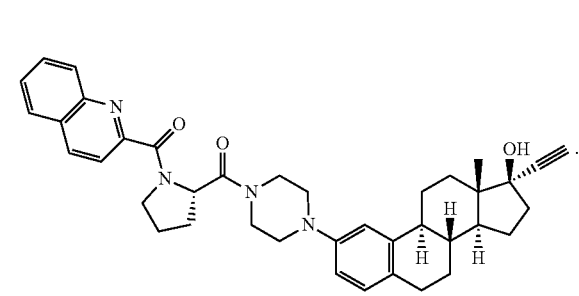

In an embodiment the aminosteroid derivative of Formula I has the structure:

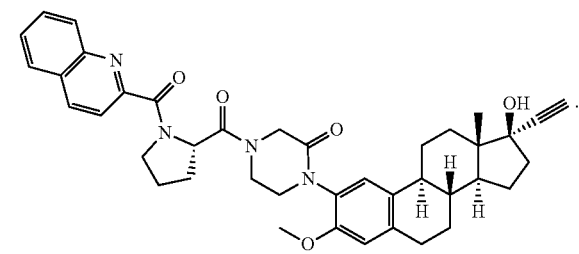

In an embodiment the aminosteroid derivative of Formula I has the structure:

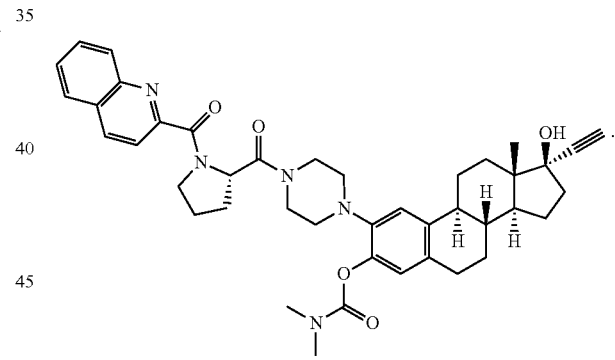

In an embodiment the aminosteroid derivative of Formula I has the structure:

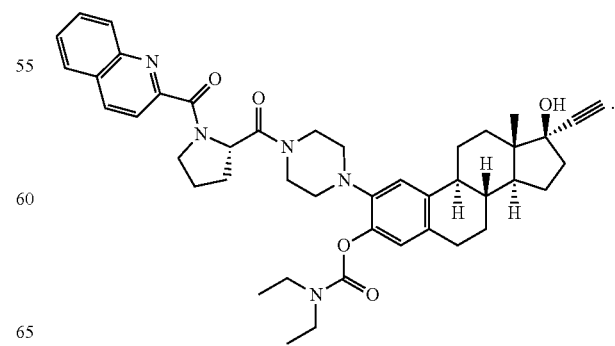

In an embodiment the aminosteroid derivative of Formula I has the structure:

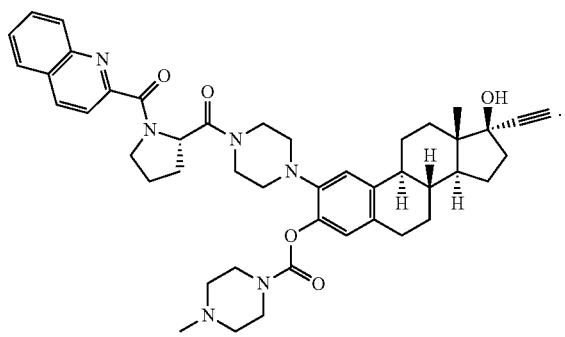

In an embodiment the aminosteroid derivative of Formula I has the structure:

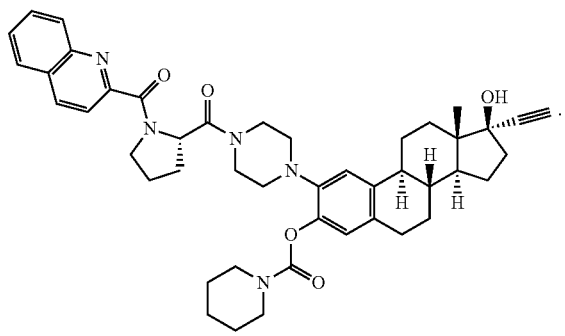

In an embodiment the aminosteroid derivative of Formula I has the structure:

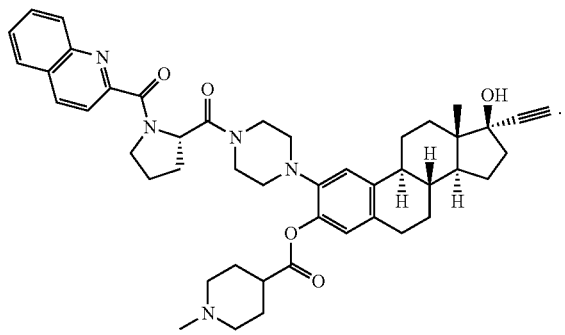

In an embodiment the aminosteroid derivative of Formula I has the structure:

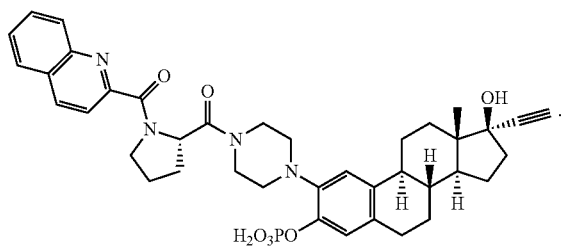

In an embodiment the aminosteroid derivative of Formula I has the structure:

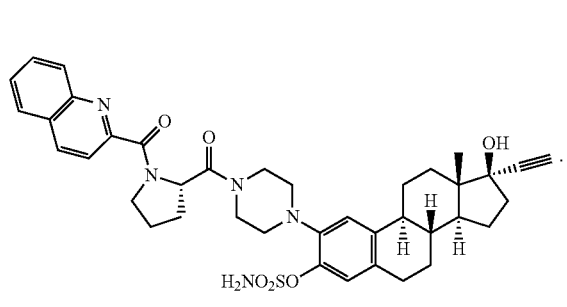

In an embodiment the aminosteroid derivative of Formula I has the structure:

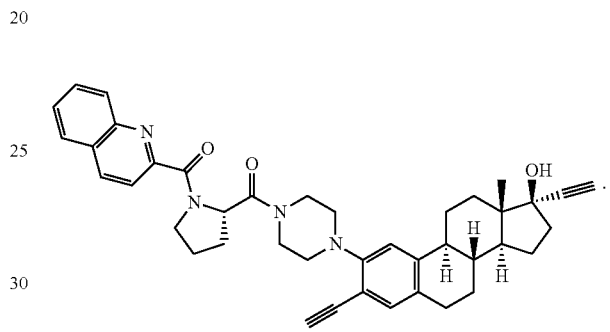

In an embodiment the aminosteroid derivative of Formula I has the structure:

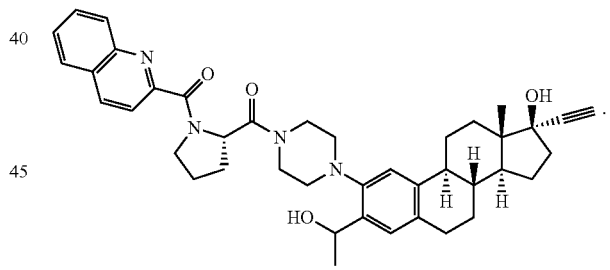

In an embodiment the aminosteroid derivative of Formula I has the structure:

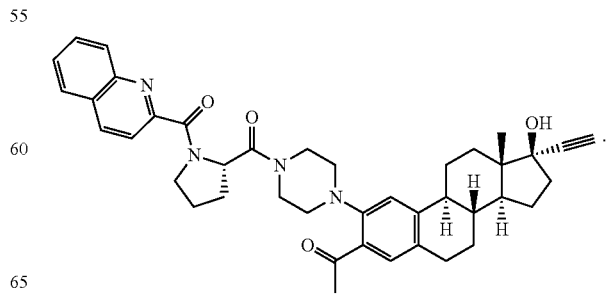

In an embodiment the aminosteroid derivative of Formula I has the structure:

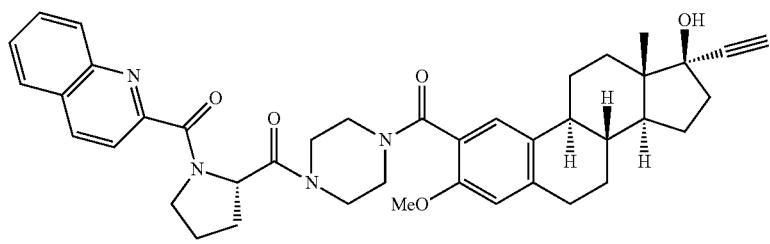

In an embodiment the aminosteroid derivative of Formula I has the structure:

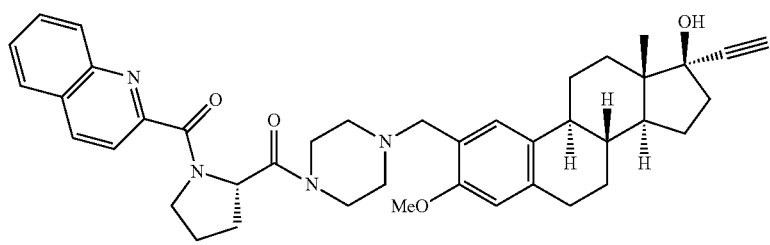

The present disclosure, in an aspect relates to an aminosteroid derivative of Formula II:

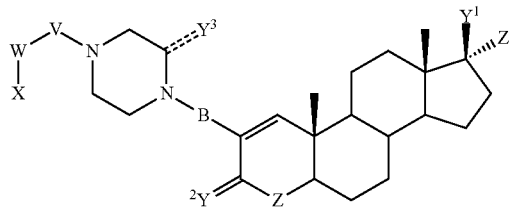

Formula II wherein:
A is $CHR^1$, $NR^1$, O or S;
B is CO, SO, $SO_2$, $CH_2$, $C(X^1)_2$, or absent;
$Y^1$ is chosen from OH, halogen, $OR^2$, $OCOR^3$, $OCONR^4R^5$ and $OSO_2NR^4R^5$;
$Y^2$ is chosen from O and S;
$Y^3$ is $H_2$ or O;
Z is H or $C\equiv CR_6$;
V is an amino acid,

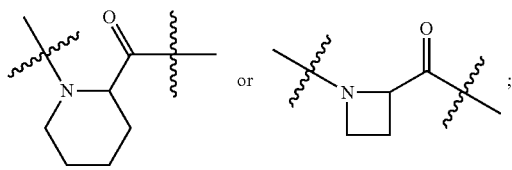 [SMILES: *C(=O)C1CCCCN1* ; *C(=O)C1CCN1*]

or

W is CO, $SO_2$, $CH_2$, CONH, CSNH, or

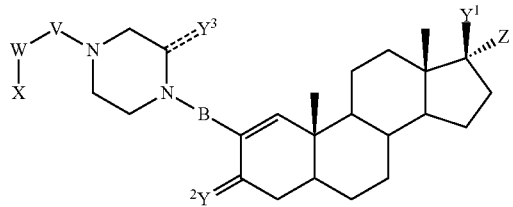

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
$X^1$ is halogen;
$R^1$ is H or alkyl;
$R^2$ is alkyl;
$R^3$ is H, alkyl or heterocyclyl;
$R^4$ and $R^5$ are independently chosen from H and alkyl; and
$R^6$ is H or alkyl;
or a pharmaceutically acceptable salt, a prodrug, an N-oxide or a solvate thereof.

The present disclosure, in an aspect relates to an aminosteroid derivative having the structure:

wherein:
B is CO, SO, $SO_2$, $CH_2$, $C(X^1)_2$, or absent;
$Y^1$ is chosen from OH, halogen, $OR^2$, $OCOR^3$, $OCONR^4R^5$ and $OSO_2NR^4R^5$;

$Y^2$ is chosen from O and S;
$Y^3$ is $H_2$ or O;
Z is H, halogen or C≡$CR_6$;
V is an amino acid,

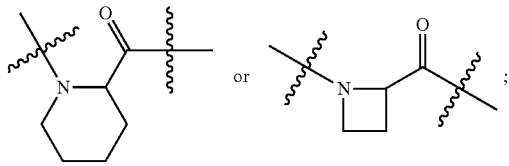 [SMILES: *C(=O)C1CCCCN1* ; *C(=O)C1CCN1*]

W is CO, $SO_2$, $CH_2$, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
$X^1$ is halogen;
$R^2$ is alkyl;
$R^3$ is H, alkyl or heterocyclyl;
$R^4$ and $R^5$ are independently chosen from H and alkyl; and
$R^6$ is H or alkyl;
or a pharmaceutically acceptable salt, a prodrug, an N-oxide or a solvate thereof.

In an embodiment the aminosteroid derivative of Formula II has a structure wherein V is proline and wherein the variables W and X are linked to form the linkage W-X, wherein W-X is chosen from

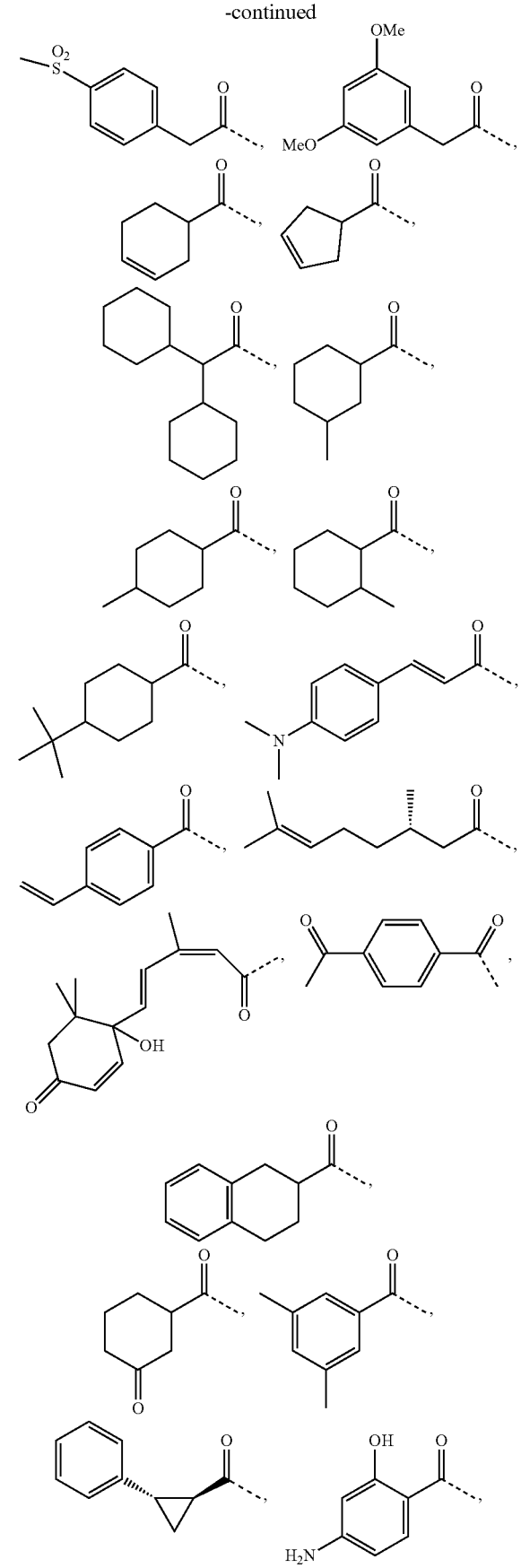

-continued

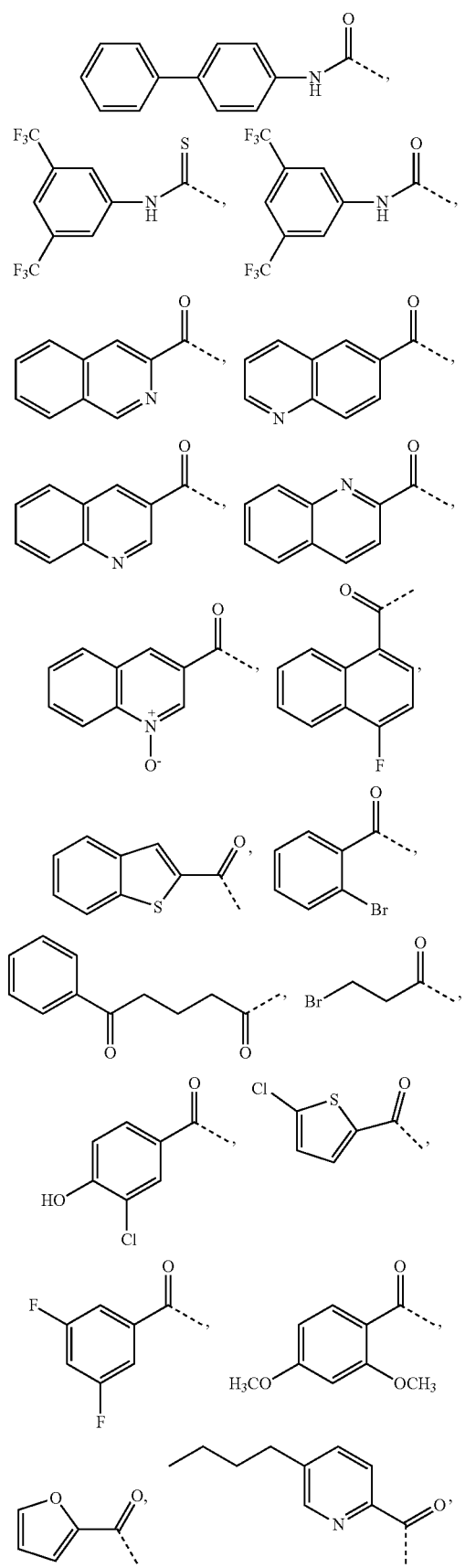
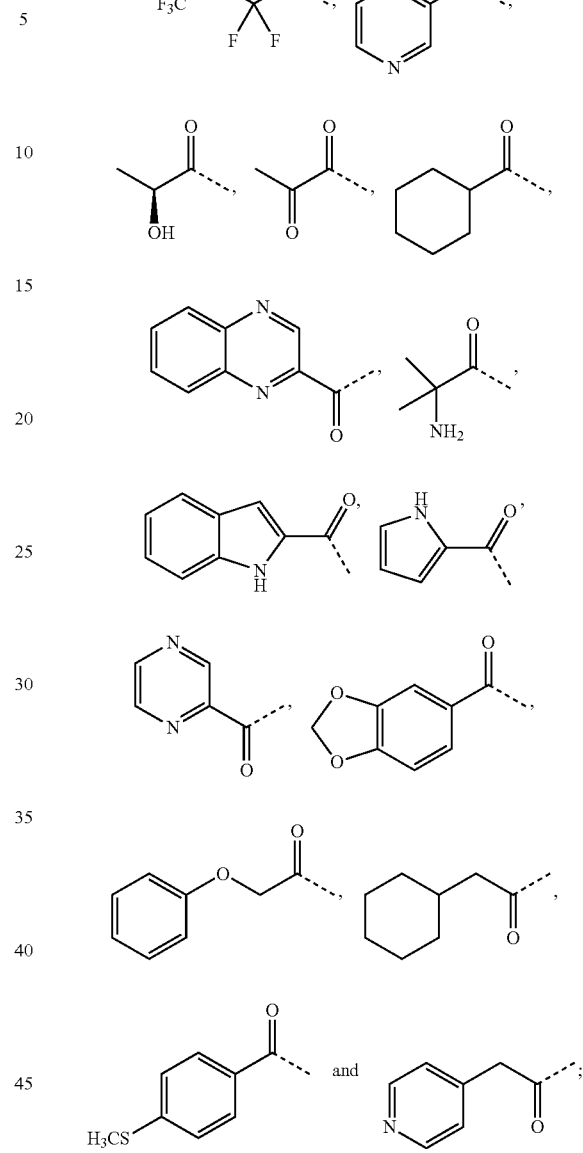
or a pharmaceutically acceptable salt, an N-oxide or a solvate thereof.
In an embodiment the aminosteroid derivative of Formula II has the structure:
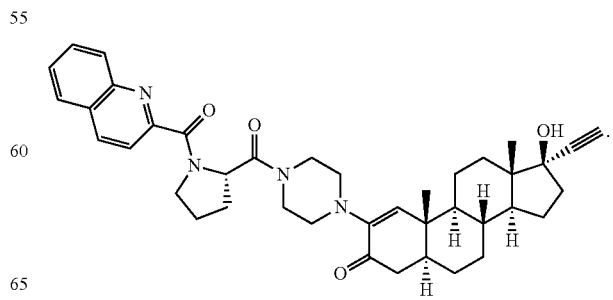

In an embodiment the aminosteroid derivative of Formula II has the structure:

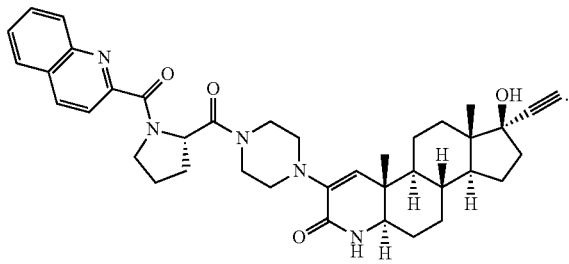

In an embodiment the aminosteroid derivative of Formula II has the structure:

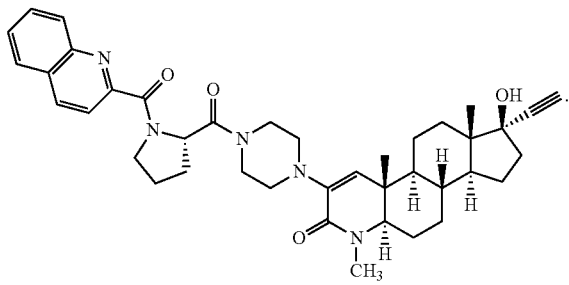

The present disclosure, in an aspect relates to an aminosteroid derivative of Formula III:

Formula III

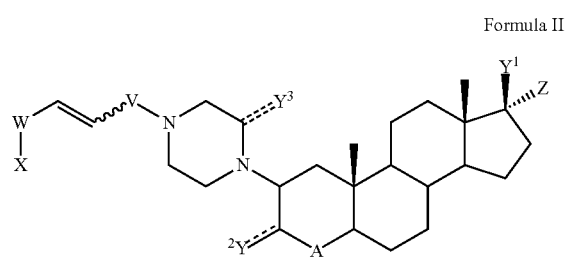

wherein:
A is $CHR^1$, $NR^1$, O or S;
$Y^1$ is chosen from OH, halogen, $OR^2$, $OCOR^3$, $OCONR^4R^5$ and $OSO_2NR^4R^5$;
$Y^2$ is chosen from H, halogen, OH, $OR_2$, OMOM (O-methoxymethyl ether), $OCOR^3$ and $OCONR^4R^5$, when $Y^2 \text{\textequiv} C$ is $Y^2$—C and
$Y^2$ is O or S when $Y^2 \text{\textequiv} C$ is $Y^2$=C;
$Y^3$ is $H_2$ or O;
Z is H or $C{\equiv}CR_6$;
V is an amino acid,

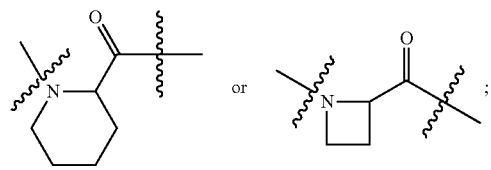

W is CO, $SO_2$, $CH_2$, CONH, CSNH, or

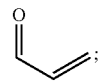

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
$R^1$ is H or alkyl;
$R^2$ is alkyl;
$R^3$ is H, alkyl or heterocyclyl;
$R^4$ and $R^5$ are independently chosen from H and alkyl; and
$R^6$ is H or alkyl;
or a pharmaceutically acceptable salt, a prodrug, an N-oxide or a solvate thereof.

The present disclosure, in an aspect relates to an aminosteroid derivative having the structure:

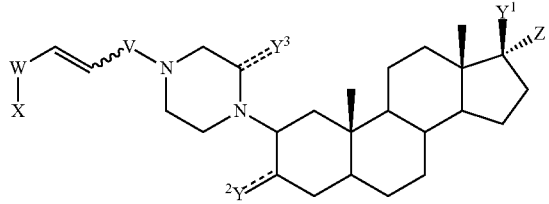

wherein:
$Y^1$ is chosen from OH, halogen, $OR^2$, $OCOR^3$, $OCONR^4R^5$ and $OSO_2NR^4R^5$;
$Y^2$ is chosen from H, halogen, OH, $OR_2$, OMOM (O-methoxymethyl ether), $OCOR^3$, $OCONR^4R^5$, $OSO_2NH_2$ or $OPO(OH)_2$, when $Y^2 \text{\textequiv} C$ is $Y^2$—C and
$Y^2$ is O or S when $Y^2 \text{\textequiv} C$ is $Y^2$=C;
$Y^3$ is $H_2$ or O;
Z is H or $C{\equiv}CR_6$;
V is an amino acid,

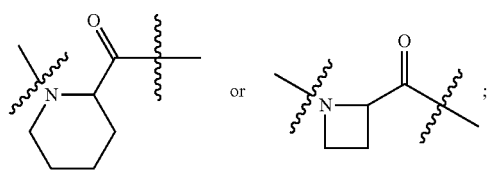

W is CO, $SO_2$, $CH_2$, CONH, CSNH, or

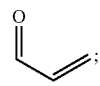

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
$R^1$ is H or alkyl;
$R^2$ is alkyl;

R[3] is H, alkyl or heterocyclyl;
R[4] and R[5] are independently chosen from H and alkyl; and
R[6] is H or alkyl;
or a pharmaceutically acceptable salt, a prodrug, an N-oxide or a solvate thereof.
In an embodiment the aminosteroid derivative of Formula III has a structure wherein V is proline and wherein the variables W and X are linked to form the linkage W-X, wherein W-X is chosen from
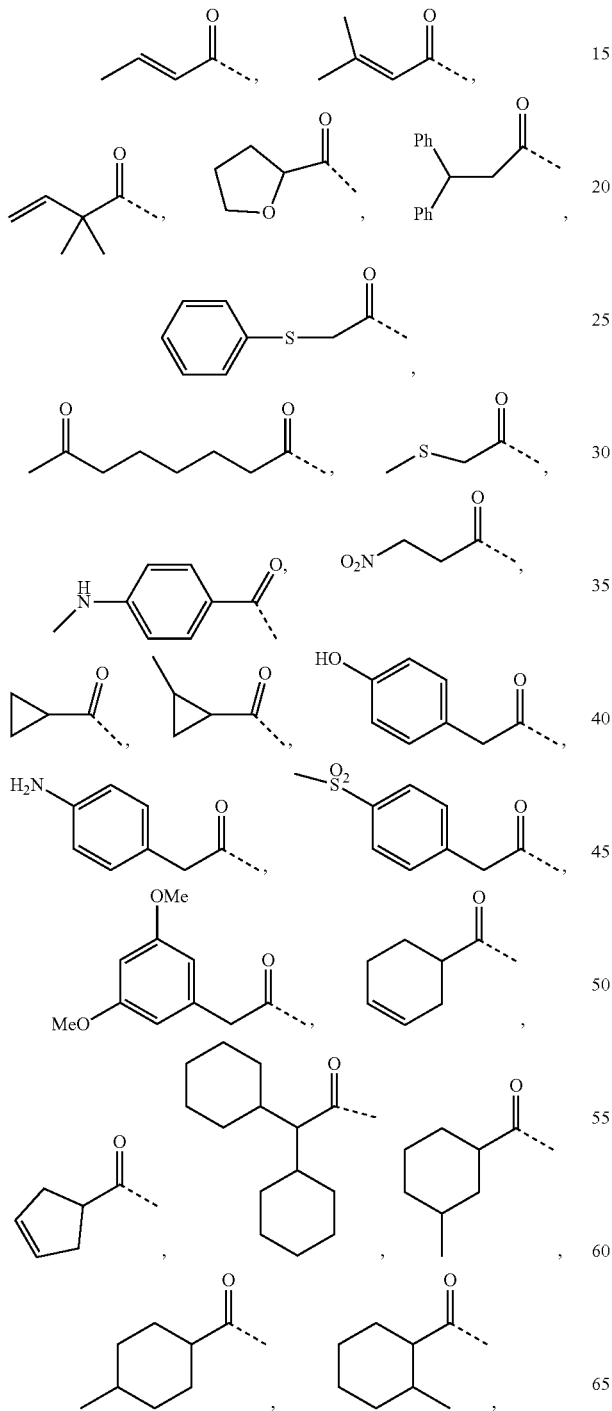
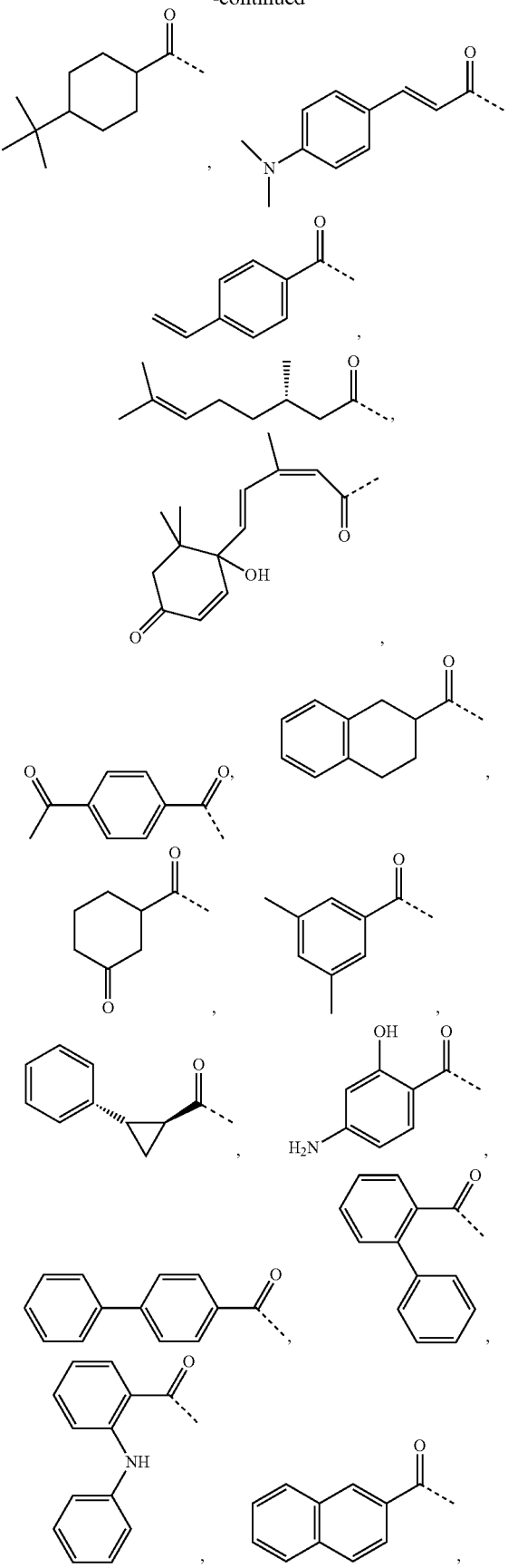

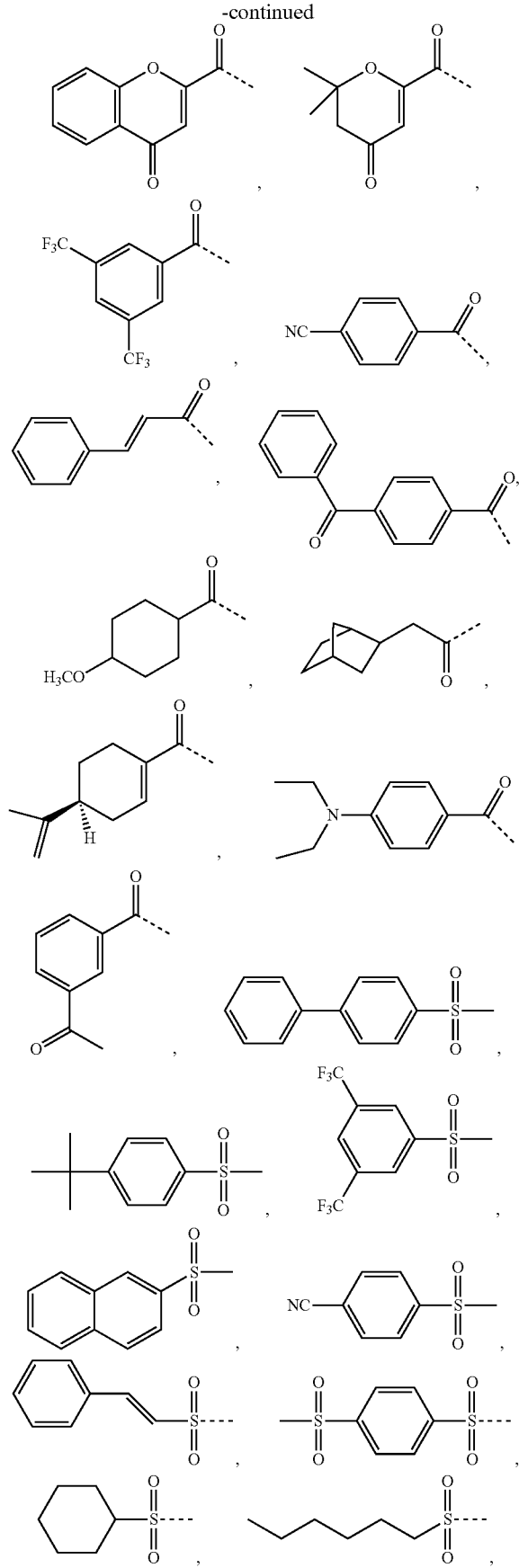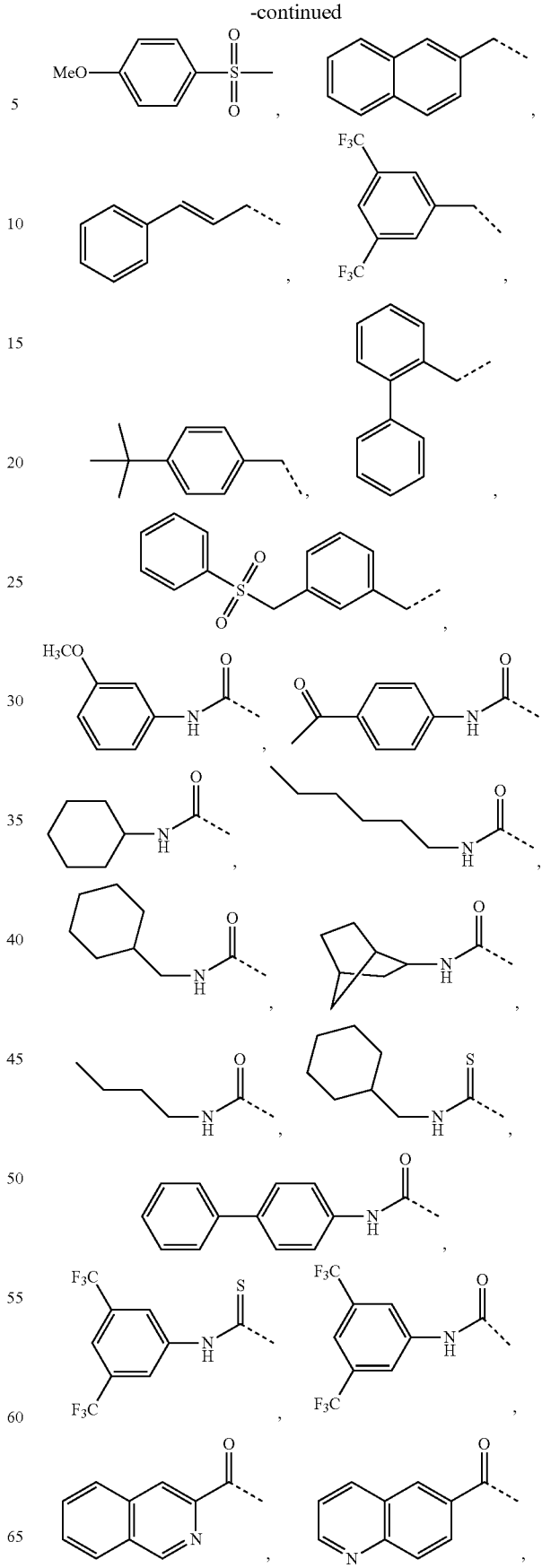

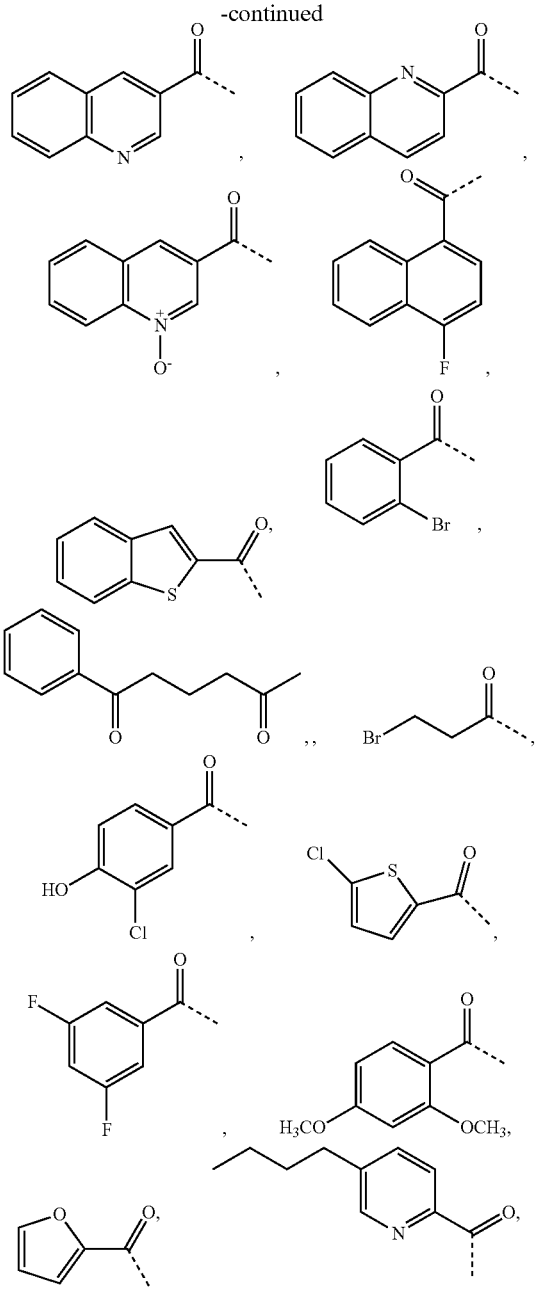
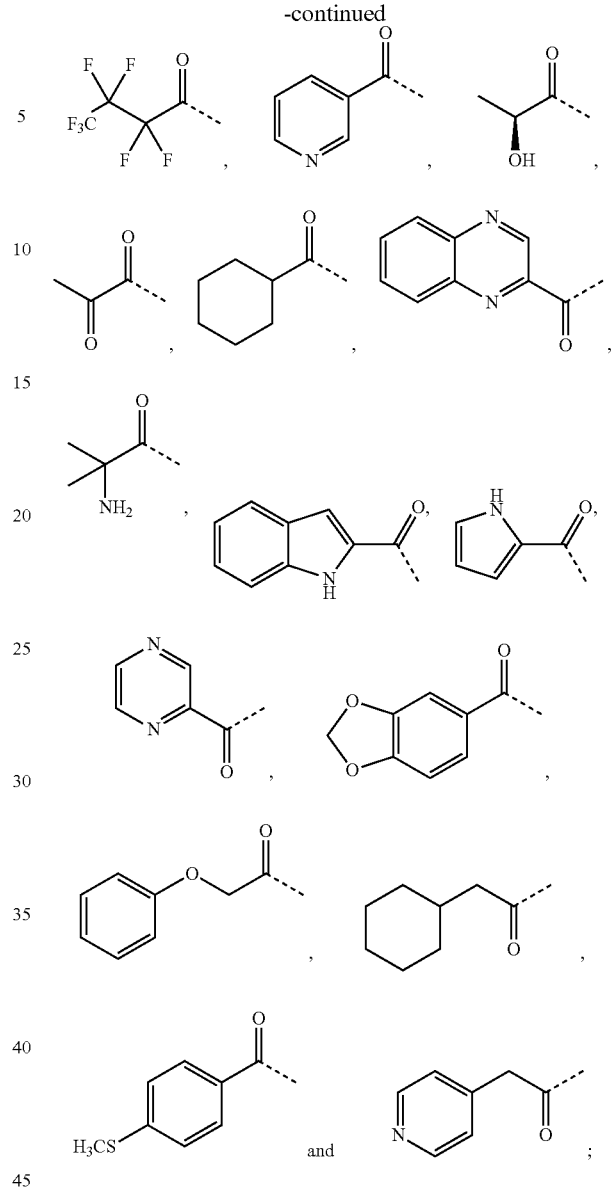
or a pharmaceutically acceptable salt, an N-oxide or a solvate thereof.
In an embodiment the aminosteroid derivative of Formula III has the structure:
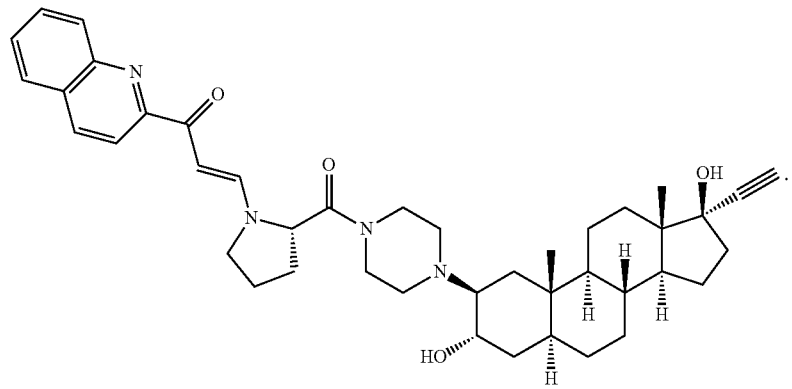

The present disclosure, in an aspect relates to an aminosteroid derivative of Formula IV:

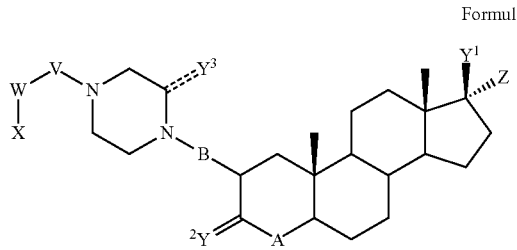

Formula IV wherein:
A is CHR¹, NR¹, O or S;
B is CO, SO₂, CH₂, C(X¹)₂, or absent;
Y¹ is chosen from OH, halogen, OR², OCOR³, OCONR⁴R⁵ and OSO₂NR⁴R⁵;
Y² is O, S;
Y³ is H₂ or O;
Z is H or C≡CR₆;
V is an amino acid,

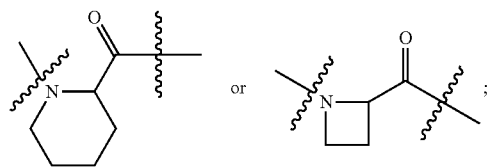

W is CO, SO₂, CH₂, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
X¹ is halogen;
R¹ is H or alkyl;
R² is alkyl;
R³ is H, alkyl or heterocyclyl;
R⁴ and R⁵ are independently chosen from H and alkyl; and
R⁶ is H or alkyl;
or a pharmaceutically acceptable salt, a prodrug, an N-oxide or a solvate thereof.

The present disclosure, in an aspect relates to an aminosteroid derivative having the structure:

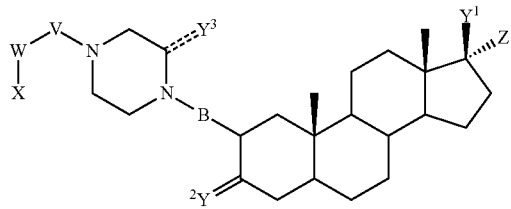

wherein:
B is CO, SO₂, CH₂, C(X¹)₂, or absent;
Y¹ is chosen from OH, halogen, OR², OCOR³, OCONR⁴R⁵ and OSO₂NR⁴R⁵;
Y² is O, S;
Y³ is H₂ or O;
Z is H or C≡CR₆;
V is an amino acid,

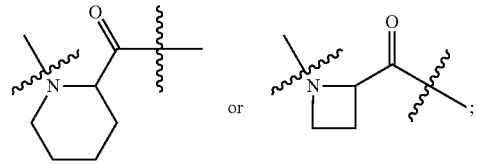

W is CO, SO₂, CH₂, CONH, CSNH, or

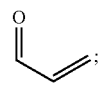

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
X¹ is halogen;
R¹ is H or alkyl;
R² is alkyl;
R³ is H, alkyl or heterocyclyl;
R⁴ and R⁵ are independently chosen from H and alkyl; and
R⁶ is H or alkyl;
or a pharmaceutically acceptable salt, a prodrug, an N-oxide or a solvate thereof.

In an embodiment the aminosteroid derivative of Formula IV has a structure wherein V is proline and wherein the variables W and X are linked to form the linkage W-X, wherein W-X is chosen from

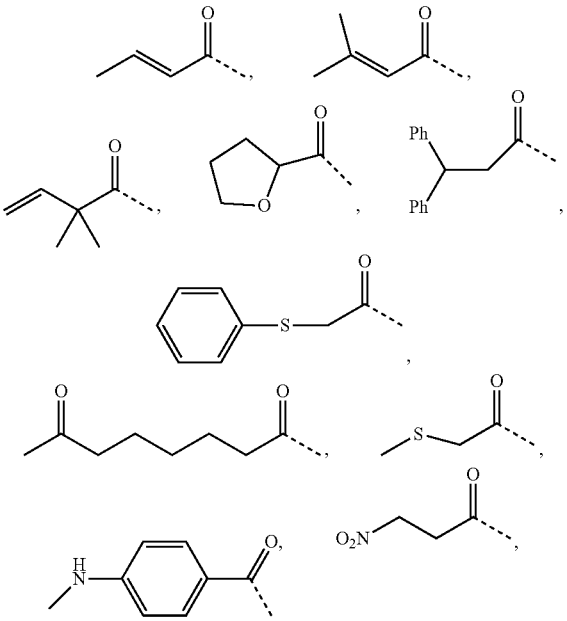

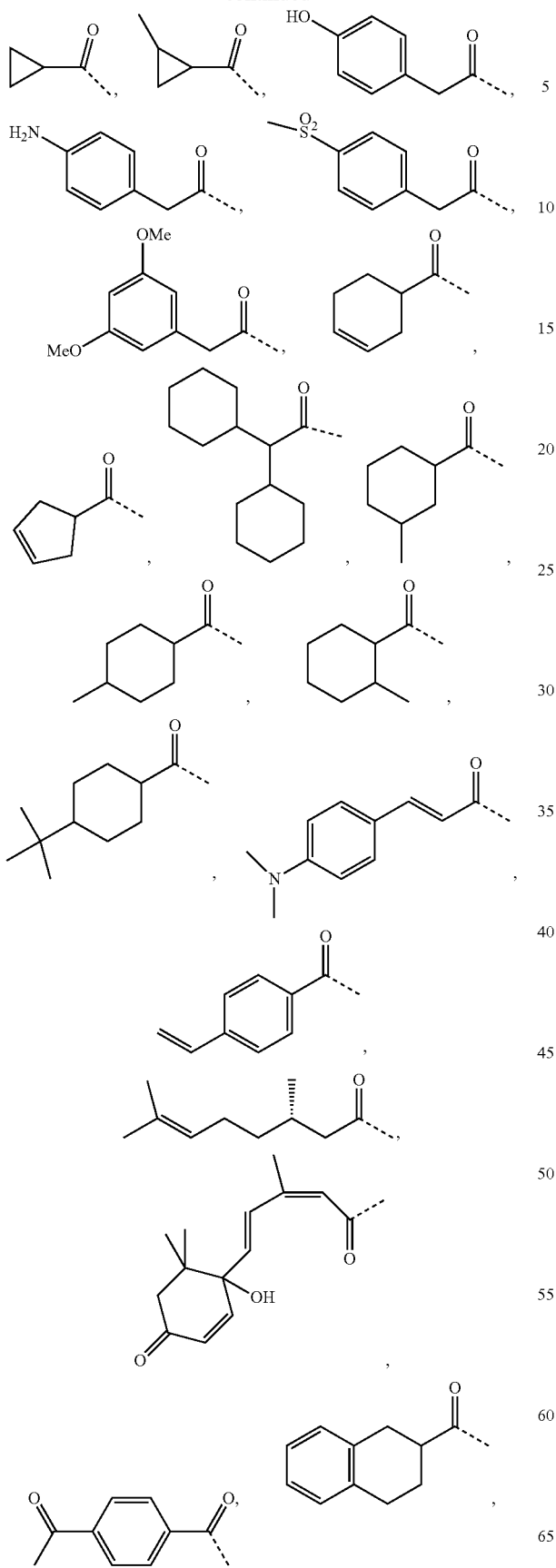
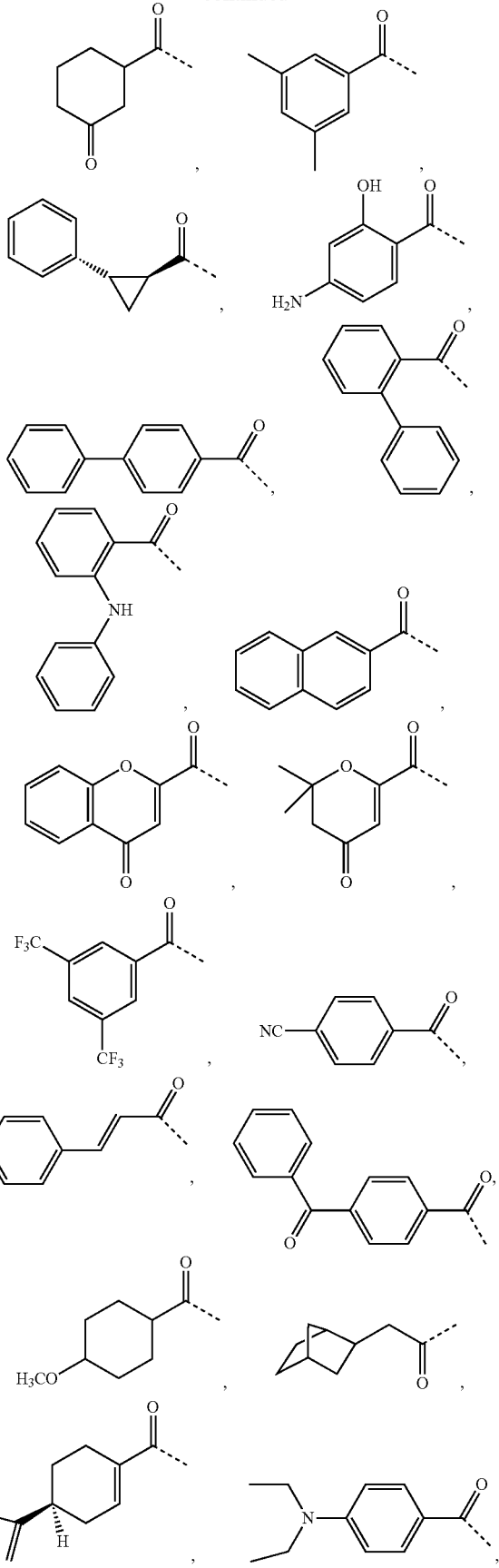

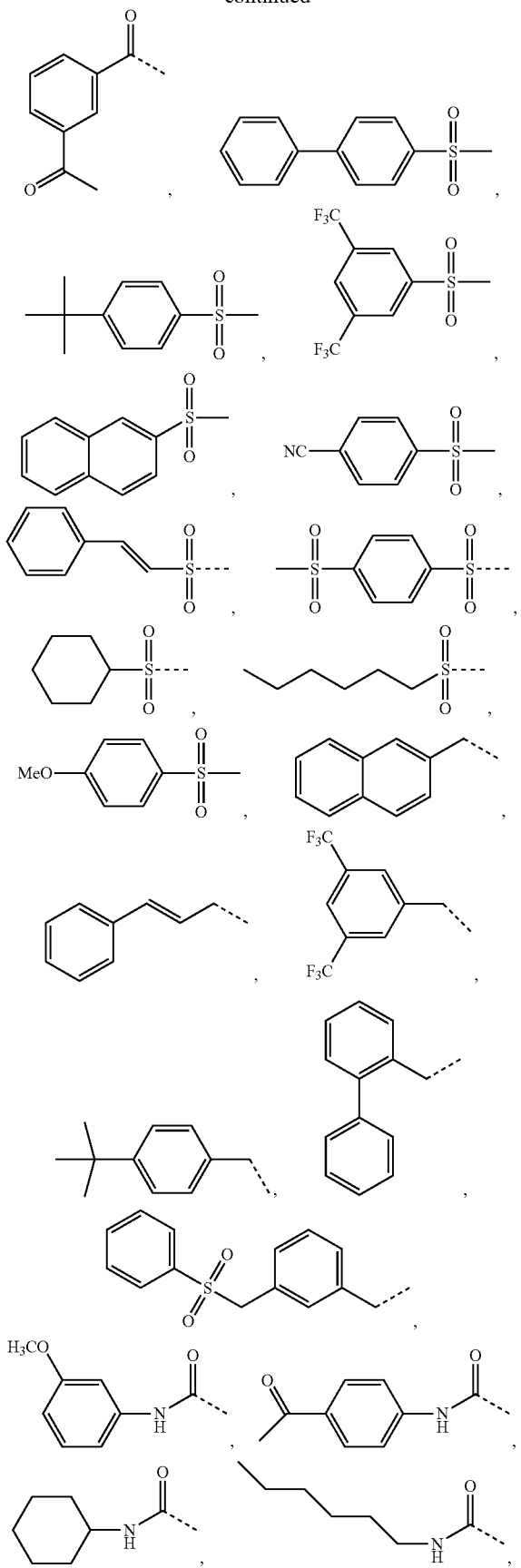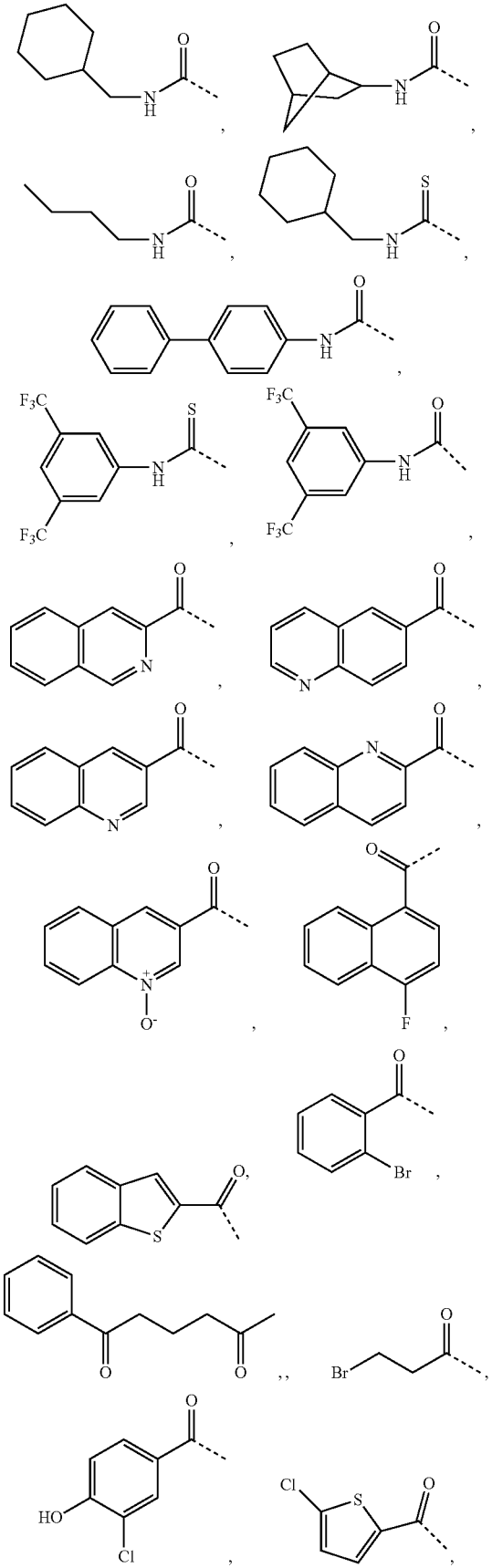

-continued

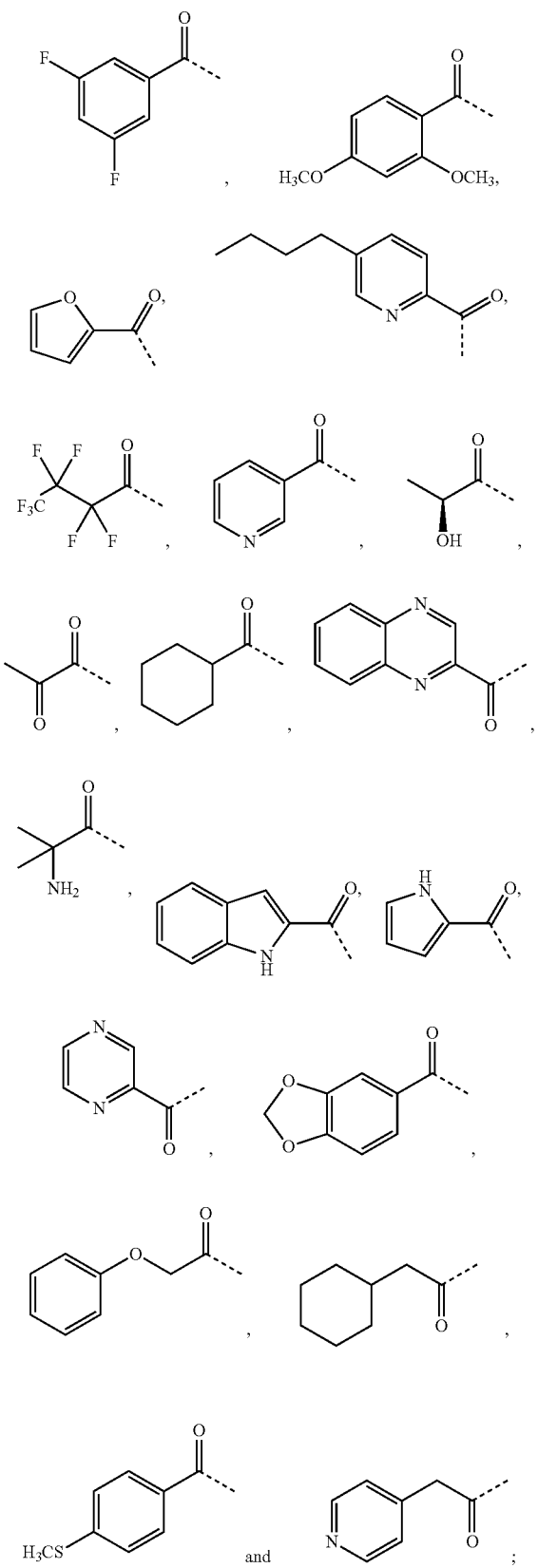

or a pharmaceutically acceptable salt, an N-oxide or a solvate thereof.

In an embodiment the aminosteroid derivative of Formula IV has the structure:

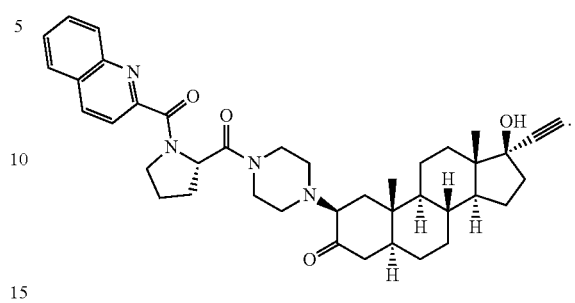

In an aspect, the present disclosure relates to a pharmaceutical composition comprising a pharmaceutically acceptable amount of an aminosteroid derivative such as disclosed herein, or a pharmaceutically acceptable salt, a prodrug, an oxide or a solvate thereof, and a pharmaceutically acceptable carrier.

In an aspect, the present disclosure relates to a pharmaceutical combination comprising an aminosteroid derivative such as disclosed herein, or a pharmaceutically acceptable salt, a prodrug, an oxide or a solvate thereof, and one or more agents selected from a taxane, an epothitone, an anti-androgen and a platinum derivative. In an embodiment of the present disclosure, the one or more agents are at least one of docetaxel, pacitaxel, taxol, ixabepitone, patupitone, sagopitone; mitoxantrone; predinisotone; dexamethasone; estramustin; vinblastin; vincristin; doxorubicin; adriamycin; idarubicin; daunorubicin; bleomycin; etoposide; cyctophosphamide; ifosfamide; procarbazine; metphalan; 5-fluorouracil; capecitabine; fludarabine; cytarabine; ara-C; 2-chloro-2"-deoxyadenosine, thioguanine, flutamide, cyproterone acetate, bicatutamide, bortezomib, cisplatin, carboplatin; chlorambucil; methotrexate or rituximab.

In an aspect, the present disclosure relates to the use of an aminosteroid derivative such as disclosed herein, or a pharmaceutically acceptable salt, a prodrug, an oxide or a solvate thereof, for the prophylaxis or treatment of a disease. In an embodiment of the present disclosure, the disease is associated with uncontrolled cell growth, proliferation and/or survival. In a further embodiment of the present disclosure, the disease comprises ovarian cancer, pancreatic cancer, leukemia, prostate cancer, breast cancer and skin cancer.

In an aspect, the present disclosure relates to the use of a pharmaceutical composition comprising a pharmaceutically acceptable amount of an aminosteroid derivative such as disclosed herein, or a pharmaceutically acceptable salt, a prodrug, an oxide or a solvate thereof, and a pharmaceutically acceptable carrier for the prophylaxis or treatment of a disease. In an embodiment of the present disclosure, the disease is associated with uncontrolled cell growth, proliferation and/or survival. In a further embodiment of the present disclosure, the disease comprises ovarian cancer, pancreatic cancer, leukemia, prostate cancer, breast cancer and skin cancer.

In an aspect, the present disclosure relates to the use of a pharmaceutical combination comprising an aminosteroid derivative such as disclosed herein, or a pharmaceutically acceptable salt, a prodrug, an oxide or a solvate thereof, and one or more agents selected from a taxane, an epothitone, an anti-androgen and a platinum derivative, for the prophylaxis or treatment of a disease. In an embodiment of the present disclosure, the disease is associated with uncontrolled cell growth, proliferation and/or survival. In a further embodiment of the present disclosure, the disease comprises ovarian cancer, pancreatic cancer, leukemia, prostate cancer, breast cancer and skin cancer. In a further embodiment of the present disclosure, the one or more agents are selected from a taxane, an epothitone, an anti-androgen and a platinum derivative. In an embodiment of the present disclosure, the one or more agents are at least one of docetaxel, pacitaxel, taxol, ixabepitone, patupitone, sagopitone; mitoxantrone; predinisotone; dexamethasone; estramustin; vinblastin; vincristin; doxorubicin; adriamycin; idarubicin; daunorubicin; bleomycin; etoposide; cyctophosphamide; ifosfamide; procarbazine; metphalan; 5-fluorouracil; capecitabine; fludarabine; cytarabine; ara-C; 2-chloro-2"-deoxyadenosine, thioguanine, flutamide, cyproterone acetate, bicatutamide, bortezomib, cisplatin, carboplatin; chlorambucil; methotrexate or rituximab.

In an aspect, the present disclosure relates to a method of treating a disease in a subject comprising administering to the subject an aminosteroid derivative such as disclosed herein or a pharmaceutically acceptable salt, a prodrug, an oxide or a solvate thereof. In an embodiment of the present disclosure, the aminosteroid derivative, or a pharmaceutically acceptable salt, a prodrug, an oxide or a solvate thereof, is administered intravenously, intra-arterially, subcutaneously, topically, or intramuscularly. In an embodiment of the present disclosure, the aminosteroid derivative, or a pharmaceutically acceptable salt, a prodrug, an oxide or a solvate thereof, is administered systemically, regionally to a tumor/disease site, locally to a tumor/disease site, into tumor/tissue vasculature or intratumorally. In a further embodiment of the present disclosure, the disease is associated with uncontrolled cell growth, proliferation and/or survival. In a further embodiment of the present disclosure, the disease comprises ovarian cancer, pancreatic cancer, leukemia, prostate cancer, breast cancer and skin cancer. In yet a further embodiment of the present disclosure, the subject is a human. In yet a further embodiment of the present disclosure, the subject is a non-human animal.

In aspect, the present disclosure relates to a method of reducing proliferation of/or inducing cell death of neoplastic cells comprising, contacting the neoplastic cells with one or more of the aminosteroid derivatives as disclosed herein, or a pharmaceutically acceptable salt, a prodrug, an oxide or a solvate thereof.

In an aspect, the present disclosure relates to the use of one or more of the aminosteroid derivatives as disclosed herein, or a pharmaceutically acceptable salt, a prodrug, an oxide or a solvate thereof, in the manufacture of a medicament for the treatment of a disease associated with uncontrolled cell growth, proliferation and/or survival. In a further embodiment of the present disclosure, the disease comprises ovarian cancer, pancreatic cancer, leukemia, prostate cancer, breast cancer and skin cancer.

In an aspect, the present disclosure relates to a pharmaceutical composition comprising an effective amount of one or more of the aminosteroid derivatives as disclosed herein, or a pharmaceutically acceptable salt, a prodrug, an oxide or a solvate thereof, in association with one or more pharmaceutically acceptable carriers, excipients or diluents.

In an aspect, the present disclosure relates to an admixture comprising an effective amount of one or more of the aminosteroid derivatives as disclosed herein, or a pharmaceutically acceptable salt, a prodrug, an oxide or a solvate thereof, in association with one or more pharmaceutically acceptable carriers, excipients or diluents.

The foregoing and other advantages and features of the present disclosure will become more apparent upon reading of the following non-restrictive description of illustrative embodiments thereof, given by way of example only with reference to the accompanying drawings/figures.

BRIEF DESCRIPTION OF THE DRAWINGS/FIGURES

In the appended drawings/figures:

FIG. 1 is an illustration of the potential metabolization sites of RM-133 by cytochromes P450 (CYPs). At least 6 functional groups at different positions on RM-133 are susceptible to phase I hepatic metabolism.

FIG. 2 is an illustration of the effect of aminosteroid RM-581-102 (compound 6) on MCF-7 tumor growth. A) Effect of a 28-day treatment on 17β-estradiol (E2)-induced growth of human MCF-7 breast tumors in ovariectomized (OVX) nude mice in accordance with an embodiment of the present disclosure. Tumor sizes are expressed as the percentage of initial tumor area (day 1 of treatment=100%). Data are expressed as the mean±SEM (n=10-12 tumors and 6-7 mice per group). RM-581 was administered by subcutaneous (s.c.) injection 6 days per week at a dose of 1530 μg (60 mg/kg on average) under E2 stimulation obtained with a 0.5 cm Silastic implant inserted s.c., and containing a 1:8 ratio of E2 and cholesterol. **p<0.01, *p<0.05 significantly different from initial size. Treatment with RM-581 (60 mg/kg, s.c.) showed a beneficial effect on MCF-7 tumor progression, leading to a complete blockade of tumor growth, and even to significant tumor regression from day 21 up to day 28. B) Initial and final body weight of the mice. Data are expressed as the mean±SD; *p<0.05 significantly different from initial weight. It is worth noticing that over a 28-day treatment period with RM-581, there were no behavioral changes, signs of toxicity and weight loss, when compared with the control groups (OVX and OVX+E2).

FIG. 3 illustrates the metabolic stability of the RM-133 analogs. The results are expressed as the % of remaining analog following treatment by a preparation of human hepatic microsomes and the Figure represents the average of 2 experiments±standard deviation. The preparation of the quaternary ammonium methyl iodide salt (androstane-based aminosteroid derivatives 6) and the N-oxide derivative (androstane-based aminosteroid derivatives 7) are modifications aimed at countering the potential for hepatic N-dealkylation.

FIG. 4 illustrates the human hepatic phase-I metabolic stability of aminosteroid derivatives RM-133, RM-581-99, RM-581-96 and RM-581-102 (10 μM) incubated for 1 h in the presence of human liver microsomes (40 μg). Results are expressed as the percentage of the remaining quantity of 10 μM RM-133, RM-581-99, RM-581-96 and RM-581-102 that remained intact after 1 h in the presence of 40 μg of human liver microsomes. Data are the average±SD of four experiments; *p<0.05. RM-581-102 is therefore significantly more stable toward phase-I hepatic metabolism than RM-133.

FIG. 5 is an illustration of the effect of aminosteroid RM-581-102 (compound 6) on PANC-1 tumor growth and the effect of treatment over a period of 27 days on tumor size in accordance with an embodiment of the present disclosure. Tumor size is expressed as the percentage of initial tumor area (day 1=100%).

FIG. 6 is an illustration of the cell survival (%) of different cancer cell lines (LAPC-4 (prostate); T-47D and MCF-7 (breast); PANC-1, BxPC3 and Hs766 (pancreatic);

OVCAR-3, Caov-3 and SKOV-3 (ovarian)) after 3 days treatment with different derivatives of RM-581 (as illustrated in Schemes 3-7) at concentrations of 5 μM (A) and 1 μM (B), in accordance with an embodiment of the present disclosure.

FIG. 7 is an illustration of the metabolic stability of various RM-581 analogs. The results are expressed as the % of remaining quantity of the compound following an incubation period of 1 h after treatment by a preparation of human hepatic microsomes and represent the average of 2 experiments±SD. The difference between two results was evaluated using a T-test; p values, which were less than 0.05, were considered as statistically significant. **$p<0.01$ and *$p<0.05$ from RM-581.

DETAILED DESCRIPTION

Glossary

Figure 1:
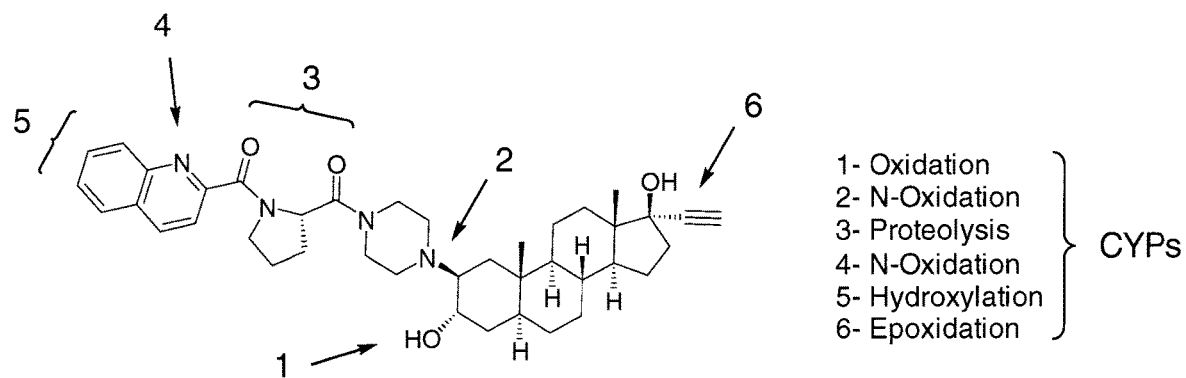
Figure 2:
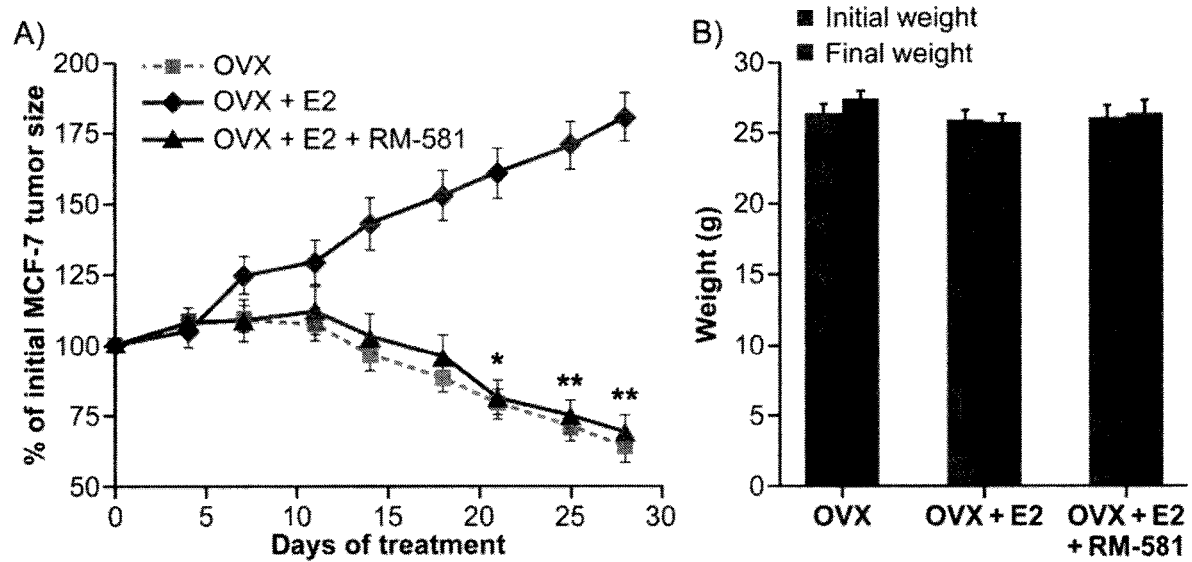

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this disclosure pertains.

The word "a" or "an" when used in conjunction with the term "comprising" in the claims and/or the disclosure may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this disclosure and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this disclosure and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 99% of the starting material or substrate is converted to product.

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups comprise from 2 to 10 carbons.

The term "alkyl" or "alk" as used herein, represents a monovalent group derived from a straight or branched chain saturated hydrocarbon comprising, unless otherwise specified, from 1 to 15 carbon atoms and is exemplified by methyl, ethyl, n- and iso-propyl, n-, sec-, iso- and tert-butyl, neopentyl and the like and may be optionally substituted with one, two, three or, in the case of alkyl groups comprising two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) OC(O)$R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) C(O)$R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) C(O)$NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) S(O)$R^E$, where $R^E$ is selected from the group consisting of (a) alkyl, (b) aryl, (c) arylalkyl, where the alkylene group comprises one to six carbon atoms, and (d) hydroxyl; (29) S(O)$_2R^E$, where $R^E$ is selected from the group consisting of (a) alkyl, (b) aryl, (c) arylalkyl, where the alkylene group comprises one to six carbon atoms, and (d) hydroxyl; (30) S(O)$_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The terms "alkoxy" or "alkyloxy," as used interchangeably herein, represent an alkyl group attached to the parent molecular group through an oxygen atom.

The term "alkylsulfinyl" as used herein, represents an alkyl group attached to the parent molecular group through an S(O) group.

The term "alkylsulfonyl," as used herein, represents an alkyl group attached to the parent molecular group through a S(O)$_2$ group.

The term "alkylthio" as used herein, represents an alkyl group attached to the parent molecular group through a sulfur atom.

The term "alkylene" as used herein, represents a saturated divalent hydrocarbon group derived from a straight or branched chain saturated hydrocarbon by the removal of two hydrogen atoms, and is exemplified by methylene, ethylene, isopropylene and the like.

The term "alkenyl," as used herein, represents monovalent straight or branched chain groups of, unless otherwise specified, from 2 to 15 carbons, such as, for example, 2 to 6 carbon atoms or 2 to 4 carbon atoms, containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) OC(O)$R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) C(O)$R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) C(O)$NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) S(O)$R^E$, where $R^E$ is selected from the group consisting of (a) alkyl, (b) aryl, (c) arylalkyl, where the alkylene group comprises one to six carbon atoms, and (d) hydroxyl; (29) S(O)$_2R^E$, where $R^E$ is selected from the group consisting of (a) alkyl, (b) aryl, (c) arylalkyl, where the alkylene group comprises one to six carbon atoms, and (d) hydroxyl; (30) S(O)$_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms; (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "alkynyl" as used herein, represents monovalent straight or branched chain groups of from two to six carbon atoms comprising a carbon-carbon triple bond and is exemplified by ethynyl, 1-propynyl, and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_1$-6 alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) $—NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "aryl" as used herein, represents mono- and/or bicyclic carbocyclic ring systems and/or multiple rings fused together and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups are independently comprised of one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where $R^B$ and $R^C$ are independently selected from the group consisting of (a) hydrogen, (b) alkyl, (c) aryl, and (d) arylalkyl, where the alkylene group comprises one to six carbon atoms; (38) $(CH_2)_qS(O)_2R^D$, where $R^D$ is selected from the group consisting of (a) alkyl, (b) aryl, and (c) arylalkyl, where the alkylene group comprises one to six carbon atoms; (39) $(CH_2)_qS(O)_2NR^ER^F$, where each of $R^E$ and $R^F$ is independently selected from the group consisting of (a) hydrogen, (b) alkyl, (c) aryl, and (d) arylalkyl, where the alkylene group comprises one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "alkaryl" represents an aryl group attached to the parent molecular group through an alkyl group.

The term "alkheterocyclyl" represents a heterocyclic group attached to the parent molecular group through an alkyl group.

The term "aryloxy" as used herein, represents an aryl group that is attached to the parent molecular group through an oxygen atom.

The term "alkoxyalkyl" as used herein means alkyl-O-alkyl-, wherein alkyl is defined above.

The term "alkoxyaryl" as used herein means alkyl-O-aryl-, wherein alkyl is defined above.

The term "alkthioalkyl" as used herein means alkyl-S-alkyl-, wherein alkyl is defined above.

The term "alkthioaryl" as used herein means alkyl-S-aryl-, wherein alkyl is defined above.

The terms "aryloyl" or "aroyl" as used interchangeably herein, represent an aryl group that is attached to the parent molecular group through a carbonyl group.

The term "carbonyl" as used herein, represents a C(O) group, which can also be represented as C=O.

The terms "carboxy" or "carboxyl," as used interchangeably herein, represents a CO$_2$H group.

The term "cycloalkyl" as used herein, represents a monovalent saturated or unsaturated non-aromatic cyclic hydrocarbon group of three to eight carbon atoms, unless otherwise specified, and is exemplified by cyclopropyl, cyclobutyl, cyclopentyl, cyclohexyl, cycloheptyl, bicyclo [2.2.1.]heptyl and the like. The cycloalkyl groups of the present disclosure can be optionally substituted with: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde) alkyl, where the alkylene group comprises one to six carbon atoms; 20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) (CH$_2$)$_q$CO$_2$R$^A$, where q is an integer ranging from zero to four and R$^A$ is selected from the group consisting of (a) alkyl, (b) aryl, and (c) arylalkyl, where the alkylene group comprises one to six carbon atoms; (37) (CH$_2$)$_q$C(O)NR$^B$R$^C$, where each of R$^B$ and R$^C$ is independently selected from the group consisting of (a) hydrogen, (b) alkyl, (c) aryl, and (d) arylalkyl, where the alkylene group comprises one to six carbon atoms; (38) (CH$_2$)$_q$S(O)$_2$R$^D$, where R$^D$ is selected from the group consisting of (a) alkyl, (b) aryl, and (c) arylalkyl, where the alkylene group comprises one to six carbon atoms; (39) (CH$_2$)$_q$S(O)$_2$NR$^E$R$^F$, where each of R$^E$ and R$^F$ is independently, selected from the group consisting of (a) hydrogen, (b) alkyl, (c) aryl, and (d) arylalkyl, where the alkylene group comprises one to six carbon atoms; (40) (CH$_2$)$_q$NR$^G$R$^H$, where each of R$^G$ and R$^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "halogen" or "halo" as used interchangeably herein, represents F, Cl, Br and I.

The term "heteroaryl" as used herein, represents that subset of heterocycles, as defined herein, which is aromatic: (i.e., containing 4n+2 pi electrons within a mono- or multicyclic ring system).

The terms "heterocycle" or "heterocyclyl" as used interchangeably herein represent a 5-, 6- or 7-membered ring, unless otherwise specified, comprising one, two, three, or four heteroatoms independently selected from the group consisting of nitrogen, oxygen, and sulfur. The 5-membered ring has from zero to two double bonds and the 6- and 7-membered rings have from zero to three double bonds. The term "heterocycle" also includes bicyclic, tricyclic, and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring such as indolyl, quinolyl, isoquinolyl, tetrahydroquinolyl, benzofuryl, benzothienyl and the like. Heterocycles include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroinidolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

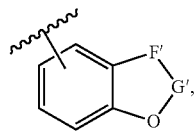

where is selected from the group consisting of $CH_2$, $CH_2O$ and O, and G' is selected from the group consisting of C(O) and $(C(R')(R''))_v$, where each of R' and R" is independently selected from the group consisting of hydrogen and alkyl of one to four carbon atoms, and v is an integer ranging from one to three, and includes groups such as 1,3-benzodioxolyl, 1,4-benzodioxanyl and the like. Any of the heterocyclic groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises from three to eight carbon atoms and the alkylene group comprises from one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises from one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises from one to six carbon atoms; (37) $(CH_2)_qC(O)NR^BR^C$, where each of $R^B$ and $R^C$ is independently selected from the group consisting of (a) hydrogen, (b) alkyl, (c) aryl, and (d) arylalkyl, where the alkylene group comprises from one to six carbon atoms; (38) $(CH_2)_qS(O)_2R^D$, where $R^D$ is selected from the group consisting of (a) alkyl, (b) aryl, and (c) arylalkyl, where the alkylene group comprises from one to six carbon atoms; (39) $(CH_2)_qS(O)_2NR^ER^F$, where each of $R^E$ and $R^F$ is independently selected from the group consisting of (a) hydrogen, (b) alkyl, (c) aryl, and (d) arylalkyl, where the alkylene group comprises from one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises from one to six carbon atoms; (h) cycloalkyl of three to eight carbon atoms, and (i) alkcycloalkyl, where the cycloalkyl group comprises from three to eight carbon atoms, and the alkylene group comprises from one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The terms "heterocyclyloxy" or "(heterocycle)oxy" as used interchangeably herein, represents a heterocyclic group, as defined herein, attached to the parent molecular group through an oxygen atom.

The term "heterocyclyloyl" or "(heterocycle)oyl" as used interchangeably herein, represents a heterocyclic group, as defined herein, attached to the parent molecular group through a carbonyl group.

The term "amino acid", as used herein, is understood as including both the L and D isomers of the naturally occurring amino acids, as well as other non-proteinaceous amino acids used in peptide chemistry to prepare synthetic analogs of peptides. Examples of naturally-occurring amino acids include, but are not limited to glycine, alanine, valine, leucine, isoleucine, serine, and threonine. Examples of non-proteinaceous amino acids include, but are not limited to norleucine, norvaline, cyclohexyl alanine, biphenyl alanine, homophenyl alanine, naphthyl alanine, pyridyl alanine, and substituted phenyl alanines (substituted with a or more substituents including but not limited to alkoxy, halogen and nitro groups). Beta and gamma amino acids are also within the scope of the term "amino acid". Amino acids protected by standard protecting groups commonly used in peptide synthesis are also within the scope of the term "amino acid". These compounds are known to persons skilled in the art of peptide chemistry.

The term "oxo" as used herein, represents =O.

The term "perfluoroalkyl" as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "heteroatom", as used herein, is understood as being oxygen, sulfur or nitrogen.

The term "sulfinyl" as used herein, represents an S(O) group.

The term "sulfonyl" as used herein, represents an $S(O)_2$ group.

The term "thioalkoxy" as used herein, represents an alkyl group attached to the parent molecular group through a sulfur atom. Exemplary unsubstituted thioalkoxy groups comprise from 1 to 6 carbon atoms.

The term "thiocarbonyl" as used herein, represents a C(S) group, which can also be represented as C=S.

The term "patient", as used herein, is understood as being any individual treated with the aminosteroid derivatives of the present disclosure.

Prodrugs and solvates of the aminosteroid derivatives of the present disclosure are also contemplated herein. The term "prodrug", as used herein, is understood as being a compound which, upon administration to a subject, undergoes chemical conversion by metabolic or chemical processes to yield a compound of the present disclosure or a salt and/or solvate thereof. Non limiting examples of prodrugs include conversion of the 3α-OH into an

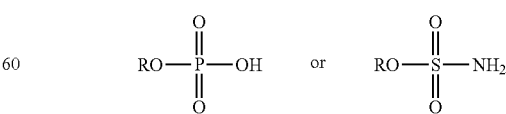

group. Solvates of the compounds of Formula I are preferably hydrates.

The term "derivative" as used herein, is understood as being a substance which comprises the same basic carbon skeleton and carbon functionality in its structure as a given compound, but can also bear one or more substituents or rings.

The term "analogue" as used herein, is understood as being a substance similar in structure to another compound but differing in some slight structural detail.

The term "salt(s)" as used herein, is understood as being acidic and/or basic salts formed with inorganic and/or organic acids or bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps.

Examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, phosphoric, 2-hydroxyethanesulfonate, lactate, maleate, mandelate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Examples of base addition salts include but are not limited to alkali metal salts and alkaline earth metal salts. Non limiting examples of alkali metal salts include lithium, sodium and potassium salts. Non-limiting examples of alkaline earth metal salts include magnesium and calcium salts.

In aspect, the present disclosure relates to pharmaceutical compositions comprising a therapeutically effective amount of one or more of the aminosteroid derivatives or pharmaceutically acceptable salts, N-oxides or solvates thereof as disclosed herein, and at least one pharmaceutically acceptable excipient, non-limiting examples of which are carriers and diluents. The term "therapeutically effective amount" is understood as being an amount of aminosteroid derivative or a pharmaceutically acceptable salt, N-oxide or solvate thereof as disclosed herein, required upon administration to a patient in order to treat a condition characterized by the uncontrolled proliferation of genetically altered tissue cells. Therapeutic methods comprise the step of treating patients in a pharmaceutically acceptable manner with the aminosteroid derivatives or pharmaceutically acceptable salts, N-oxides or solvates thereof as disclosed herein, or with compositions comprising such aminosteroid derivatives or pharmaceutically acceptable salts, N-oxides or solvates thereof. Such compositions may be in the form of tablets, coated tablets, capsules, caplets, powders, granules, lozenges, suppositories, reconstitutable powders, syrups, liquid preparations such as oral or sterile parenteral solutions or suspensions, as well as injectable formulations and transdermal formulations.

The aminosteroid derivatives or pharmaceutically acceptable salts, N-oxides or solvates thereof of the present disclosure may be administered alone or in combination with pharmaceutically acceptable carriers. The proportion of each carrier is determined by the solubility and chemical nature of the compound, the route of administration, and standard pharmaceutical practice. In order to ensure consistency of administration, in an embodiment of the present disclosure, the pharmaceutical composition is in the form of a unit dose. The unit dose presentation forms for oral administration may be tablets, coated tablets and capsules and may contain conventional excipients. Non-limiting examples of conventional excipients include binding agents such as acacia, gelatin, sorbitol, or polyvinylpyrrolidone; fillers such as lactose, dextrose, saccharose, sugar, maize-starch, calcium phosphate, sorbitol or glycine; tableting lubricants such as talc, stearic acid, calcium or magnesium stearate, polyethylene glycols, gums, gels; disintegrants such as starch, polyvinylpyrrolidone, sodium starch glycollate or microcrystalline cellulose; or pharmaceutically acceptable wetting agents such as sodium lauryl sulphate.

The aminosteroid derivatives or pharmaceutically acceptable salts, N-oxides or solvates thereof of the present disclosure may be injected parenterally; this being intramuscularly, intravenously, subcutaneously or intraperitoneally. For parenteral administration, the aminosteroid derivatives or pharmaceutically acceptable salts, N-oxides or solvates thereof may be used in the form of sterile solutions containing solutes for example, sufficient saline or glucose to make the solution isotonic.

The aminosteroid derivatives or pharmaceutically acceptable salts, N-oxides or solvates thereof of the present disclosure may also be administered topically such as via transdermal routes using dermal or skin patches.

The aminosteroid derivatives or pharmaceutically acceptable salts, N-oxides or solvates thereof may be administered orally in the form of tablets, coated tablets, capsules, or granules, containing suitable excipients non-limiting examples of which are starch, lactose, white sugar and the like. The aminosteroid derivatives or pharmaceutically acceptable salts, N-oxides or solvates thereof may be administered orally in the form of solutions which may contain coloring and/or flavoring agents. The aminosteroid derivatives or pharmaceutically acceptable salts, N-oxides or solvates thereof may also be administered sublingually in the form of tracheas or lozenges in which the active ingredient(s) is/are mixed with sugar or corn syrups, flavoring agents and dyes, and then dehydrated sufficiently to make the mixture suitable for pressing into solid form.

The solid oral compositions may be prepared by conventional methods of blending, granulation, compression, coating, filling, tableting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, suspensions, syrups, or elixirs, or may be presented as a dry product for reconstitution with water or other suitable vehicle before use. Such liquid preparations may or may not contain conventional additives. Non limiting examples of conventional additives include suspending agents such as sorbitol, cyclodextrins, syrup, natural gums, agar, methyl cellulose, gelatin, pectin, sodium alginate, hydroxyethylcellulose, carboxymethylcellulose, aluminum stearate gel, or hydrogenated edible fats; emulsifying agents such as sorbitan monooleate or acaci; non-aqueous vehicles (which may include edible oils) such as almond oil, fractionated coconut oil, oily esters selected from the group consisting of glycerine, propylene glycol, ethylene glycol, and ethyl alcohol; preservatives such as for instance methyl para-hydroxybenzoate, ethyl para-hydroxybenzoate, n-propyl parahydroxybenzoate, n-butyl parahydroxybenzoate or sorbic acid; and, if desired conventional flavoring such as saccharose, glycerol, mannitol, sorbitol, or coloring agents.

For parenteral administration, fluid unit dosage forms may be prepared by utilizing the aminosteroid derivatives or pharmaceutically acceptable salts, N-oxides or solvates thereof and a sterile vehicle (i.e. sterile water) and, depending on the concentration employed, the aminosteroid derivatives or pharmaceutically acceptable salts, N-oxides or solvates thereof may be either suspended or dissolved in the vehicle. Other suitable vehicles may include olive oil, ethyl oleate, and glycols. If needed, a suitable quantity of lidocaine hydrochloride may also be included. Once in solution, the aminosteroid derivatives or pharmaceutically acceptable salts, N-oxides or solvates thereof may be injected and filter sterilized before filling a suitable vial or ampoule followed by subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying). Parenteral suspensions may be prepared in substantially the same manner, except that the aminosteroid derivatives or pharmaceutically acceptable salts or N-oxides thereof should be suspended in the vehicle rather than being dissolved, and, further, sterilization is not achievable by filtration. The aminosteroid derivatives or pharmaceutically acceptable salts, N-oxides or solvates thereof may be sterilized, however, by exposing it to ethylene oxide before suspending it in the sterile vehicle. A surfactant or wetting solution may be advantageously included in the composition to facilitate uniform distribution of the aminosteroid derivatives or pharmaceutically acceptable salts, N-oxides or solvates thereof.

The aminosteroid derivatives or pharmaceutically acceptable salts, N-oxides or solvates thereof may be administered in the form of suppositories. Suppositories may contain pharmaceutically acceptable vehicles such as cocoa butter, polyethylene glycol, sorbitan, esters of fatty acids, lecithin and the like.

The pharmaceutical compositions of the present disclosure comprise a pharmaceutically effective amount of at least one aminosteroid derivative or pharmaceutically acceptable salt, N-oxide or solvate thereof as disclosed herein and one or more pharmaceutically acceptable carriers, excipients or diluents. In an embodiment of the present disclosure, the pharmaceutical compositions contain from about 0.1% to about 99% by weight of an aminosteroid derivative or pharmaceutically acceptable salt, N-oxide or solvate thereof as disclosed herein. In a further embodiment of the present disclosure, the pharmaceutical compositions contain from about 10% to about 60% by weight of an aminosteroid derivative or pharmaceutically acceptable salt, N-oxide or solvate thereof as disclosed herein, depending on which method of administration is employed. Physicians will determine the most-suitable dosage of the present therapeutic agents (the aminosteroid derivatives or pharmaceutically acceptable salts, N-oxides or solvates thereof). Dosages may vary with the mode of administration and the particular aminosteroid derivative chosen. In addition, the dosage may vary with the particular patient under treatment. The dosage of the aminosteroid derivative or pharmaceutically acceptable salt, N-oxide or solvate thereof used in the treatment may vary, depending on the relative efficacy of the compound and the judgment of the treating physician.

In an embodiment of the present disclosure the pharmaceutical compositions comprise a therapeutically effective amount of one or more of the aminosteroid derivatives or pharmaceutically acceptable salts, N-oxides or solvates thereof as disclosed herein, and at least one pharmaceutically acceptable excipient, non-limiting examples of which are carriers and diluents.

It is contemplated that any embodiment discussed in this disclosure can be implemented with respect to any method or composition of the disclosure, and vice versa. Furthermore, compositions of the disclosure can be used to achieve the methods of the disclosure.

Representative, non-limiting examples of specific aminosteroids in accordance with the present disclosure and methods of preparing same are described below.

Synthesis of Estrane-Aminosteroid Derivatives

In accordance with an embodiment of the present disclosure, Scheme 1 illustrates the synthesis of selected estrane-based aminosteroid derivatives 4-6.

Scheme 1:

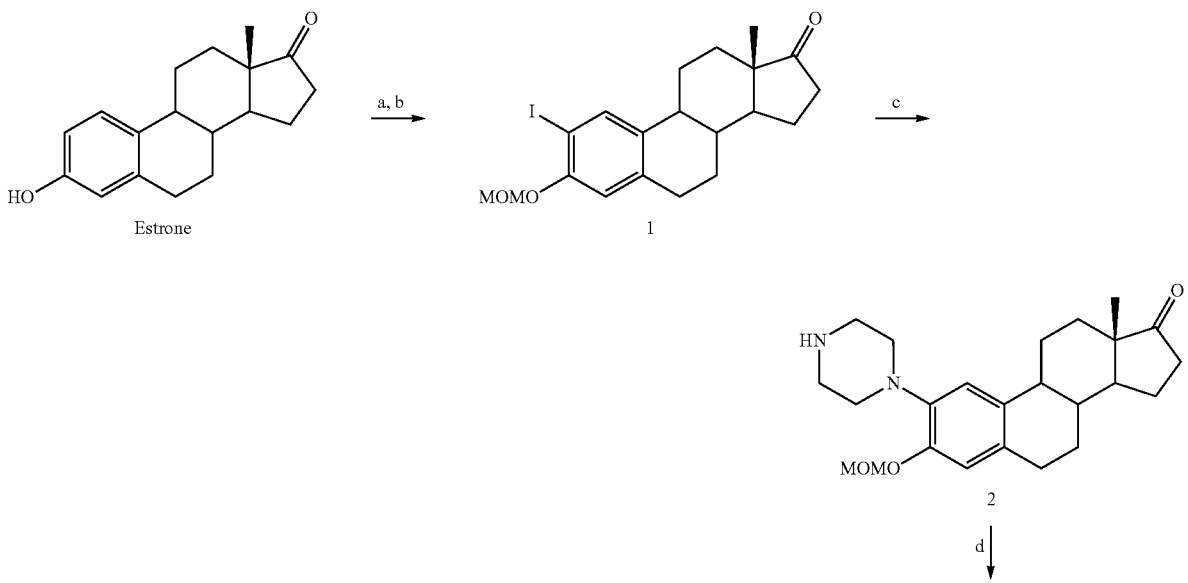

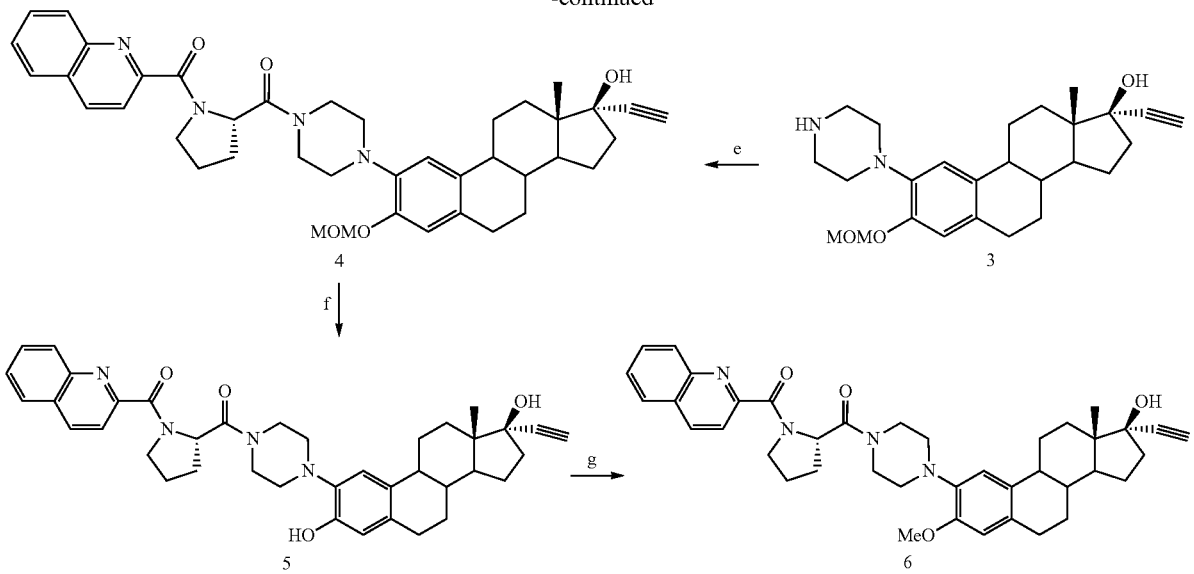

Reagents and conditions: (a) MOM—Cl, K₂CO₃, ACN, reflux, 72 h; (b) CF₃CO₂Ag, NaHCO₃, I₂, DCM, 1 h, -30° C.; (c) piperazine, K₂CO₃, CuI, L-Proline, DMSO, 120° C., overnight; (d) i) TMS-acetylene, MeLi, THF, rt, 3 h; ii) K₂CO₃, MeOH, overnight; (e) 1-(quinolin-2-ylcarbonyl)-L-proline, HBTU, DIPEA, DMF, rt, overnight; (f) HCl 10% aq in MeOH, 60° C.; (g) CH₃I, K₂CO₃, acetone, overnight.

In accordance with an embodiment of the present disclosure, Scheme 2 illustrates a further synthesis of estrane-based aminosteroid derivative 6 (RM-581).

Scheme 2:

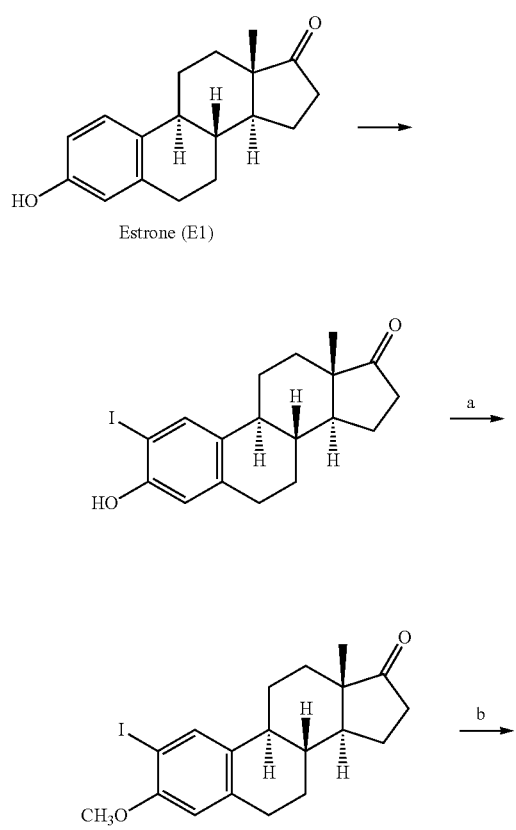

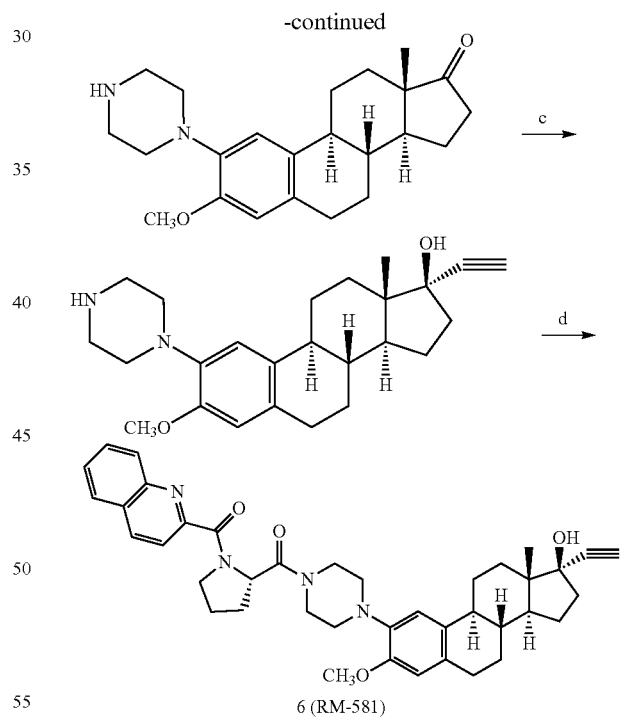

6 (RM-581)

Reagents and conditions: (a) MeI, Cs₂CO₃, acetonitrile, reflux, 2.5 h; (b) piperazine, K₂CO₃, CuI, L-proline, DMSO, 120° C., overnight; (c) i) TMA-acetylene, MeLi, THF, rt, overnight; ii) K₂CO₃, MeOH, rt, 5 h; (d) 1-(quinolin-2-ylcarbonyl)-L-proline TFA salt, HBTU, DIPEA, DMF, rt, overnight.

Preparation of Various Estrane-Based Derivatives

Since many chemically similar structures may elicit different biological responses and offer the potential for significant therapeutic advances, the impact of chemical modifications at strategic positions on the estrane scaffold on anticancer activity, metabolic stability and aqueous solubility was further explored. Accordingly, in accordance with various embodiments of the present disclosure, a series of novel derivatives at position $C_3$ and $C_2$ of RM-581-OH were prepared as illustrated hereinbelow in Schemes 3-7. The addition of a phosphate group on RM-581-OH (Scheme 3; compound 5) provided for significant enhancement of water solubility without adversely affecting the antiproliferative properties of the compound. Moreover, the phosphate derivative 5 showed a stability similar to its phenolic counterpart in a liver microsomal assay.

Scheme 3:

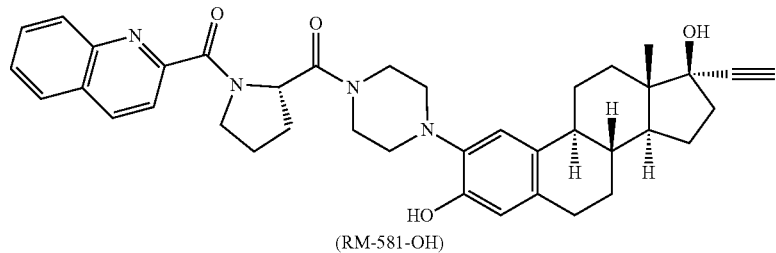

(RM-581-OH)

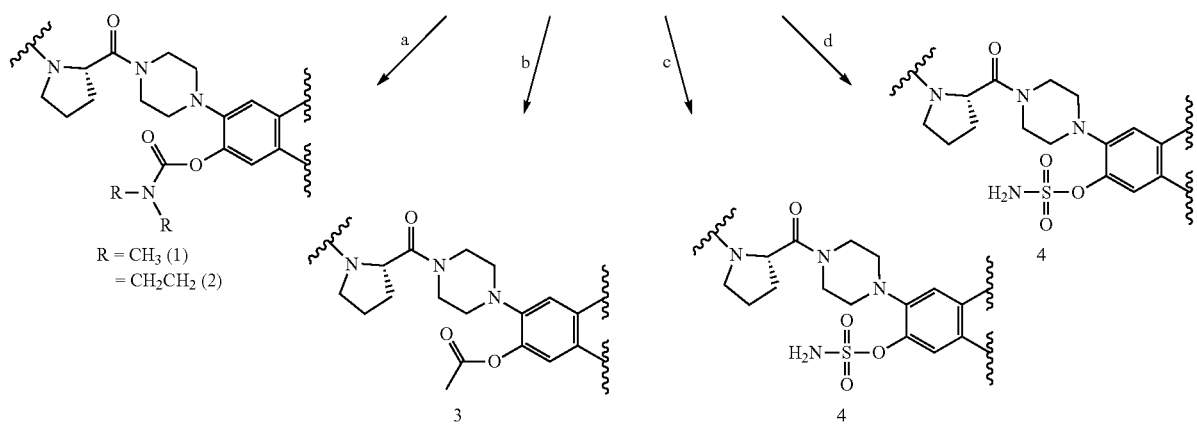

Reagents and conditions: (a) dimethyl or diethylcarbamoylchloride, pyridine, 80° C.; (b) acetic anhydride, pyridine, 80° C.; (c) sulfamoylchloride, DCM, DBMP, rt.; (d) i) POCl₃, pyridine, DCM, 0° C.; ii) Acetone/H₂O (1:1), rt.

Scheme 4:

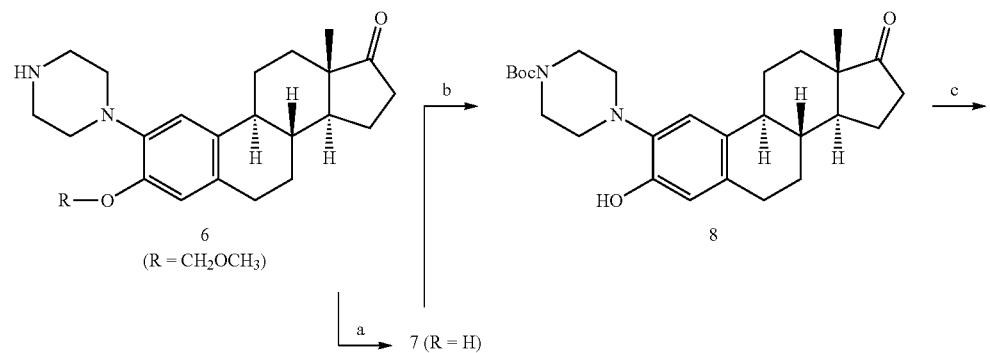

57 58
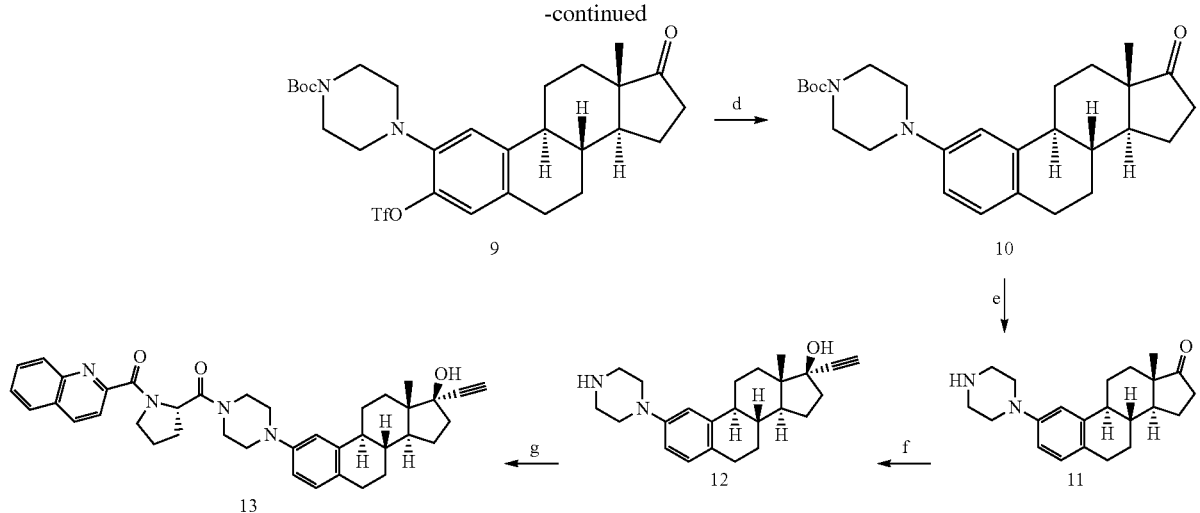
Reagents and conditions: (a) HCl 10% aq/MeOH (1:9), 70° C.; (b) NaHCO$_3$, THF/Dioxane/H$_2$O, di-t-butyl-dicarbonate, rt; (c) Triflic anhydride, pyridine, DMC, rt; (d) Formic acid, PPh$_3$, Pd(OAc)$_2$, DMF, 40° C.; (e) TFA/DCM (1:1), rt, 12 h; (f) i) TMS-acetylene, MeLi, ether, -78° C. to rt; ii) K$_2$CO$_3$, MeOH, rt: (g) 1-(quinolin-2-ylcarbonyl)-L-proline TFA salt, HBTU, DIPEA, DMF, rt, overnight.
Scheme 5:
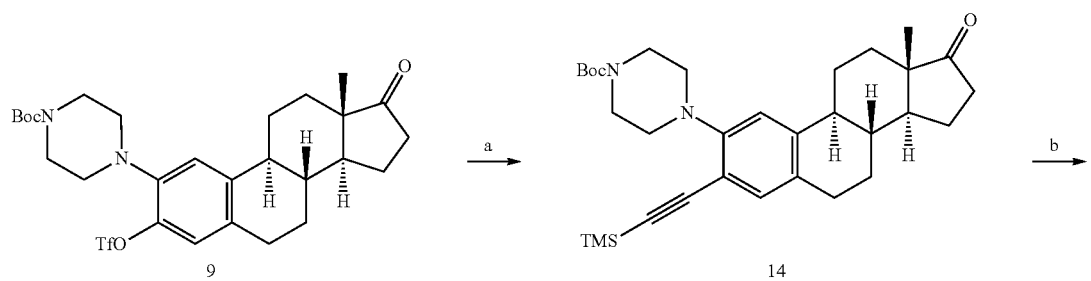
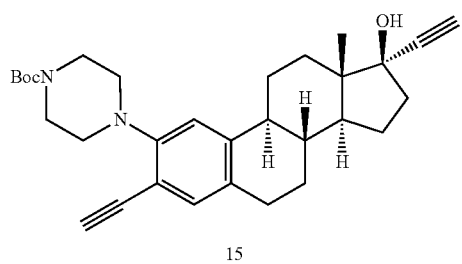

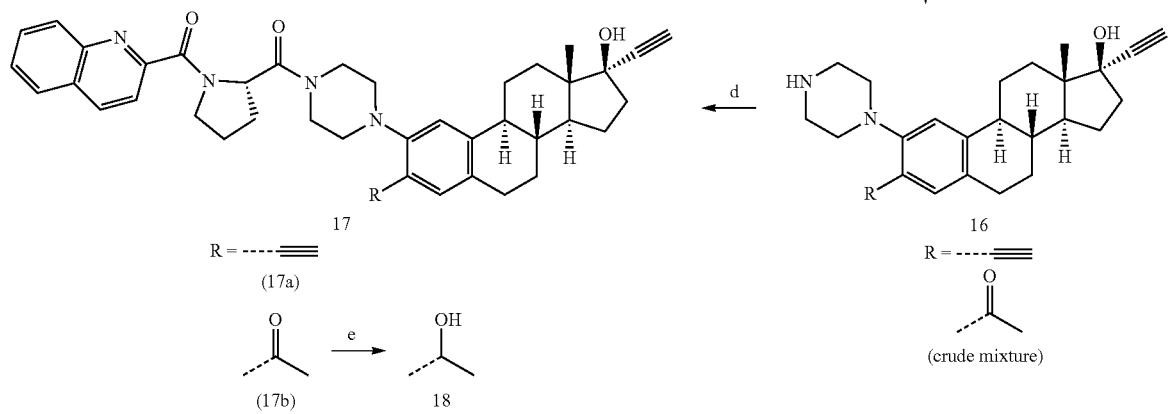

Reagents and conditions: (a) TMS-acetylene, CuI, Pd(PPh3)2Cl2, Et3N, DMF, 80° C.;
(b) i) TMS-acetylene, MeLi, Ether/THF, ii) K2CO3, MeOH, rt; (c) TFA/DCM (2:8);
(d) 1-(quinolin-2-ylcarbonyl)-L-proline TFA salt, HBTU, DIPEA, DMF, rt, overnight;
(e) NaBH4, MeOH, rt.

Scheme 6:

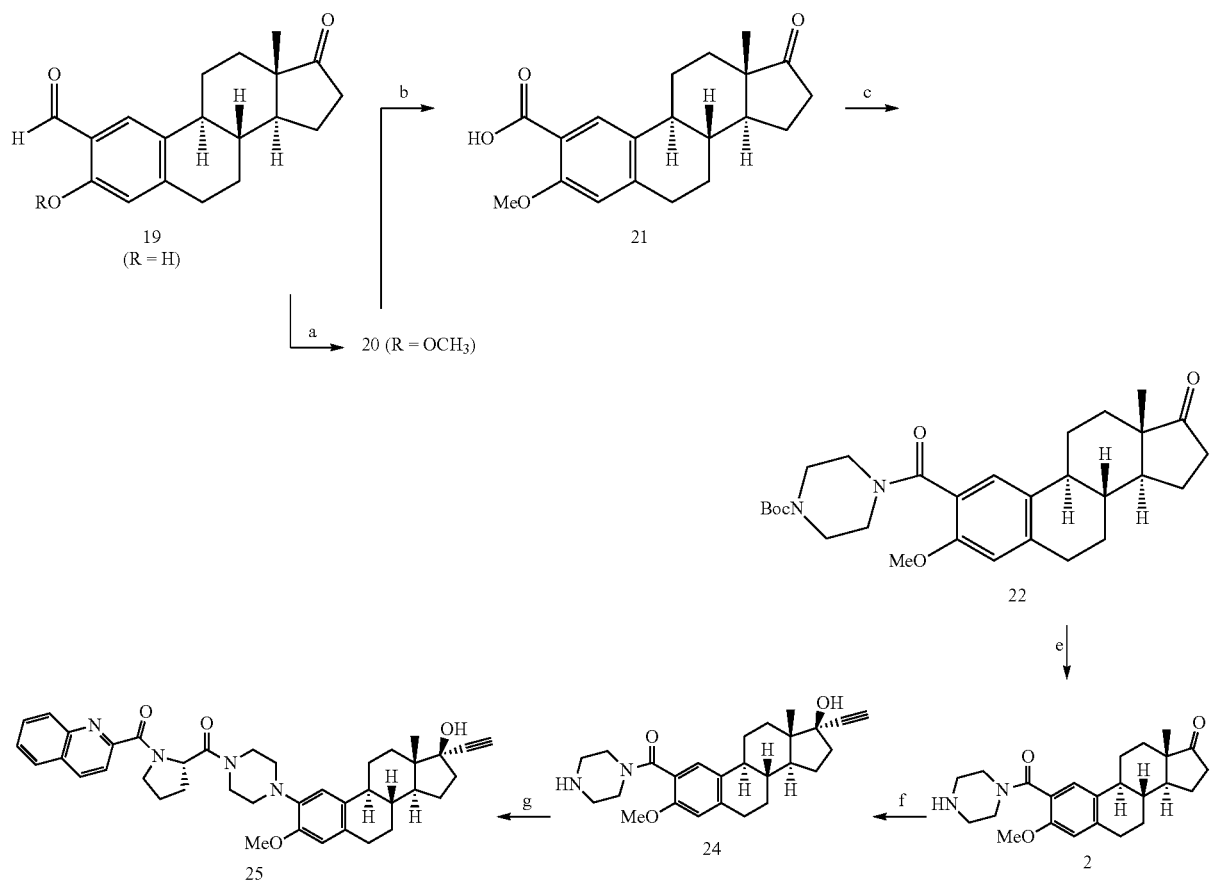

Reagents and conditions: (a) K2CO3, CH3I, acetone, rt; (b) TEMPO, iodobenzene dicaetate, DCM/H2O (2:1); (c) 1-Boc-piperazine, HBTU, DIPEA, DMF, rt; (d) i) TFA/DCM (20%); ii) NaHCO3 aq; (i) i) TMS-acetylene, MeLi, Ether/THF, ii) K2CO3, MeOH, rt; (f) 1-(quinolin-2-ylcarbonyl)-L proline TFA salt, HBTU, DIPEA, DMF, rt, overnight.

Scheme 7:

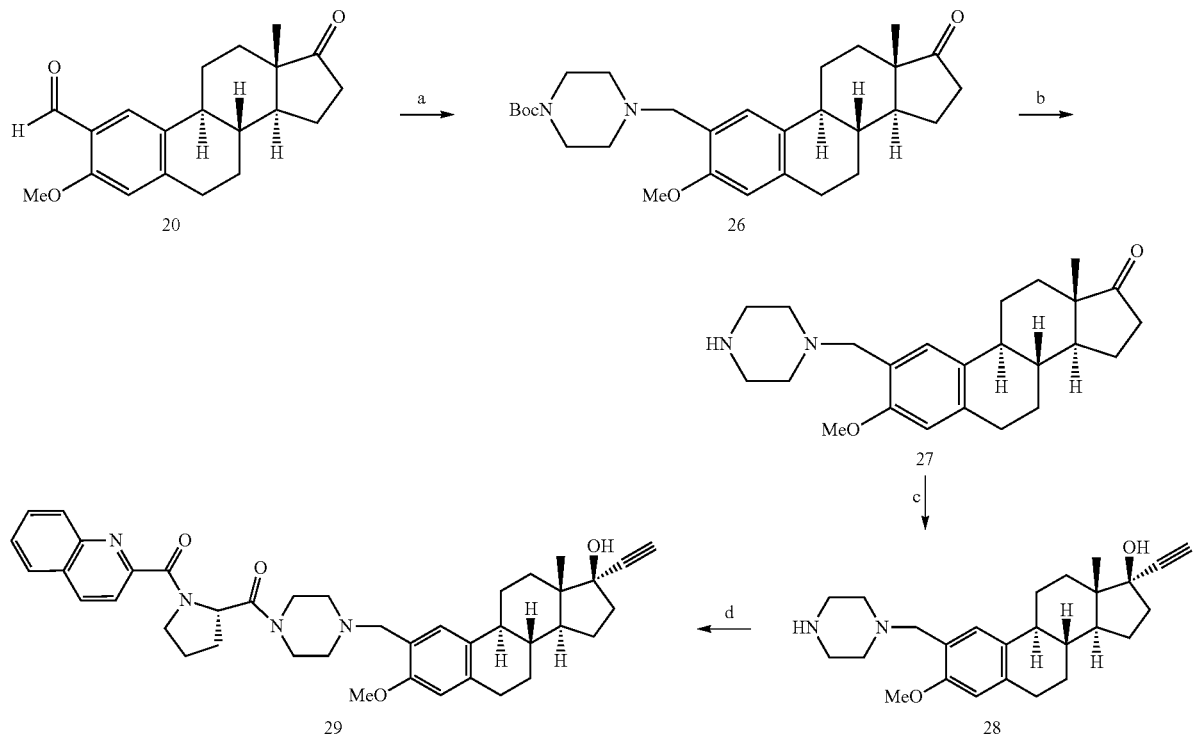

Reagents and conditions: (a) 1-Boc-piperazine; NaBH$_3$CN, 1% AcOH (0.2M in DMF);
(b) TFA/DCM (2:8), rt; (c) TMS-acetylene, MeLi, Ether/THF, ii) K$_2$CO$_3$, MeOH, rt;
(d) 1-(quinolin-2-ylcarbonyl)-L-proline TFA salt, HBTU, DIPEA, DMF, rt, overnight.

Figure 6:
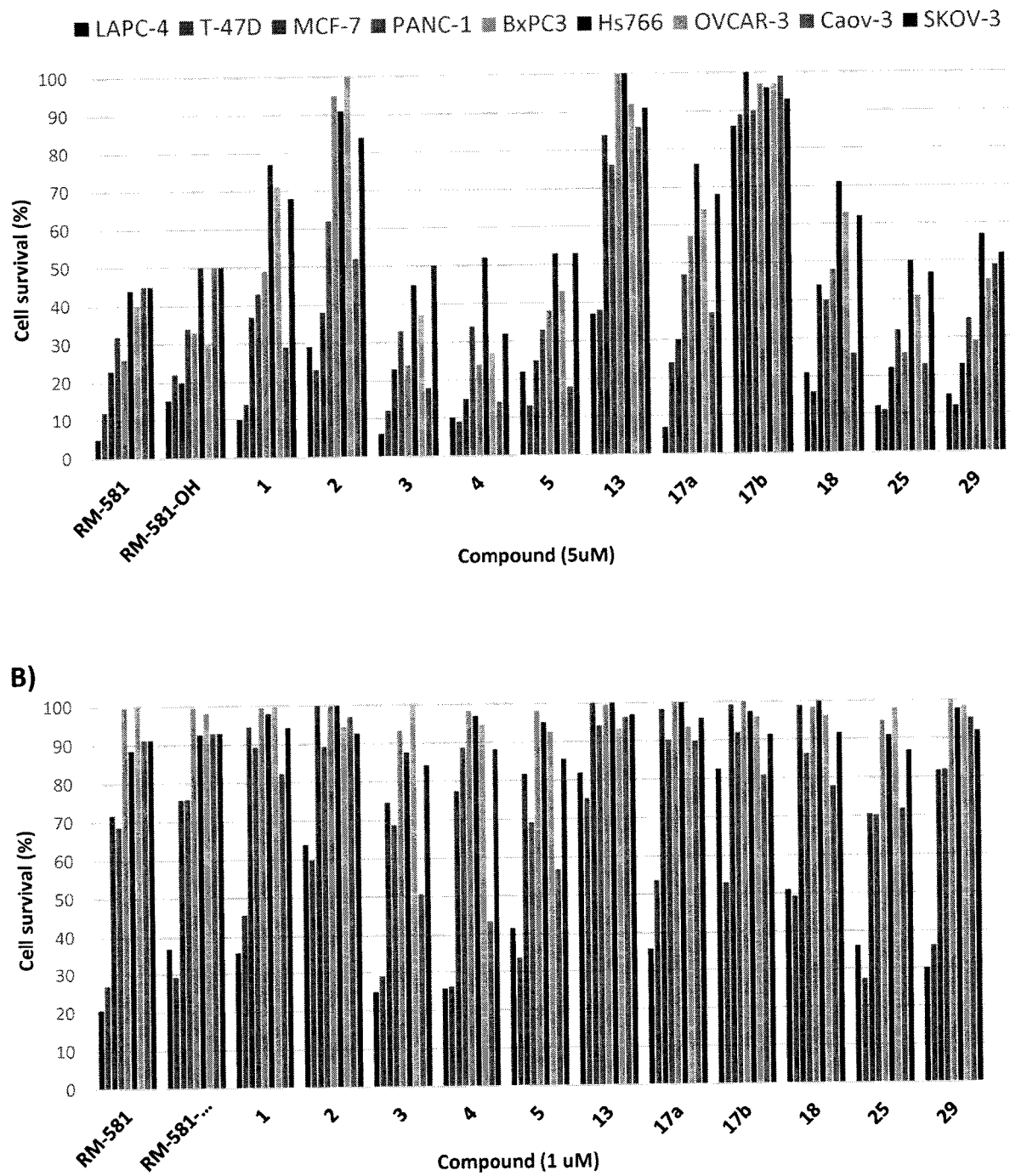

The new series of compounds 1-5, 13, 17a, 17b, 18, 25 and 29 (Schemes 3-7) as well as RM-581 and RM-581-OH were screened for their cytotoxic activities at two concentrations (5 and 1 μM) on four different cancer types (pancreatic, ovary, breast and prostate). Included were different representative cell lines for each type of cancer studied (pancreatic: PANC-1, BxPC-3 and Hs766; ovaries: OVCAR-3, Caov3 and SKOV3; breast: MCF-7 and T-47D), except for prostate cancer where only LAPC-4 was used at the screening assay step (FIG. 6).

Independently of the cancer cell line tested, compounds 2, 13 and 17b showed a marked weaker cytotoxic activity. Compounds 1, 3, 4, 5, 17a, 18, 25 and 29 showed only slight differences in their respective levels of activity. The observation of a close and repetitive pattern of activity among a series of anticancer molecules for different cancer cell types is indeed very interesting and it is surmised that such a repetitive pattern is indicative of a sensitive and common check point of cancer is being targeted. Moreover, this observation seems to point to a fine regulation of a molecular target essential for cancer cell survival.

A higher anticancer activity of the compounds tested for the breast and prostate cancer cell lines was observed. These higher levels of activity in the screening assays were subsequently confirmed by the determination of the respective IC$_{50}$ values for selected compounds of the series (i.e. 3, 4, 5, 25 and 29) (Table 1). Lower values for prostate cancer (IC$_{50}$=0.3-2.6; mean value=1.0 μM) and breast cancer (IC$_{50}$=0.2-2.6; mean value=0.9 μM) were observed relative to pancreatic (IC$_{50}$=2.6-3.9; mean value=4.4 μM) and ovarian (IC$_{50}$=3.1-5.2; mean value=2.9 μM) cell lines.

TABLE 1

IC$_{50}$ values for selected aminosteroid derivatives on different cancer cell lines.

| | IC50 (μM) Prostate cancer | | | IC50 (μM) Breast cancer | | IC50 (μM) Ovarian cancer | IC50 (μM) Pancreatic cancer |
|---|---|---|---|---|---|---|---|
| Compound | PC-3 | LAPC-4 | LNCaP | MCF-7 | T-47D | OVCAR-3 | PANC-1 |
| RM-581 | 1.6 ± 0.3 | 0.6 ± 0.3 | 1.2 ± 0.6 | 2.6 ± 0.3 | 0.5 ± 0.05 | 5.0 ± 0.5 | 3.9 ± 0.9 |
| RM-581-OH | 1.4 ± 0.4 | 0.4 ± 0.1 | 1.1 ± 0.4 | 1.4 ± 0.2 | 0.5 ± 0.2 | 4.4 ± 0.6 | 3.1 ± 0.2 |
| 3 | 1.4 ± 0.3 | 0.5 ± 0.4 | 0.8 ± 0.3 | 1.4 ± 0.1 | 0.4 ± 0.2 | 3.9 ± 0.4 | 2.8 ± 0.7 |
| 4 | 1.6 ± 0.1 | 0.3 ± 0.2 | 0.9 ± 0.3 | 1.2 ± 0.4 | 0.2 ± 0.01 | 3.1 ± 0.5 | 3.0 ± 0.2 |

TABLE 1-continued

IC$_{50}$ values for selected aminosteroid derivatives on different cancer cell lines.

| | IC50 (μM) Prostate cancer | | | IC50 (μM) Breast cancer | | IC50 (μM) Ovarian cancer | IC50 (μM) Pancreatic cancer |
|---|---|---|---|---|---|---|---|
| Compound | PC-3 | LAPC-4 | LNCaP | MCF-7 | T-47D | OVCAR-3 | PANC-1 |
| 5 | 1.3 ± 0.05 | 0.3 ± 0.07 | 0.6 ± 0.05 | 1.5 ± 0.3 | 0.3 ± 0.05 | 4.6 ± 0.7 | 2.6 ± 0.1 |
| 25 | 1.7 ± 0.4 | 0.5 ± 0.2 | 0.8 ± 0.2 | 2.2 ± 0.1 | 0.3 ± 0.2 | 5.2 ± 1.6 | 3.5 ± 0.4 |
| 29 | 1.7 ± 0.3 | 0.7 ± 0.2 | 1.3 ± 0.5 | 2.3 ± 0.6 | 0.4 ± 0.2 | 5.0 ± 0.2 | 2.6 ± 0.7 |

It is important to note that small structural modifications at position $C_3$ of the steroid core resulted in significant losses of activity (cytotoxic potency) as observed for $C_3$ derivatives 2, 13 and 17. In the case of aminosteroid derivative 2, the greater steric hindrance of its N-diethylcarbamate group relative to N-dimethylcarbamate 1, points to a rather limited steric tolerance at position $C_3$. Moreover, the presence of the $C_3$ oxygen seems to have a direct impact on cytotoxic activity as demonstrated by the important loss of activity observed for aminosteroid derivative 13. It is surmised that the oxygen at position $C_3$ may actively participate in hydrogen bonding interactions, resulting in a more favourable configuration of the aminosteroids derivatives. The addition of a spacer group at position $C_2$ of the steroid core (i.e. a carbonyl (compound 25) or a methylene group (compound 29)) seems well tolerated as no loss of activity was recorded for the latter compounds. Indeed, displacement of the side chain by an additional carbon atom seems well tolerated, without adversely affecting the cytotoxic activity.

Figure 7:
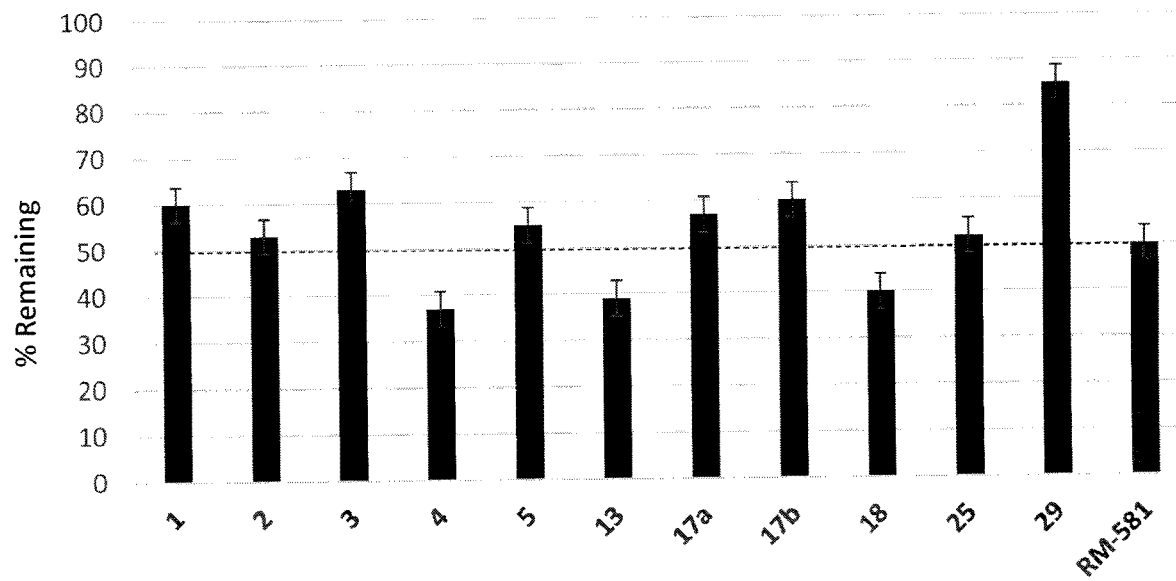

Compounds 1-5, 13, 17a, 17b, 18, 25 and 29 (Schemes 3-7) as well as RM-581 were screened for their metabolic stability in human liver microsomes (FIG. 7). The percentage of remaining compound after an incubation period of 1 h was relative similar for compounds 1-3, 5, 17a, 17b and 25, whereas compounds 4, 13 and 18 exhibited slightly lower values. Compound 29 exhibited the highest percentage of remaining compound indicative of an increased metabolic stability. Interestingly, no trace of the phenolic metabolite RM-581-OH could be observed in the case of compounds 1, 2, 3, 4, and 5, showing a significant stability of these potential prodrugs to hydrolysis.

Figure 8:
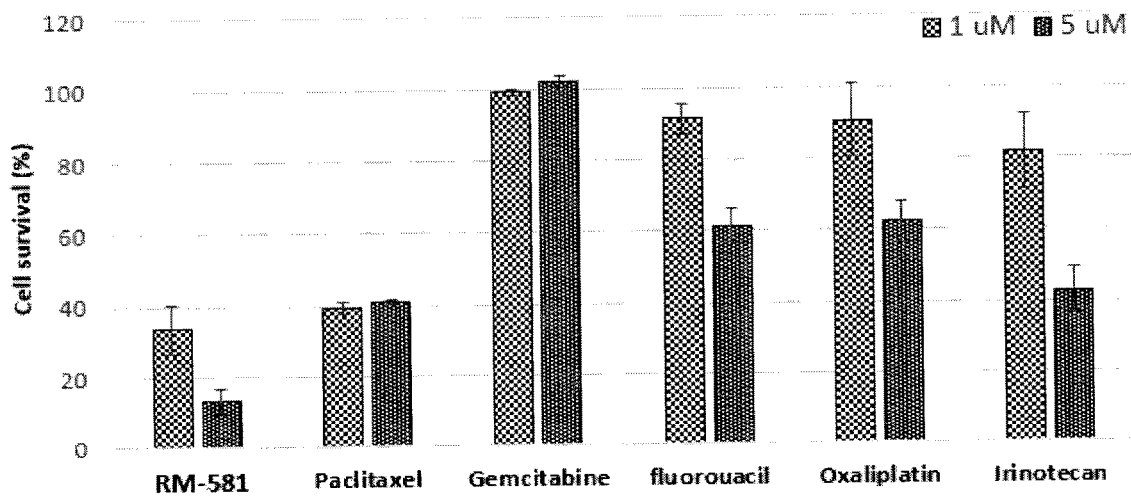
FIG. 8 is an illustration of the cytotoxic effect of RM-581 and selected anticancer clinical drugs (Paclitaxel, Gemcitabine, Fluorouacil, Oxaliplatin and Irinotecan) on the viability of T47D breast cancer cells after 72 h of treatment at concentrations of 1 and 5 μM respectively, in accordance with an embodiment of the present disclosure.
Figure 9:
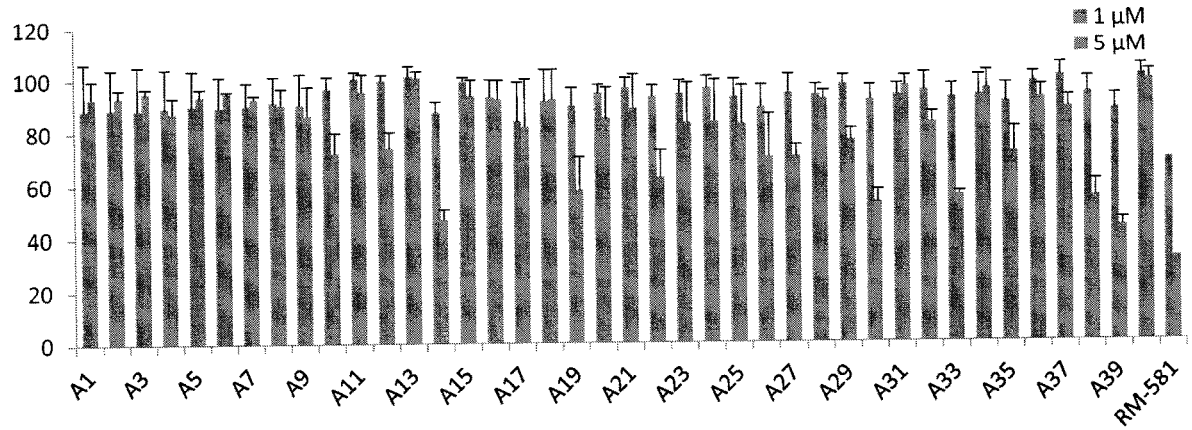
FIG. 9 is an illustration of the cell survival (%) on cancer cell lines PANC-1, BxPC3 and Hs766 (pancreatic) after 3 days treatment with different derivatives of RM-581 (A1-A40—Table 1) at concentrations of 5 μM and 1 μM respectively, in accordance with an embodiment of the present disclosure.
Figure 9:
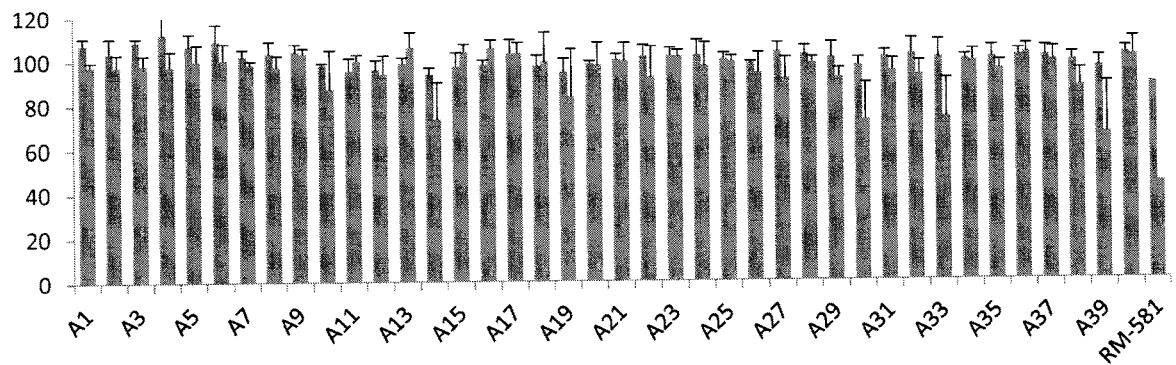
Figure 9:
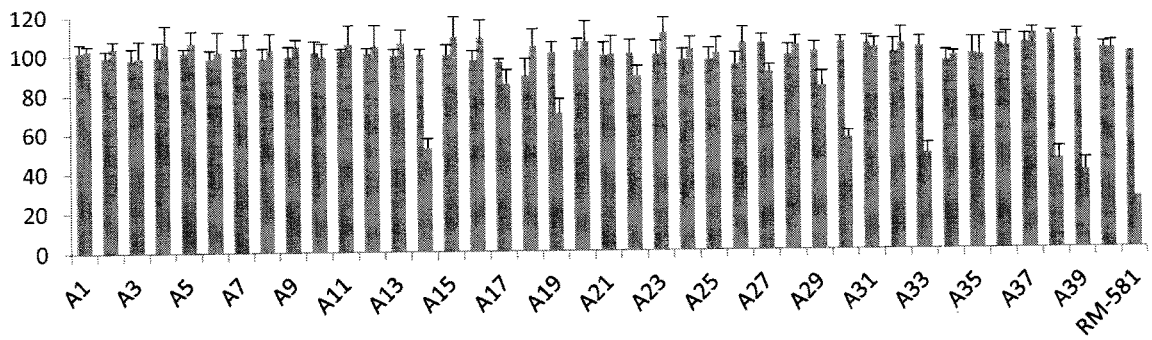
Figure 10:
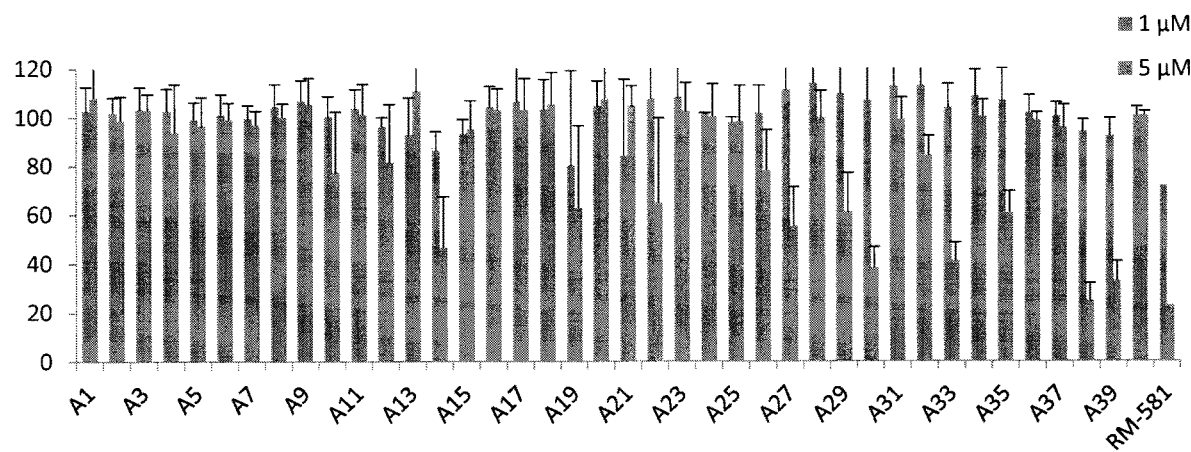
FIG. 10 is an illustration of the cell survival (%) on cancer cell lines T-47D and MCF-7 (breast) after 3 days treatment with different derivatives of RM-581 (A1-A40—Table 1) at concentrations of 5 μM and 1 μM respectively, in accordance with an embodiment of the present disclosure.
Figure 10:
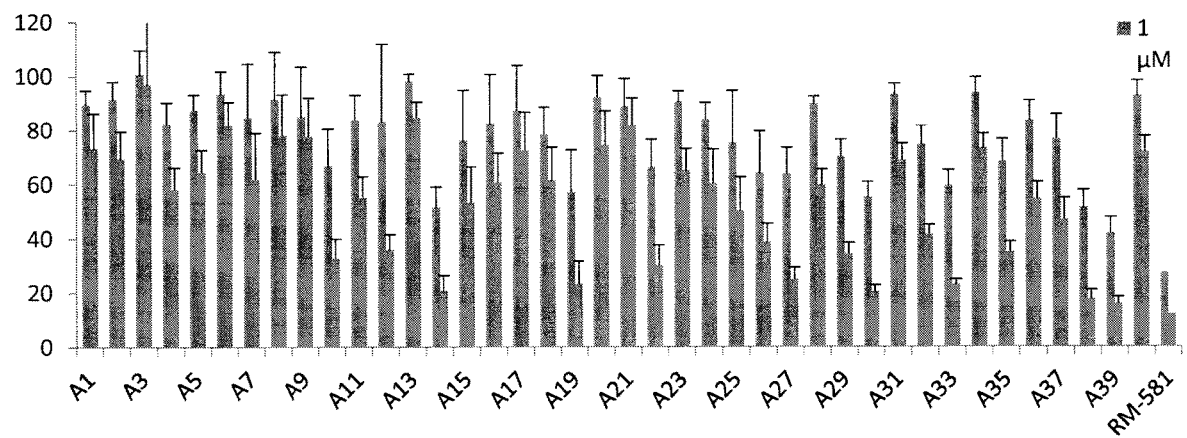
Figure 11:
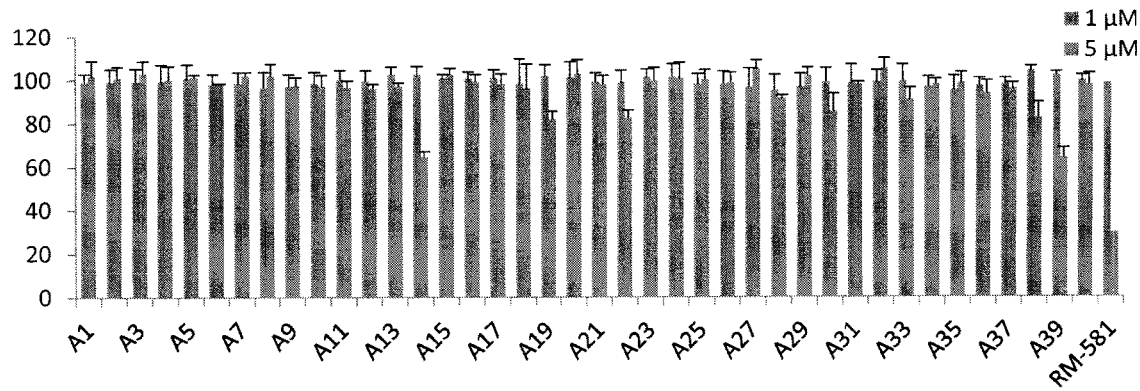
FIG. 11 is an illustration of the cell survival (%) on cancer cell lines OVCAR-3, Caov-3 and SKOV-3 (ovarian) after 3 days treatment with different derivatives of RM-581 (A1-A40—Table 1) at concentrations of 5 μM and 1 μM respectively, in accordance with an embodiment of the present disclosure.
Figure 11:
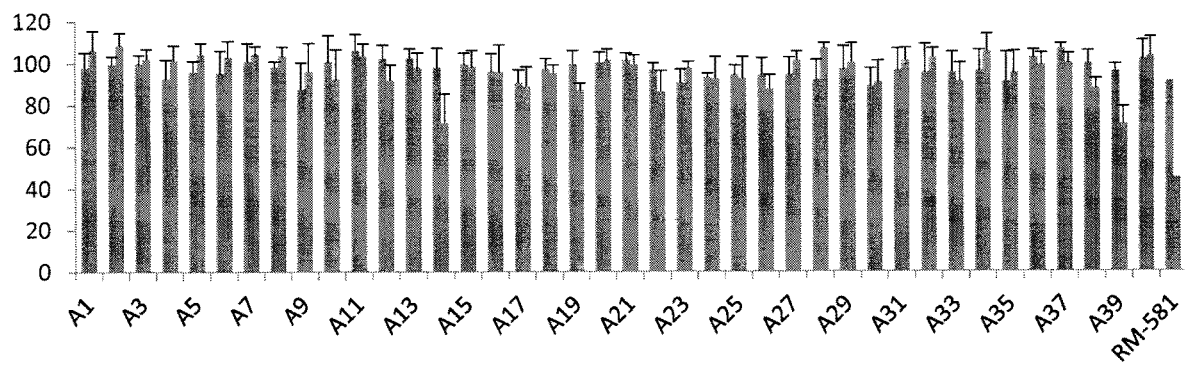
Figure 11:
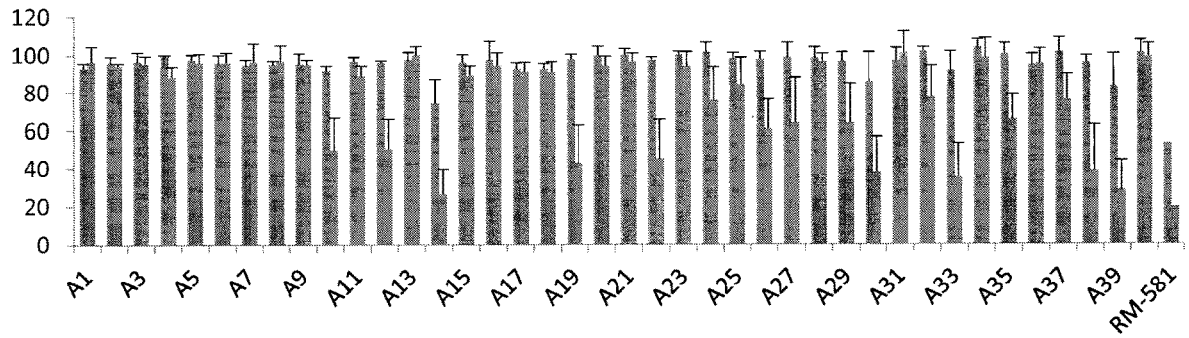
Figure 12:
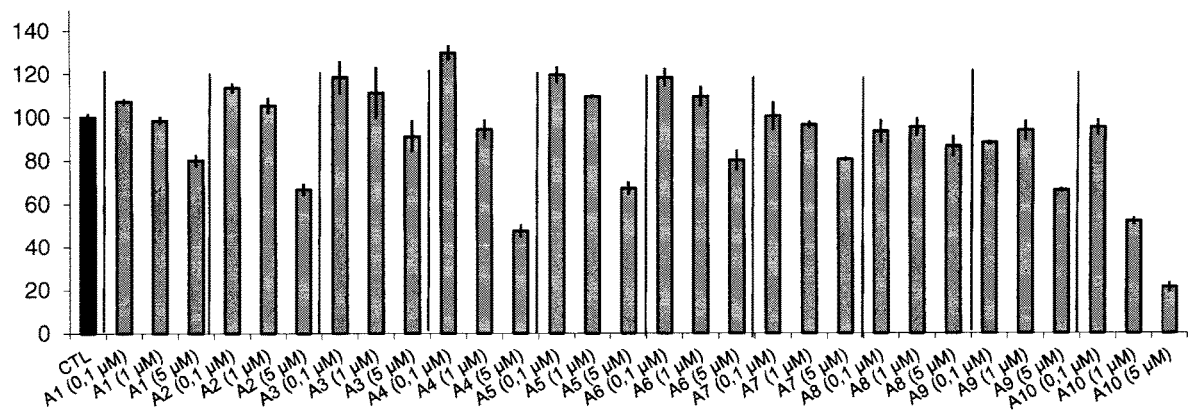
FIG. 12 is an illustration of the cell survival (%) on cancer cell line LAPC-4 (prostate) after 7 days treatment with different derivatives of RM-581 (A1-A40—Table 1) at concentrations of 0.1 μM, 5 μM and 1 μM respectively, in accordance with an embodiment of the present disclosure.
Figure 12:
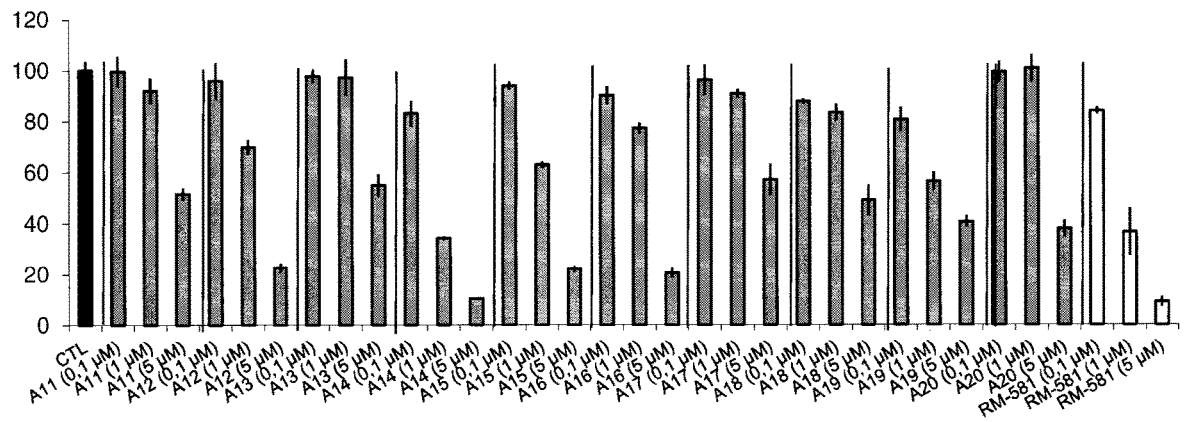
Figure 12:
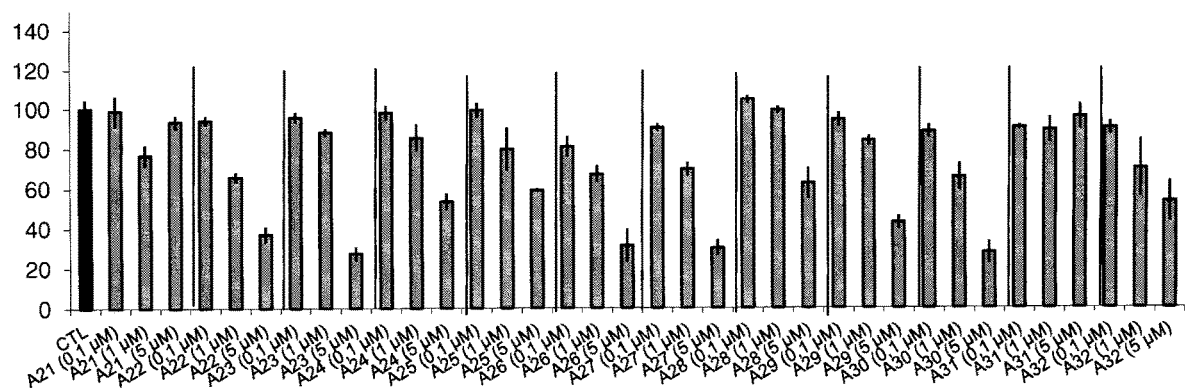
Figure 12:
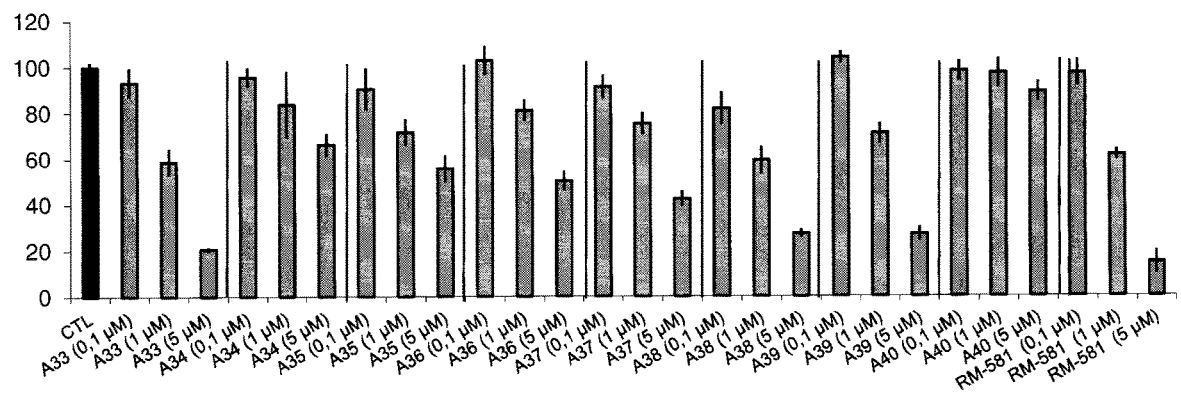

The cytotoxic activity of RM-581 was compared with those of selected known antineoplastic agents in the T-47D breast cancer cell line at two concentrations (1.0 and 5 μM) (FIG. 8). RM-581 displayed stronger cytotoxic activities at both concentrations relative to the known antineoplastic agents tested (i.e. paclitaxel, gemcitabine, fluorouacil, oxaliplatin and irinotecan). This observation is particularly interesting, highlighting the potential of the compounds of the present disclosure over other drugs and their associated mechanism of action (paclitaxel-microtubule stabilizer; gemcitabine and fluorouacil-thymidylate synthetase inhibitor; irinotecan-topoisomerase I inhibitor).

Preparation of Selected Estrane-Based Aminosteroid Derivatives by Solid Phase Synthesis In accordance with an embodiment of the present disclosure, Schemes 8 and 9 illustrate general procedures for the preparation of estrane-based aminosteroid derivatives by solid phase synthesis.

Scheme 8:

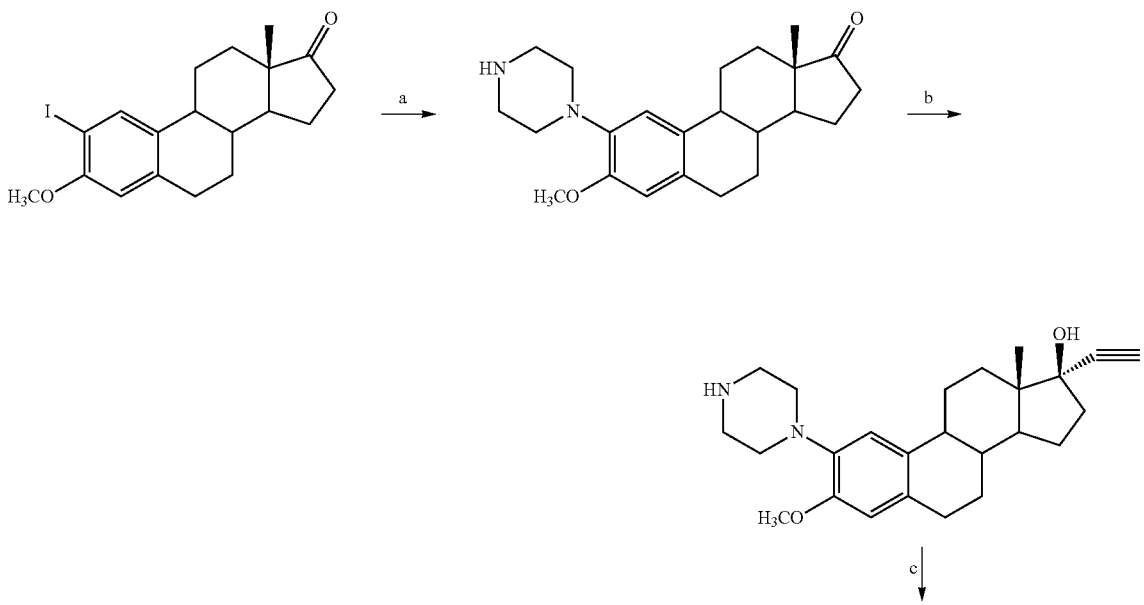

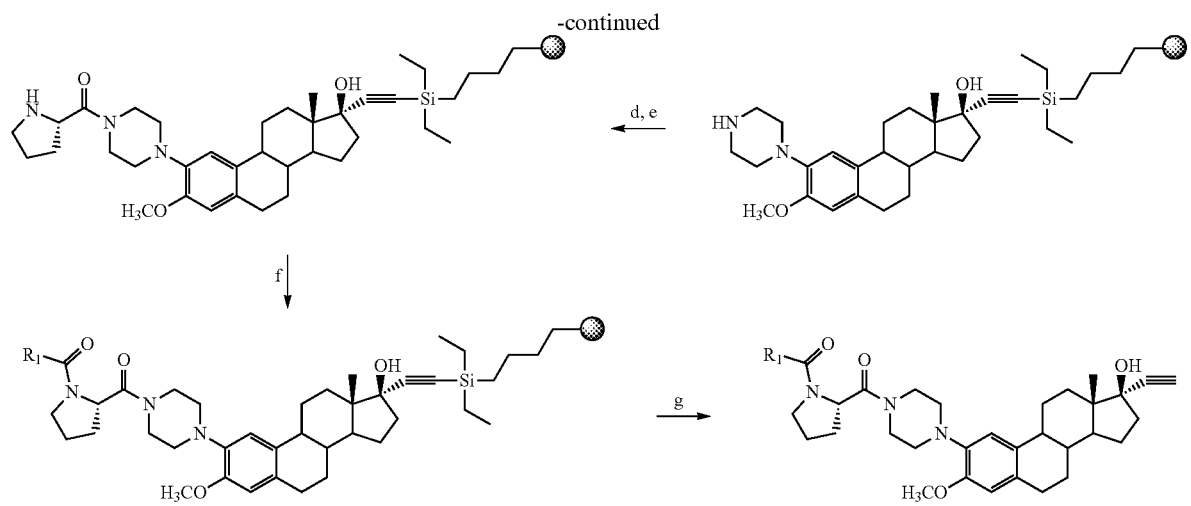

Reagents and conditions: Piperazine, K$_2$CO$_3$, CuI, L-Proline, DMSO, 120° C., overnight; (b) i) TMS-acetylene, MeLi, THF, rt, 3 h; ii) K$_2$CO$_3$, MeOH, overnight; (c) i) MeLi, THF, 0° C. to rt, 85 min; ii) PS-DES,1,3-dichloro-5,5-dimethylhydantoin, DCM, rt, 1 h; iii) PS-DES-Cl, THF, rt, overnight; (d) L-proline-Fmoc, HBTU, DIPEA, DMF, rt, overnight; (e) Piperidine 20%, DMF, rt, 1 h; (f) R$^1$—COOH, HBTU, DIPEA, DMF, rt, overnight; (g) HCl, MeOH, DCM, rt, overnight.

With reference to Scheme 8, non-limiting examples of R$^1$ include alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy. With further reference to Scheme 8, selected examples of R$^1$CO include:

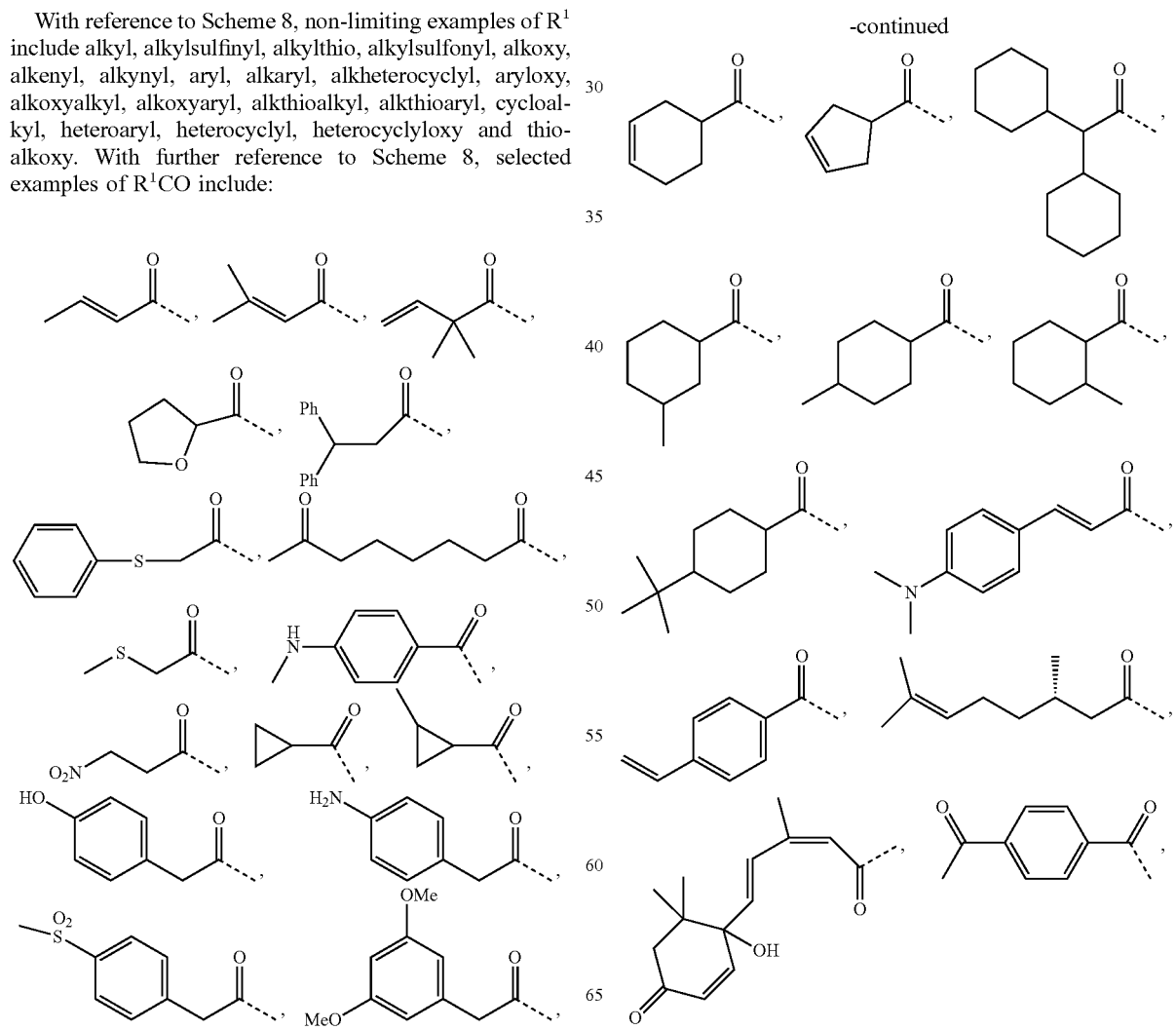

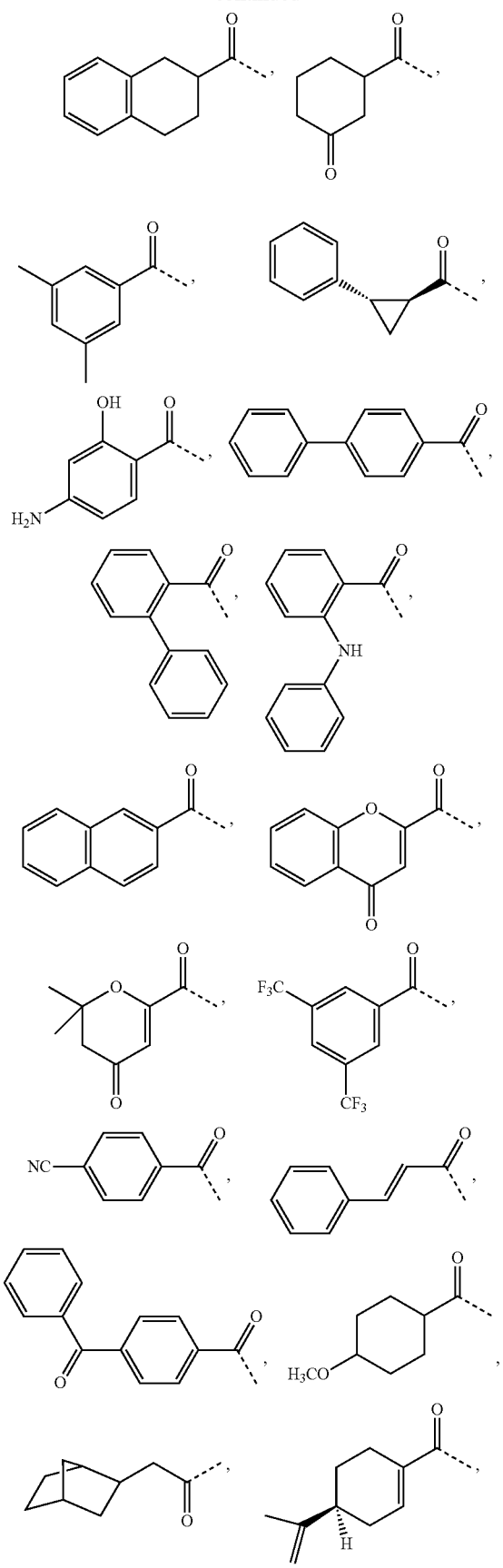
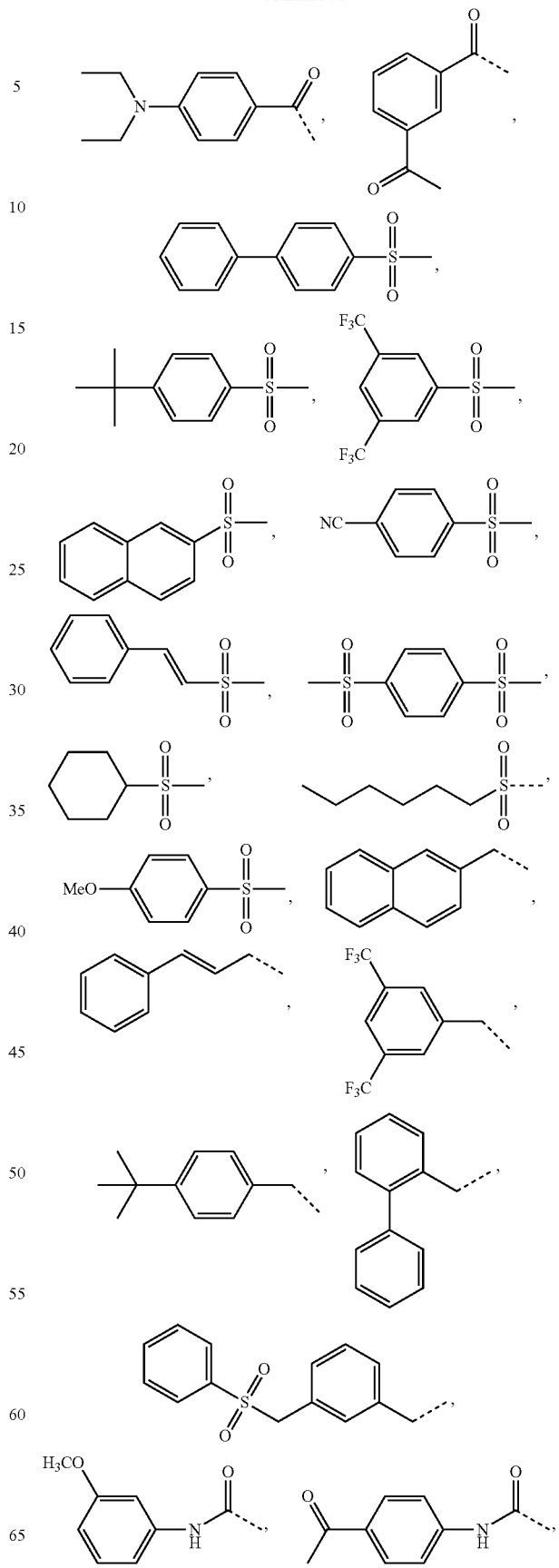

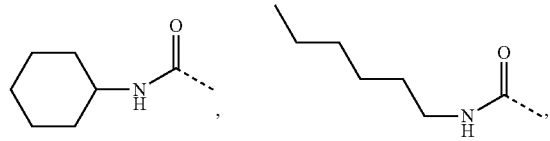
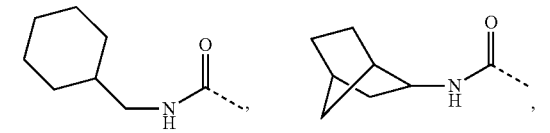
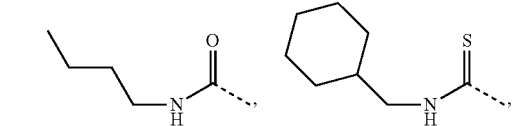
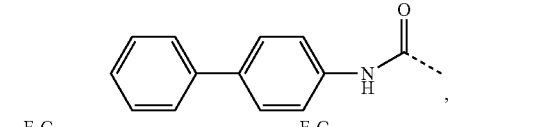
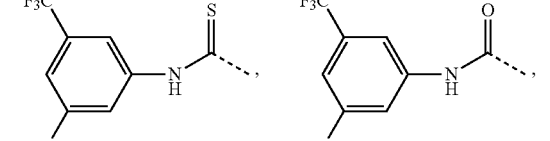
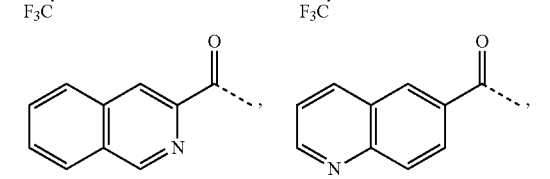
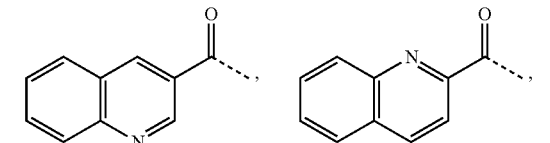
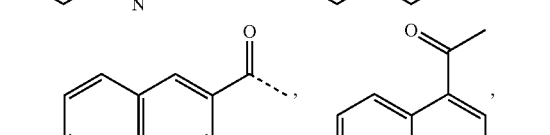
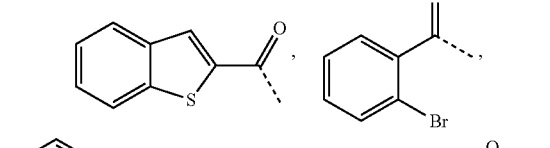
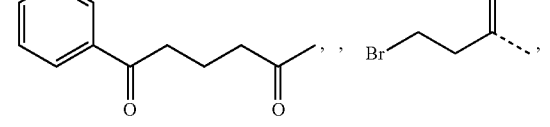
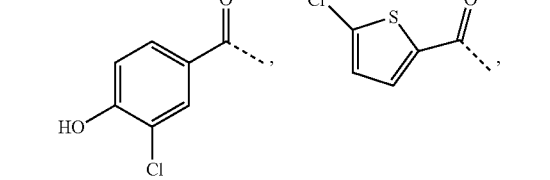
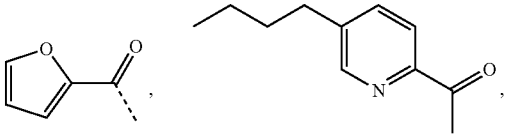
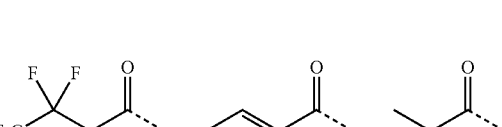
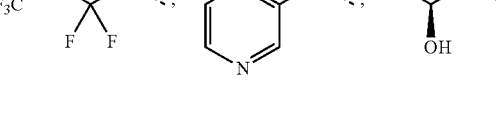
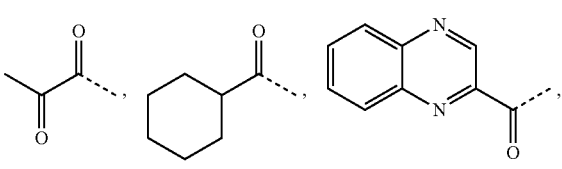
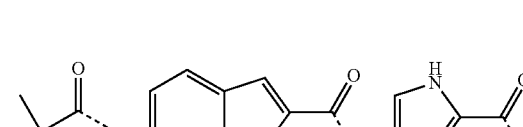
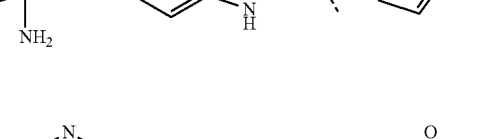
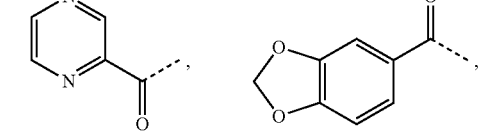
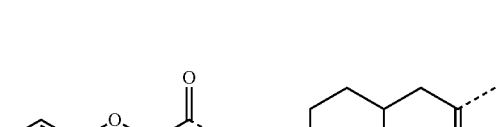
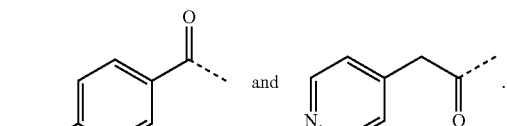

Scheme 9:

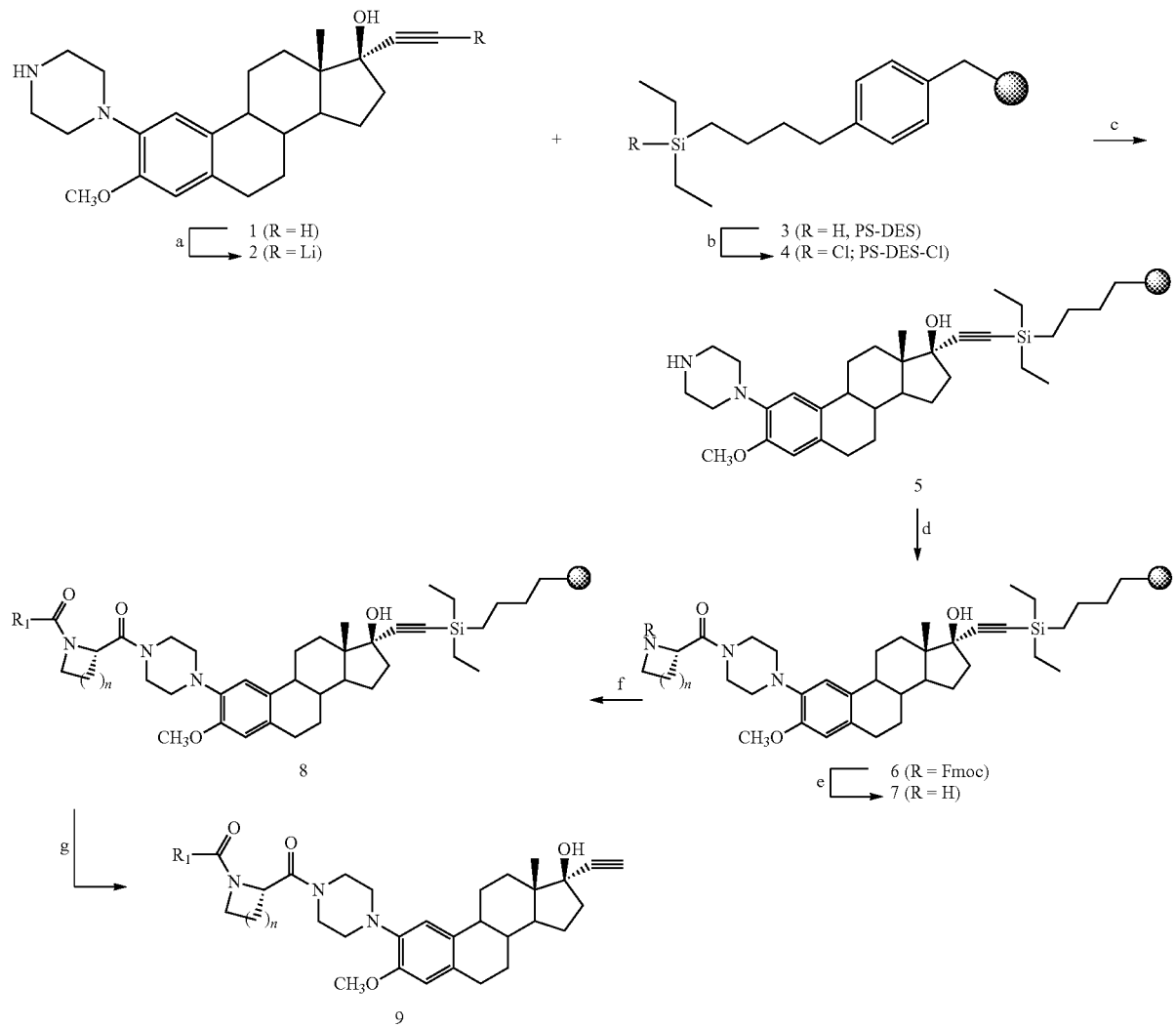

Reagents and conditions: (a) MeLi, THF, 0° C. to rt, 1.5 h; (b) 1,3-dichloro-5,5-dimethylhydantoin, DCM, rt, 1 h; (c) THF, rt, overnight; (d) L-azetidine-Fmoc (n = 1), L-proline-Fmoc (n = 2) or L-homoproline-Fmoc (n = 3), HBTU, DIPEA, DMF, rt, 4 h (2 coupling cycles); (e) piperidine 20%, DMF, rt, 1 h; (f) R$^1$—COOH, HBTU, DIPEA, DMF, rt, 3 h; (g) HCl, MeOH, DCM, rt, overnight.

With reference to Scheme 9, non-limiting examples of R$^1$ include alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy. With further reference to Scheme 9, selected examples of R$^1$CO include:

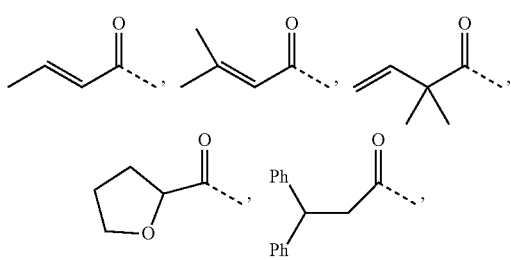

-continued

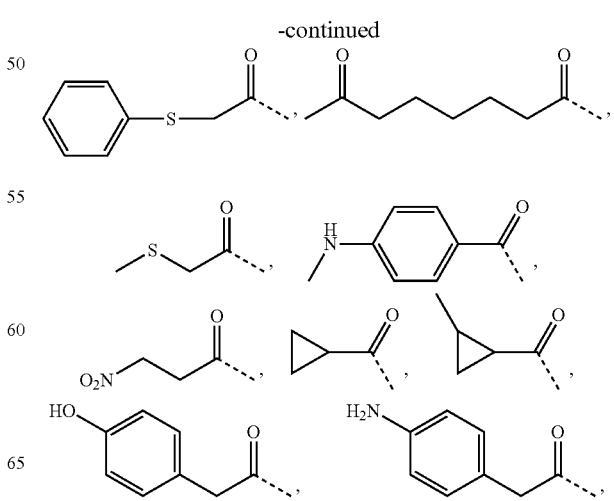

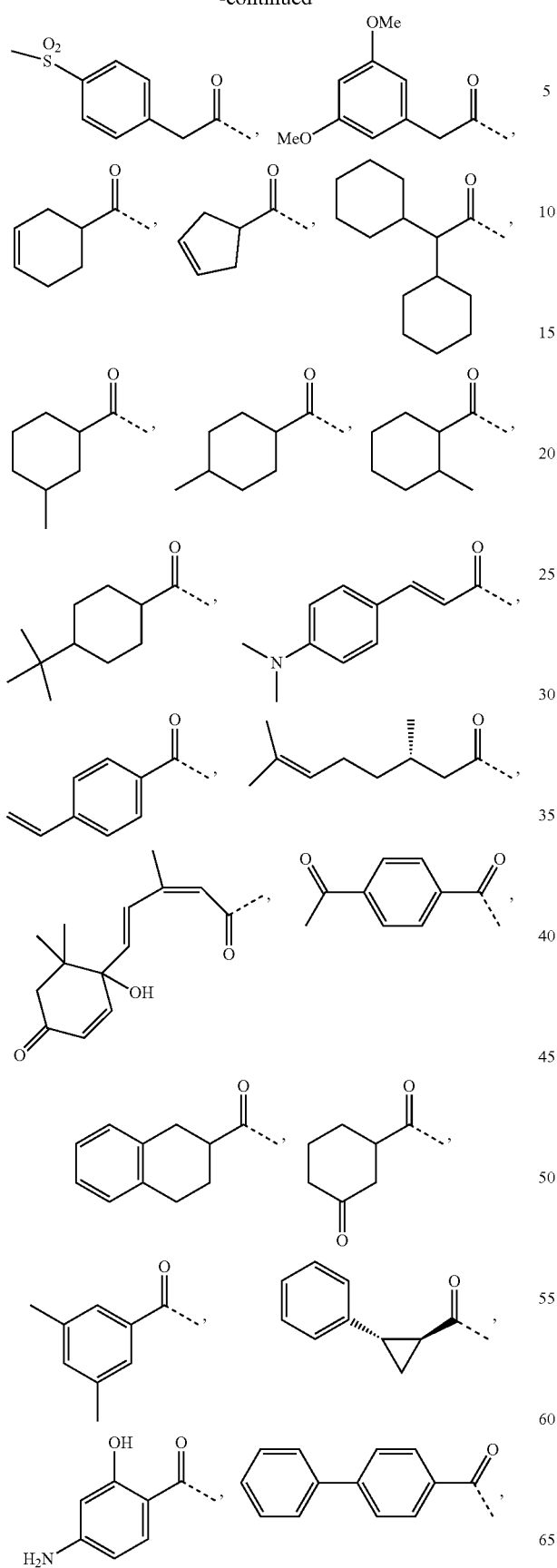
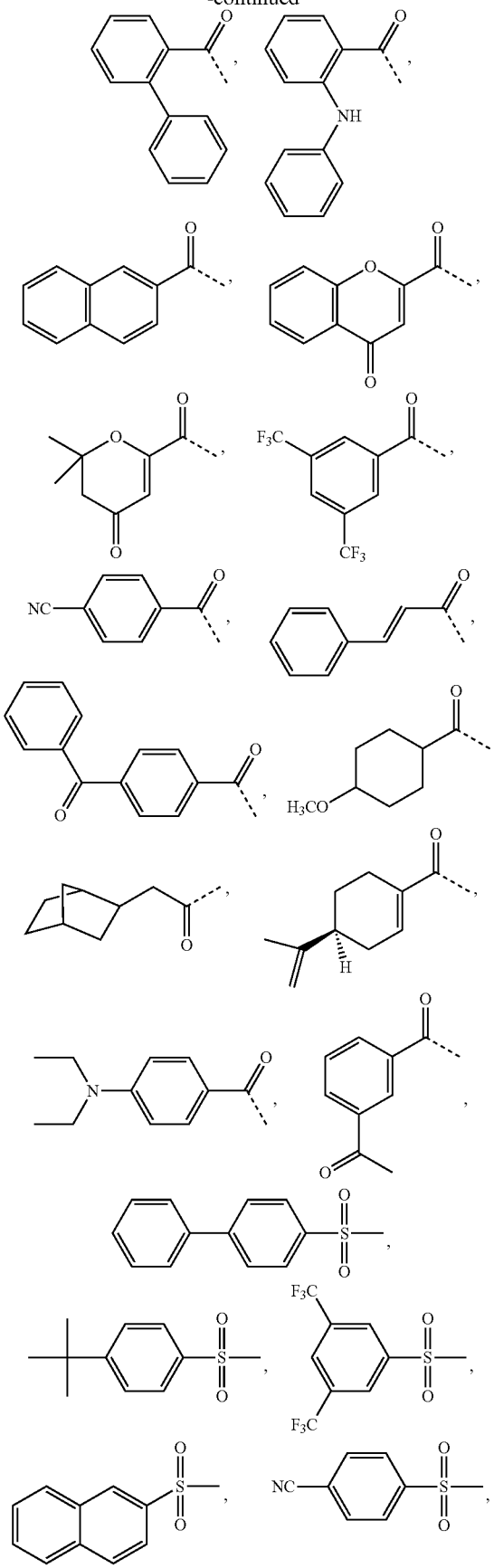

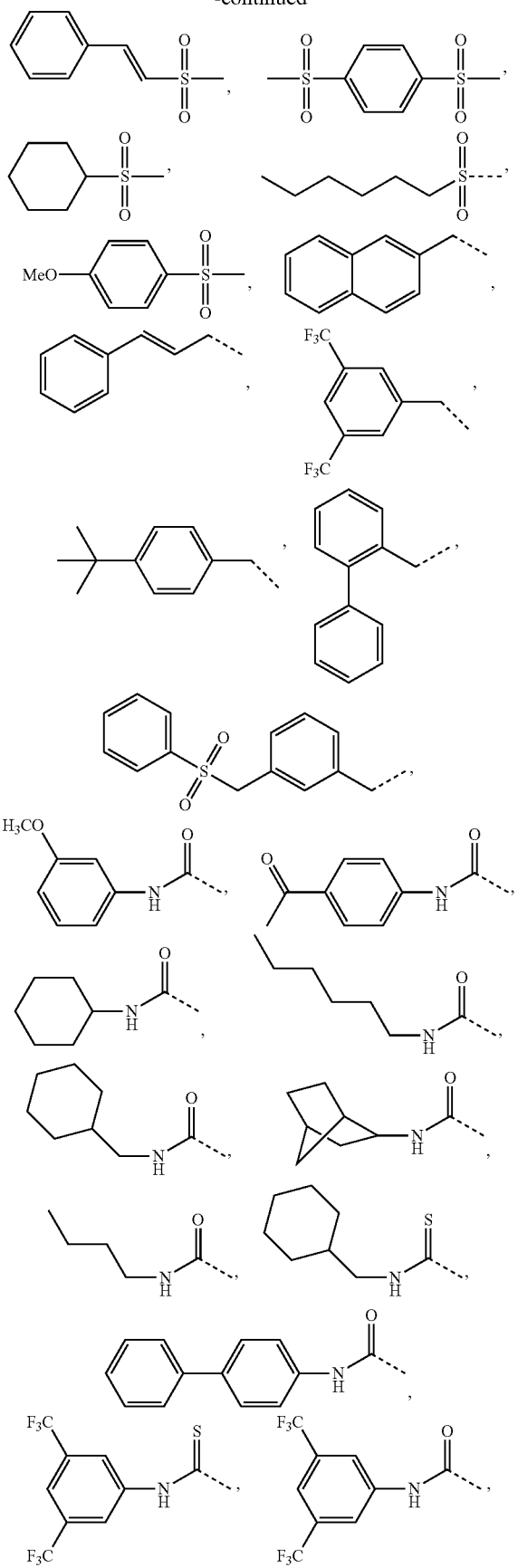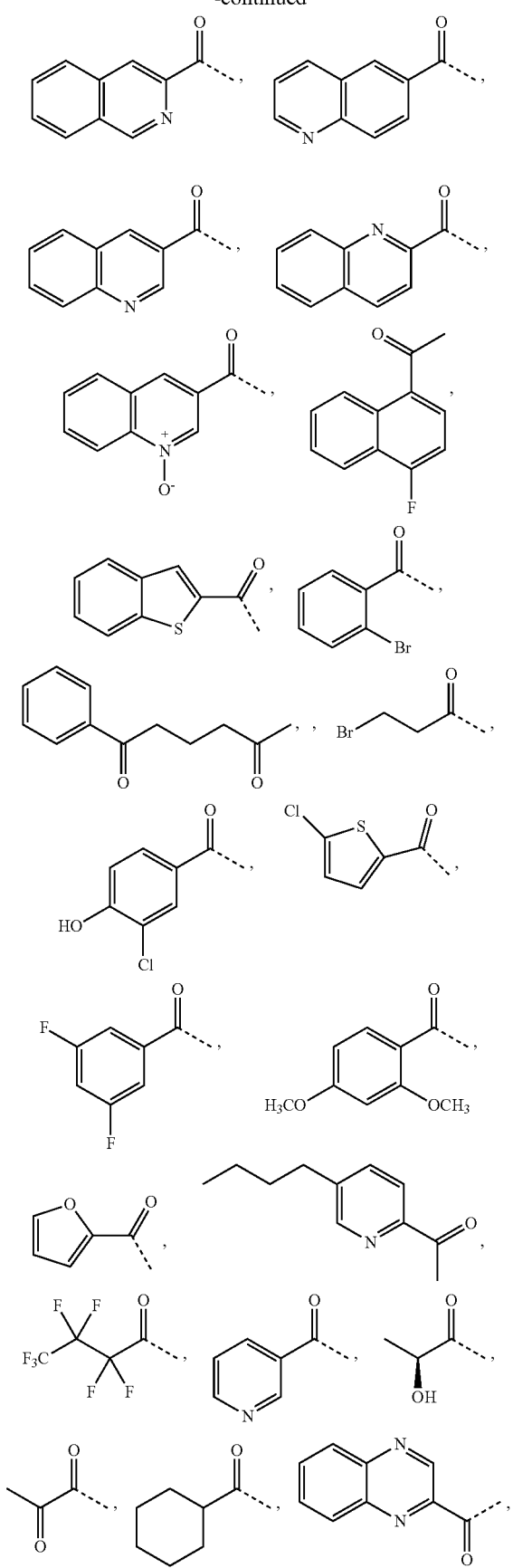

-continued

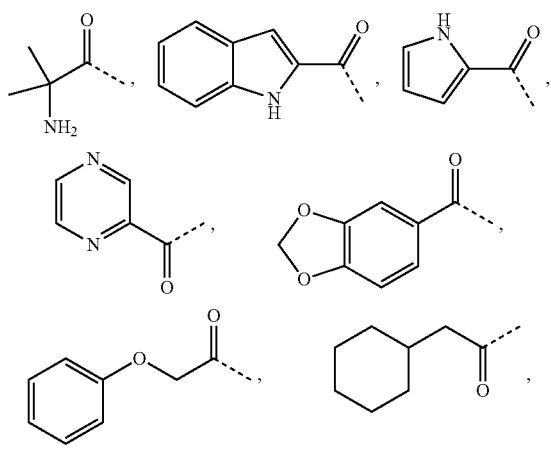

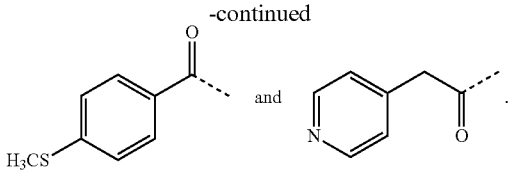

Selected derivatives (A1-A40) in accordance with an embodiment of the present disclosure are illustrated in Table 2. The new series of compounds A1-A40 as well as RM-581 were screened for their cytotoxic activities at two concentrations (5 and 1 μM) on three different cancer cell lines (pancreatic, ovary and breast) and at concentrations (0.1, 1.0 and 5 M) on prostate cancer cells. Different representative cell lines were tested for each cancer-type studied (pancreatic: PANC-1, BxPC-3 and Hs766; ovaries: OVCAR-3, Caov3 and SKOV3; breast: MCF-7 and T-47D), except for prostate cancer where only LAPC-4 cells were used at the screening assay step (FIGS. 9-12).

TABLE 2

Selected aminosteroid derivatives

| # | R | M.M. (g/mol) | Chemical formula | Purity (%) |
|---|---|---|---|---|
| A1 | | 559.75 | $C_{34}H_{45}N_3O_4$ | 87.5 |
| A2 | | 573.78 | $C_{35}H_{47}N_3O_4$ | 83.7 |
| A3 | | 589.78 | $C_{35}H_{47}N_3O_5$ | 82.0 |
| A4 | | 641.87 | $C_{38}H_{47}N_3O_4S$ | 74.7 |
| A5 | | 624.83 | $C_{38}H_{48}N_4O_4$ | 81.3 |
| A6 | | 559.75 | $C_{34}H_{45}N_3O_4$ | 82.2 |
| A7 | | 625.81 | $C_{38}H_{47}N_3O_5$ | 79.2 |

TABLE 2-continued
Selected aminosteroid derivatives
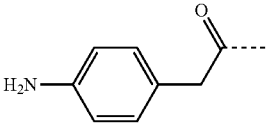
| # | R | M.M. (g/mol) | Chemical formula | Purity (%) |
|---|---|---|---|---|
| A8 | 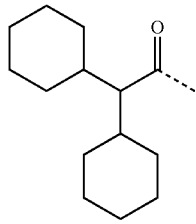 | 624.83 | $C_{38}H_{48}N_4O_4$ | 73.5 |
| A9 | 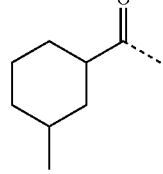 | 698.00 | $C_{44}H_{63}N_3O_4$ | 77.2 |
| A10 | 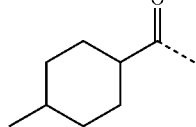 | 615.86 | $C_{38}H_{53}N_3O_4$ | 78.4 |
| A11 | 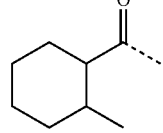 | 615.86 | $C_{38}H_{53}N_3O_4$ | 77.9 |
| A12 | 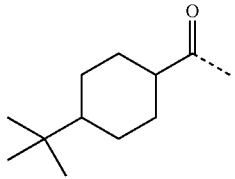 | 615.86 | $C_{38}H_{53}N_3O_4$ | 81.4 |
| A13 | 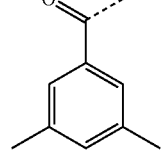 | 657.94 | $C_{41}H_{59}N_3O_4$ | 80.6 |
| A14 |  | 623.84 | $C_{39}H_{49}N_3O_4$ | 79.4 |

TABLE 2-continued

Selected aminosteroid derivatives

| # | R | M.M. (g/mol) | Chemical formula | Purity (%) |
|---|---|---|---|---|
| A15 | (trans-2-phenylcyclopropyl)carbonyl | 635.85 | $C_{40}H_{49}N_3O_4$ | 85.6 |
| A16 | 4-biphenylcarbonyl | 671.88 | $C_{43}H_{49}N_3O_4$ | 83.2 |
| A17 | 2-(phenylamino)cyclohexa-2,4-dien-1-ylcarbonyl | 686.90 | $C_{43}H_{50}N_4O_4$ | 81.8 |
| A18 | 3,5-bis(trifluoromethyl)benzoyl | 731.78 | $C_{39}H_{43}F_6N_3O_4$ | 77.1 |
| A19 | cinnamoyl | 621.82 | $C_{39}H_{47}N_3O_4$ | 85.1 |
| A20 | 4-benzoylbenzoyl | 699.89 | $C_{44}H_{49}N_3O_5$ | 81.6 |
| A21 | 4-methoxycyclohexylcarbonyl | 631.86 | $C_{38}H_{53}N_3O_5$ | 80.1 |
| A22 | (norbornan-2-yl)acetyl | 627.87 | $C_{39}H_{53}N_3O_4$ | 79.5 |

TABLE 2-continued
Selected aminosteroid derivatives
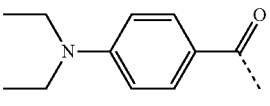
| # | R | M.M. (g/mol) | Chemical formula | Purity (%) |
|---|---|---|---|---|
| A23 | 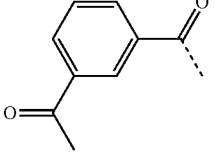 | 666.91 | $C_{41}H_{54}N_4O_4$ | 81.1 |
| A24 | 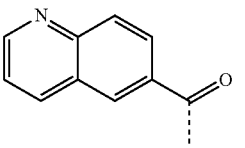 | 637.82 | $C_{39}H_{47}N_3O_5$ | 84.7 |
| A25 | 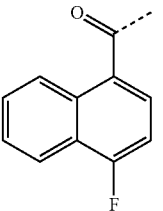 | 646.83 | $C_{40}H_{46}N_4O_4$ | 86.9 |
| A26 | 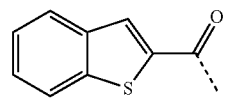 | 663.83 | $C_{41}H_{46}FN_3O_4$ | 86.5 |
| A27 | 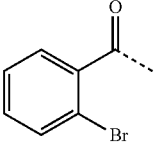 | 651.87 | $C_{39}H_{45}N_3O_4S$ | 82.7 |
| A28 | 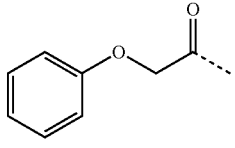 | 674.68 | $C_{37}H_{44}BrN_3O_4$ | 82.8 |
| A29 | 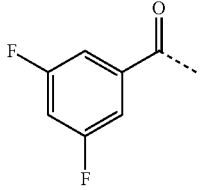 | 625.81 | $C_{38}H_{47}N_3O_5$ | 77.0 |
| A30 | | 631.76 | $C_{37}H_{43}F_2N_3O_4$ | 85.0 |

TABLE 2-continued
Selected aminosteroid derivatives
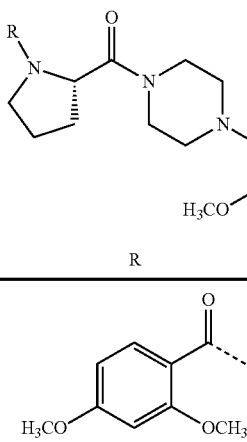
| # | R | M.M. (g/mol) | Chemical formula | Purity (%) |
|---|---|---|---|---|
| A31 | 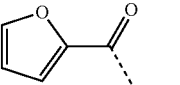 | 655.84 | $C_{39}H_{49}N_3O_6$ | 88.7 |
| A32 | 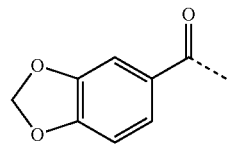 | 585.75 | $C_{35}H_{43}N_3O_5$ | 83.8 |
| A33 | 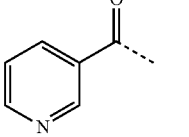 | 639.79 | $C_{38}H_{45}N_3O_6$ | 85.4 |
| A34 | 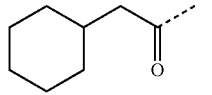 | 596.77 | $C_{36}H_{44}N_4O_4$ | 77.0 |
| A35 | 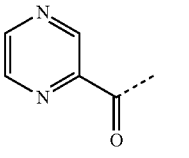 | 615.86 | $C_{38}H_{53}N_3O_4$ | 87.1 |
| A36 | 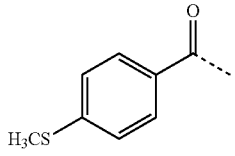 | 597.76 | $C_{35}H_{43}N_5O_4$ | 85.4 |
| A37 | 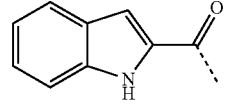 | 641.87 | $C_{38}H_{47}N_3O_4S$ | 81.8 |
| A38 | 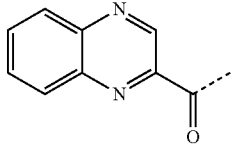 | 634.82 | $C_{39}H_{46}N_4O_4$ | 84.2 |
| A39 | | 647.82 | $C_{39}H_{45}N_5O_4$ | 80.1 |

TABLE 2-continued

Selected aminosteroid derivatives

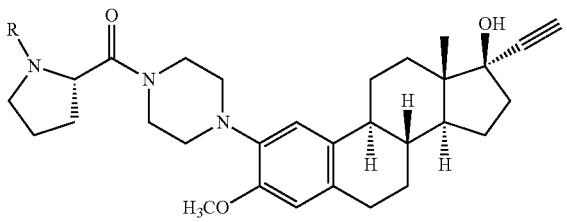

| # | R | M.M. (g/mol) | Chemical formula | Purity (%) |
|---|---|---|---|---|
| A40 | 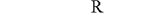 | 610.80 | $C_{37}H_{46}N_4O_4$ | 80.7 |

Anticancer Activity of Selected Estrane-Based Aminosteroid Derivatives

The estrane-based aminosteroid derivatives 4-6 (Scheme 1) displayed good antiproliferative activities on the OVCAR-3, PANC-1, HL-60 and LAPC-4 cell lines, respectively. (Table 3).

TABLE 3

Antiproliferative activity of derivatives 4-6 on 4 cancer cell lines as well as their relative toxicity on human normal cells.

| Estrane-based aminosteroid derivative | IC50 (µM) | | | | | |
|---|---|---|---|---|---|---|
| | Cancer Cell Lines | | | | Normal Cells | |
| | OVCAR-3 | PANC-1 | HL-60 | LAPC-4 | Ovary | Kidney |
| 1 | 6.4 | 9.6 | 4.3 | 1.3 | Non-toxic at ≥50 µM | Non-toxic at ≥50 µM |
| 2 | 3.2 | 5.8 | 6.1 | 0.5 | Non-toxic at ≥50 µM | Non-toxic at ≥50 µM |
| 3 | 3.4 | 5.7 | 4.3 | 0.6 | Non-toxic at ≥50 µM | Non-toxic at ≥50 µM |

1: RM-581-96 (derivative 4);
2: RM-581-99 (derivative 5);
3: RM-581-102 (derivative 6)

Selectivity of RM-581-102 for Cancer Cells Over Normal Cells

A selectivity index (SI) for RM-581-102 was calculated as the ratio of its $IC_{50}$ value in MCF-10A cells, a cell line used as a model for normal breast cells, versus its $IC_{50}$ value in MCF-7 breast cancer cells (Table 4). In this setup, RM-581-102 triggered only a mildly toxic effect on MCF-10A cells with an $IC_{50}$ of 16.8 µM, which leads to an SI of 15.3. RM-133 displayed an $IC_{50}$ of 3.0 µM in MCF-10A cells, resulting in a SI of 3.0. Therefore, RM-581-102 was shown to be 5.1 times more selective compared to RM-133 in the in vitro MCF-7 and MCF-10A cell models. Moreover, this lower cytotoxicity for normal cells was confirmed using primary renal proximal tubule epithelial cells (RPTEC), in which RM-581-102 was non-toxic at doses as high as 50 µM in comparison to RM-133 which displayed an $IC_{50}$ of 22.2 µM. It would thus appear that the replacement of the 5α-androstane-3α,17β-diol backbone by that of mestranol, is beneficial for the selectivity of these aminosteroid derivatives.

TABLE 4

Cytotoxic activity of RM-133 and RM-581-102 on MCF-7, MCF-10A and RPTEC cells.

| Compound | $IC_{50}$ (µM)[a] | | Selectivity Index | $IC_{50}$ (µM)[a] |
| --- | --- | --- | --- | --- |
| | MCF-7 | MCF-10A | | RPTEC |
| RM-133 | 1.0 ± 0.1 | 3.0 ± 0.6 | 3.0 | 22.2 ± 4.8 |
| RM-581-102 | 1.1 ± 0.1 | 16.8 ± 3.2 | 15.3 | >50.0 |

[a]Data represent the average of two experiments performed in triplicate (±SD).

Plasma concentration of RM-133 and RM-581-102

The plasmatic concentration (AUC) of RM-581-102 was determined following four different methods of administration (s.c., p.o., i.v. and i.p.) at the following concentrations: 60 mg/kg of body weight in 0.1 mL for s.c. and p.o. administration; 2 mg/kg of body weight in 0.02 mL for i.v. caudal administration; and 20 mg/kg of body weight in 0.1 mL for i.p. administration. For the s.c., p.o. and i.p. administrations, RM-581-102 was first dissolved in DMSO followed by the addition of propylene glycol to obtain a final concentration of DMSO of 8%. Regarding the i.v. administration, RM-581-102 was first dissolved in DMSO (8%) followed by the addition of DMA (38%) and propylene glycol (60%). For the i.v. administration, the mice were fasted over a period of 8 h before injection of RM-581-102. Blood samples for the determination of RM-581-102 plasma concentrations were collected by cardiac puncture at target intervals ranging from 5 min to 24 h post-dose administration from 3 mice/time point (Table 5).

TABLE 5

Plasmatic concentration of RM-133 and RM-581-102 in mice as per the mode of administration.

| Administration mode | $AUC_{0-24\,h}$ (ng·h/mL) | Plasmatic concentration (ng/mL) at 3 h | |
| --- | --- | --- | --- |
| | RM-581-102 | RM-581-102 | RM-133 |
| SC (60 mg/kg) | 7760 | 600 | 500 |
| PO (60 mg/kg) | 5545 | 550 | 50 |
| IP (20 mg/kg) | 11440 | 5300 | 5400 |
| IV (2 mg/kg) | 595 | 300 | 100 |

Synthesis of Androstane-Aminosteroid Derivatives

In accordance with an embodiment of the present disclosure, Scheme 10 illustrates the synthesis of selected androstane-based aminosteroid derivatives 1-7. Androstane-based aminosteroid derivatives 1-7 were all obtained in a single chemical step starting from the aminosteroid derivative RM-133. Considering the formation of by-products with similar polarities, preparative HPLC or preparative TLC purification was used to obtain a sufficient purity level of compounds 1, 2, 4 and 5 for biological assays. Flash column chromatography was however found to be efficient to purify compounds 3, 6 and 7. Androstane-based aminosteroid derivative 1 was obtained by oxidation of the 3α-OH of RM-133 using 2-iodoxybenzoic acid (IBX) in DMSO followed by in situ dehydrogenation. Oxidation of the 3α-OH of RM-133 using tetrapropylammonium perruthenate (TPAP) as the oxidation agent provided the corresponding androstane-based aminosteroid derivative 2. Androstane-based aminosteroid derivative 3 was obtained by protection of the 3α-OH of RM-133 using N,N-dimethylcarbamoyl chloride in pyridine with heating at 80° C. Androstane-based aminosteroid derivatives 4 and 5 were obtained by reaction of the 3α-OH of RM-133 (derivative 4) or by reaction of both the 3α-OH and 17α-OH of RM-133 (derivative 5) using acetic anhydride as the acetylating reagent. The N-methyl quaternary ammonium salt of RM-133, androstane-based aminosteroid derivative 6, was obtained through a Menshutkin reaction by treating RM-133 with a large excess of methyl iodide in acetonitrile at room temperature for 3 days. Oxone® (potassium peroxymonosulfate) in a mixture of methanol and water was used to selectively oxidize the tertiary amine of RM-133 providing the corresponding androstane-based aminosteroid derivative 7.

Scheme 10:
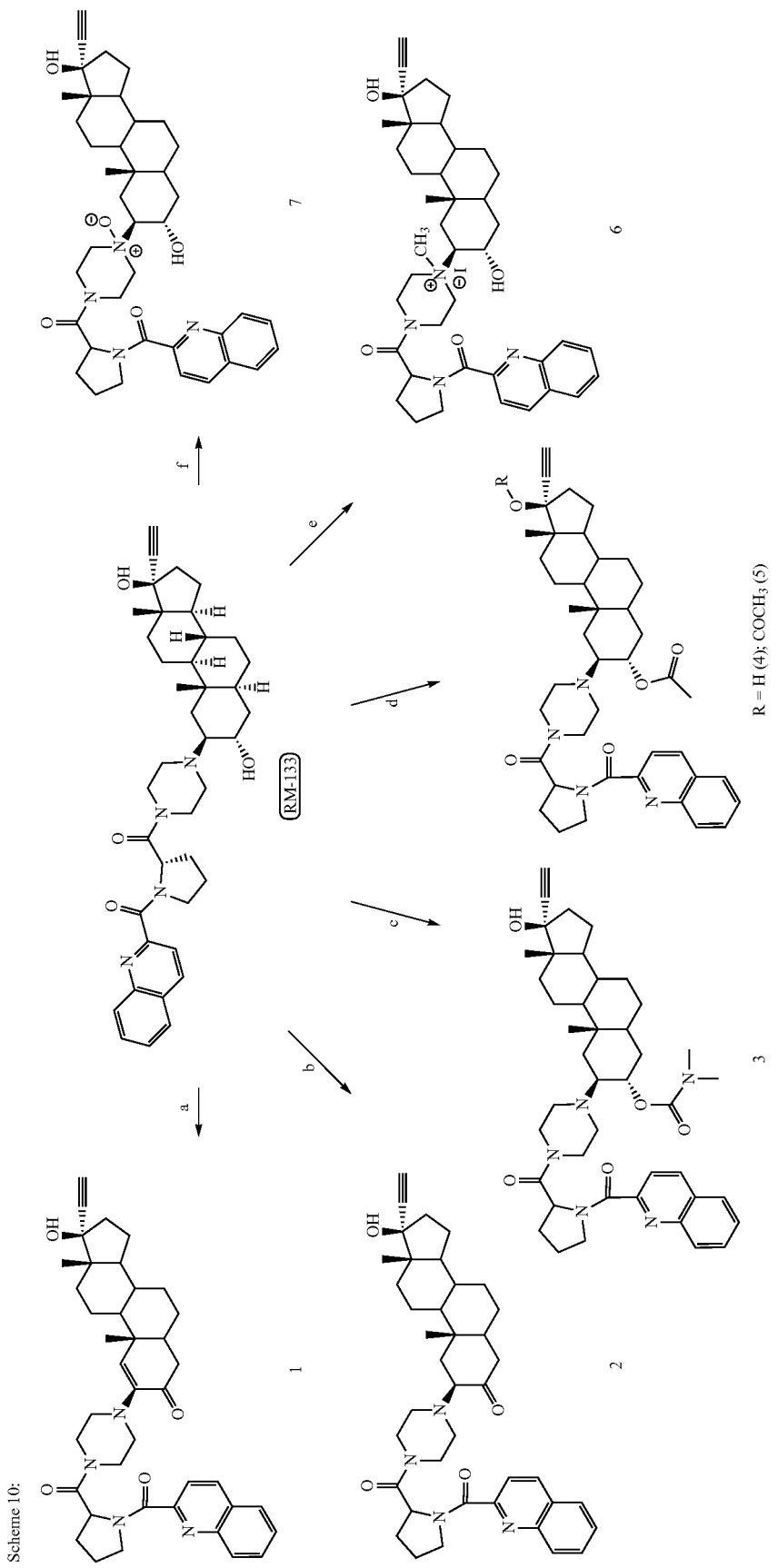
Reagents and conditions: (a) IBX, DMSO/toluene (1:3); (b) TPAP, NMO, molecular sieve, DCM, 0° C. to rt; (c) N,N-Dimethylcarbamoyl chloride, pyridine (1:1), 80° C.; (d) Acetic anhydride, pyridine (1:1), 80° C.; (e) CH₃I, ACN, rt; (f) Oxone, MeOH/H₂O (4:1), rt.

Synthesis of Androstane-Aminosteroid Derivatives

In accordance with an embodiment of the present disclosure, Scheme 11 illustrates the synthesis of selected androstane-based aminosteroid derivative 15 as well as steroids 11 and 12 lacking the 2β-side chain. Steroid 11 was generated in 2 steps from epiandrosterone (epi-ADT) by first reacting epi-ADT with lithium trimethylsilylacetylide followed by hydrolysing the silylated protecting group. Protection of the 3α-OH of 11 using N,N-dimethylcarbamoyl chloride in pyridine with heating at 80° C. provided steroid 12. In order to investigate to positional importance of the side-chain at position 2β on the activity and stability of the androstane-based aminosteroid derivatives, aminosteroid derivative 14 comprising a side-chain at position 3β was prepared. Accordingly, steroid 13 was readily transformed by a reductive amination to provide the aforementioned aminosteroid derivative 14 having a 3β-N-Boc-1-piperazine side chain. Boc-hydrolysis followed by an acylation reaction with the activated ester of the uronium form of 1-(quinolin-2-ylcarbonyl)-L-proline (9) provided androstane-based aminosteroid derivative 15.

Scheme 11:

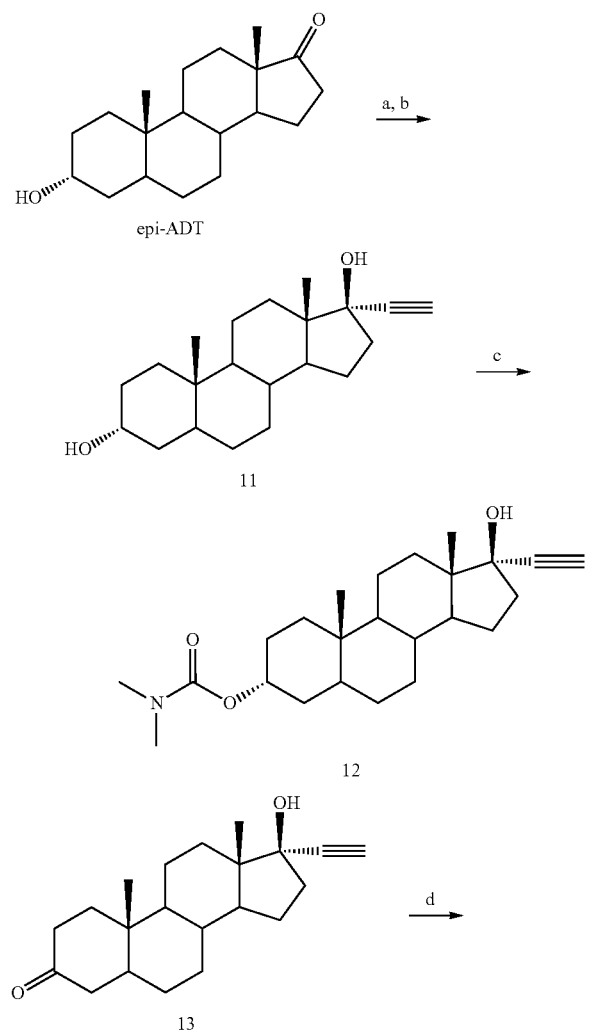

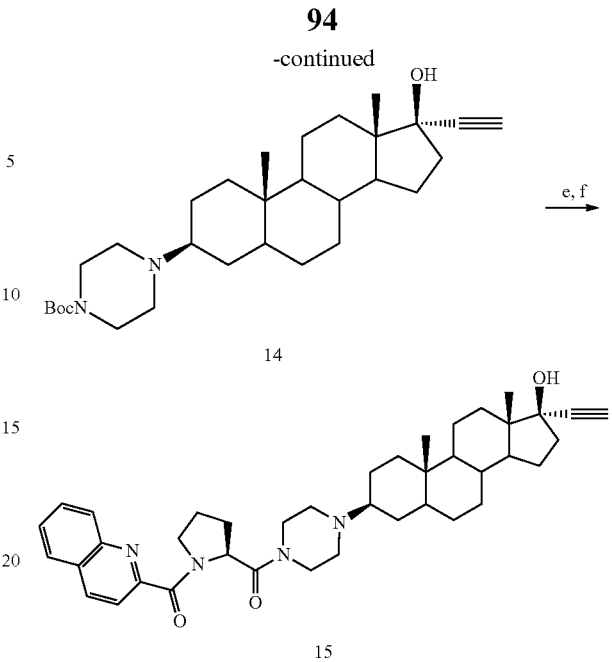

Reagent and conditions: (a) Trimethylsilylacetylene, MeLi, THF/diethylether (1:1), 0° C. to rt; (b) 5% K$_2$CO$_3$ in MeOH, rt; (c) N,N-Dimethylcarbamoyl chloride, pyridine, 80° C.; (d) N-Boc-1-piperazine, NaBH$_3$CN, AcOH, molecular sieve, MeOH/DCM (8:2), rt; (e) 25% TFA/DCM (1:1) in EtOAc, rt; (f) 9, HBTU, DIPEA, DMF, rt.

Synthesis of the 2-Side Chain of RM-133

In accordance with an embodiment of the present disclosure, Scheme 12 illustrates the synthesis of the 2β-side chain (compound 10) of androstane-based aminosteroid derivative RM-133. Compound 10 was obtained by coupling N-methylpiperazine with the uronium form of 1-(quinolin-2-ylcarbonyl)-L-proline (9). Compound 9 was obtained by the condensation of quinaldic acid with proline t-butylester followed by deprotection of the proline t-butyl ester moiety using trifluoroacetic acid. The presence of 2 rotamers for compound 10 was confirmed by $^1$H NMR analysis, as illustrated by the signal splitting and the observation of the associated characteristic signals (5.08 and 5.69 ppm) corresponding to the NCHCO of proline. A similar signal splitting was also observed when the side chain was attached to the steroid core. For example, both methyl-19 and methyl-18 appear as split signals in the $^1$H NMR spectrum of RM-133.

Scheme 12:

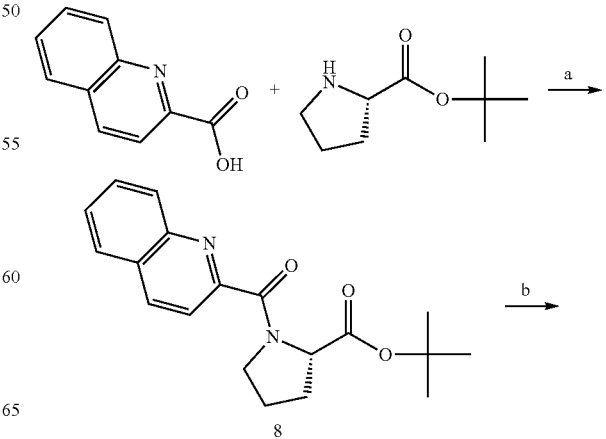

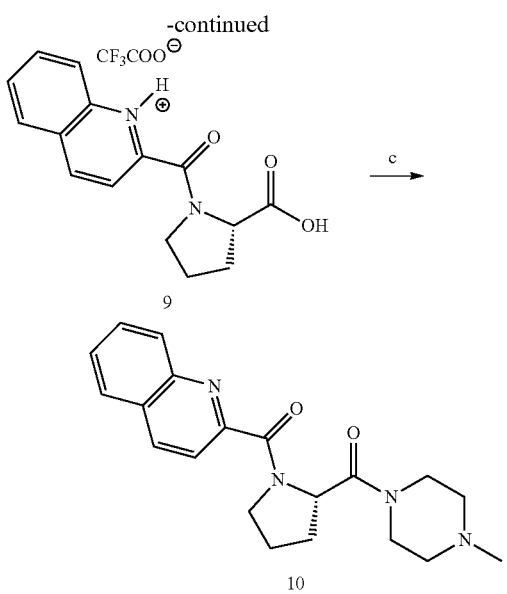

Reagent and conditions: (a)PyBOP, HOBt, DIPEA, DMF, rt; (b) TFA/DCM (95:5); (c) HBTU, N-methylpiperazine, DIPEA, DMF, rt.

Anticancer Activity of RM-133 Analogs

The RM-133 analogs (Schemes 10 and 11) displayed a wide range of antiproliferative activities (Table 6). Androstane-based aminosteroid derivative 1 (enone) displayed a significantly enhanced activity relative to RM-133, exhibiting a 2.3, 11.3 and 22.9-fold increase on the HL-60, PANC-1 and OVCAR-3 cell lines, respectively. Androstane-based aminosteroid derivative 2 (ketone) displayed an enhanced activity (2-fold) only on the OVCAR-3 cell line, while displaying a similar activity relative to RM-133 on the HL-60 and PANC-1 cell lines. It is believed that the enhanced activity of enone 1 relative to the ketone 2 is a result of a conformational change in the steroid structure rendering the A-ring more planar. Moreover, the presence of the enone functionality makes derivative 1 more susceptible to Michael-type addition reactions. Protecting the 3α-OH of the parent molecule as a potential carbamate or ester prodrug group, resulted in only a small effect on the antiproliferative efficiency of the parent molecule RM-133. Indeed, the androstane-based aminosteroid derivative 3 (3-carbamate) displayed a similar activity relative to RM-133 on the HL-60 and PANC-1 cell lines (0.9 and 0.7-fold respectively). However, derivative 3 only displayed a 0.3 fold activity relative to RM-133 on the OVCAR-3 cell line. Androstane-based aminosteroid derivative 4 (3-ester) displayed a similar activity relative to RM-133 on the HL-60, PANC-1 and OVCAR-3 cell lines (1.1, 1.1 and 1.4 fold). Androstane-based aminosteroid derivative 5 (3,17-diester) displayed an activity similar to RM-133 only on the HL-60 cell line. However, derivative 5 only displayed a 0.3 and 0.4 fold activity relative to RM-133 on the PANC-1 and OVCAR-3 cell lines. A significant loss of activity on the HL-60, PANC-1 and OVCAR-3 cell lines relative to RM-133 was observed for androstane-based aminosteroid derivatives 6 ($CH_3$-salt) and 7 (N-oxime). The 2β-side chain (compound 10) of androstane-based aminosteroid derivative RM-133 was found to be completely inactive on the HL-60, PANC-1 and OVCAR-3 cell lines relative to RM-133. Androstane-based aminosteroid derivative 15 (side-chain at 3β) was found to be completely inactive on the HL-60, PANC-1 and OVCAR-3 cell lines relative to RM-133. Finally, steroids 11 and 12, lacking the 2β-side chain, were also found to be inactive on the HL-60, PANC-1 and OVCAR-3 cell lines relative to RM-133. These results suggest that both a 2β-side chain and a steroid core be provided for anticancer activity.

TABLE 6

Antiproliferative activity of RM-133 and its analogs on 3 cancer cell lines.

| | $IC_{50}$ (µM) | | |
| --- | --- | --- | --- |
| RM-133 and its Analogs | HL-60 (leukemia) | PANC-1 (pancreas cancer) | OVCAR-3 (ovarian cancer) |
| RM-133 | 7.25 | 6.64 | 5.50 |
| 1 (enone) | 3.16 | 0.59 | 0.24 |
| 2 (ketone) | 6.52 | 7.01 | 2.75 |
| 3 (3-carbamate) | 7.95 | 9.99 | 20.0 |
| 4 (3-ester) | 6.44 | 6.24 | 3.83 |
| 5 (3,17-diester) | 6.44 | 25.0 | 13.1 |
| 6 ($CH_3$-salt) | >50.0 | >50.0 | >50.0 |
| 7 (N-oxime) | 43.7 | >50.0 | 29.9 |
| 10 (side-chain only) | >50.0 | >50.0 | >50.0 |
| 11 (no side-chain; and 3α-OH) | >50.0 | >50.0 | >50.0 |
| 12 (no side-chain; and 3-carbamate) | 15.2 | >50.0 | 48.1 |
| 15 (side-chain at 3β) | >50.0 | >50.0 | >50.0 |

Toxicity of RM-133 Analogs on Normal Cells

In accordance with the anticancer activities reported in Table 6, androstane-based aminosteroid derivatives 1-5 were selected and tested for their toxicity on primary pancreas, primary ovary and renal proximal tubule epithelial cells (RPTEC) (Table 7). Renal proximal tubule epithelial cells have been widely used in drug discovery processes as a good indicator of potential renal toxicity. Androstane-based aminosteroid derivative 3 (3-carbamate) and androstane-based aminosteroid derivative 4 (3-ester) displayed very low toxicity on the normal cell types tested. Moreover, carbamate derivative 3 did not trigger any loss of cell viability even at concentrations as high as 50 µM. Ester derivative 4 was observed to be 3.2 and 2.9 times less toxic relative to RM-133 in primary pancreas and ovary cells, respectively. Androstane-based aminosteroid derivative 5 (3,17-diester) displayed increased toxicity relative to the mono-ester derivative 4 (3-ester). However, derivative 5 was observed to be 1.8 and 1.7 times less toxic relative to RM-133 in primary pancreas and ovary cells, respectively. Androstane-based aminosteroid derivative 2 (3-ketone) displayed a similar toxicity relative to RM-133 in primary ovary cells and was observed to be 1.7 times more toxic in primary pancreas cells. Androstane-based aminosteroid derivative 1 (enone) was observed to be 4.3 and 1.6 times more toxic relative to RM-133 in primary pancreas and ovary cells, respectively. Finally, only derivative 1 was observed to be more cytotoxic (5.0 fold) relative to RM-133 in primary renal proximal tubule epithelial cells (RPTEC), a robust and predictive cell model for in vitro ADME and toxicity studies.

Selectivity of RM-133 enone analogue 1 (Scheme 10) and RM-581 and RM-581-OH for Cancer Cells over Normal Cells The cytotoxic activity of enone 1, RM-581 and RM-581-OH was assessed on four different cancer types (prostate, breast, ovarian and pancreatic) and on renal proximal tubule epithelial cells (RPTEC). Also included were different representative cell lines for each cancer-type studied (prostate: PC-3, LAPC-4 and LNCaP; breast: MCF-7 and T-47D; ovarian: OVCAR-3; pancreatic: PANC-1). The results are summarized hereinbelow in Table 7.

TABLE 7

Antiproliferative activity of enone 1, RM-581 and RM-581-OH on 4 cancer cell lines.

| Compound | IC$_{50}$ (μM) Prostate cancer | | | IC$_{50}$ (μM) Breast cancer | | IC$_{50}$ (μM) Ovarian cancer | IC$_{50}$ (μM) Pancreatic cancer | IC$_{50}$ (μM) Normal (kidney) |
|---|---|---|---|---|---|---|---|---|
| | PC-3 | LAPC-4 | LNCaP | MCF-7 | T-47D | OVCAR-3 | PANC-1 | RPTEC |
| RM-581 | 1.6 | 0.6 | 1.2 | 2.6 | 0.5 | 5.0 | 3.9 | >50 |
| RM-581-OH | 1.4 | 0.4 | 1.1 | 1.4 | 0.5 | 4.4 | 3.1 | — |
| Enone 1 | 0.002 | 0.03 | 0.002 | — | — | 0.24 | 0.6 | 4.5-15.3 |

Selectivity of RM-133 and analogs for Cancer Cells over Normal Cells

The selectivity of RM-133 and its analogs was assessed on 3 human normal cell types (primary pancreas normal cells, primary ovary normal cells and renal proximal tubule epithelial cells (RPTEC)). The selectivity of RM-133 was greatly enhanced by modification of the 3α-hydroxy group. This was particularly true for androstane-based aminosteroid derivative 3 (3-carbamate) for which a selectivity index (SI) for pancreas cancer cells of >5.0 and a selectivity index (SI) for ovary cancer cells of >2.5 was determined and no cytotoxicity was observed for normal cells at the higher concentration tested (50 μM). Similarly, a selectivity index (SI) for ovary cancer cells of 38 and a selectivity index (SI) for pancreas cancer cells of 3.7 was determined for androstane-based aminosteroid derivative 1 (enone). Androstane-based aminosteroid derivative 2 (3-ketone) displayed good selectivity (SI=5.5) for ovary cancer cells but shows little selectivity (SI=0.8) for pancreas cancer cells (Table 8). Androstane-based aminosteroid derivative 4 (3-ester) displayed good selectivity for both pancreas and ovary cancer cells (SI=4.8 and 11.0, respectively). Androstane-based aminosteroid derivative 5 (3,17-diester) displayed the lowest SI values of all compounds tested.

Metabolic Stability of RM-133 Analogs in Human Microsomes

Figure 3:
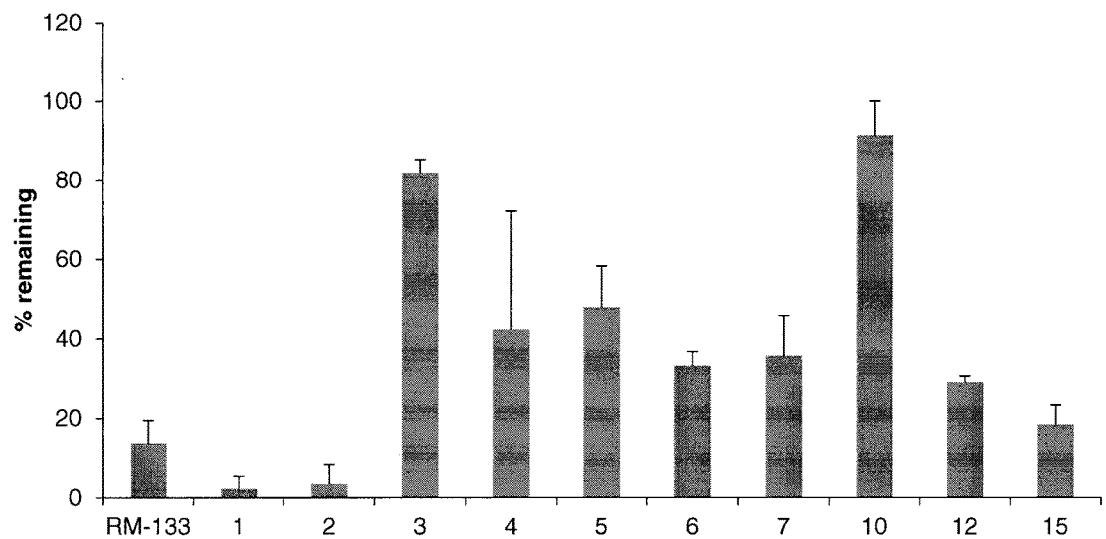
Figure 4:
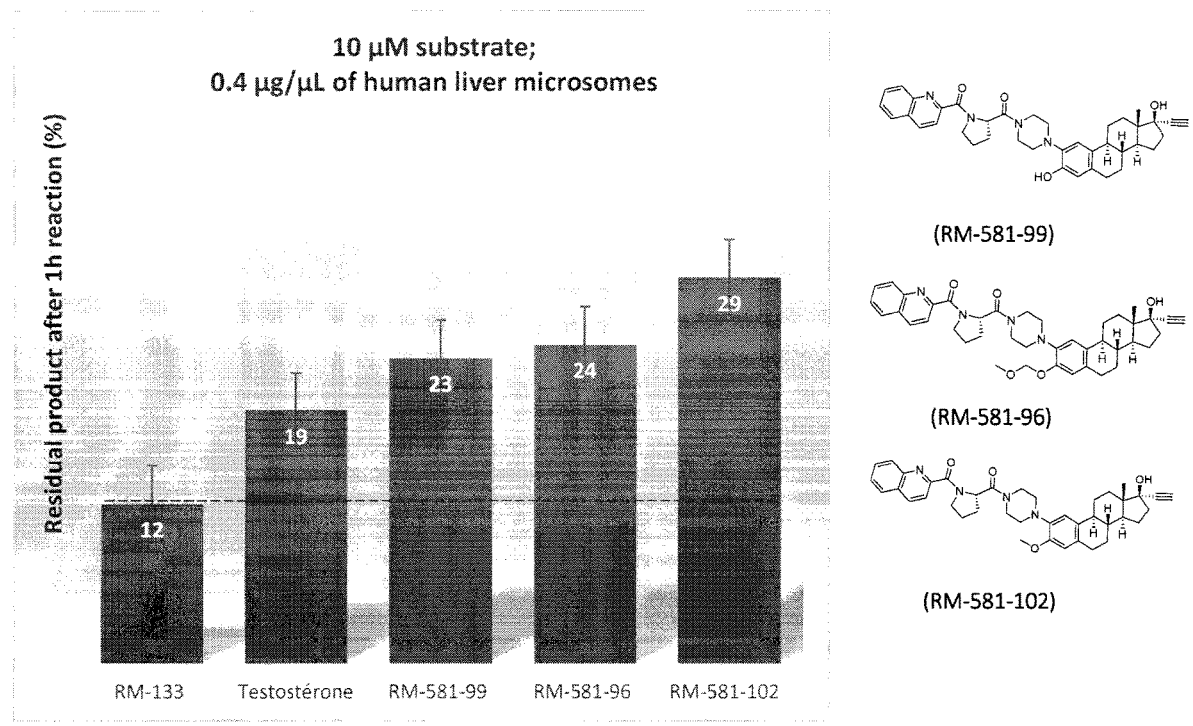

The oxidation of the 3α-hydroxy group of RM-133 to the corresponding androstane-based aminosteroid derivative 2 (3-ketone) or androstane-based aminosteroid derivative 1 (enone) significantly reduces the metabolic stability of the compounds (FIG. 3). Other modifications to the 3α-hydroxy group of RM-133 however proved beneficial to the metabolic stability of the compounds (3-carbamate, 3-ester, 3,17-diester). Androstane-based aminosteroid derivative 3 (3-carbamate) displayed a 5.9-fold increased metabolic stability relative to RM-133. Androstane-based aminosteroid derivative 4 (3-ester) and androstane-based aminosteroid derivative 5 (3,17-diester) displayed a 3.1 and 3.5-fold increased metabolic stability respectively relative to RM-133. It is hypothesized that the enhanced metabolic stability observed for derivative 3 (3-carbamate) relative to derivative 4 (3-ester) is a result of increased steric hindrance imparted by the larger N-dimethylcarbamate over the smaller methyl ester group causing a lower affinity of the analog for CYP enzymes. Generation of the N-methyl quaternary ammonium salt of RM-133 (derivative 6) or oxidation of the tertiary amine of RM-133 (derivative 7) proved beneficial to the metabolic stability of the compounds. The protective effect imparted by these modifications is likely the result of countering the potential for hepatic N-dealkylation and/or N-oxidation. A lower affinity of these analogs for CYP enzymes could further explain the observed metabolic stability. Androstane-based aminosteroid derivative 6 (CH$_3$-salt) and androstane-based aminosteroid derivative 7 (N-oxime) displayed a 2.4 and 2.6-fold increased metabolic stability respectively relative to RM-133. Finally, androstane-based aminosteroid derivative 15 (side-chain at 3β) displayed little to no variation on the metabolic stability relative to RM-133. The 2β-side chain (compound 10) of androstane-based aminosteroid derivative RM-133 was found to be more stable than steroid 12 lacking the 2β-side chain or RM-133 itself (FIG. 3).

TABLE 8

Toxicity of RM-133 analogs on human normal cells and their selectivity index

| RM-133 and its Analogs | IC$_{50}$ (μM) Primary pancreas (normal cells) | IC$_{50}$ (μM) PANC-1 (cancer cells) | Selectivity Index* Pancreas | IC$_{50}$ (μM) Primary Ovary (normal cells) | IC$_{50}$ (μM) OVCAR-3 (cancer cells) | Selectivity Index* Ovary | IC$_{50}$ (μM) RPTEC (normal cells) |
|---|---|---|---|---|---|---|---|
| RM-133 | 9.46 | 6.64 | 1.4 | 14.6 | 5.50 | 2.7 | 22.2 |
| 1 (enone) | 2.20 | 0.59 | 3.7 | 9.12 | 0.24 | 38 | 4.55 |
| 2 (ketone) | 5.41 | 7.01 | 0.8 | 15.0 | 2.75 | 5.5 | 20.7 |
| 3 (3-carbamate) | >50.0 | 9.99 | >5.0 | >50.0 | 20.0 | >2.5 | 24.2 |
| 4 (3-ester) | 30.1 | 6.24 | 4.8 | 42.0 | 3.83 | 11 | 32.1 |
| 5 (3,17-diester) | 16.6 | 25.0 | 0.7 | 25.4 | 13.1 | 1.9 | 45.5 |

*Selectivity Index (SI) = IC$_{50}$ normal cells/IC$_{50}$ cancer cells

Biological Assays
Celle Culture

HL-60 (acute promyelocytic leukemia), BxPC-3 (pancreas cancer), LNCaP (prostate cancer) and PC3 (prostate cancer) cells were routinely grown in suspension in RPMI 1640 (Sigma, Saint Louis, Mo., USA) containing L-glutamine (2 nM), antibiotics (100 IU penicillin/mL, 100 µg streptomycin/mL) and supplemented with 10% fetal bovine serum (FBS). LAPC4 (prostate cancer) cells were grown in IMDM containing L-glutamine (2 nM), antibiotics (100 IU penicillin/mL, 100 µg streptomycin/mL) and supplemented with 10% FBS. OVCAR-3 cells (ovarian cancer) were maintained in RPMI 1640 containing L-glutamine (2 nM), antibiotics (100 IU penicillin/mL, 50 or 100 µg streptomycin sulphate/mL), insulin (50 ng/mL), estradiol (1 nM) and supplemented with 20% FBS. Human pancreas cancer cells (PANC-1) were obtained from the American Type Culture Collection (ATCC, Rockville, Md., USA) and were routinely grown in suspension in 90% DME-F12 (Sigma, Saint Louis, USA) supplemented with L-glutamine (2 nM), antibiotics (100 IU penicillin/mL, 100 µg streptomycin/mL) and supplemented with 10% (v/v) foetal bovine serum (FBS) and maintained in a 175 cm$^2$ culture flask under a 5% $CO_2$ humidified atmosphere at 37° C. SKOV-3 cells were routinely grown in McCoy's 5a Medium Modified containing L-glutamine (2 nM), antibiotics (100 IU penicillin/mL, 100 µg streptomycin/mL) and supplemented with 10% FBS. Human primary epithelial pancreas and ovary cells were obtained from Cedarlane (Chicago, Ill., USA) and were cultured in the manufacturer recommended medium. Human renal proximal tubule epithelial cells (RPTEC) were obtained from Lonza (Mississauga, ON, Canada) and were maintained in DMEM-F12 supplemented as previously reported [4]. The cell lines were all maintained under a 5% $CO_2$ humidified atmosphere at 37° C. and the culture medium was changed every 2 to 3 days and the cells were split once a week to maintain cell propagation.

Cell Proliferation Assays

The cell proliferation assay was performed using 3-(4,5-dimethylthiazol-2-yl)-5-(3-carboxymethoxyphenyl)2-(4-sulfophenyl)-2H-tetrazolium (MTS) (Cell Titer 96 Aqueous, Promega, Nepean, ON, Canada) as previously described [3, 4, 5]. Briefly, cells were plated in triplicate in 96-well plates ($1 \times 10^4$ cells/well) in appropriate culture medium (total of 90 µL). Before each treatment, the cells were incubated at 37° C. in a 5% $CO_2$ humidified atmosphere for 24 h. The different aminosteroids were dissolved in methanol (50 mM). The stock solutions were diluted at multiple concentrations with culture media in order to obtain the desired final concentration followed by the addition of 10 µL to each well, and the mixture incubated for 3 days. Following treatment, MTS (10 µL) was added to each well and the mixture was incubated for 4 h. The plates were subsequently analyzed at 490 nm using a Tecan Infinite® M-200 microplate reader (Mannedorf, Switzerland) and the $IC_{50}$ values (50% cell growth inhibition) were calculated using GraphPad Prism® 6 software. Selectivity was calculated by dividing the $IC_{50}$ obtained for a specific primary cell by the $IC_{50}$ for the related cancer cell line.

Metabolic Stability Assays

The metabolic stability of RM-133 and various RM-581 analogs was evaluated using a classical human liver microsomal assay [6]. Assays were performed at 37° C. for 1 h, with or without 10 mM NADPH in the presence of 40 µg of human liver microsome from Corning (Melrose, Mass., USA) and 10 µM of aminosteroid substrate in a final 100 µL volume of 50 mM Tris buffer (pH 7.4) supplemented with 10 mM $MgCl_2$. Assays were ended by adding 100 µL of MeOH followed by centrifugation at 13,000 g for 10 min to obtain a pellet of proteins. The supernatant of 2 assays was pooled and submitted to HPLC-MS analysis (Shimadzu LCMS-2020 APCI, Alltima HP C18 (250 mm×4.6 mm, 5 µm) column, MeOH:$H_2O$ gradient). Remaining substrate (expressed in %) was calculated by dividing the area under the curve of the substrate for the assays without NADPH by the area under the curve of the substrate for the assays with NADPH and multiplied by 100. Values represent the average of 2 independent experiments.

Animal and Tumor Inoculation

42 Homozygous female nu/nu Br athymic mice (24-42 days old) were obtained from Charles River (Saint-Constant, Canada). Mice (4-5/cage) were housed in vinyl cages equipped with air lids, which were kept in laminar airflow hoods and maintained under pathogen-limiting conditions. The photoperiod was 12 h of light and 12 h of darkness (lights on at 07:15). Cages, bedding and food (Agway Pro-Lab R-M-H Diet 4018, Agway Inc. C.G., Syracuse, N.Y.) were autoclaved before use. Water was autoclaved and provided ad libitum. After 5 days, $5 \times 10^6$ PANC-1 cells (passage X) cells were inoculated s.c. in 0.1 mL of DME-F12 medium+30% Matrigel on both flanks of each mouse through a 2.5 cm long 25-gauge needle. After 19 days, randomization and treatment were started.

Treatment

One day prior to initiation of treatment, all mice were randomly assigned to seven groups (with respect to tumor size for tumor-bearing mice): 3 mice (6 tumors) for the p.o. control group; 3 mice (6 tumors) for the s.c. control group; 3 mice (6 tumors) for the i.p. control group; 6 mice (9 tumors) for the group of animals receiving RM-581-102 by p.o. administration of 1.48 mg (60 mg/kg on average) suspended in 0.1 mL; 7 mice (11 tumors) for the group of animals receiving RM-581-102 by s.c. injection of 1.48 mg (60 mg/kg on average) suspended in 0.1 mL; 7 mice (12 tumors) for the group of animals receiving RM-581-102 by i.p. injection of 0.25 mg (10 mg/kg on average) suspended in 0.1 mL; and 8 mice (12 tumors) for the group of animals receiving Docetaxel by i.p. injection of 0.099 mg (4 mg/kg on average) suspended in 0.1 mL. RM-581-102 was administered to the animals 6 days per week and docetaxel was given 2 times per week. All animals in the control group received 0.1 mL of the vehicle alone: propylene glycol with 8% of DMSO over a period of 27 days. All solutions were prepared one day prior to initiation of treatment, stored at 4° C. and used under constant agitation.

Tumor Measurement and Necropsy

Figure 5:
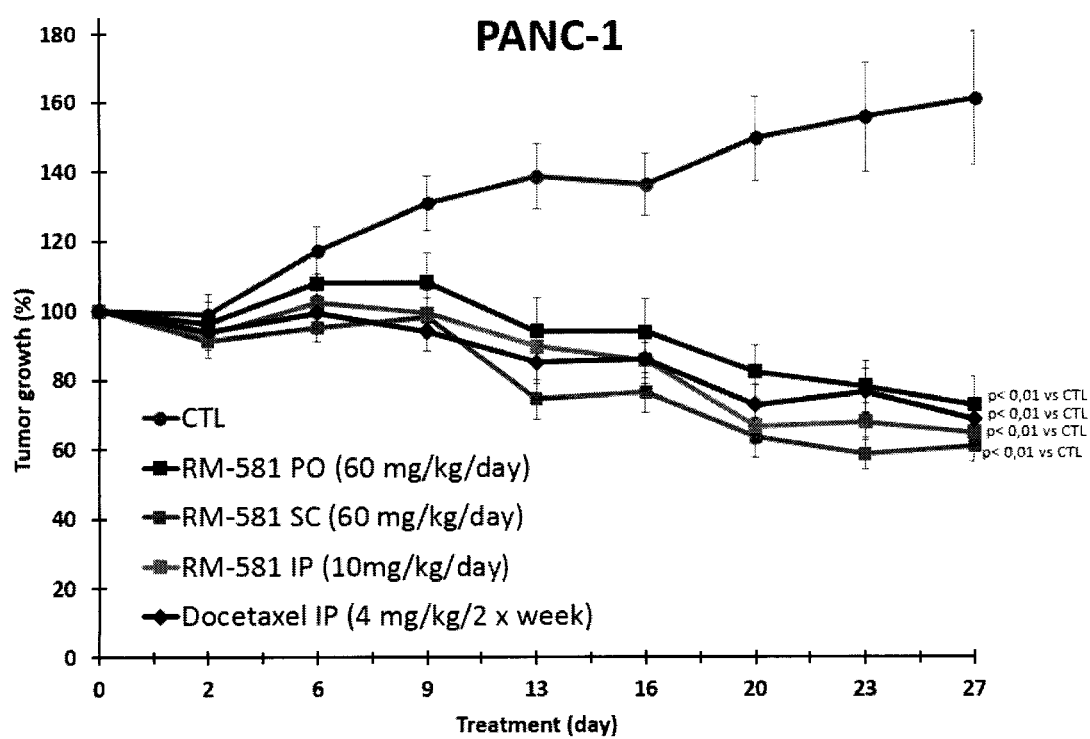

The tumors were measured two times per week. Two perpendicular diameters were recorded and the tumor area (mm$^2$) was calculated using the formula L/2×W/2×π. The area measured on the first day of treatment was taken as 100% (FIG. 5). After 27 days of treatment and 3 h after the last treatment, the animals were anesthetized with isoflurane and killed by exsanguination (cardiac puncture). The uterus, pancreas and tumors were removed and immediately frozen at −80° C. until analysis. The liver, intestine and the kidneys were removed and immediately fixed until analysis.

Pharmacokinetic study of RM-581-102 in mice

Plasmatic concentration (AUC) of RM-581-102 after a single administration in mice.

Animals: Six to seven week-old female Balb/c mice weighing approximately 18 g were obtained from Charles-River, Inc (St-Constant, Qc., Canada). The animals were acclimatized to environmental conditions (temperature: 22±3° C.; humidity: 50±20%; 12-h light/12-h dark cycles, lights on at 07:15 h) for at least 5 days before starting the experiment. The animals were housed three per cage and were allowed free access to water and a certified commercial rodent food (Rodent diet #T.2018.15, Harlan Teklad, Madison, Wis., U.S.A.). The experiments with the animals were conducted in an animal facility approved by the Canadian Council on Animal Care (CCAC) and the Association for Assessment and Accreditation of Laboratory Animal Care. The study was performed in accordance with the CCAC Guide for Care and Use of Experimental Animals. Institutional approval was obtained.

Assay: The pharmacokinetic study was carried out following four different methods of administration (s.c., p.o., i.v. and i.p.) of RM-581-102 at the following concentrations: 60 mg/kg of body weight in 0.1 mL for s.c. and p.o. administration; 2 mg/kg of body weight in 0.02 mL for i.v. caudal administration; and 20 mg/kg of body weight in 0.1 mL for i.p. administration. For the s.c., p.o. and i.p. administrations, RM-581-102 was first dissolved in DMSO followed by the addition of propylene glycol to obtain a final concentration of DMSO of 8%. Regarding the i.v. administration, RM-581-102 was first dissolved in DMSO (8%) followed by the addition of DMA (38%) and propylene glycol (60%). For the i.v. administration, the mice were fasted over a period of 8 h before injection of RM-581-102. Blood samples for the determination of RM-581-102 plasma concentrations were collected by cardiac puncture at target intervals ranging from 5 minutes to 24 hours post-dose administration from 3 mice/time point. The blood samples were collected in Microvette® potassium-EDTA (ethylenediamine tetra-acetic acid)-coated tubes (Sarstedt AG & Co, Germany) and centrifuged at 3200 rpm for 10 minutes at 4° C. The plasma was subsequently collected and stored at −80° C. until analysis by liquid chromatography/mass spectrometry/mass spectrometry (LC/MS/MS).

Measurement of RM-581-102 in plasma

The plasma concentrations of RM-581-102 was determined by LC/MS/MS analysis using a procedure developed at CHUQ (CHUL)—Research Center (Bioanalytical Service). For extraction from the plasma, a plasma sample (100 µL) was transferred to individual tubes and 600 µL of ammonium acetate (1 mM) was added. A methanolic solution (50 µL) containing a deuterated steroid internal standard was then added to each tube. Samples were then transferred on Strata-X SPE columns (Phenomenex, Torrance, Calif., USA) and each column was washed with water and methanol:water (10:90, v/v). RM-581-102 was then eluted with 5 mL of methanol containing 1 mM ammonium acetate. Methanol was subsequently evaporated at 45° C. under an inert atmosphere and the dried residue was reconstituted in 100 µL of methanol:water (85:15, v/v). The compounds were eluted at a flow rate of 0.8 mL/min. RM-581-102 was detected using an API 4000 mass spectrometer, equipped with TurbolonSpray (Applied Biosystems, Canada). ESI in positive ion mode.

EXPERIMENTAL

General: Unless otherwise noted, starting materials and reactants were obtained commercially and were used as such or purified by standard techniques. Butyldiethylsilane (PS-DES) resin with a loading capacity of 1.47 mmol/g was supplied by Biotage (Charlotte, N.C., USA). Chemical reagents were purchased from Sigma-Aldrich Canada Ltd. (Oakville, ON, Canada), Matrix Innovation (Québec, QC, Canada), Alfa Aesar (Wood Hill, Mass., USA), Chem-Impex Int'l. Inc. (Wood Dale, Ill., USA) and AAPPTec (Louisville, Ky., USA). The usual solvents were obtained from Fisher Scientific (Montréal, QC, Canada) and were used as received. Anhydrous dichloromethane (DCM), diethylether, dimethylformamide (DMF), dimethylsulfoxide (DMSO) and tetrahydrofuran (THF) were obtained from Sigma-Aldrich. Ethyl acetate (EtOAc), hexanes and methanol (MeOH) were purchased from Fisher Scientific. The loading of steroid 1 on PS-DES-Cl (resin 4) (Scheme 9) was performed in peptide synthesis vessels equipped with frit for vacuum filtration (ChemGlass Inc., Vineland, N.J., USA). The steps giving final compounds 9 (Scheme 9) were realized with an AAPPTec Solution automated organic synthesizer (Louisville, Ky., USA) using a solid-phase reaction block (96 wells). Thin-layer chromatography (TLC) and flash-column chromatography were performed on 0.20-mm silica gel 60 $F_{254}$ plates (E. Merck; Darmstadt, Germany) and with 230-400 mesh ASTM silica gel 60 (Silicycle, Québec, QC, Canada), respectively. Infrared (IR) spectra were recorded on a MB 3000 ABB FTIR spectrometer (Québec, QC, Canada), and only the most significant bands are reported in $cm^1$. Nuclear magnetic resonance (NMR) spectra were recorded at 400 MHz for $^1H$ and 100.6 MHz for $^{13}C$ using a Bruker Avance 400 digital spectrometer (Billerica, Mass., USA). The chemical shifts (δ) are expressed in ppm and referenced to chloroform-d (7.26 and 77.0 ppm), dimethylsulfoxide-d6 (2.49 and 39.5 ppm), methanol-d4 (3.31 ppm and 49.0 ppm) or acetone-d6 (2.05 and 28.9 ppm) for $^1H$ and $^{13}C$ NMR, respectively. When required, all glassware was flame dried and allowed to cool under a stream of dry argon. The purity of the final compounds to be tested was determined with a Shimadzu HPLC apparatus using a Shimadzu SPD-M20A photodiode array detector, an Altima HP C18 reversed-phase column (250 mm×4.6 mm, 5 m), and a solvent gradient of MeOH:water. The wavelength of the UV detector was selected between 190 and 205 nm. For some compounds, a preparative HPLC purification was performed using the Shimadzu HPLC apparatus equipped with a Phenomenex® C18 reversed-phase column (250 mm×21.2 mm, 4 m) and a solvent gradient of MeOH (70%):water (30%) to methanol (100%) over a 60 min run. Low-resolution mass spectra (LRMS) were recorded on a Shimadzu apparatus (Kyoto, Japan) equipped with an APCI (atomic pressure chemical ionization) turbo ion-spray source. The chemical names of steroid derivatives were generated with ACD/Laboratories (Chemist Version) software (Toronto, ON, Canada) which uses IUPAC nomenclature.

With reference to Schemes 1 and 2, a number of non-limiting examples illustrating the preparation of selected estrane-based aminosteroid derivatives (4-6) in accordance with various embodiments of the present disclosure, are illustrated in the following sections.

3-(methoxymethoxy)-2-(piperazin-1-yl)estra-1(10), 2,4-trien-17-one (2)

2-Iodo-3-(methoxymethoxy)estra-1(10),2,4-trien-17-one (1) (1.5 g, 3.4 mmol), piperazine (2.33 g, 34 mmol), $K_2CO_3$ (0.92 g, 6.8 mmol), CuI (66 mg, 0.34 mmol) and L-proline (78 mg, 0.68 mmol) were added in a dried flask under argon atmosphere, followed by the addition of anhydrous DMSO (9 mL). The resulting solution was stirred and heated at 120° C. overnight. After cooling, the reaction was poured into water. The resulting mixture was extracted with EtOAc, washed with brine, dried over sodium sulfate, filtered, and evaporated under reduced pressure. The crude compound was purified by flash chromatography with DCM/methanol/

TEA (89:10:1) as eluent to give the desired compound 2 as a light yellow solid (440 mg, 34%). IR (KBr) v: 3441 (NH), 1736 (C=O); $^1$H NMR (Acetone-$d_6$) δ: 0.91 (s, $CH_3$-18), 1.42-2.48 (m, residual CH and $CH_2$), 2.80 (m, $CH_2$-6), 3.00 (broad d, J=4.9 Hz, 4×$CH_2$N), 3.48 (s, $OCH_2$—$OCH_3$), 5.17 (s, $OCH_2$—$OCH_3$), 6.76 (s, CH-1), 6.87 (s, CH-4); $^{13}$C NMR (Acetone-$d_6$) δ: 14.1, 22.1, 26.7, 27.4, 32.7, 36.1, 39.2, 45.3, 46.7, 48.4, 48.7, 51.1, 51.5, 56.2, 96.2, 116.5, 118.8, 118.9, 131.3, 134.6, 142.1, 149.0, 175.7, 219.5.

(17β)-17-ethynyl-3-(methoxymethoxy)-2-(piperazin-1-yl)estra-1(10),2,4-trien-17-ol (3)

To a solution of trimethylsilylacetylene (320 µL, 3.26 mmol) in anhydrous THF (10 mL) was added MeLi (1.65 mL, 2.64 mmol, from 1.6 M solution in ether) at 0° C. under argon atmosphere. The solution was stirred at room temperature for 1 h and cooled again at 0° C. This cold solution was then added to a solution of compound 2 (250 mg, 0.65 mmol) in anhydrous THF (10 mL). The resulting solution was allowed to return to room temperature and stirred for 4 h. The solution was then poured into water, extracted with EtOAc, washed with brine, dried over sodium sulfate, filtered, and evaporated under reduced pressure. The crude compound was dissolved in a 5% $K_2CO_3$ solution in MeOH (20 mL) and stirred overnight. The resulting solution was poured into water, neutralised to pH 7, extracted with EtOAc, washed with brine, dried over sodium sulfate, filtered, and evaporated under reduced pressure to give the desired compound 3 as a light yellow solid 236 mg (88%). IR (KBr) v: 3286 and 3441 (NH and OH), 2098 (very weak peak, C≡C); $^1$H NMR (Acetone-$d_6$) δ: 0.91 (s, $CH_3$-18), 1.42-2.40 (m, residual CH and $CH_2$), 2.6-3.0 (broad m, 4×$CH_2$N), 2.97 (s, C≡CH), 3.48 (s, $OCH_2$—$OCH_3$), 5.16 (s, $OCH_2$—$OCH_3$), 6.73 (s, CH-1), 6.88 (s, CH-4); $^{13}$C NMR (Acetone-$d_6$) δ: 13.4, 23.5, 27.3, 28.2, 33.8, 39.9, 40.5, 45.1, 47.2, 47.9, 50.3, 51.6, 53.0, 56.2, 74.5, 79.6, 89.3, 96.2, 116.5, 118.5, 131.2, 135.0, 142.4.

{4-[(17β)-17-ethynyl-17-hydroxy-3-(methoxymethoxy)estra-1(10),2,4-trien-2-yl]piperazin-1-yl}[(2S)-1-(quinolin-2-ylcarbonyl)pyrrolidin-2-yl]methanone (4)

To a solution of 1-(quinolin-2-ylcarbonyl)-L-proline in anhydrous DMF (10 mL) was added, at room temperature, HBTU (829 mg, 2.2 mmol). The solution was stirred for 10 min and compound 3 (225 mg, 0.55 mmol) was added, followed by the addition of DIPEA (782 µL, 4.5 mmol). The solution was stirred for 48 h at room temperature. The resulting mixture was poured into water, extracted with EtOAc, washed with brine, dried over sodium sulfate, filtered, and evaporated under reduced pressure. The crude compound was purified by flash chromatography with DCM/methanol (95:5) as eluent to give the desired compound 4 as light yellow amorphous solid (101 mg, 24%). IR (KBr) v: 3410 (OH), 1643 (CON); $^1$H NMR (Acetone-$d_6$) δ: 0.90 and 0.94 (2s, $CH_3$-18), 1.25-4.19 (m, residual CH and $CH_2$), 2.82 (broad d, J=13.6 Hz, $CH_2$NCO), 2.97 and 3.01 (s, C≡CH), 3.44 and 3.51 (2s, $OCH_2$—$OCH_3$), 5.11 and 5.22 (2s, $OCH_2$—$OCH_3$), 5.22 and 5.91 (m, NCHCO of proline, two rotamers), 6.59 and 6.77 (2s, CH-1, two rotamers), 6.72 and 6.95 (2s, CH-4, two rotamers), 7.63 and 7.67 (2t, J=7.0 Hz, CH of quinoline), 7.80 (t, J=7.0 Hz, CH of quinoline), 7.87 and 7.91 (2d, J=8.6 Hz, CH of quinoline, two rotamers), 7.98 and 8.02 (2d, J=7.6 Hz, CH of quinoline, two rotamers), 8.12 (d, J=8.4 Hz, CH of quinoline), 8.37 and 8.44 (2d, J=8.5 Hz, CH of quinoline, two rotamers); $^{13}$C NMR (Acetone-$d_6$) δ: 13.2 (13.3), 23.1, 23.5, 26.0, 27.3, 27.5, 28.1, 28.2, 32.3, 33.8, 40.0, 40.4, 42.7, 45.0, 46.0, 47.9, 48.8, 50.3, 50.5, 51.4 (51.5), 51.7 (52.1), 57.3, 58.5, 60.0, 74.5, 79.6 (79.7), 89.3, 96.1 (96.2), 116.6 (116.9), 118.5 (118.7), 121.8 (122.3), 128.3, 128.5 (128.7), 128.8, 130.4 (130.5), 134.9, 137.3 (137.6), 146.9, 148.8, 155.7, 167.3, 171.0, 175.7; LRMS for $C_{41}H_{49}N_4O_5$ [M+H]+: 677.9; HPLC purity: 94.8%.

{4-[(17β)-17-ethynyl-3,17-dihydroxyestra-1(10),2,4-trien-2-yl]piperazin-1-yl}[(2S)-1-(quinolin-2-ylcarbonyl)pyrrolidin-2-yl]methanone (5)

To a solution of compound 4 (42 mg, 0.06 mmol) in MeOH (4 mL) was added 0.4 mL of HCl (10% aq). The solution was heated at 60° C. for 3 h. The resulting solution was poured into water, neutralised to pH 7 with NaHCO₃ (saturated solution), extracted with EtOAc, washed with brine, dried over sodium sulfate, filtered, and evaporated under reduced pressure to give the desired compound 5 as white solid (30 mg, 75%). IR (KBr) v: 3402 and 3294 (OH), 1636 (CON); $^1$H NMR (Acetone-$d_6$) δ: 0.90 and 0.94 (2s, $CH_3$-18), 1.31-4.40 (m, residual CH and $CH_2$), 2.83 (broad d, J=13.2 Hz, $CH_2$NCO), 2.97 and 3.01 (s, C≡CH), 5.22 and 5.98 (m, NCHCO of proline, two rotamers), 6.51 and 6.57 (2s, CH-1, two rotamers), 6.73 (2s, CH-4), 7.26 (s, OH of phenol), 7.66 (m, CH of quinoline), 7.83 (m, CH of quinoline), 7.85 (m, CH of quinoline), 8.02 (d, J=8.2 Hz, CH of quinoline), 8.14 (m, CH of quinoline), 8.39 and 8.44 (2d, J=8.5 Hz, CH of quinoline, two rotamers); $^{13}$C NMR (Acetone-$d_6$) δ: 13.2, 23.1, 26.0, 28.1, 28.2, 33.8, 40.0, 40.5, 42.6, 44.9, 46.0, 46.8, 47.9, 48.9, 50.3, 52.6 (52.7), 58.5, 60.1, 75.4, 79.6 (79.7), 89.3, 115.5, 118.2 (118.7), 128.3, 128.7, 129.1, 130.4 (130.5), 132.2 (132.3), 134.4 (134.6), 137.3 (137.6), 141.4 (141.7), 146.8, 149.8, 155.5, 167.1, 171.0, 175.7; LRMS for $C_{39}H_{45}N_4O_4$ [M+H]+: 633.8; HPLC purity: 93.8%.

{4-[(17β)-17-ethynyl-17-hydroxy-3-methoxyestra-1(10),2,4-trien-2-yl]piperazin-1-yl}[(2S)-1-(quinolin-2-ylcarbonyl)pyrrolidin-2-yl]methanone (6)

To a solution of compound 5 (18 mg, 0.03 mmol) in acetone (2 mL) was added $K_2CO_3$ (28 mg, 0.2 mmol) and MeI (18 µL, 0.3 mmol). The suspension was heated at 70° C. in a sealed vial. The resulting solution was poured into water, neutralised to pH 7, extracted with EtOAc, washed with brine, dried over sodium sulfate, filtered, and evaporated under reduced pressure. The crude compound was purified by preparative HPLC using a gradient of water/methanol (3:7 to 0:100) as eluent to give the desired compound 6 as white solid (4 mg, 21%). IR (KBr) v: 3410 and 3294 (OH), 1643 (CON); $^1$H NMR (Acetone-d6) δ: 0.90 and 0.93 (2s, $CH_3$-18), 1.28-4.39 (m, residual CH and $CH_2$), 2.82 (broad d, J=13.6 Hz, $CH_2$NCO), 2.97 and 3.02 (s, C≡CH), 3.75 and 3.78 (2s, $OCH_3$), 5.20 and 5.92 (m, NCHCO of proline, two rotamers), 6.55 and 6.65 (2s, CH-1, two rotamers), 6.58 and 6.90 (2s, CH-4, two rotamers), 7.63 and 7.65 (2t, J=7.0 Hz, CH of quinoline), 7.80 (t, J=7.0 Hz, CH of quinoline), 7.87 and 7.91 (2d, J=8.5 Hz, CH of quinoline, two rotamers), 7.98 and 8.02 (2d, J=8.2 Hz, CH of quinoline, two rotamers), 8.12 (d, J=8.4 Hz, CH of quinoline), 8.37 and 8.44 (2d, J=8.5 Hz, CH of quinoline, two rotamers); $^{13}$C NMR (CDCl₃) δ: 12.7, 22.4 (22.8), 26.6, 27.2, 29.0, 29.2 (29.3), 29.4, 31.7, 32.7, 39.0, 39.4, 42.0, 43.7 (43.8), 45.2, 47.1, 48.3, 49.4, 49.9, 50.6, 50.8 (51.0), 51.2, 55.3 (55.4), 57.6, 59.3, 79.8, 87.5, 111.7, 115.4 (115.8), 121.5 (121.6), 127.5 (127.7), 128.2 (128.3), 129.3 (129.8), 131.6 (131.8), 132.1 (132.3), 136.8, 138.4, 145.9 (146.5), 150.0 (150.2), 153.5 (154.1), 166.2 (166.6), 170.0 (170.3); LRMS for $C_{40}H_{47}N_4O_4$ [M+H]+: 647.9; HPLC purity: 99.6%.

2-Iodo-3-methoxyestra-1,3,5(10)-trien-17-one

To a solution of 2-iodo-estra-1,3,5(10)-trien-17-one (9.0 g, 22.7 mmol) and $Cs_2CO_3$ (14.8 g, 45.4 mmol) in ACN (250 mL) was added MeI (11.3 mL, 181.6 mmol). The resulting mixture was stirred and heated under reflux for 2.5 h. After cooling, the reaction mixture was poured into water, neutralized to pH7 and extracted with EtOAc. The organic phase was washed with water, dried over $MgSO_4$, filtered, and evaporated under reduced pressure. The crude compound was purified by flash chromatography with hexanes/EtOAc (8:2 to 5:5) as eluent to give the title compound as a white solid (7.66 g, 82%). IR (KBr): v: 1736 cm$^1$ (C=O); $^1$H NMR (CDCl$_3$) δ: 0.91 (s, CH$_3$-18), 1.37-2.40 (m, residual CH and CH$_2$), 2.51 (dd, J$_1$=8.6 Hz, J$_2$=18.8 Hz, 163-CH), 2.88 (m, CH$_2$-6), 3.84 (s, OCH$_3$), 6.55 (s, CH-4), 7.65 ppm (s, CH-1); $^{13}$C NMR (CDCl$_3$) δ: 13.8, 21.5, 25.9, 26.3, 29.6, 31.4, 35.8, 38.1, 43.6, 47.9, 50.2, 56.3, 82.7, 111.3, 134.3, 136.4, 138.1, 156.0, 221.0 ppm; HRMS for $C_{19}H_{24}IO_2$ [M+H]+: 411.08155 (calculated), 411.07973 (found).

3-Methoxy-2-(piperazin-1-yl)estra-1,3,5(10)-trien-17-one

The iodo compound (5.22 g, 12.7 mmol), piperazine (32.8 g, 381 mmol), $K_2CO_3$ (3.51 g, 25.4 mmol), CuI (242 mg, 1.27 mmol) and L-proline (292 mg, 2.54 mmol) were added in a dried flask under argon atmosphere, followed by the addition of anhydrous DMSO (25 mL). The resulting solution was stirred and heated at 120° C. overnight. After cooling, the reaction mixture was poured into water and the resulting mixture was extracted with EtOAc. The organic phase was washed with brine, dried over MgSO$_4$, filtered, and evaporated under reduced pressure. The crude compound was purified by flash chromatography with DCM/MeOH/TEA (94:5:1) as eluent to give the title compound as a light brown oil (3.17 g, 68%). IR (KBr) v: 3440 (NH), 1736 (C=O); $^1$H NMR (CDCl$_3$) δ: 0.90 (s, CH$_3$-18), 1.35-2.42 (m, residual CH and CH$_2$), 2.49 (dd, J$_1$=8.5 Hz, J$_2$=18.9 Hz, 16β-CH), 2.86 (m, CH$_2$-6), 3.09 (broad d, 4×CH$_2$N), 3.82 (s, OCH$_3$), 6.57 (s, CH-4), 6.85 (s, CH-1); $^{13}$C NMR (CDCl$_3$) δ: 13.9, 21.6, 26.1, 26.6, 29.2, 31.6, 35.9, 38.4, 44.2, 45.8 (2C), 48.0, 50.3, 51.4 (2C), 55.4, 111.7, 115.6, 131.1, 131.6, 139.2, 150.4, 221.0; HRMS for $C_{23}H_{33}N_2O_2$ [M+H]+: 369.25365 (calculated), 369.25256 (found).

17α-Ethynyl-3-methoxy-2-(piperazin-1-yl)estra-1,3,5(10)-trien-17β-ol

To a solution of trimethylsilylacetylene (4.8 mL, 34.1 mmol) in anhydrous diethyl ether (200 mL) under an argon atmosphere was added MeLi (16 mL, 25.6 mmol, from 1.6 M solution in diethyl ether) at 0° C. The solution was stirred at room temperature for 1 h and cooled again at 0 C before the addition of a solution of 3-methoxy-2-(piperazin-1-yl) estra-1,3,5(10)-trien-17-one_(3.14 g, 8.52 mmol) in anhydrous THF (200 mL). The resulting solution was allowed to return to room temperature and stirred overnight under an argon atmosphere. The solution was then poured into water and extracted with EtOAc. The organic phase was washed with brine, dried over MgSO$_4$, filtered, and evaporated under reduced pressure. The crude compound was dissolved in a 5% K$_2$CO$_3$ solution in MeOH (220 mL) and stirred overnight while at room temperature. The resulting solution was filtered to remove the excess K$_2$CO$_3$ and evaporated under reduced pressure until a volume of MeOH of about 30 mL. This mixture was then poured into water, neutralized to pH 7 and extracted with EtOAc and DCM. The organic layers were individually washed with brine, dried over MgSO$_4$, filtered, and evaporated under reduced pressure and finally combined. The crude compound was purified by flash chromatography with DCM/MeOH/TEA (94:5:1) as eluent to give the title compound as a brown yellow solid (2.24 g, 67%). IR (KBr) v: 3295 and 3390 (NH and OH), 2098 (weak peak, C≡C); $^1$H NMR (CDCl$_3$) δ: 0.88 (s, CH$_3$-18), 1.30-2.50 (m, residual CH and CH$_2$), 2.59 (s, C≡CH), 2.80 (m, CH$_2$-6), 2.98 and 3.06 (2s broad, 4×CH$_2$N), 3.82 (s, OCH$_3$), 6.56 (s, CH-4), 6.88 (s, CH-1); $^{13}$C NMR (CDCl$_3$) δ: 12.7, 22.7, 26.5, 27.3, 29.4, 32.9, 39.0, 39.4, 43.8, 46.1 (2C), 47.1, 49.4, 52.0 (2C), 55.4, 73.8, 79.6, 87.7, 111.6, 115.5, 131.1, 132.1, 139.4, 150.2; HRMS for $C_{25}H_{35}N_2O_2$[M+H]+: 395.26930 (calculated), 395.26787 (found).

{4-[17α-Ethynyl-17I-hydroxy-3-methoxyestra-1,3,5(10)-trien-2-yl]piperazin-1-yl}[(2S)-1-(quinolin-2-ylcarbonyl)pyrrolidin-2-yl]methanone (6; RM-581)

To a solution of 1-(quinolin-2-ylcarbonyl)-L-proline TFA salt (586 mg, 1.52 mmol) in anhydrous DMF (20 mL) was added at room temperature HBTU (578 mg, 1.52 mmol). The solution was stirred for 10 min and 17α-ethynyl-3-methoxy-2-(piperazin-1-yl)estra-1,3,5(10)-trien-17β-ol (500 mg, 1.27 mmol) was added, followed by the addition of diisopropylethylamine (DIPEA) (1.32 mL, 7.62 mmol). The solution was stirred overnight at room temperature under argon atmosphere. The resulting mixture was poured into water, extracted with EtOAc, washed with brine, dried over MgSO$_4$, filtered, and evaporated under reduced pressure. The crude compound was purified twice by flash chromatography with DCM/MeOH (97:3 to 95:5) and then with hexanes/acetone (5:5) as eluent to give RM-581 as a light yellow amorphous solid (490 mg, 60%). IR (KBr) v: 3410 (OH), 1643 (CON), 2098 (weak peak, C=C; $^1$H NMR (acetone-d$_6$) δ: 0.90 and 0.93 (2s, CH$_3$-18), 1.25-2.60 (m, residual CH and CH$_2$), 2.97 and 3.02 (2s, C≡CH), 2.76 (m, CH$_2$-6), 2.80-4.20 (m broad, 5×CH$_2$N), 3.75 and 3.83 (2s, OCH$_3$), 5.20 and 5.92 (2m, NCHCO of proline, two rotamers), 6.55, 6.58, 6.65 and 6.90 (4s, CH-1 and CH-4, two rotamers), 7.63 and 7.69 (2t, J=8.0 Hz, CH of quinoline), 7.80 (t, J=8.4 Hz, CH of quinoline), 7.88 and 7.91 (2d, J=8.5 Hz, CH of quinoline, two rotamers), 7.98 and 8.02 (2d, J=8.0 Hz, CH of quinoline, two rotamers), 8.12 (d, J=8.4 Hz, CH of quinoline), 8.37 and 8.44 (2d, J=8.5 Hz, CH of quinoline, two rotamers); $^{13}$C NMR (CDCl$_3$) δ: 12.7, 22.4 (22.8), 26.6, 27.2, 29.0, 29.2 (29.3), 29.4, 31.7, 32.7, 39.0, 39.4, 42.0, 43.7 (43.8), 45.2, 47.1, 48.3, 49.4, 49.9, 50.6, 50.8 (51.0), 51.2, 55.3 (55.4), 57.6, 59.3, 79.8, 87.5, 111.7, 115.4 (115.8), 121.5 (121.6), 127.5 (127.7), 128.2 (128.3), 129.3 (129.8), 131.6 (131.8), 132.1 (132.3), 136.8, 138.0 (138.4), 145.9 (146.5), 150.0 (150.2), 153.5 (154.1), 166.2 (166.6), 170.0 (170.3); HRMS for $C_{40}H_{47}N_4O_4$ [M+H]+: 647.35918 (calculated), 647.35675 (found); HPLC purity: 99.6% (determined using a Shimadzu HPLC apparatus using a Shimadzu SPD-M20A photodiode array detector, an Altima HP C18 reversed-phase column (250 mm×4.6 mm, 5 am), and a solvent gradient of MeOH:H$_2$O. The wavelength of the UV detector was selected at 205 nm).

With reference to Schemes 3-7, a number of non-limiting examples illustrating the preparation of selected estrane-based aminosteroid derivatives in accordance with various embodiments of the present disclosure, are described in the following sections.

(17β)-17-ethynyl-17-hydroxy-2-{4-[1-(quinolin-2-ylcarbonyl)-L-prolyl]piperazin-1-yl}estra-1,3,5(10)-trien-3-yl dimethylcarbamate (1)

To a solution of RM-581-OH (50 mg, 0.08 mmol) in dry pyridine (2 mL) was added N-dimethylcarbamyl chloride (75 µL, 0.82 mmol). The solution was heated in a sealed vial at 80° C. over a period of 16 h. After cooling, the solution was carefully poured into water (50 mL) and stirred for 5 min. The resulting mixture was extracted with EtOAc and the organic phase washed with brine, dried over sodium sulfate, filtered and evaporated under reduced pressure. Purification by flash chromatography using acetone/hexane (6:4) gave compound 1 as a white solid (20 mg, 36%). IR (KBr) v: 3425 (OH), 2106 (weak, C≡CH), 1720 (OCON), 1643 (NCO); $^1$H NMR (Acetone-$d_6$) δ: 0.91 and 0.95 (2s, $CH_3$-18), 1.29-2.70 (m, residual CH and $CH_2$, 2×$CH_2$ of piperazine, 1×$CH_2$ of proline, 2α-CH), 2.81 (m, $CH_2$-6), 3.02 and 3.06 (2s, C≡CH), 2.80-4.20 (m broad, 5×$CH_2$N), 4.36 and 4.40 (2s, OH of two rotamers), 5.12 and 5.93 (2m, NCHCO of proline, two rotamers), 6.70 (s, CH-4), 6.73 and 7.10 (2s, CH-1 two rotamers), 7.66 and 7.68 (2t, J=8.0 Hz, CH of quinoline), 7.83 (t, J=8.3 Hz, CH of quinoline), 7.88 and 7.91 (2d, J=8.5 Hz, CH of quinoline, two rotamers), 8.00 and 8.02 (2d, J=7.3 Hz, CH of quinoline, two rotamers), 8.12 (d, J=8.3 Hz, CH of quinoline), 8.38 and 8.44 (2d, J=8.5 Hz, CH of quinoline, two rotamers); LRMS for $C_{42}H_{50}N_5O_5$ [M+H]+: 704.8; HPLC purity: 99.0%.

(17β)-17-ethynyl-17-hydroxy-2-{4-[1-(quinolin-2-ylcarbonyl)-L-prolyl]piperazin-1-yl}estra-1,3,5(10)-trien-3-yl diethylcarbamate (2)

To a solution of RM-581-OH (60 mg, 0.09 mmol) in dry pyridine (2 mL) was added N-diethylcarbamyl chloride (130 µL, 1.0 mmol). The solution was heated in a sealed vial at 80° C. over a period of 16 h. After cooling, the solution was carefully poured into water (50 mL) and stirred for 5 min. The resulting mixture was extracted with EtOAc and the organic phase washed with brine, dried over sodium sulfate, filtered and evaporated under reduced pressure. Purification by flash chromatography using acetone/hexane (1:1) followed by preparative HPLC gave compound 2 as a white solid (22 mg, 32%). IR (KBr) v: 3425 (OH), 2098 (weak, C≡CH), 1713 (OCON), 1643 (NCO); $^1$H NMR (Acetone-$d_6$) δ: 0.91 and 0.95 (2s, $CH_3$-18), 1.11-2.70 (m, residual CH and $CH_2$, 2×$CH_2$ of piperazine, 1×$CH_2$ of proline, 2α-CH), 2.81 (m, $CH_2$-6), 2.98 and 3.02 (2s, C≡CH), 2.80-4.20 (m broad, 5×$CH_2$N), 4.36 and 4.40 (2s, OH of two rotamers), 5.19 and 5.95 (2m, NCHCO of proline, two rotamers), 6.70 (is, CH-4), 6.73 and 7.10 (2s, CH-1 two rotamers), 7.66 and 7.68 (2t, J=8.0 Hz, CH of quinoline), 7.83 (t, J=8.3 Hz, CH of quinoline), 7.88 and 7.91 (2d, J=8.5 Hz, CH of quinoline, two rotamers), 8.00 and 8.02 (2d, J=7.3 Hz, CH of quinoline, two rotamers), 8.11 (d, J=8.3 Hz, CH of quinoline), 8.38 and 8.44 (2d, J=8.5 Hz, CH of quinoline, two rotamers); LRMS for $C_{44}H_{54}N_5O_5$ [M+H]+: 732.4; HPLC purity: 99.3%.

(17β)-17-ethynyl-17-hydroxy-2-{4-[1-(quinolin-2-ylcarbonyl)-L-prolyl]piperazin-1-yl}estra-1,3,5(10)-trien-3-yl acetate (3)

To a solution of RM-581-OH (80 mg, 0.13 mmol) in dry pyridine (2 mL) was added acetic anhydride (150 µL, 1.6 mmol). The solution was heated in a sealed vial at 80° C. over a period of 16 h. After cooling, the solution was carefully poured into water (50 mL) and stirred for 5 min. The resulting mixture was extracted with EtOAc and the organic phase washed with brine, dried over sodium sulfate, filtered and evaporated under reduced pressure. Purification by flash chromatography using acetone/hexane (1:1) followed by preparative HPLC gave compound 3 as a white solid (35 mg, 37%). IR (KBr) v: 3410 (OH), 2106 (weak, C≡CH), 1759 (OCOCH$_3$), 1643 (NCO); $^1$H NMR (Acetone-$d_6$) δ: 0.91 and 0.95 (2s, $CH_3$-18), 1.11-2.70 (m, residual CH and $CH_2$, 2×$CH_2$ of piperazine, 1×$CH_2$ of proline, 2α-CH), 2.20 and 2.31 (2 s, OCOCH$_3$ of two rotamers), 2.81 (m, $CH_2$-6), 2.98 and 3.02 (2s, C≡CH), 2.80-4.20 (m broad, 5×$CH_2$N), 4.36 and 4.40 (2s, OH of two rotamers), 5.20 and 5.91 (2m, NCHCO of proline, two rotamers), 6.68 (is, CH-4), 6.75 and 7.12 (2s, CH-1 two rotamers), 7.65 and 7.69 (2t, J=8.0 Hz, CH of quinoline), 7.83 (t, J=8.3 Hz, CH of quinoline), 7.88 and 7.91 (2d, J=8.5 Hz, CH of quinoline, two rotamers), 8.00 and 8.02 (2d, J=7.3 Hz, CH of quinoline, two rotamers), 8.13 (d, J=8.3 Hz, CH of quinoline), 8.38 and 8.44 (2d, J=8.5 Hz, CH of quinoline, two rotamers); LRMS for $C_{41}H_{47}N_4O_5$ [M+H]+: 676.5; HPLC purity: 92.4%.

(17β)-17-ethynyl-17-hydroxy-2-{4-[1-(quinolin-2-ylcarbonyl)-L-prolyl]piperazin-1-yl}estra-1,3,5(10)-trien-3-yl sulfamate (4)

To a solution of RM-581-OH (100 mg, 0.16 mmol) in dichloromethane (20 mL) at room temperature was added 2,6-di-tert-butyl-4-methylpyridine (98 mg, 0.48 mmol) followed by the addition of two portions of sulfamoyl chloride (109 mg, 94 mmol) at 15 min intervals. The solution was subsequently stirred at room temperature over a period of 2 h. The solution was then poured into water (150 mL), extracted with DCM, filtered using a phase separator syringe and evaporated under reduced pressure. Purification by flash chromatography using DCM/MeOH (9:1) gave compound 4 as a pale yellow solid (40 mg, 35%). IR (KBr) v: 3387 (OH), 3288 and 3070 (NH$_2$), 2106 (weak, C≡CH), 1638 (NCO); $^1$H NMR (Acetone-$d_6$) δ: 0.91 and 0.95 (2s, $CH_3$-18), 1.07-2.54 (m, residual CH and $CH_2$, 2×$CH_2$ of piperazine, 1×$CH_2$ of proline, 2α-CH), 2.81 (m, $CH_2$-6), 2.98 and 3.02 (2s, C≡CH), 2.80-4.20 (m broad, 5×$CH_2$N), 4.38 and 4.42 (2s, OH of two rotamers), 5.20 and 5.92 (2m, NCHCO of proline, two rotamers), 6.72 (is, CH-4), 6.85 and 7.06 (2 broad s, SO$_2$NH$_2$) 7.00 and 7.10 (2s, CH-1 two rotamers), 7.63 and 7.69 (2t, J=8.0 Hz, CH of quinoline), 7.80 (t, J=8.4 Hz, CH of quinoline), 7.88 and 7.91 (2d, J=8.5 Hz, CH of quinoline, two rotamers), 8.02 and 8.04 (2d, J=7.3 Hz, CH of quinoline, two rotamers), 8.13 (d, J=8.3 Hz, CH of quinoline), 8.37 and 8.45 (2d, J=8.5 Hz, CH of quinoline, two rotamers); LRMS for $C_{39}H_{46}N_5O_6S$ [M+H]+: 712.5; HPLC purity: 94.5%.

(17β)-17-ethynyl-17-hydroxy-2-{4-[1-(quinolin-2-ylcarbonyl)-L-prolyl]piperazin-1-yl}estra-1,3,5(10)-trien-3-yl dihydrogen phosphate (5)

To a solution of RM-581-OH (100 mg, 0.16 mmol) in DCM (1 mL) under an argon atmosphere at 0° C. was added pyridine (250 µL, 3.1 mmol) followed by a dropwise addition of POCl$_3$ (150 µL, 0.59 mmol). The solution was stirred at room temperature over a period of 2 h. A mixture of acetone/H$_2$O (1:1) was then added and the resulting solution stirred for 15 min. The solution was subsequently poured into water, extracted with DCM and EtOAc. The organic phases were combined, dried over sodium sulfate, filtered and evaporated under reduced pressure. Purification by preparative HPLC gave compound 5 as a white solid (13 mg, 12%). IR (KBr) ν: 3410 and 3294 (OH), 2106 (weak, C≡CH), 1628 (NCO); $^1$H NMR (CD$_3$OD) δ: 0.86 and 0.91 (2s, CH$_3$-18), 1.29-2.54 (m, residual CH and CH$_2$, 2×CH$_2$ of piperazine, 1×CH$_2$ of proline, 2α-CH), 2.83 (m, CH$_2$-6), 2.92 and 2.96 (2s, C≡CH), 3.13-4.35 (m broad, 5×CH$_2$N), 5.25 and 5.79 (2m, NCHCO of proline, two rotamers), 6.76 and 7.40 (is, CH-1), 7.07 and 7.12 (2s, CH-4 two rotamers), 7.63 and 7.69 (2t, J=8.2 Hz, CH of quinoline), 7.85 (t, J=8.4 Hz, CH of quinoline), 7.95 and 7.97 (2d, J=8.5 Hz, CH of quinoline, two rotamers), 8.11 (d, J=8.3 Hz, CH of quinoline), 8.39 and 8.46 (2d, J=8.5 Hz, CH of quinoline, two rotamers); LRMS for C$_{39}$H$_{46}$N$_4$O$_7$P [M+H]+: 713.4; HPLC purity: 99.9%.

3-Hydroxy-2-(piperazin-1-yl)estra-1,3,5(10)-trien-17-one (7)

A solution of aqueous HCl (10%) in MeOH (9:1) was added to compound 6 (2.25 g, 5.6 mmol) and the mixture was stirred at 70° C. over a period of 16 h. The resulting solution was then poured into water, neutralized to pH 7, extracted with EtOAc, washed with brine, dried over sodium sulfate, filtered and evaporated under reduced pressure. The crude compound was directly used without further purification. Compound 7 was obtained as a white solid (2.0 g). IR (KBr) ν: 3310 (OH), 1736 (C=O); $^1$H NMR (Acetone-d$_6$) δ: 0.90 (s, CH$_3$-18), 1.29-2.48 (m, residual CH and CH$_2$), 2.81 (m, CH$_2$-6), 2.80-3.03 (broad m, 4×CH$_2$ piperazine and CH$_2$-6), 6.54 (s, CH-1), 7.08 (s, CH-4); LRMS for C$_{22}$H$_{31}$N$_2$O$_2$ [M+H]+: 355.6.

tert-Butyl 4-[3-hydroxy-17-oxoestra-1,3,5(10)-trien-2-yl]piperazine-1-carboxylate (8)

To a solution of compound 7 (1.50 g, 4.23 mmol) in a mixture of THF/dioxane/H$_2$O (25/25/25 mL) was added sodium bicarbonate (543 mg, 6.46 mmol) and di-t-butyldicarbonate (1.21 g, 5.54 mmol). The solution was stirred at room temperature over a period of 16 h. The resulting solution was subsequently poured into water, extracted with EtOAc, washed with brine, dried over sodium sulfate, filtered and evaporated under reduced pressure. The crude compound was directly used without further purification. Compound 8 was obtained as a white solid (2.0 g). IR (KBr) ν: 3371 (OH), 1736 (C=O), 1690 (NCOO); $^1$H NMR (Acetone-d$_6$) δ: 0.90 (s, CH$_3$-18), 1.46 and 1.51 (2s, (CH$_3$)$_3$OCON), 1.29-2.48 (m, residual CH and CH$_2$), 2.81 (m, 2×CH$_2$N of piperazine, CH$_2$-6), 3.59 (m, 2×CH$_2$NCO), 6.56 (s, CH-1), 7.08 (s, CH-4), 7.35 (s, OH); LRMS for C$_{27}$H$_{39}$N$_2$O$_4$ [M+H]+: 455.4.

tert-Butyl 4-[17-oxo-3-{[(trifluoromethyl)sulfonyl]oxy}estra-1,3,5(10)-trien-2-yl]piperazine-1-carboxylate (9)

To a solution of compound 8 (2.2 g, 4.84 mmol) at 0° C. in DCM (150 mL) was added, under an argon atmosphere, TEA (2.1 mL, 15.0 mmol) and trifluoromethanesulfonic anhydride (1.29 mL, 7.68 mmol). The solution was stirred at 0° C. over a period of 20 min (until completion of the reaction). The resulting solution was poured into water, extracted two times with DCM, filtered using a phase separator syringe and evaporated under reduced pressure. The crude compound was purified by flash chromatography using EtOAc/hexanes (1:9) with 1% TEA to give a pale yellow amorphous solid (675 mg, 24%). IR (KBr) ν: 1744 (C=O), 1697 (NCOO); $^1$H NMR (Acetone-d$_6$) δ: 0.92 (s, CH$_3$-18), 1.46 and 1.52 (2s, (CH$_3$)$_3$OCON), 1.18-2.53 (m, residual CH and CH$_2$), 2.81 (m, 2×CH$_2$N of piperazine, CH$_2$-6), 3.57 (m, 2×CH$_2$NCO), 7.05 (s, CH-1), 7.29 (s, CH-4); LRMS for C$_{28}$H$_{38}$F$_3$N$_2$O$_6$S [M+H]+: 587.3.

tert-Butyl 4-[17-oxoestra-1,3,5(10)-trien-2-yl]piperazine-1-carboxylate (10)

To a solution of compound 9 (110 mg, 0.19 mmol) in anhydrous DMF (3 mL), under an argon atmosphere at room temperature, was added TEA (109 μL, 0.78 mmol), formic acid (30 μL, 0.78 mmol), triphenylphosphine (16 mg, 0.06 mmol) and Pd(OAc)$_2$ (5 mg, 0.02 mmol). The resulting solution was subsequently stirred at 40° C. over a period of 48 h. The resulting solution was poured into water, extracted two times with EtOAc, dried over sodium sulfate, filtered and evaporated under reduced pressure. The crude compound was purified by flash chromatography using EtOAc/hexanes (1:9) to give a white amorphous solid (52 mg) containing 30% of inseparable starting material 9. IR (KBr) ν: 1736 (C=O), 1697 (NCOO); $^1$H NMR (Acetone-d$_6$) δ: 0.91 (s, CH$_3$-18), 1.46 (s, (CH$_3$)$_3$OCON), 1.26-2.52 (m, residual CH and CH$_2$), 2.81 (m, 2×CH$_2$N of piperazine, CH$_2$-6), 2.94 and 3.08 (m, 2×CH$_2$N), 3.53 (m, 2×CH$_2$NCO), 6.77 (d, CH-3, J=8.2 Hz), 6.94 (s, CH-1), 6.95 (d, CH-4, J=8.4 Hz); LRMS for C$_{27}$H$_{39}$N$_2$O$_3$ [M+H]+: 439.3.

2-(piperazin-1-yl)estra-1,3,5(10)-trien-17-one (11)

To a solution of compound 10 (45 mg, 0.10 mmol) in DCM (8 mL) was added TFA (2 mL) at room temperature. The solution was then stirred for 30 min and poured into a 10% bicarbonate solution (50 mL). The resulting solution was subsequently extracted with DCM, filtered using a phase separator syringe and evaporated under reduced pressure. The crude compound was directly used without further purification. IR (KBr) ν: 1736 (C=O); $^1$H NMR (Acetone-d$_6$) δ: 0.91 and 0.92 (2s, CH$_3$-18), 1.07-2.57 (m, residual CH and CH$_2$), 2.79-3.18 (m, 4×CH$_2$N of piperazine and CH$_2$-6), 6.76 (d, CH-3, J=8.2 Hz), 6.94 (m, CH$_1$ and CH-4); LRMS for C$_{22}$H$_{31}$N$_2$O [M+H]+: 339.2.

(17β)-17-ethynyl-2-(piperazin-1-yl)estra-1,3,5(10)-trien-17-ol (12)

To a solution of trimethylsilylacetylene (46 mg, 65 μL, 0.47 mmol) in anhydrous ether (5 mL) was added MeLi 1.6 M (236 μL, 0.38 mmol) at 0° C. The cold bath was removed and the solution was stirred over a period of 1 h under an argon atmosphere. A solution of compound 11 (32 mg, 0.14 mmol) in anhydrous THF (10 mL) was then added to the latter solution while at 0° C. The resulting solution was then allowed to return to room temperature and stirred over a period of 4 h. The resulting solution was subsequently poured into water, extracted two times with EtOAc, dried over sodium sulfate, filtered and evaporated under reduced pressure. The crude compound was submitted to an aqueous solution of potassium carbonate 5% in MeOH (3 mL) and stirred overnight. The resulting solution was filtered, poured into water, extracted three times with DCM, filtered using a phase separator syringe and evaporated. The crude compound was directly used without further purification. IR (KBr) ν: 3302 (OH), 2106 (weak, C≡CH); $^1$H NMR (Acetone-d$_6$) δ: 0.91 and 0.92 (2s, CH$_3$-18), 1.13-2.55 (m, residual CH and CH$_2$), 2.85 (m, 2×CH$_2$N of piperazine, CH$_2$-6), 2.94 and 3.08 (m, 2×CH$_2$N), 3.53 (m, 2×CH$_2$NCO), 6.77 (d, CH-3, J=8.2 Hz), 6.94 (s, CH-1), 6.95 (d, CH-4, J=8.4 Hz); LRMS for C$_{24}$H$_{33}$N$_2$O [M+H]$^+$: 365.3.

{4-[(17β)-17-ethynyl-17-hydroxyestra-1,3,5(10)-trien-2-yl]piperazin-1-yl}[(2S)-1-(quinolin-2-ylcarbonyl)pyrrolidin-2-yl]methanone (13)

To a solution of the TFA salt of 1-(quinolin-2-ylcarbonyl)-L-proline (42 mg, 0.11 mmol) in anhydrous DMF (2 mL) was added at room temperature, HBTU (41 mg, 0.11 mmol) and DIPEA (38 μL, 0.22 mmol). The solution was stirred for 5 min and then a solution of compound 12 (20 mg, 0.55 mmol) in DMF (1 mL) was added. The resulting solution was stirred overnight and then poured into water, extracted three times with EtOAc, washed with brine, dried over sodium sulfate, filtered and evaporated under reduced pressure. Purification by preparative HPLC afforded compound 13 (5 mg, 15%). IR (KBr) ν: 3410 (OH), 2106 (weak, C≡CH), 1643 (NCO); $^1$H NMR (CDCl$_3$) δ: 0.91 (s, CH$_3$-18), 1.29-2.54 (m, residual CH and CH$_2$, 2×CH$_2$ of piperazine, 1×CH$_2$ of proline, 2α-CH), 2.82 (m, CH$_2$-6), 2.98 and 2.99 (2s, C≡CH), 2.80-4.20 (m broad, 5×CH$_2$N), 4.36 (s, OH), 5.20 and 5.93 (2m, NCHCO of proline, two rotamers), 6.58 and 6.78 (2 dd, J$_1$=8.1 Hz; J$_2$=2.2 Hz, CH-3, two rotamers), 6.77 and 7.00 (2s, CH-1, two rotamers), 6.90 and 6.95 (2d, J=8.3 Hz, CH-4 two rotamers), 7.60 and 7.71 (2t, J=8.1 Hz, CH of quinoline, two rotamers), 7.76 and 7.84 (2t, J=8.4 Hz, CH of quinoline), 7.89 and 7.90 (2d, J=8.5 Hz, CH of quinoline, two rotamers), 7.95 and 8.02 (2d J=7.9 Hz, CH of quinoline, two rotamers), 8.08 and 8.12 (2d, J=8.6 Hz, CH of quinoline, two rotamers), 8.36 and 8.44 (2d, J=8.5 Hz, CH of quinoline, two rotamers); LRMS for C$_{39}$H$_{45}$N$_4$O$_3$ [M+H]$^+$: 618.2; HPLC purity: 96.4%.

tert-Butyl 4-{17-oxo-3-[(trimethylsilyl)ethynyl]estra-1,3,5(10)-trien-2-yl}piperazine-1-carboxylate (14)

To a solution of compound 9 (509 mg, 0.91 mmol) in anhydrous DMF (4 mL) was added Pd(dppf)$_2$Cl$_2$ (133 mg, 0.18 mmol), CuI (35 mg, 0.18 mmol), trimethylsilylacetylene (1.26 mL, 9.1 mmol) and TEA (764 μL, 5.6 mmol). The solution was stirred at 80° C. over a period of 72 h. The resulting solution was poured into water, extracted with EtOAc, washed with brine, dried over sodium sulfate, filtered and evaporated under reduced pressure. The crude compound was subsequently purified by flash chromatography using EtOAc/hexanes (1:9) to give compound 14 as white amorphous solid (112 mg, 23%). IR (KBr) ν: 1744 (C=O), 1697 (NCOO); $^1$H NMR (Acetone-d$_6$) δ: 0.24 (s, (CH$_3$)$_3$Si), 0.90 (s, CH$_3$-18), 1.46 (s, (CH$_3$)$_3$OCON), 1.29-2.48 (m, residual CH and CH$_2$), 2.81 (m, CH$_2$-6), 3.10 (m, 2×CH$_2$N of piperazine), 3.59 (m, 2×CH$_2$NCO), 6.92 (s, CH-1), 7.12 (s, CH-4); LRMS for C$_{32}$H$_{46}$N$_2$O$_3$Si [M+H]$^+$: 535.5.

t-Butyl 4-[3-ethynyl-17-oxoestra-1, 35(10)-trien-2-yl]piperazine-1-carboxylate To a solution of trimethylsilylacetylene (142 μL, 1.03 mmol) in anhydrous ether (7.5 mL) under an argon atmosphere at 0° C. was added dropwise a solution of methyl lithium 1.6 M in diethyl ether (514 μL, 0.82 mmol). The solution was subsequently stirred for 5 min at 0° C. and then allowed to return to room temperature and stirred over a period of 1 h. To the latter solution was then added a solution of compound 14 (110 mg, 0.21 mmol) in anhydrous THF (7.5 mL) at 0° C. The solution was then stirred at room temperature over a period of 12 h. The resulting solution was poured into water, extracted with EtOAc, washed with brine, dried over sodium sulfate, filtered and evaporated under reduced pressure. The crude compound was then dissolved in MeOH (5 mL) and potassium carbonate was added (500 mg). The solution was stirred over a period of 4 h at room temperature. The resulting solution was filtered and then poured into water, extracted three times with EtOAc, washed with brine, dried over sodium sulfate, filtered and evaporated under reduced pressure to give compound 15 as pale yellow amorphous solid (69 mg, 69%). IR (KBr) ν: 3433 and 3402 (OH), 2098 (weak, C≡CH), 1682 (NCOO); $^1$H NMR (Acetone-d$_6$) δ: 0.90 (s, CH$_3$-18), 1.46 (s, (CH$_3$)$_3$OCON), 1.29-2.48 (m, residual CH and CH$_2$), 2.80 (m, CH$_2$-6), 2.98 (s, 17α-C≡CH), 3.08 (m, 2×CH$_2$N of piperazine), 3.54 (m, 2×CH$_2$NCO), 3.81 (s, 3-C≡CH), 4.37 (s, OH), 6.96 (s, CH-1), 7.14 (s, CH-4); LRMS for C$_{31}$H$_{40}$N$_2$O$_3$ [M+H]$^+$: 489.7.

3-ethynyl-2-(piperazin-1-yl)estra-1,3,5(10)-trien-17-one (16a) and 3-acetyl-2-(piperazin-1-yl)estra-1,3,5(10)-trien-17-one (16b)

To a solution of compound 15 (65 mg, 0.13 mmol) in DCM (5 mL) was added TFA (1 mL). The solution was stirred at room temperature over a period of 1 h. The resulting solution was neutralized at pH 7 with a saturated solution of aqueous bicarbonate, filtered using a phase separator syringe and evaporated under reduce pressure. The crude mixture of compounds 16a and 16b (20:80 as evaluated by $^1$H NMR, 55 mg) was directly used without further purification (separation by chromatography being very difficult). 16a: $^1$H NMR (Acetone-d$_6$) δ: 0.91 (s, CH$_3$-18), 1.29-2.46 (m, residual CH and CH$_2$), 2.81 (m, CH$_2$-6 and CH$_2$NH of piperazine), 2.99 (s, 17α-C≡CH), 3.36 (m, CH$_2$NH of piperazine), 3.47 (m, 2×CH$_2$N of piperazine), 3.89 (s, 3-C≡CH), 7.02 (s, CH-1), 7.12 (s, CH-4); 16b: $^1$H NMR (Acetone-d$_6$) δ:0.91 (s, CH$_3$-18), 1.29-2.46 (m, residual CH and CH$_2$), 2.60 (s, CH$_3$CO), 2.81 (m, CH$_2$-6 and CH$_2$NH of piperazine), 2.99 (s, 17α-C≡CH), 3.36 (m, CH$_2$NH of piperazine), 3.47 (m, 2×CH$_2$N of piperazine), 3.89 (s, 3-C≡CH), 7.21 (s, CH-1 and CH-4); LRMS for C$_{26}$H$_{32}$N$_2$O (16a) [M+H]$^+$: 389.2 and C$_{26}$H$_{34}$N$_2$O$_2$ (16b) [M+H]$^+$: 407.6.

Synthesis of Compounds 17a and 17b

To a solution of the TFA salt of 1-(quinolin-2-ylcarbonyl)-L-proline (64 mg, 0.17 mmol) in anhydrous DMF (3 mL) was added at room temperature, HBTU (63 mg, 0.17 mmol) and DIPEA (112 μL, 0.64 mmol). The solution was stirred for 5 min and then a solution comprising a mixture of compound 16a and 16b (50 mg, 0.55 mmol) in DMF (1 mL) was added. The resulting solution was stirred overnight and then poured into water, extracted three times with EtOAc, washed with brine, dried over sodium sulfate, filtered and evaporated under reduced pressure. Purification by preparative HPLC afforded pure compounds 17a (7 mg) and 17b (20 mg) as light yellow amorphous solids.

{4-[(17β)-3,17-diethynyl-17-hydroxyestra-1,3,5(10)-trien-2-yl]piperazin-1-yl}[(2S)-1-(quinolin-2-ylcarbonyl)pyrrolidin-2-yl]methanone (17a)

IR (KBr) ν: 3379 (OH), 2098 (weak, C≡CH), 1643 (NCO); $^1$H NMR (Acetone-d$_6$) δ: 0.91 and 0.94 (2s, CH$_3$-

18, two conformers), 1.29-2.67 (m, residual CH and CH$_2$, 2×CH$_2$ of piperazine, 1×CH$_2$ of proline, 2α-CH), 2.75 (m, CH$_2$-6), 2.98 and 3.02 (2s, 17α-C≡CH), 2.80-4.20 (m broad, 5×CH$_2$N), 3.77 (s, 3-C≡CH), 4.40 (s, OH), 5.23 and 5.93 (2m, NCHCO of proline, two rotamers), 6.64 and 7.00 (2 s, CH-1, two rotamers), 7.10 and 7.16 (2s, CH-4, two rotamers), 7.63 and 7.69 (2t, J=8.1 Hz, CH of quinoline, two rotamers), 7.80 (t, J=8.4 Hz, CH of quinoline), 7.88 and 7.91 (2d, J=8.5 Hz, CH of quinoline, two rotamers), 7.98 and 8.02 (2d, J=7.9 Hz, CH of quinoline, two rotamers), 8.13 (2d, J=8.6 Hz, CH of quinoline, two rotamers), 8.37 and 8.44 (2d, J=8.5 Hz, CH of quinoline, two rotamers); LRMS for C$_{41}$H$_{44}$N$_4$O$_3$ [M+H]$^+$: 641.4; HPLC purity: 97.0%.

1-[(17β)-17-ethynyl-17-hydroxy-2-(4-{[(2S)-1-(quinolin-2-ylcarbonyl)pyrrolidin-2-yl]carbonyl}piperazin-1-yl)estra-1,3,5(10)-trien-3-yl]ethanone (17b)

IR (KBr) ν: 3402 (OH), 2106 (weak, C≡CH), 1651 (NCO and COCH$_3$); $^1$H NMR (CDCl$_3$) δ: 0.82 (m, 1H), 0.89 and 0.93 (2s, CH$_3$-18, two conformers), 1.24-2.69 (m, residual CH and CH$_2$, 2×CH$_2$ of piperazine, 1×CH$_2$ of proline, 2α-CH), 2.82 (m, CH$_2$-6), 2.53 and 2.68 (2s, CH$_3$CO, two conformers), 2.61 and 2.64 (2s, 17α-C≡CH), 2.80-4.20 (m broad, 5×CH$_2$N), 5.16 and 5.81 (2m, NCHCO of proline, two rotamers), 6.69 and 7.04 (2 s, CH-1, two rotamers), 7.16 and 7.21 (2s, CH-4, two rotamers), 7.58 (2dt, J$_1$=Hz, J$_2$=Hz, CH of quinoline), 7.72 (2dt, J$_1$=Hz, J$_2$=Hz, CH of quinoline), 7.84 (t, J=7.5 Hz, CH of quinoline), 8.02 (m, 2×CH of quinoline), 8.12 (d, J=8.6 Hz, 0.5 CH of quinoline from one rotamer), 8.24 (m, CH of quinoline); LRMS for C$_{41}$H$_{46}$N$_4$O$_4$ [M+H]$^+$: 659.8; HPLC purity: 98.2%.

{4-[(17β)-17-ethynyl-17-hydroxy-3-(1-hydroxyethyl)estra-1,35(10)-trien-2-yl]piperazin-1-yl}[(2S)-1-(quinolin-2-ylcarbonyl)pyrrolidin-2-yl]methanone (18)

To a solution of compound 17b (10 mg, 0.015 mmol) in MeOH/DCM (3:1; 4 mL) was added NaBH$_4$ (4 mg, 0.11 mmol). The solution was then stirred at room temperature over a period of 1 h. The resulting solution was subsequently poured into water (50 mL), extracted two times with EtOAc, washed with brine, dried over sodium sulfate, filtered and evaporated under reduced pressure to give compound 18 as white amorphous solid (10 mg, 99%). IR (KBr) ν: 3418 (OH), 2106 (weak, C≡CH), 1697 (NCO), 1643 (NCO); $^1$H NMR (Acetone-d$_6$) δ: 0.88 and 0.96 (m, CH$_3$-18 and residual CH), 1.24-3.10 (m, residual CH and CH$_2$, CH$_3$CH—OH, 2×CH$_2$ of piperazine, 1×CH$_2$ of proline, 2α-CH, CH$_2$-6), 2.98 and 3.02 (2s, 17α-C≡CH), 3.15-4.50 (m broad, 5×CH$_2$N and CH—OH), 5.14 (OH), 5.24 and 5.97 (2m, NCHCO of proline, two rotamers), 6.80 and 7.17 (2 s, CH-1, two rotamers), 7.13 and 7.22 (2s, CH-4, two rotamers), 7.69 (m, CH of quinoline), 7.88 (m, CH of quinoline), 7.92 (m, CH of quinoline), 8.02 (dd, J$_1$=8.2 Hz, J$_2$=2.2 Hz, CH of quinoline), 8.14 (m, CH of quinoline), 8.40 and 8.45 (2d, J=8.5 Hz, CH of quinoline, two rotamers); LRMS for C$_{41}$H$_{46}$N$_4$O$_4$ [M+H]$^+$: 661.4; HPLC purity: mixture of two isomers (45.4% and 53.5%).

3-Methoxy-17-oxoestra-1,3,5(10)-triene-2-carbaldehyde (20)

To a solution of compound 19 (500 mg, 1.68 mmol) in acetone (50 mL) was added potassium carbonate (1.16 g, 8.39 mmol) and MeI (1.05 mL, 16.8 mmol). The solution was stirred at room temperature overnight. The resulting solution was then poured into water (250 mL), extracted two times with EtOAc, washed with brine, dried over sodium sulfate, filtered and evaporated under reduced pressure. The crude compound was purified by flash chromatography using EtOAc/Hexanes (3:7) to give 20 as a white solid (515 mg, 96%). IR (KBr) ν: 1736 (C=O), 1682 (CH=O); $^1$H NMR (CDCl$_3$) δ: 0.91 (s, CH$_3$-18), 1.41-1.68 (m, residual CH and CH$_2$), 1.94-2.44 (m, residual CH and CH$_2$), 2.97 (m, CH$_2$-6), 3.89 (OCH$_3$), 6.70 (s, CH-1), 7.76 (s, CH-4), 10.39 (CHO); LRMS for C$_{20}$H$_{24}$O$_3$[M+H]$^+$: 313.1.

3-Methoxy-17-oxoestra-1,3,5(10)-triene-2-carboxylic acid (21)

To a solution of compound 20 (145 mg, 0.46 mmol) in a mixture of DCM/H$_2$O (2:1) (9 mL) was added iodobenzene diacetate (188 mg, 0.58 mmol) and TEMPO (16 mg, 0.102 mmol). The solution was then stirred vigorously at room temperature over a period of 48 h. The resulting solution was subsequently diluted with DCM (10 mL), poured into water (50 mL) and filtered using a phase separator syringe. The crude compound was purified by flash chromatography using EtOAc/Hexanes (4:6) to give 21 as white solid (70 mg, 47%). IR (KBr) ν: 3279 (COOH), 1736 (C=O); $^1$H NMR (CDCl$_3$) δ: 0.91 (s, CH$_3$-18), 1.42-1.68 (m, residual CH and CH$_2$), 1.94-2.54 (m, residual CH and CH$_2$), 2.97 (m, CH$_2$-6), 4.04 (OCH$_3$), 6.76 (s, CH-1), 8.09 (s, CH-4), 10.7 (broad s, COOH); LRMS for C$_{20}$H$_{25}$O$_4$[M+H]$^+$: 329.1.

tert-Butyl 4-{[3-methoxy-17-oxoestra-1,3,5(10)-trien-2-yl]carbonyl}piperazine-1-carboxylate (22)

To a solution of compound 21 (65 mg, 0.20 mmol) in anhydrous DMF (6 mL) was added HBTU (157 mg, 0.41 mmol). The solution was stirred for 5 min before the addition of 1-Boc-piperazine (78 mg, 0.41 mmol) and DIPEA (150 μL, 0.84 mmol). The solution was then stirred at room temperature overnight. The resulting solution was subsequently poured into water (150 mL), extracted two times with EtOAc, the organic phase washed with water and brine, dried with sodium sulfate, filtered and evaporated under reduced pressure. The crude compound was purified by flash chromatography using EtOAc/Hexanes (1:1) to give 22 as white solid (76 mg, 93%). IR (KBr) ν: 1736 (C=O), 1697 (NCOO), 1636 (NCO); $^1$H NMR (Acetone-d$_6$) δ: 0.91 (s, CH$_3$-18), 1.44 (s, (CH$_3$)$_3$COCO), 1.44-2.48 (m, residual CH and CH$_2$), 2.93 (m, CH$_2$-6), 3.18-3.68 (m, 4×CH$_2$NCO), 3.81 (OCH$_3$), 6.77 (s, CH-1), 7.13 (s, CH-4); LRMS for C$_{29}$H$_{41}$N$_2$O$_5$ [M+H]$^+$: 497.4.

3-Methoxy-2-(piperazin-1-ylcarbonyl)estra-1,3,5 (10)-trien-17-one (23)

To compound 22 (70 mg, 0.14 mmol) was added a TFA/DCM (20%) solution (3 mL). The resulting solution was then stirred for 1 h at room temperature and diluted with DCM (25 mL) before being slowly poured into a mixture of ice and a saturated NaHCO$_3$ solution. The organic phase was filtered using a phase separator syringe and then evaporated under reduced pressure. The resulting crude compound (55 mg, 99%) was used directly without further purification. IR (KBr) ν: 3448 and 3325 (NH), 1736 (C=O), 1628 (NCO); $^1$H NMR (Acetone-d$_6$) δ: 0.91 (s, CH$_3$-18), 1.07-2.48 (m, residual CH and CH$_2$), 2.78-3.70 (m, CH$_2$-6 and 4×CH$_2$NCO), 3.80 (OCH$_3$), 6.76 (s, CH-1), 7.11 (s, CH-4); LRMS for C$_{24}$H$_{33}$N$_2$O$_3$ [M+H]$^+$: 397.2.

[(17β)-17-ethynyl-17-hydroxy-3-methoxyestra-1,3,5(10)-trien-2-yl](piperazin-1-yl)methanone (24)

To a solution of trimethylsilylacetylene (96 µL, 0.692 mmol) in anhydrous ether (7.5 mL) was added at 0° C. MeLi (1.6 M in ether) (347 µL, 0.55 mmol). The solution was stirred at 0° C. for 5 min and then allowed to return to room temperature and stirred for an additional 55 min. To the latter solution was then added a solution of compound 23 (51 mg, 0.128 mmol) in THF (15 mL) and stirred for 5 min at 0° C. and then overnight at room temperature. The resulting solution was poured into water, extracted two times with EtOAc, washed with brine, dried over sodium sulfate and evaporated under reduced pressure. The crude product (42 mg) was then diluted in MeOH (10 mL), followed by the addition of potassium carbonate (50 mg). The resulting solution was then stirred vigorously overnight. The resulting suspension was subsequently poured into water (100 mL), extracted three times with EtOAc, the organic phase was washed with brine, dried over sodium sulfate and evaporated under reduced pressure to give compound 24. The resulting crude compound was used directly without further purification. IR (KBr) ν: 3302 (NH), 2106 (weak, C≡CH), 1620 (NCO); $^1$H NMR (Acetone-d$_6$) δ: 0.88 (broad s, CH$_3$-18), 1.13-2.63 (m, residual CH and CH$_2$), 2.78-3.70 (m, CH$_2$-6 and 4×CH$_2$NCO), 3.79 (OCH$_3$), 6.60 (broad s, CH-1), 7.16 (broad s, CH-4); LRMS for C$_{26}$H$_{35}$N$_2$O$_3$ [M+H]$^+$: 423.3.

[(17β)-17-ethynyl-17-hydroxy-3-methoxyestra-1,3,5(10)-trien-2-yl](4-{[(2S)-1-(quinolin-2-ylcarbonyl)pyrrolidin-2-yl]carbonyl}piperazin-1-yl)methanone (25)

To a solution of the TFA salt of 1-(quinolin-2-ylcarbonyl)-L-proline (68 mg, 0.18 mmol) in anhydrous DMF (2 mL) was added at room temperature HBTU (67 mg, 0.18 mmol) and DIPEA (62 µL, 0.36 mmol). The solution was stirred for 5 min and then a solution of compound 24 (35 mg, 0.083 mmol) in DMF (1 mL) was added. The resulting solution was stirred overnight and then poured into water, extracted three times with EtOAc, washed with brine, dried over sodium sulfate, filtered and evaporated under reduced pressure. Purification by preparative HPLC afforded compound 25 (30 mg, 54%). IR (KBr) ν: 3410 (OH), 2106 (weak, C≡CH), 1628 (NCO); $^1$H NMR (CDCl$_3$) δ: 0.86 (broad s, CH$_3$-18), 1.25-2.45 (m, residual CH and CH$_2$, 2×CH$_2$ of piperazine, 1×CH$_2$ of proline, 2α-CH), 2.60 (s, C≡CH), 2.86 (m, CH$_2$-6), 2.99-4.28 (m broad, 5×CH$_2$N), 5.06 and 5.14 (2m, NCHCO of proline, two rotamers), 5.73 and 5.91 (2m, NCHCO of proline, two rotamers), 6.58 (m, CH-1), 7.12 (m, CH-4), 7.61 (t, J=7.1 Hz, CH of quinoline), 7.75 (t, J=8.3 Hz, CH of quinoline), 7.85 (d, J=8.0 Hz, CH of quinoline), 7.96 (d J=8.0 Hz, CH of quinoline), 8.07 (m, CH of quinoline), 8.24 (d, J=8.4 Hz, CH of quinoline); LRMS for C$_{41}$H$_{47}$N$_4$O$_5$ [M+H]$^+$: 675.4; HPLC purity: 100.0%.

tert-Butyl 4-{[3-methoxy-17-oxoestra-1,3,5(10)-trien-2-yl]methyl}piperazine-1-carboxylate (26)

To a solution of 1-boc-piperazine (308 mg, 1.65 mmol) in DMF/acetic acid (99:1) (0.2M) was added compound 20 (515 mg, 1.65 mmol) previously dissolved in DMF/acetic acid (99:1). The resulting solution was stirred for 1 h under an argon atmosphere while at room temperature and then a solution of sodium cyanoborohydride (207 mg, 3.29 mmol) in DCM/MeOH/acetic acid (75:24:1) (3 mL) (1.0 M) was added. The resulting solution was stirred overnight and then poured into water, extracted three times with DCM, filtered using a phase separator syringe and evaporated under reduced pressure. The crude compound was purified by flash chromatography using EtOAc/Hexanes (3:7) to give compound 26 (479 mg, 60%). IR (KBr) ν: 1736 (C=O), 1697 (NCOO); $^1$H NMR (CDCl$_3$) δ: 0.91 (s, CH$_3$-18), 1.44 (s, (CH$_3$)$_3$COCO), 1.44-2.48 (m, residual CH and CH$_2$, 2×CH$_2$N), 2.93 (m, CH$_2$-6), 3.44-3.59 (m, 2×CH$_2$NCO and PhCH$_2$N), 3.81 (OCH$_3$), 6.60 (s, CH-1), 7.23 (s, CH-4); LRMS for C$_{29}$H$_{43}$N$_2$O$_4$ [M+H]$^+$: 483.7.

3-Methoxy-2-(piperazin-1-ylmethyl)estra-1,3,5(10)-trien-17-one (27)

To compound 26 (120 mg, 0.25 mmol) was added a TFA/DCM solution (20%, 5 mL). The resulting solution was then stirred over a period of 1 h while at room temperature and diluted with DCM (25 mL) before being slowly poured into a mixture of ice and a saturated NaHCO$_3$ solution. The organic phase was filtered using a phase separator syringe and evaporated under reduced pressure. The crude compound was purified by flash chromatography using DCM/MeOH (9:1) to give compound 27 (58 mg, 61%). IR (KBr) ν: 3348 and 3310 (NH), 1736 (C=O); $^1$H NMR (CDCl$_3$) δ: 0.91 (s, CH$_3$-18), 1.38-2.56 (m, residual CH and CH$_2$), 2.69 (m, 2×CH$_2$N), 2.88 (m, CH$_2$-6), 3.11 (broad t, J=4.9 Hz, 2×CH$_2$NH), 3.60 (m, PhCH$_2$N), 3.77 (OCH$_3$), 6.60 (s, CH-1), 7.20 (s, CH-4); LRMS for C$_{24}$H$_{35}$N$_2$O$_2$ [M+H]$^+$: 383.7.

(17β)-17-ethynyl-3-methoxy-2-(piperazin-1-ylmethyl)estra-1,3,5(10)-trien-17-ol (28)

To a solution of trimethysilylacetylene (56 mg, 79 µL, 0.57 mmol) in anhydrous ether (7.5 mL) was added MeLi (1.6 M in ether) (347 µL, 0.56 mmol) at 0° C. The cold bath was removed and the solution was stirred for 1 h under an argon atmosphere. A solution of compound 27 (50 mg, 0.13 mmol) in anhydrous THF (15 mL) was then added to the later solution at 0° C. The resulting solution was allowed to return to room temperature and stirred over a period of 4 h. The solution was subsequently poured into water, extracted two times with EtOAc, dried over sodium sulfate, filtered and evaporated under reduced pressure. The crude compound was submitted to an aqueous solution of potassium carbonate 5% in MeOH (10 mL) and stirred overnight. The resulting solution was filtered, poured into water, extracted three times with DCM, filtered using a phase separator syringe and evaporated. The crude compound (26 mg, 49%) was directly used without further purification. IR (KBr) ν: 3302 (NH), 2106 (weak, C≡CH); $^1$H NMR (CDCl$_3$) δ: 0.88 (s, CH$_3$-18), 1.13-2.77 (m, residual CH and CH$_2$, 2×CH$_2$N), 2.60 (s, C≡CH), 2.86 (m, CH$_2$-6), 3.18-3.70 (m, 2×CH$_2$NH and PhCH$_2$N), 3.78 (OCH$_3$), 6.59 (s, CH-1), 7.22 (s, CH-4); LRMS for C$_{26}$H$_{37}$N$_2$O$_2$ [M+H]$^+$: 409.3.

(4-{[(17(1)-17-ethynyl-17-hydroxy-3-methoxyestra-1,3,5(10)-trien-2-yl]methyl}piperazin-1-yl)[(2S)-1-(quinolin-2-ylcarbonyl)pyrrolidin-2-yl]methanone (29)

To a solution of the TFA salt of 1-(quinolin-2-ylcarbonyl)-L-proline (45 mg, 0.12 mmol) in anhydrous DMF (2 mL) was added at room temperature HBTU (44 mg, 0.12 mmol)

and DIPEA (40 µL, 0.23 mmol). The solution was stirred for 5 min and then a solution of compound 28 (22 mg, 0.06 mmol) in DMF (1 mL) was added. The resulting solution was stirred overnight and then poured into water, extracted three times with EtOAc, washed with brine, dried over sodium sulfate, filtered and evaporated under reduced pressure. Purification by preparative HPLC afforded compound 29 (4 mg, 11%). IR (KBr) ν: 3418 (OH), 2106 (weak, C≡CH), 1697 (NCO); $^1$H NMR (Acetone-$d_6$) δ: 0.90 (s, $CH_3$-18), 1.29-2.50 (m, residual CH and $CH_2$), 2.8 (m, under solvent peak, $CH_2$-6), 2.99 (s, C≡CH), 3.10-4.20 (m broad, 5×$CH_2$N and $CH_2$N-Ph), 3.77 and 3.79 (2s, $OCH_3$, two rotamers), 4.36 (s, OH), 5.11 and 5.84 (2m, NCHCO of proline, two rotamers), 6.64, 6.67 (2s, CH-1 two rotamers), 7.17 and 7.33 (2s, CH-4, two rotamers), 7.68 (t, J=6.9 Hz, CH of quinoline), 7.80 (t, J=6.9 Hz, CH of quinoline), 7.87 and 7.89 (2d, J=8.5 Hz, CH of quinoline, two conformers), 8.01 (d, J=8.4 Hz, CH of quinoline), 8.07 and 8.11 (2d, J=8.4 Hz, CH of quinoline, two conformers), 8.37 and 8.44 (2d, J=8.0 Hz, CH of quinoline, two rotamers); LRMS for $C_{41}H_{49}N_4O_4$ [M+H]$^+$: 661.5; HPLC purity: 98.2%.

With reference to Schemes 8 and 9, a number of non-limiting examples illustrating the preparation of selected estrane-based aminosteroid derivatives by means of solid phase synthesis and in accordance with various embodiments of the present disclosure, are described in the following sections.

Coupling of Compound 1 to PS-DES Resin 3 (Synthesis of Resin 5)

To a solution of compound 1 (2.88 g, 7.3 mmol) in dry THF (35 mL) under an argon atmosphere at 0° C. was added dropwise a methyl lithium solution (1.6 M) in diethyl ether (13.7 mL, 21.9 mmol), followed by the addition of DMSO (10 mL). The resulting mixture was stirred over a period of 1.5 h at room temperature to generate 2. To PS-DES resin 3 (2.48 g, 3.65 mmol), previously dried under vacuum and swollen in dry DCM (14 mL), was added a solution of 1,3-dichloro-5,5-dimethylhydantoin (2.09 g, 10.6 mmol) in dry DCM (26 mL) under an argon atmosphere. The resulting solution was stirred over a period of 1 h at room temperature and the activated PS-DES-Cl resin 4 was then washed twice with dry DCM (100 mL) and once with dry THF (100 mL). Organolithium 2 was immediately added to the activated resin 4 and the mixture was stirred overnight at room temperature under an argon atmosphere. The resin was then washed successively with DCM (100 mL), MeOH (100 mL), $H_2O$ (100 mL), MeOH (100 mL) and DCM (100 mL) and then dried overnight under vacuum to give resin 5 (36% loading).

Addition of Amino Acids and Carboxylic Acids (Solid-Phase Synthesis of Resins

Portions of resin 5 (~100 mg) were placed in 4 mL-reactor wells of an automated synthesizer reaction block (96-well format) (AAPPTec). To each well was added a solution of the appropriate Fmoc-protected amino acid (Fmoc-L-azetidine (n=1), Fmoc-L-proline (n=2), Fmoc-L-homoproline) (n=3) (0.3 M), 2-(1H-benzotriazol-1-yl)-1,1,3,3-tetramethyluronium hexafluorophosphate (HBTU) (0.5 M) and N,N-diisopropylethylamine (DIPEA) (1 M) in DMF (1 mL). The suspensions were vortexed at 600 rpm over a period of 4 h; the wells were then filtered using the vacuum system and resins 6 were washed with DMF (2 mL). The wells were filtered again and a second cycle of amino acid coupling of the resins 6 with amino acids was achieved as described above. The deprotection of the Fmoc group of resins 6 was carried out by adding to each well a solution of piperidine (20%, v/v) in DMF (5 mL) (2 deprotection cycles). The suspensions were vortexed at 600 rpm over a period of 1 h; the wells were then filtered and the resins 7 washed with DMF and ethanol (EtOH). To introduce a second level of molecular diversity, a solution of the appropriate carboxylic acid ($R^1$—COOH) (0.5 M), HBTU (0.5 M) and DIPEA (1 M) in DMF (1 mL) was added to each well. The suspensions were vortexed at 600 rpm over a period of 3 h; the wells were then filtered and the resins 8 washed with DCM and EtOH.

Cleavage of the Resin-Bound Aminosteroid Derivatives from Resins 8

To each resin 8 was added a solution of HCl-MeOH-DCM (1:9:30) (2.5 mL) and the resulting suspensions were vortexed at 600 rpm over a total period of 24 h. The resins were filtered and washed with DCM and a solution of MeOH-DCM (1:1) (1.5 mL). The filtrates were neutralized with a saturated aqueous solution of $NaHCO_3$(2 mL). The biphasic solutions were subsequently treated with a phase separator syringe (Biotage, Uppsala, Sweden) and the organic solutions evaporated under reduced pressure to give the respective aminosteroid derivatives 9.

Characterization of Compounds A1-A40 (Table 1)

(2E)-1-[(2S)-2-({4-[(17α)-17-Hydroxy-3-methoxy-19-norpregna-1(10),2,4-trien-20-yn-2-yl]piperazin-1-yl}carbonyl)pyrrolidin-1-yl]but-2-en-1-one (A1)

$^1$H NMR (CDCl$_3$) δ: 0.89 (s, $CH_3$-18), 1.25-2.40 (m, residual CH and $CH_2$), 1.87 and 1.88 (2d, J=6.9 Hz, $CH_3$CH=CH), 2.606 and 2.611 (2s, C≡CH), 2.81 (m, $CH_2$-6), 2.95-3.20 (m, 2×$CH_2$N), 3.60-3.90 (m, 3×$CH_2$NCO), 3.83 (s, $OCH_3$), 4.77 and 5.00 (2m, NHCO of Pro), 6.19 (d, J=15.0 Hz, CH=CHCO), 6.58 (s, CH-1), 6.85 (s, CH-4), 6.94 (m, $CH_3$CH=CH); LRMS for $C_{34}H_{46}N_3O_4$ [M+H]$^+$: 560.7; HPLC purity: 87.5%.

1-[(2S)-2-({4-[(17α)-17-Hydroxy-3-methoxy-19-norpregna-1 (10),2,4-trien-20-yn-2-yl]piperazin-1-yl}carbonyl)pyrrolidin-1-yl]-3-methylbut-2-en-1-one (A2)

$^1$H NMR (CDCl$_3$) δ: 0.89 (s, $CH_3$-18), 1.25-2.38 (m, residual CH and $CH_2$), 1.85 and 1.86 (2d, $CH_3$C), 2.08 and 2.09 (2d, J=1.0 Hz, $CH_3$CCH), 2.60 and 2.61 (2s, C≡CH), 2.81 (m, $CH_2$-6), 2.90-3.20 (m, 2×$CH_2$N), 3.55-3.88 (m, 3×$CH_2$NCO), 3.83 and 3.84 (2 s, $OCH_3$), 4.69 and 4.99 (2m, NHCO of Pro), 5.86 (s, ($CH_3$)$_2$C≡CH), 6.58 (s, CH-1), 6.85 (s, CH-4); LRMS for $C_{35}H_{48}N_3O_4$ [M+H]$^+$: 574.8; HPLC purity: 83.7%.

{4-[(17α)-17-Hydroxy-3-methoxy-19-norpregna-1 (10),2,4-trien-20-yn-2-yl]piperazin-1-yl}{(2S)-1-[(2S)-tetrahydrofuran-2-ylcarbonyl]pyrrolidin-2-yl}methanone (A3)

$^1$H NMR (CDCl$_3$) δ: 0.89 (s, $CH_3$-18), 1.25-2.38 (m, residual CH and $CH_2$), 2.60 and 2.61 (2s, C≡CH), 2.81 (m, $CH_2$-6), 2.95-3.20 (m, 2×$CH_2$N), 3.60-3.90 (m, 3×$CH_2$NCO), 3.83 and 3.84 (2s, $OCH_3$), 3.85 (t, J=8.5 Hz, $CH_2$O), 4.25 and 4.61 (2m, $CH_2$CHO), 4.63 and 4.94 (2m, NHCO of Pro), 6.58 (s, CH-1), 6.85 (s, CH-4); LRMS for $C_{35}H_{48}N_3O_5$ [M+H]$^+$: 590.8; HPLC purity: 82.0%.

1-[(2S)-2-({4-[(17a)-17-Hydroxy-3-methoxy-19-norpregna-1 (10),2,4-trien-20-yn-2-yl]piperazin-1-yl}carbonyl)pyrrolidin-1-yl]-2-(phenylsulfanyl)ethanone (A4)

$^1$H NMR (CDCl$_3$) δ: 0.89 (s, $CH_3$-18), 1.25-2.40 (m, residual CH and $CH_2$), 2.60 and 2.61 (2 s, C≡CH), 2.81 (m, CH$_2$-6), 2.95-3.18 (m, 2×CH$_2$N), 3.60-3.90 (m, 3×CH$_2$NCO), 3.72 and 3.76 (2s, CH$_2$S), 3.83 and 3.84 (2s, OCH$_3$), 4.84 and 4.94 (2m, NHCO of Pro), 6.58 (s, CH-1), 6.84 (s, CH-4), 7.24 (m, 3×CH of Ph), 7.46 (d, J=8.3 Hz, 2×CH of Ph); LRMS for C$_{38}$H$_{48}$N$_3$O$_4$S [M+H]$^+$: 642.3; HPLC purity: 74.7%.

{4-[(17α)-17-Hydroxy-3-methoxy-19-norpregna-1
(10),2,4-trien-20-yn-2-yl]piperazin-1-yl}{(2S)-1-[4-
(methylamino)benzoyl]pyrrolidin-2-yl}methanone
(A5)

$^1$H NMR (CDCl$_3$) δ: 0.88 (s, CH$_3$-18), 1.25-2.40 (m, residual CH and CH$_2$), 2.61 (s, C≡CH), 2.81 (m, CH$_2$-6), 2.86 (s, CH$_3$NH), 2.95-3.20 (m, 2×CH$_2$N), 3.62-3.98 (m, 3×CH$_2$NCO), 3.82 and 3.83 (2s, OCH$_3$), 4.93 and 5.17 (2m, NHCO of proline), 6.55 (d, J=8.7 Hz, 2×CH of Ar), 6.57 (s, CH-1), 6.85 (s, CH-4), 7.53 (d, J=6.9 Hz, 2×CH of Ar); LRMS for C$_{38}$H$_{49}$N$_4$O$_4$ [M+H]$^+$: 625.8; HPLC purity: 81.3%.

Cyclopropyl[(2S)-2-({4-[(17α)-17-hydroxy-3-
methoxy-19-norpregna-1 (10),2,4-trien-20-yn-2-yl]
piperazin-1-yl}carbonyl)pyrrolidin-1-yl]methanone
(A6)

$^1$H NMR (CDCl$_3$) δ: 0.88 (s, CH$_3$-18), 0.77 and 0.79 (2s, 2×H of (CH$_2$)$_2$CHCO), 0.85-2.40 (m, residual CH and CH$_2$), 2.60 and 2.61 (2s, C≡CH), 2.80 (m, CH$_2$-6), 2.95-3.15 (m, 2×CH$_2$N), 3.60-3.95 (m, 3×CH$_2$NCO), 3.83 and 3.84 (2s, OCH$_3$), 4.90 and 4.95 (2m, NHCO of Pro), 6.57 (s, CH-1), 6.84 (s, CH-4); LRMS for C$_{34}$H$_{46}$N$_3$O$_4$ [M+H]$^+$: 560.3; HPLC purity: 82.2%.

1-[(2S)-2-({4-[(17α)-17-Hydroxy-3-methoxy-19-
norpregna-1 (10),2,4-trien-20-yn-2-yl]piperazin-1-
yl}carbonyl)pyrrolidin-1-yl]-2-(4-hydroxyphenyl)
ethanone (A7)

$^1$H NMR (CDCl$_3$) δ: 0.87 (s, CH$_3$-18), 1.23-2.37 (m, residual CH and CH$_2$), 2.61 and 2.62 (2s, C≡CH), 2.80 (m, CH$_2$-6), 2.95-3.15 (m, 2×CH$_2$N), 3.52-4.00 (m, 3×CH$_2$NCO), 3.55 (s, PhCH$_2$CON), 3.82 and 3.84 (2s, OCH$_3$), 4.62 and 4.96 (2m, NHCO of Pro), 6.56 (s, CH-1), 6.63 and 6.77 (2d, J=8.4 Hz, 2×CH Ar), 6.83 (s, CH-4), 7.02 and 7.12 (2d, J=8.4 Hz, 2×CH of Ar); LRMS for C$_{38}$H$_{48}$N$_3$O$_5$ [M+H]$^+$: 626.4; HPLC purity: 79.2%.

2-(4-Aminophenyl)-1-[(2S)-2-({4-[(17α)-17-hy-
droxy-3-methoxy-19-norpregna-1(10),2,4-trien-20-
yn-2-yl]piperazin-1-yl}carbonyl)pyrrolidin-1-yl]
ethanone (A8)

$^1$H NMR (CDCl$_3$) δ: 0.88 (s, CH$_3$-18), 1.25-2.38 (m, residual CH and CH$_2$), 2.60 and 2.61 (2s, C≡CH), 2.81 (m, CH$_2$-6), 2.95-3.15 (m, 2×CH$_2$N), 3.48-3.85 (m, 3×CH$_2$NCO), 3.61 (s, PhCH$_2$CON), 3.83 and 3.84 (2s, OCH$_3$), 4.56 and 4.94 (2m, NHCO of Pro), 6.57 (s, CH-1), 6.64 and 7.08 (2d, J=8.3 Hz, 2×CH of Ar), 6.84 (s, CH-4), 6.71 and 7.35 (2d, J=8.3 Hz, 2×CH of Ar); LRMS for C$_{38}$H$_{49}$N$_4$O$_4$ [M+H]$^+$: 625.4; HPLC purity: 73.5%.

2,2-Dicyclohexyl-1-[(2S)-2-({4-[(17α)-17-hydroxy-
3-methoxy-19-norpregna-1(10),2,4-trien-20-yn-2-yl]
piperazin-1-yl}carbonyl)pyrrolidin-1-yl]ethanone
(A9)

$^1$H NMR (CDCl$_3$) δ: 0.89 (s, CH$_3$-18), 0.90-2.38 (m, residual CH and CH$_2$), 2.60 and 2.61 (2s, C≡CH), 2.81 (m, CH$_2$-6), 2.90-3.20 (m, 2×CH$_2$N), 3.58-3.90 (m, 3×CH$_2$NCO), 3.84 (s, OCH$_3$), 5.01 (m, NHCO of Pro), 6.57 (s, CH-1), 6.84 (s, CH-4); LRMS for C$_{44}$H$_{64}$N$_3$O$_4$ [M+H]$^+$: 699.6; HPLC purity: 77.2%.

{4-[(17α)-17-Hydroxy-3-methoxy-19-norpregna-1
(10),2,4-trien-20-yn-2-yl]piperazin-1-yl}{(2S)-1-[(3-
methylcyclohexyl)carbonyl]pyrrolidin-2-
yl}methanone (A10)

$^1$H NMR (CDCl$_3$) δ: 0.89 (s, CH$_3$-18), 0.90 (d, J=6.6 Hz, CH$_3$CH), 0.90-2.47 (m, residual CH and CH$_2$), 2.60 and 2.61 (2s, C≡CH), 2.80 (m, CH$_2$-6), 2.95-3.15 (m, 2×CH$_2$N), 3.55-3.90 (m, 3×CH$_2$NCO), 3.84 (s, OCH$_3$), 4.93 (m, NHCO of Pro), 6.57 (s, CH-1), 6.84 (s, CH-4); LRMS for C$_{38}$H$_{54}$N$_3$O$_4$ [M+H]$^+$: 616.8; HPLC purity: 78.4%.

{4-[(17α)-17-Hydroxy-3-methoxy-19-norpregna-1
(10),2,4-trien-20-yn-2-yl]piperazin-1-yl}{(2S)-1-[(4-
methylcyclohexyl)carbonyl]pyrrolidin-2-
yl}methanone (A11)

$^1$H NMR (CDCl$_3$) δ: 0.89 (s, CH$_3$-18), 0.97 (d, J=7.1 Hz, CH$_3$CH), 1.25-2.50 (m, residual CH and CH$_2$), 2.61 (s, C≡CH), 2.81 (m, CH$_2$-6), 2.95-3.15 (m, 2×CH$_2$N), 3.55-3.85 (m, 3×CH$_2$NCO), 3.84 (s, OCH$_3$), 4.94 (m, NHCO of Pro), 6.57 (s, CH-1), 6.84 (s, CH-4); LRMS for C$_{38}$H$_{54}$N$_3$O$_4$ [M+H]$^+$: 616.8; HPLC purity: 77.9%.

{4-[(17α)-17-Hydroxy-3-methoxy-19-norpregna-1
(10),2,4-trien-20-yn-2-yl]piperazin-1-yl}{(2S)-1-[(2-
methylcyclohexyl)carbonyl]pyrrolidin-2-
yl}methanone (A12)

$^1$H NMR (CDCl$_3$) δ: 0.89 (s, CH$_3$-18), 0.95 and 0.99 (2d, J=7.0 Hz, CH$_3$CH), 1.25-2.38 (m, residual CH and CH$_2$), 2.60 and 2.61 (2s, C≡CH), 2.80 (m, CH$_2$-6), 2.95-3.15 (m, 2×CH$_2$N), 3.60-3.85 (m, 3×CH$_2$NCO), 3.84 (s, OCH$_3$), 4.96 (m, NHCO of Pro), 6.57 (s, CH-1), 6.84 (s, CH-4); LRMS for C$_{38}$H$_{54}$N$_3$O$_4$ [M+H]$^+$: 616.8; HPLC purity: 81.4%.

(4-tert-Butylcyclohexyl)[(2S)-2-({4-[(17α)-17-hy-
droxy-3-methoxy-19-norpregna-1(10),2,4-trien-20-
yn-2-yl]piperazin-1-yl}carbonyl)pyrrolidin-1-yl]
methanone (A13)

$^1$H NMR (CDCl$_3$) δ: 0.84 (s, (CH$_3$)$_3$C), 0.89 (s, CH$_3$-18), 0.90-2.38 (m, residual CH and CH$_2$), 2.60 and 2.61 (2s, C≡CH), 2.81 (m, CH$_2$-6), 2.95-3.20 (m, 2×CH$_2$N), 3.55-3.88 (m, 3×CH$_2$NCO), 3.83 (s, OCH$_3$), 4.95 (m, NHCO of Pro), 6.57 (s, CH-1), 6.84 (s, CH-4); LRMS for C$_{41}$H$_{60}$N$_3$O$_4$ [M+H]$^+$: 658.5; HPLC purity: 80.6%.

[(2S)-1-(3,5-Dimethylbenzoyl)pyrrolidin-2-yl]{4-
[(17α)-17-hydroxy-3-methoxy-19-norpregna-1(10),
2,4-trien-20-yn-2-yl]piperazin-1-yl}methanone
(A14)

$^1$H NMR (CDCl$_3$) δ: 0.88 (s, CH$_3$-18), 1.25-2.37 (m, residual CH and CH$_2$), 2.32 (s, 2×CH$_3$ of Ar), 2.60 and 2.62 (2s, C≡CH), 2.80 (m, CH$_2$-6), 2.95-3.20 (m, 2×CH$_2$N), 3.50-4.00 (m, 3×CH$_2$NCO), 3.84 (s, OCH$_3$), 4.57 and 5.14 (2m, NHCO of Pro), 6.58 (s, CH-1), 6.86 (s, CH-4), 7.04 (s, CH of Ar), 7.19 (s, 2×CH of Ar); LRMS for C$_{39}$H$_{50}$N$_3$O$_4$ [M+H]$^+$: 624.4; HPLC purity: 79.4%.

{4-[(17α)-17-Hydroxy-3-methoxy-19-norpregna-1 (10),2,4-trien-20-yn-2-yl]piperazin-1-yl}[(2S)-1-{[(1R,2R)-2-phenylcyclopropyl]carbonyl}pyrrolidin-2-yl]methanone (A15)

$^1$H NMR (CDCl$_3$) δ: 0.89 (s, CH$_3$-18), 1.25-2.50 (m, residual CH and CH$_2$), 2.60 and 2.61 (2s, C≡CH), 2.80 (m, CH$_2$-6), 2.95-3.15 (m, 2×CH$_2$N), 3.50-3.95 (m, 3×CH$_2$NCO), 3.84 (s, OCH$_3$), 4.78 and 4.97 (2m, NHCO of Pro), 6.58 (s, CH-1), 6.85 (s, CH-4), 7.10-7.30 (m, 5×CH of Ar); LRMS for C$_{40}$H$_{50}$N$_3$O$_4$[M+H]$^+$: 636.8; HPLC purity: 85.6%.

Biphenyl-4-yl[(2S)-2-({4-[(17α)-17-hydroxy-3-methoxy-19-norpregna-1 (10),2,4-trien-20-yn-2-yl] piperazin-1-yl}carbonyl)pyrrolidin-1-yl]methanone (A16)

$^1$H NMR (CDCl$_3$) δ: 0.88 (s, CH$_3$-18), 1.25-2.35 (m, residual CH and CH$_2$), 2.60 (s, C≡CH), 2.82 (m, CH$_2$-6), 2.95-3.22 (m, 2×CH$_2$N), 3.60-4.00 (m, 3×CH$_2$NCO), 3.85 (s, OCH$_3$), 4.65 and 5.18 (2m, NHCO of Pro), 6.58 (s, CH-1), 6.87 (s, CH-4), 7.35-7.70 (m, 9×CH of biphenyl); LRMS for C$_{43}$H$_{50}$N$_3$O$_4$[M+H]$^+$: 672.8; HPLC purity: 83.2%.

{4-[(17α)-17-Hydroxy-3-methoxy-19-norpregna-1 (10),2,4-trien-20-yn-2-yl]piperazin-1-yl}{(2S)-1-[2-(phenylamino)benzoyl]pyrrolidin-2-yl}methanone (A17)

$^1$H NMR (CDCl$_3$) δ: 0.88 (s, CH$_3$-18), 1.25-2.38 (m, residual CH and CH$_2$), 2.61 (s, C≡CH), 2.82 (m, CH$_2$-6), 2.95-3.20 (m, 2×CH$_2$N), 3.45-3.97 (m, 3×CH$_2$NCO), 3.85 (s, OCH$_3$), 4.74 and 5.14 (2m, NHCO of Pro), 6.59 (s, CH-1), 6.83 (t, J=7.4 Hz, 2×CH of diphenylamine), 6.87 (s, CH-4), 6.93 (m, CH of diphenylamine), 7.25 (m, 4×CH of diphenylamine), 7.33 and 7.40 (2d, J$_A$=7.5 Hz and J$_B$=8.3 Hz, 2×CH of diphenylamine), 8.04 (s, NH); LRMS for C$_{43}$H$_{51}$N$_4$O$_4$ [M+H]$^+$: 687.8; HPLC purity: 81.8%.

{(2S)-1-[3,5-Bis(trifluoromethyl)benzoyl]pyrrolidin-2-yl}{4-[(17α)-17-hydroxy-3-methoxy-19-norpregna-1(10),2,4-trien-20-yn-2-yl]piperazin-1-yl}methanone (A18)

$^1$H NMR (CDCl$_3$) δ: 0.88 (s, CH$_3$-18), 1.25-2.37 (m, residual CH and CH$_2$), 2.60 and 2.61 (2s, C≡CH), 2.82 (m, CH$_2$-6), 2.95-3.20 (m, 2×CH$_2$N), 3.48-4.00 (m, 3×CH$_2$NCO), 3.84 and 3.85 (2s, OCH$_3$), 4.46 and 5.12 (2m, NHCO of Pro), 6.59 (s, CH-1), 6.87 (s, CH-4), 7.94 (s, CH of Ar), 8.08 (s, 2×CH of Ar); LRMS for C$_{39}$H$_{44}$F$_6$N$_3$O$_4$ [M+H]$^+$: 733.1; HPLC purity: 77.1%.

(2E)-1-[(2S)-2-({4-[(17α)-17-Hydroxy-3-methoxy-19-norpregna-1(10),2,4-trien-20-yn-2-yl]piperazin-1-yl}carbonyl)pyrrolidin-1-yl]-3-phenylprop-2-en-1-one (A19)

$^1$H NMR (CDCl$_3$) δ: 0.89 (s, CH$_3$-18), 1.25-2.38 (m, residual CH and CH$_2$), 2.60 and 2.61 (2s, C≡CH), 2.82 (m, CH$_2$-6), 2.95-3.20 (m, 2×CH$_2$N), 3.70-3.97 (m, 3×CH$_2$NCO), 3.85 (s, OCH$_3$), 4.89 and 5.07 (2m, NHCO of Pro), 6.58 (s, CH-1), 6.79 (d, J=15.5 Hz, CH=CHCO), 6.87 (s, CH-4), 7.36 and 7.52 (2m, 5×CH of Ph), 7.71 (d, J=15.5 Hz, CH=CHCO); LRMS for C$_{39}$H$_{48}$N$_3$O$_4$ [M+H]$^+$: 622.8; HPLC purity: 85.1%.

[(2S)-1-(4-Benzoylbenzoyl)pyrrolidin-2-yl]{4-[(17α)-17-hydroxy-3-methoxy-19-norpregna-1(10),2,4-trien-20-yn-2-yl]piperazin-1-yl}methanone (A20)

$^1$H NMR (CDCl$_3$) δ: 0.88 (s, CH$_3$-18), 1.25-2.38 (m, residual CH and CH$_2$), 2.60 and 2.61 (2s, C≡CH), 2.81 (m, CH$_2$-6), 2.95-3.20 (m, 2×CH$_2$N), 3.50-4.00 (m, 3×CH$_2$NCO), 3.85 (s, OCH$_3$), 4.58 and 5.15 (2m, NHCO of Pro), 6.59 (s, CH-1), 6.87 (s, CH-4), 7.47-7.85 (m, 9×CH of benzophenone); LRMS for C$_{44}$H$_{50}$N$_3$O$_5$[M+H]$^+$: 700.4; HPLC purity: 81.6%.

{4-[(17α)-17Hydroxy-3-methoxy-19-norpregna-1 (10),2,4-trien-20-yn-2-yl]piperazin-1-yl}{(2S)-1-[(4-methoxycyclohexyl)carbonyl]pyrrolidin-2-yl}methanone (A21)

$^1$H NMR (CDCl$_3$) δ: 0.88 (s, CH$_3$-18), 1.10-2.50 (m, residual CH and CH$_2$), 2.61 (s, C≡CH), 2.81 (m, CH$_2$-6), 2.95-3.20 (m, 2×CH$_2$N), 3.27 and 3.35 (2s, CH$_3$OCH), 3.45-3.90 (m, 3×CH$_2$NCO and CH$_3$OCH), 3.83 (s, OCH$_3$), 4.73 and 4.94 (2m, NHCO of Pro), 6.57 (s, CH-1), 6.84 (s, CH-4); LRMS for C$_{38}$H$_{54}$N$_3$O$_5$ [M+H]$^+$: 632.9; HPLC purity: 80.1%.

2-[(1R)-Bicyclo[2.2.1]hept-2-yl]-1-[(2S)-2-({4-[(17α)-17-hydroxy-3-methoxy-19-norpregna-1(10), 2,4-trien-20-yn-2-yl]piperazin-1-yl}carbonyl)pyrrolidin-1-yl]ethanone (A22)

$^1$H NMR (CDCl$_3$) δ: 0.89 (s, CH$_3$-18), 0.95-2.40 (m, residual CH and CH$_2$), 2.61 (s, C≡CH), 2.81 (m, CH$_2$-6), 2.90-3.15 (m, 2×CH$_2$N), 3.48-3.90 (m, 3×CH$_2$NCO), 3.83 (s, OCH$_3$), 4.66 and 4.96 (2m, NHCO of Pro), 6.57 (s, CH-1), 6.85 (s, CH-4); LRMS for C$_{39}$H$_{54}$N$_3$O$_4$ [M+H]$^+$: 629.1; HPLC purity: 79.5%.

{(2S)-1-[4-(Diethylamino)benzoyl]pyrrolidin-2-yl} [4-[(17α)-17-hydroxy-3-methoxy-19-norpregna-1 (10),2,4-trien-20-yn-2-yl]piperazin-1-yl]methanone (A23)

$^1$H NMR (CDCl$_3$) δ: 0.88 (s, CH$_3$-18), 1.16 (t, J=6.8 Hz, 2×CH$_3$CH$_2$N), 1.25-2.38 (m, residual CH and CH$_2$), 2.61 (s, C≡CH), 2.80 (m, CH$_2$-6), 2.95-3.20 (m, 2×CH$_2$N), 3.37 (q, J=6.6 Hz, 2×CH$_3$CH$_2$N), 3.60-4.02 (m, 3×CH$_2$NCO), 3.83 (s, OCH$_3$), 5.19 (m, NHCO of Pro), 6.57 (s, CH-1), 6.60 (d, J=8.5 Hz, 2×CH of Ar), 6.85 (s, CH-4), 7.55 (d, J=6.6 Hz, 2×CH of Ar); LRMS for C$_{41}$H$_{55}$N$_4$O$_4$ [M+H]$^+$: 667.8; HPLC purity: 81.1%.

1-(3-{[(2S)-2-({4-[(17α)-17-Hydroxy-3-methoxy-19-norpregna-1(10),2,4-trien-20-yn-2-yl]piperazin-1-yl}carbonyl)pyrrolidin-1-yl]carbonyl}phenyl)ethanone (A24)

$^1$H NMR (CDCl$_3$) δ: 0.88 (s, CH$_3$-18), 1.25-2.37 (m, residual CH and CH$_2$), 2.60 and 2.61 (2s, C≡CH), 2.58 and 2.63 (2s, CH$_3$CO), 2.82 (m, CH$_2$-6), 2.95-3.21 (m, 2×CH$_2$N), 3.52-4.00 (m, 3×CH$_2$NCO), 3.85 (s, OCH$_3$), 4.56 and 5.14 (2m, NHCO of Pro), 6.58 (s, CH-1), 6.87 (s, CH-4), 7.52 (t, J=7.7 Hz, CH of Ar), 7.81 (d, J=7.7 Hz, CH of Ar), 8.03 (d, J=7.9 Hz, CH of Ar), 8.17 (s, CH of Ar); LRMS for C$_{39}$H$_{48}$N$_3$O$_5$ [M+H]$^+$: 638.7; HPLC purity: 84.7%.

{4-[(17α)-17-Hydroxy-3-methoxy-19-norpregna-1 (10),2,4-trien-20-yn-2-yl]piperazin-1-yl}[(2S)-1-(quinolin-6-ylcarbonyl)pyrrolidin-2-yl]methanone (A25)

$^1$H NMR (CDCl$_3$) δ: 0.88 (s, CH$_3$-18), 1.25-2.36 (m, residual CH and CH$_2$), 2.60 (s, C≡CH), 2.82 (m, CH$_2$-6), 2.95-3.22 (m broad, 2×CH$_2$N), 3.54-4.02 (m, 3×CH$_2$NCO), 3.85 (s, OCH$_3$), 4.60 and 5.20 (2m, NCHCO of Pro), 6.59 (s, CH-1), 6.87 (s, CH-4), 7.45, 7.93 and 8.15 and 8.97 (4m, 6×CH of quinoline); LRMS for C$_{40}$H$_{47}$N$_4$O$_4$ [M+H]$^+$: 647.3; HPLC purity: 86.9%.

(4-Fluoronaphthalen-1-yl)[(2S)-2-({4-[(17α)-17-hydroxy-3-methoxy-19-norpregna-1(10), 2,4-trien-20-yn-2-yl]piperazin-1-yl}carbonyl)pyrrolidin-1-yl]methanone (A26)

$^1$H NMR (CDCl$_3$) δ: 0.88 (s, CH$_3$-18), 1.25-2.37 (m, residual CH and CH$_2$), 2.60 (s, C≡CH), 2.82 (m, CH$_2$-6), 2.95-3.23 (m broad, 2×CH$_2$N), 3.74-4.03 (m, 3×CH$_2$NCO), 3.86 (s, OCH$_3$), 4.92 and 5.23 (2m, NCHCO of Pro), 6.59 (s, CH-1), 6.88 (s, CH-4), 7.15 (m, CH of Ar), 7.48 (m, CH of Ar), 7.58 (t, J=8.1 Hz, CH of Ar), 7.66 (t, J=7.1 Hz, CH of Ar), 8.13 (d, J=8.3 Hz, CH of Ar), 8.37 (d, J=7.3 Hz, CH of Ar); LRMS for C$_{41}$H$_{47}$FN$_3$O$_4$[M+H]$^+$: 664.7; HPLC purity: 86.5%.

1-Benzothiophen-2-yl[(2S)-2-({4-[(17α)-17-hydroxy-3-methoxy-19-norpregna-1(10),2,4-trien-20-yn-2-yl]piperazin-1-yl}carbonyl)pyrrolidin-1-yl]methanone (A27)

$^1$H NMR (CDCl$_3$) δ: 0.89 (s, CH$_3$-18), 1.25-2.36 (m, residual CH and CH$_2$), 2.60 and 2.61 (2s, C≡CH), 2.82 (m, CH$_2$-6), 2.95-3.20 (m broad, 2×CH$_2$N), 3.72-4.12 (m, 3×CH$_2$NCO), 3.84 (s, OCH$_3$), 5.00 and 5.19 (2m, NCHCO of Pro), 6.58 (s, CH-1), 6.87 (s, CH-4), 7.40 (m, 2×CH of Ar), 7.80 (s, CH=CS), 7.84 (m, 2×CH of Ar); LRMS for C$_{39}$H$_{46}$N$_3$O$_4$S [M+H]$^+$: 652.8; HPLC purity: 82.7%.

[(2S)-1-(2-Bromobenzoyl)pyrrolidin-2-yl]{4-[(17α)-17-hydroxy-3-methoxy-19-norpregna-1(10),2,4-trien-20-yn-2-yl]piperazin-1-yl}methanone (A28)

$^1$H NMR (CDCl$_3$) δ: 0.88 (s, CH$_3$-18), 1.25-2.37 (m, residual CH and CH$_2$), 2.60 and 2.62 (2s, C≡CH), 2.80 (m, CH$_2$-6), 2.95-3.20 (m broad, 2×CH$_2$N), 3.25-4.03 (m, 3×CH$_2$NCO), 3.85 (s, OCH$_3$), 4.45 and 5.15 (2m, NCHCO of Pro), 6.58 (s, CH-1), 6.86 (s, CH-4), 7.14-7.44 (m, 3×CH of Ar), 7.53 and 7.57 (2d, J=7.5 Hz, CH of Ar); LRMS for C$_{37}$H$_{45}$Br$^{81}$N$_3$O$_4$ [M+H]$^+$: 676.0; HPLC purity: 82.8%.

1-[(2S)-2-({4-[(17α)-17-Hydroxy-3-methoxy-19-norpregna-1 (10),2,4-trien-20-yn-2-yl]piperazin-1-yl}carbonyl)pyrrolidin-1-yl]-2-phenoxyethanone (A29)

$^1$H NMR (CDCl$_3$) δ: 0.88 (s, CH$_3$-18), 1.25-2.38 (m, residual CH and CH$_2$), 2.61 (s, C≡CH), 2.80 (m, CH$_2$-6), 2.95-3.15 (m broad, 2×CH$_2$N), 3.64-3.95 (m, 3×CH$_2$NCO), 3.83 (s, OCH$_3$), 4.65 and 4.75 (2d of AB system, J=14.0 Hz, OCH$_2$), 4.92 and 4.98 (2m, NCHCO of Pro), 6.57 (s, CH-1), 6.84 (s, CH-4), 6.88-7.00 (m, 3×CH of Ar), 7.29 (m, 2×CH of Ar); LRMS for C$_{38}$H$_{48}$N$_3$O$_5$ [M+H]$^+$: 626.3; HPLC purity: 77.0%.

[(2S)-1-(3,5-Difluorobenzoyl)pyrrolidin-2-yl]{4-[(17α)-17-hydroxy-3-methoxy-19-norpregna-1(10),2,4-trien-20-yn-2-yl]piperazin-1-yl}methanone (A30)

$^1$H NMR (CDCl$_3$) δ: 0.88 (s, CH$_3$-18), 1.25-2.38 (m, residual CH and CH$_2$), 2.61 (s, C≡CH), 2.80 (m, CH$_2$-6), 2.95-3.20 (m broad, 2×CH$_2$N), 3.50-4.00 (m, 3×CH$_2$NCO), 3.84 (s, OCH$_3$), 4.50 and 5.09 (2m, NCHCO of Pro), 6.58 (s, CH-1), 6.86 (s, CH-4), 6.75-6.90 (m, CH of Ar), 6.96 and 7.13 (2m, 2×CH of Ar); LRMS for C$_{37}$H$_{44}$F$_2$N$_3$O$_4$ [M+H]$^+$: 632.5; HPLC purity: 85.0%.

[(2S)-1-(2,4-Dimethoxybenzoyl)pyrrolidin-2-yl]{4-[(17α)-17-hydroxy-3-methoxy-19-norpregna-1(10), 2,4-trien-20-yn-2-yl]piperazin-1-yl}methanone (A31)

$^1$H NMR (CDCl$_3$) δ: 0.88 (s, CH$_3$-18), 1.25-2.37 (m, residual CH and CH$_2$), 2.60 (s, C≡CH), 2.80 (m, CH$_2$-6), 2.95-3.20 (m broad, 2×CH$_2$N), 3.37-4.00 (m, 3×CH$_2$NCO), 3.82, 3.83 and 3.84 (3s, 3× OCH$_3$), 4.54 and 5.12 (2m, NCHCO of Pro), 6.58 (s, CH-1), 6.86 (s, CH-4), 6.41-6.51 (m, 2×CH of Ar), 7.18 and 7.32 (2d, J=8.3 Hz, CH of Ar); LRMS for C$_{39}$H$_{50}$N$_3$O$_6$[M+H]$^+$: 656.4; HPLC purity: 88.7%.

Furan-2-yl[(2S)-2-({4-[(17α)-17-hydroxy-3-methoxy-19-norpregna-1(10),2,4-trien-20-yn-2-yl]piperazin-1-yl}carbonyl)pyrrolidin-1-yl]methanone (A32)

$^1$H NMR (CDCl$_3$) δ: 0.89 (s, CH$_3$-18), 1.25-2.37 (m, residual CH and CH$_2$), 2.61 (s, C≡CH), 2.82 (m, CH$_2$-6), 2.95-3.20 (m broad, 2×CH$_2$N), 3.68-4.15 (m, 3×CH$_2$NCO), 3.84 (s, OCH$_3$), 4.93 and 5.12 (2m, NCHCO of Pro), 6.48 (m, CH of furan), 6.58 (s, CH-1), 6.86 (s, CH-4), 7.11 (d, J=3.2 Hz, CH of furan), 7.51 (d, J=0.8 Hz, CH of furan); LRMS for C$_{35}$H$_{44}$N$_3$O$_5$ [M+H]$^+$: 586.7; HPLC purity: 83.8%.

1,3-Benzodioxol-5-yl[(2S)-2-({4-[(17α)-17-hydroxy-3-methoxy-19-norpregna-1(10),2,4-trien-20-yn-2-yl]piperazin-1-yl}carbonyl)pyrrolidin-1-yl]methanone (A33)

$^1$H NMR (CDCl$_3$) δ: 0.88 (s, CH$_3$-18), 1.25-2.36 (m, residual CH and CH$_2$), 2.61 (s, C≡CH), 2.80 (m, CH$_2$-6), 2.95-3.20 (m broad, 2×CH$_2$N), 3.60-4.00 (m, 3×CH$_2$NCO), 3.84 (s, OCH$_3$), 4.61 and 5.12 (2m, NCHCO of Pro), 5.99 (s, OCH$_2$O), 6.58 (s, CH-1), 6.81 (d, J=8.0 Hz, CH of Ar), 6.86 (s, CH-4), 7.11 (s, CH of Ar), 7.16 (d, J=8.1 Hz, CH of Ar); LRMS for C$_{38}$H$_{46}$N$_3$O$_6$ [M+H]$^+$: 640.8; HPLC purity: 85.4%.

{4-[(17α)-17-Hydroxy-3-methoxy-19-norpregna-1 (10),2,4-trien-20-yn-2-yl]piperazin-1-yl}[(2S)-1-(pyridin-3-ylcarbonyl)pyrrolidin-2-yl]methanone (A34)

$^1$H NMR (CDCl$_3$) δ: 0.88 (s, CH$_3$-18), 1.25-2.38 (m, residual CH and CH$_2$), 2.60 (s, C≡CH), 2.81 (m, CH$_2$-6), 2.95-3.20 (m broad, 2×CH$_2$N), 3.60-3.98 (m, 3×CH$_2$NCO), 3.84 (s, OCH$_3$), 4.58 and 5.14 (2m, NCHCO of Pro), 6.58 (s, CH-1), 6.86 (s, CH-4), 7.35 (m, CH of pyr), 7.94 (m, CH of pyr), 8.67 (m, CH of pyr), 8.86 (s, CH of pyr); LRMS for C$_{36}$H$_{45}$N$_4$O$_4$ [M+H]$^+$: 597.3; HPLC purity: 77.0%.

2-Cyclohexyl-1-[(2S)-2-({4-[(17α)-17-hydroxy-3-methoxy-19-norpregna-1(10),2,4-trien-20-yn-2-yl]piperazin-1-yl}carbonyl)pyrrolidin-1-yl]ethanone (A35)

$^1$H NMR (CDCl$_3$) δ: 0.89 (s, CH$_3$-18), 0.80-2.38 (m, residual CH and CH$_2$), 2.19 and 2.23 (2d, J=7.2 Hz, CH$_2$Cy), 2.61 (s, C≡CH), 2.80 (m, CH$_2$-6), 2.95-3.15 (m broad, 2×CH$_2$N), 3.51-3.90 (m, 3×CH$_2$NCO), 3.83 (s, OCH$_3$), 4.69 and 4.95 (2m, NCHCO of Pro), 6.57 (s, CH-1), 6.85 (s, CH-4); LRMS for C$_{38}$H$_{54}$N$_3$O$_4$ [M+H]$^+$: 616.4; HPLC purity: 87.1%.

{4-[(17α)-17-Hydroxy-3-methoxy-19-norpregna-1(10),2,4-trien-20-yn-2-yl]piperazin-1-yl}[(2S)-1-(pyrazin-2-ylcarbonyl)pyrrolidin-2-yl]methanone (A36)

$^1$H NMR (CDCl$_3$) δ: 0.89 and 0.90 (2s, CH$_3$-18), 1.25-2.40 (m, residual CH and CH$_2$), 2.61 (s, C≡CH), 2.82 (m, CH$_2$-6), 2.88-3.23 (m broad, 2×CH$_2$N), 3.55-4.12 (m, 3×CH$_2$NCO), 3.85 (s, OCH$_3$), 5.14 and 5.61 (2m, NCHCO of Pro), 6.59 and 6.60 (2s, CH-1), 6.83 and 6.87 (2s, CH-4), 8.42, 8.57 and 8.64 (3m, 2×CH of pyrazine), 9.19 and 9.31 (2s, CH of pyrazine); LRMS for C$_{35}$H$_{44}$N$_5$O$_4$ [M+H]$^+$: 598.7; HPLC purity: 85.4%.

{4-[(17α)-17-Hydroxy-3-methoxy-19-norpregna-1(10),2,4-trien-20-yn-2-yl]piperazin-1-yl}{(2S)-1-[4-(methylsulfanyl)benzoyl]pyrrolidin-2-yl}methanone (A37)

$^1$H NMR (CDCl$_3$) δ: 0.88 (s, CH$_3$-18), 1.25-2.40 (m, residual CH and CH$_2$), 2.50 (s, SCH$_3$), 2.60 (s, C≡CH), 2.80 (m, CH$_2$-6), 2.95-3.20 (m broad, 2×CH$_2$N), 3.55-3.98 (m, 3×CH$_2$NCO), 3.84 (s, OCH$_3$), 4.58 and 5.14 (2m, NCHCO of Pro), 6.58 (s, CH-1), 6.86 (s, CH-4), 7.24 (d, J=8.3 Hz, 2×CH of Ar), 7.54 (d, J=8.3 Hz, 2×CH of Ar); LRMS for C$_{38}$H$_{48}$N$_3$O$_4$S [M+H]$^+$: 642.8; HPLC purity: 81.8%.

{4-[(17α)-17-Hydroxy-3-methoxy-19-norpregna-1(10),2,4-trien-20-yn-2-yl]piperazin-1-yl}[(2S)-1-(1H-indol-2-ylcarbonyl)pyrrolidin-2-yl]methanone (A38)

$^1$H NMR (CDCl$_3$) δ: 0.89 (s, CH$_3$-18), 1.25-2.37 (m, residual CH and CH$_2$), 2.60 and 2.61 (2s, C≡CH), 2.82 (m, CH$_2$-6), 2.95-3.25 (m broad, 2×CH$_2$N), 3.60-4.20 (m, 3×CH$_2$NCO), 3.85 (s, OCH$_3$), 4.92 and 5.19 (2m, NCHCO of Pro), 6.59 (s, CH-1), 6.87 (s, CH-4), 6.98 (s, CH=CNH), 7.14 (t, J=7.4 Hz, CH of indole), 7.28 (d, J=7.3 Hz, CH of indole), 7.40 (d, J=8.2 Hz, CH of indole), 7.68 (d, J=7.9 Hz, CH of indole), 9.29 (s, NH); LRMS for C$_{39}$H$_{47}$N$_4$O$_4$ [M+H]$^+$: 635.5; HPLC purity: 84.2%.

{4-[(17α)-17-Hydroxy-3-methoxy-19-norpregna-1(10),2,4-trien-20-yn-2-yl]piperazin-1-yl}[(2S)-1-(quinoxalin-2-ylcarbonyl)pyrrolidin-2-yl]methanone (A39)

$^1$H NMR (CDCl$_3$) δ: 0.89 and 0.91 (2s, CH$_3$-18), 1.25-2.50 (m, residual CH and CH$_2$), 2.61 and 2.63 (2s, C≡CH), 2.80 (m, CH$_2$-6), 2.95-3.37 (m broad, 2×CH$_2$N), 3.60-4.30 (m, 3×CH$_2$NCO), 3.81 and 3.85 (2s, OCH$_3$), 5.20 and 5.74 (2m, NCHCO of Pro), 6.57, 6.59, 6.65 and 6.88 (4s, CH-1 and CH-4), 7.75-8.18 (m broad, 4×CH of quinoxaline), 9.43 and 9.46 (2s, CH of quinoxaline); LRMS for C$_{39}$H$_{46}$N$_5$O$_4$ [M+H]$^+$: 648.4; HPLC purity: 80.1%.

1-[(2S)-2-({4-[(17α)-17-Hydroxy-3-methoxy-19-norpregna-1(10),2,4-trien-20-yn-2-yl]piperazin-1-yl}carbonyl)pyrrolidin-1-yl]-2-(pyridin-4-yl)ethanone (A40)

$^1$H NMR (CDCl$_3$) δ: 0.88 (s, CH$_3$-18), 1.25-2.37 (m, residual CH and CH$_2$), 2.61 (s, C≡CH), 2.80 (m, CH$_2$-6), 2.95-3.15 (m broad, 2×CH$_2$N), 3.52-3.90 (m, 3×CH$_2$NCO), 3.83 (s, OCH$_3$), 4.60 and 4.96 (2m, NCHCO of Pro), 6.57 (s, CH-1), 6.84 (s, CH-4), 7.27 (m, 2×CH of pyr), 8.55 (d, J=6.1 Hz, 2×CH of pyr); LRMS for C$_{37}$H$_{47}$N$_4$O$_4$ [M+H]$^+$: 611.4; HPLC purity: 80.7%.

With reference to Schemes 10 and 11, a number of non-limiting examples illustrating the preparation of selected pregnane-based aminosteroid derivatives (1-7 and 15) in accordance with the present disclosure, are illustrated in the following sections.

(5α,17α)-17-hydroxy-2-(4-{[(2S)-1-(quinolin-2-ylcarbonyl)pyrrolidin-2-yl]carbonyl}piperazin-1-yl)pregn-1-en-20-yn-3-one (1)

To a solution of RM-133 (50 mg, 0.077 mmol) in DMSO (0.8 mL) and toluene (0.2 mL) was added 2-iodoxybenzoic acid (64 mg, 0.229 mmol). The reaction mixture was then heated at 80° C. for 90 min and the resulting solution was poured in water and extracted with EtOAc. The organic phase was washed with brine, dried over sodium sulfate, filtered and evaporated under reduced pressure. The crude compound was first purified by flash chromatography (DCM/MeOH, 95:5) to give a mixture of starting material and desired compound. A preparative HPLC purification was performed to provide pure compound 1 as a white solid (9 mg, 18%); IR (KBr) ν: 3410 (OH), 2098 (C≡CH, very weak), 1651 (CON and enone); $^1$H NMR (CDCl$_3$) δ: 0.88 and 0.90 (2s, CH$_3$-19), 0.96 and 1.00 (2s, CH$_3$-18), 0.80-2.10 (m, residual CH and CH$_2$), 2.15-2.55 (broad m, 2×CH$_2$N of piperazine, 1×CH$_2$ of proline), 2.58 and 2.60 (2s, C≡CH), 2.70-4.23 (broad m, 3×CH$_2$NCO), 5.13 (dd, J$_1$=3.3 Hz and J$_2$=8.0 Hz, NCHCO of proline, one of 2 rotamers), 5.80 (dd, J$_1$=4.1 Hz and J$_2$=8.5 Hz, NCHCO of proline, one of 2 rotamers), 5.94 and 6.22 (2s, CH of enone), 7.59 (m, CH of quinoline), 7.72 (m, CH of quinoline), 7.85 (t$_{app}$, J=6.6 Hz, CH of quinoline), 7.95 and 7.99 (2d, J=8.5 Hz, CH of quinoline), 8.00 and 8.12 (2d, J=8.1 Hz, CH of quinoline), 8.20 and 8.24 (2d, J=8.7 Hz, CH of quinoline); $^{13}$C NMR (CDCl$_3$) δ: 12.9, 13.9, 21.2, 22.5, 23.0, 25.4, 27.0, 29.0, 30.7, 31.7, 32.6 (32.7), 36.2, 38.3 (38.4), 38.9 (2C), 41.5 (41.7, 41.9 and 42.2), 43.6 (43.7), 44.9, 45.8, 47.0 (2C), 48.2, 49.5 (49.8, 49.9 and 50.2), 50.4 (50.5), 50.7 (2C), 57.4, 59.1, 74.1, 79.7, 87.3 (87.4), 120.9 (121.7), 127.5 (127.6), 127.6 (127.8), 128.2 (128.3), 129.3, 129.7 (129.9), 136.6 (136.7, 136.8 and 136.8), 144.9, 145.1, 145.9 (146.5), 154.2, 166.2, 170.1, ~195; LRMS for C$_{40}$H$_{49}$N$_4$O$_4$ [M+H]$^+$: 649.4; HPLC purity: 100.0%.

(2β,5α,17α)-17-hydroxy-2-(4-{[(2S)-1-(quinolin-2-ylcarbonyl)pyrrolidin-2-yl]carbonyl}piperazin-1-yl)pregn-20-yn-3-one (2)

To a solution of RM-133 (40 mg, 0.062 mmol) in DCM (2 mL) at 0° C. was added N-methylmorpholine N-oxide (10.8 mg, 0.09 mmol), molecular sieves (30 mg) and tetrapropylammonium perruthenate (TPAP) (4 mg, 0.012 mmol). The solution was stirred for 30 min at 0° C., then allowed to return to room temperature and stirred overnight. The resulting solution was filtered on silica gel using a mixture of DCM/MeOH (95:5) as eluent. The crude compound was finally purified by preparative TLC using DCM/MeOH (95:5) as eluent to provide compound 2 as a white solid (6 mg, 15%); IR (KBr) ν: 3410 (OH), 1713 (C=O), 1643 (CON); $^1$H NMR (CDCl$_3$) δ: 0.87 and 0.88 (2s, CH$_3$-19), 1.05 and 1.08 (2s, CH$_3$-18), 0.76-2.10 (m, residual CH and CH$_2$), 2.11-2.65 (broad m, 2×CH$_2$N of piperazine, 1×CH$_2$ of proline), 2.58 (s, C≡CH), 2.75-4.25 (broad m, 3×CH$_2$NCO), 5.11 (dd, J$_1$=3.5 Hz and J$_2$=8.5 Hz, NCHCO of proline, one of 2 rotamers), 5.85 (m, NCHCO of proline, one of 2 rotamers), 7.59 (m, CH of quinoline), 7.74 (t$_{app}$, J=7.4 Hz, CH of quinoline), 7.84 (t$_{app}$, J=6.6 Hz, CH of quinoline), 8.00 (t$_{app}$, J=9.5 Hz, CH of quinoline), 8.05 and 8.11 (2d, J=8.1 Hz, CH of quinoline), 8.21 and 8.23 (2d, J=9.0 Hz, CH of quinoline); $^{13}$C NMR (CDCl$_3$) δ: 12.7, 12.8, 22.3, 23.1, 25.3, 29.0, 31.8, 32.5, 35.5, 36.7, 38.9, 41.1, 42.1, 44.9, 45.5, 46.8, 47.7, 48.4, 49.3, 49.9, 50.4 (50.5), 50.2, 53.8, 57.6, 59.4, 67.8 (67.9), 74.1, 79.7 (79.8), 87.4, 121.0 (121.7), 127.5, 127.6 (2C), 127.7, 128.2 (128.3), 129.4, 129.7 (129.8), 129.9, 136.7 (136.8), 145.9 (146.5), 166.2, 170.4, ~220; LRMS for C$_{40}$H$_{51}$N$_4$O$_4$ [M+H]$^+$: 651.5; HPLC purity: 90.3%.

(2β,3α,5α,17α)-17-hydroxy-2-{4-[1-(quinolin-2-ylcarbonyl)-L-prolyl]piperazin-1-yl}pregn-20-yn-3-yl dimethylcarbamate (3)

To a solution of RM-133 (100 mg, 0.15 mmol) in dry pyridine (1.5 mL) was added N-dimethylcarbamyl chloride (1.5 mL, 16.3 mmol). The solution was heated at 80° C. in a sealed vial for 16h. After cooling, the solution was carefully poured into water (50 mL) and stirred for 5 min. The resulting mixture was extracted with EtOAc and the organic phase washed with brine, dried over sodium sulfate, filtered and evaporated under reduced pressure. A preparative HPLC purification was performed to provide compound 3 as a white solid (31 mg, 28%). IR (KBr) ν: 3425 (OH), 1697 (OCON), 1643 (CON); $^1$H NMR (CDCl$_3$) δ: 0.82 and 0.84 (2s, CH$_3$-19), 0.94 and 1.05 (2s, CH$_3$-18), 0.67-2.40 (m, residual CH and CH$_2$, 2×CH$_2$ of piperazine, 1×CH$_2$ of proline, 2α-CH), 2.58 (s, C≡CH), 2.92 (s, CON(CH$_3$)$_2$), 3.09-4.23 (broad m, 3×CH$_2$NCO), 5.01 and 5.15 (2s, 313-CH, 5.09 (dd, J$_1$=3.3 Hz and J$_2$=8.0 Hz, NCHCO of proline, one of 2 rotamers), 5.74 (dd, J$_1$=4.1 Hz and J$_2$=8.5 Hz, NCHCO of proline, one of 2 rotamers), 7.57 (m, CH of quinoline), 7.72 (m, CH of quinoline), 7.85 (t$_{app}$, J=6.6 Hz, CH of quinoline), 7.95 (t$_{app}$, J=7.0 Hz, CH of quinoline), 8.00 and 8.12 (2d, J=8.5 Hz, CH of quinoline), 8.22 (t$_{app}$, J=8.7 Hz, CH of quinoline); $^{13}$C NMR (CDCl$_3$) δ: 12.7, 12.8, 20.7, 22.4, 23.1, 25.3, 27.4, 29.0, 30.0 (2C), 31.4, 31.7, 32.7, 33.7, 35.5, 36.0 (36.1), 38.9, 40.9, 41.9 (42.2), 45.1, 45.8, 46.8 (46.9), 48.3, 49.9 (50.6), 50.8 and 51.2), 54.6 (54.7), 57.5, 59.2, 62.8 (62.9), 69.8 (70.1), 73.8, 79.9 (2C), 87.7, 121.0 (121.7), 127.4 (127.6), 127.8, 128.2 (128.3), 129.3, 129.6, 129.7 (129.9), 136.7 (136.8), 145.9 (146.4), 153.5 (154.1), 156.0 (156.1), 166.2 (166.6), 170.0 (170.4); LRMS for C$_{43}$H$_{58}$N$_5$O$_5$ [M+H]$^+$: 724.9; HPLC purity: 83.3%.

Monoacetate 4 and di-acetate 5

To a solution of RM-133 (50 mg, 0.077 mmol) in dry pyridine (2.5 mL) was added acetic anhydride (2.5 mL, 26.4 mmol). The solution was heated in a sealed vial at 80° C. for 16h. After cooling, the solution was poured into water (50 mL) and stirred for 5 min. The resulting mixture was extracted with EtOAc, washed with brine, dried over sodium sulfate, filtered and evaporated under reduced pressure. A preparative HPLC purification was performed to separate compound 4 (RT=43.0 min) and compound 5 (RT=51.1 min).

(2α,3α,5α,17α)-17-hydroxy-2-{4-[1-(quinolin-2-ylcarbonyl)-L-prolyl]piperazin-1-yl}pregn-20-yn-3-yl acetate (4)

White solid (8 mg, 15%); IR (KBr) ν: 3433 (OH), 1728 (OCOCH$_3$), 1643 (CON); $^1$H NMR (CDCl$_3$) δ: 0.83 and 0.84 (2s, CH$_3$-19), 0.92 and 1.05 (2s, CH$_3$-18), 0.70-2.45 (m, residual CH and CH$_2$), 2.04 and 2.06 (2s, OCOCH$_3$), 2.56 (s, C≡CH), 2.75-4.26 (broad m, 3×CH$_2$NCO), 5.09 and 5.25 (2s broad, 313-CH), 5.10 (dd, J$_1$=3.3 Hz and J$_2$=8.0 Hz, NCHCO of proline, one of 2 rotamers), 5.74 (dd, J$_1$=4.1 Hz and J$_2$=8.5 Hz, NCHCO of proline, one of 2 rotamers), 7.57 (m, CH of quinoline), 7.72 (m, CH of quinoline), 7.83 (m, CH of quinoline), 7.95 (m, CH of quinoline), 8.00 and 8.11 (2d, J=8.5 Hz, CH of quinoline), 8.22 (t$_{app}$, J=9.0 Hz, CH of quinoline); $^{13}$C NMR (CDCl$_3$) δ: 12.8, 12.9, 20.7, 21.4 (21.5), 22.4, 23.0, 25.3, 27.3 (27.4), 29.0, 29.8 (29.9), 31.3, 31.6, 32.7, 33.5 (33.8), 35.5, 35.9 (36.0), 38.9, 40.3 (40.4), 42.0 (42.2), 45.1, 45.8, 46.8 (46.9), 48.2, 49.9, 50.2, 50.5, 50.6 (50.7), 51.0, 54.4 (54.5), 57.5, 59.1, 62.4 (62.5), 69.0 (69.3), 73.8 (2C), 79.9 (2C), 87.6, 121.0 (121.7), 127.4 (127.6), 127.7 (127.9), 128.2 (128.3), 129.3, 129.6, 129.7 (129.9), 136.7 (136.8), 145.9 (146.5), 153.5 (154.2), 166.1, 166.7, 170.0, 170.3, 170.5; LRMS for C$_{42}$H$_{55}$N$_4$O$_4$ [M+H]$^+$: 695.4; HPLC purity: 95.7%.

(2β,3α,5α,17α)-2-{4-[1-(quinolin-2-ylcarbonyl)-L-prolyl]piperazin-1-yl}pregn-20-yne-3,17-diyl diacetate (5)

White solid (13 mg, 23%); IR (KBr) ν: 3448 (OH), 1736 (OCOCH$_3$), 1651 (CON); $^1$H NMR (CDCl$_3$) δ: 0.85 and 0.86 (2s, CH$_3$-19), 0.92 and 1.04 (2s, CH$_3$-18), 0.73-2.47 (m, residual CH and CH$_2$), 2.03 and 2.04 (2s, OCOCH$_3$), 2.05 and 2.07 (2s, OCOCH$_3$), 2.59 (s, C≡CH), 2.68-4.26 (broad m, 3×CH$_2$NCO), 5.09 and 5.25 (2s broad, 33-CH), 5.10 (dd, J$_1$=3.3 Hz and J$_2$=8.6 Hz, NCHCO of proline, one of 2 rotamers), 5.75 (dd, J$_1$=3.8 Hz and J$_2$=8.3 Hz, NCHCO of proline, one of 2 rotamers), 7.57 (m, CH of quinoline), 7.72 (m, CH of quinoline), 7.84 (m, CH of quinoline), 7.96 and 8.00 (2d, J=8.5 Hz, CH of quinoline), 7.99 and 8.11 (2d, J=8.5 Hz, CH of quinoline), 8.22 (t$_{app}$, J=9.0 Hz, CH of quinoline); $^{13}$C NMR (CDCl$_3$) δ: 12.9, 13.0, 13.5, 20.7, 21.4 (21.5), 22.4, 23.5, 25.3, 27.4, 29.0, 29.8 (29.9), 31.3, 31.6, 33.0, 33.5, 35.2, 35.8 (36.0), 37.3, 40.2 (40.4), 42.0 (42.2), 45.1, 45.8, 47.6 (2C), 48.2, 48.8, 49.9, 50.2, 50.6, 51.0, 54.3 (54.4), 57.5, 59.1, 62.5 (62.6), 69.0 (69.2), 74.6 (2C), 83.5, 84.5 (2C), 121.0 (121.7), 127.4 (127.6), 127.9, 128.3, 129.3, 129.6, 129.7 (129.9), 136.7 (136.8), 145.9 (146.5), 153.5 (154.2), 166.6, 169.7, 170.3, 170.5; LRMS for C$_{44}$H$_{57}$N$_4$O$_6$ [M+H]$^+$: 737.6; HPLC purity: 93.6%.

(2β,3α,5α,17α)-3,17-dihydroxy-2-(1-methyl-4-t[(2S)-1-(quinolin-2-ylcarbonyl) pyrrolidin-2-yl]carbonylpiperazin-1-ium-1-yl)pregn-20-yne iodide (6)

To a solution of RM-133 (40 mg, 0.062 mmol) in anhydrous acetonitrile (3 mL) was added methyl iodide (750 μL, 11.8 mmol). The solution was stirred at room temperature for 3 days and was the evaporated under reduced pressure. The crude compound was purified by flash chromatography with DCM/MeOH (95:5) as eluent to provide the desired compound 6 as a yellow solid (19 mg, 39%); IR (KBr) ν: 3410 (OH), 1620 (CON); $^1$H NMR (CD$_3$OD) δ: 0.82 and 0.84 (2s, CH$_3$-19), 1.02 (s, CH$_3$-18), 0.80-2.50 (m, residual CH and CH$_2$), 2.85 and 2.87 (2s, C≡CH), 2.91, 3.09 and 3.23 (3s, N$^+$(I$^-$)CH$_3$), 3.05-4.40 (broad m, 3×CH$_2$NCO, 3β-CH), 5.17 and 5.80 (2m, NCHCO of proline, 2 rotamers), 7.70 (t$_{app}$, J=7.0 Hz, CH of quinoline), 7.84 (m, 2×CH of quinoline), 8.00 (d, J=7.8 Hz, CH of quinoline), 8.11 (d, J=8.7 Hz, CH of quinoline), 8.46 (dd, J$_1$=8.5 Hz, J$_2$=3.0 Hz, CH of quinoline); $^{13}$C NMR (CD$_3$OD) δ: 13.4, 18.2, 23.5, 23.9, 26.5 (26.6), 28.8, 30.0, 32.0, 34.0, 37.4, 37.6, 38.1, 38.3, 39.1, 39.4, 39.6, 39.8, 40.9, 41.3, 42.1, 48.1, 51.4, 51.7, 57.3, (57.4), 58.6, 58.9, 59.6, 60.0, 63.4, 66.7 (66.9), 74.8, 75.5, 80.2, 88.8, 121.3, 129.1, 129.3 (129.4), 129.9, 130.4, 131.6, 138.7, 147.2 (147.9), 154.4, 168.2, 172.8; LRMS for C$_{41}$H$_{55}$N$_4$O$_4$I [M+H+I]$^+$: 795.3; HPLC purity: 96.6%.

{4-[(2β,3α,5α,17α)-3,17-dihydroxypregn-20-yn-2-yl]-4-oxidopiperazin-1-yl}[(2S)-1-(quinolin-2-ylcarbonyl)pyrrolidin-2-yl]methanone (7)

To a solution of RM-133 (50 mg, 0.077 mmol) in a mixture of MeOH/H$_2$O (4:1) (1 mL) was added Oxone® (25 mg, 0.164 mmol). The solution was stirred for 2h at room temperature. The resulting mixture was extracted with EtOAc, washed with brine, dried over sodium sulfate, filtered and evaporated under reduced pressure. The crude compound was purified by flash chromatography with DCM/MeOH (9:1) as eluent to provide the desired compound 7 as a white solid (12 mg, 24%); IR (KBr) ν: 3418 (OH), 1628 (CON); $^1$H NMR (CD$_3$OD) δ: 0.79 and 0.82 (2s, CH$_3$-19), 0.93 and 0.97 (2s, CH$_3$-18), 0.75-2.50 (m, residual CH and CH$_2$), 2.86 and 2.87 (2s, C≡CH), 3.05-4.53 (broad m, 3×CH$_2$NCO, 3β-CH), 5.10, 5.20, 5.75 and 6.05 (4m, NCHCO of proline, mixture of rotamers), 7.68 (m, CH of quinoline), 7.85 (m, 2×CH of quinoline), 7.98 (m, CH of quinoline), 8.11 (d, J=8.5 Hz, CH of quinoline), 8.41 (m, CH of quinoline); $^{13}$C NMR (CD$_3$OD) δ: 13.4, 17.8, 23.3, 23.9, 26.6, 29.2, 31.9, 32.2, 32.9, 33.9 (34.0), 36.9, 37.4 (37.5), 37.6 (37.7), 37.9 (38.0), 38.1, 38.3, 39.8, 39.9, 40.2, 41.9, 48.7, 51.4, 51.5 (51.6), 56.8 (56.9), 57.9, 59.4, 61.4, 63.3, 66.5, 74.7, 79.5 (79.6), 80.3, 88.8, 121.5, 122.1, 129.1 (2C), 129.3 (129.4), 129.8, 130.2 (130.4), 131.5 (131.7), 138.4 (138.5), 147.8, 154.2 (154.5), 168.0 (172.8), 173.0; LRMS for C$_{40}$H$_{53}$N$_4$O$_5$ [M+H]$^+$: 669.4 (weak) and for C$_{40}$H$_{51}$N$_4$O$_4$ [M+H-H$_2$O]$^+$: 651.4; HPLC purity: 96.8%.

(3α,5α,17α)-pregn-20-yne-3,17-diol (11)

To a solution of trimethysilylacetylene (0.4 mL, 2.76 mmol) in anhydrous diethylether (20 mL) was added MeLi (1.6 M, 1.3 mL, 2.08 mmol) under an argon atmosphere at 0° C. The mixture was then allowed to return at room temperature and was stirred for 1h. The mixture was then cooled again at 0° C. before the addition of a solution of androsterone (200 mg, 0.69 mmol) in anhydrous THF (20 mL) and stirred at room temperature overnight. The reaction mixture was poured into water, extracted with EtOAc, washed with brine, dried over sodium sulfate, filtered and evaporated under reduced pressure. The crude compound was dissolved in a solution of potassium carbonate (5%) in MeOH and stirred for 3h. The solution was poured into water, extracted 3 times with DCM and 2 times with EtOAc. Each organic phase was washed with water, combined, dried over sodium sulfate, filtered and evaporated under reduced pressure. The crude compound was purified by flash chromatography with hexanes/EtOAc (9:1 to 8:2) as eluent to provide compound 11 as a white solid (152 mg, 70%). IR (KBr) ν: 3379 (OH); $^1$H NMR (CDCl$_3$) δ: 0.79 (s, CH$_3$-19), 0.83 (s, CH$_3$-18), 0.76-1.72 (m, residual CH and CH$_2$), 1.94 (m, 1H), 2.26 (m, 1H), 2.57 (s, C≡CH), 4.04 (broad t, J=2.4 Hz, 3-17-CH); $^{13}$C NMR (CDCl$_3$) δ: 11.2, 12.8, 20.4, 23.1, 28.4, 29.0, 31.5, 32.2, 32.7, 35.8, 36.1 (2C), 38.9, 39.1, 46.9, 50.5, 53.9, 66.5, 73.9, 79.9, 87.6.

Synthesis of (3α,5α,17α)-17-hydroxypregn-20-yn-3-yl dimethylcarbamate (12)

To a solution of compound 11 (50 mg, 0.16 mmol) in pyridine (1 mL) was added N-dimethylcarbamyl chloride (1 mL) and the solution was heated under microwave at 90° C. for 7h. After cooling, the solution was carefully poured into water (50 mL) and stirred for 5 min. The resulting mixture was extracted with EtOAc, washed with brine, dried over sodium sulfate, filtered and evaporated under reduced pressure. The crude compound was purified by flash chromatography with hexanes/EtOAc (8:2) as eluent to provide an amorphous white solid (38 mg) as a 92:8 mixture of monocarbamate and dicarbamate derivatives (yields of 57% and 5% respectively). A preparative HPLC purification was subsequently carried out to obtain the monocarbamate derivative (compound 12). IR (KBr) ν: 3418 (OH), 1682 (OCON); $^1$H NMR (CDCl$_3$) δ: 0.81 (s, CH$_3$-19), 0.84 (s, CH$_3$-18), 0.72-1.76 (m, residual CH and CH$_2$), 1.94 (m, 1H), 2.26 (m, 1H), 2.57 (s, C≡CH), 2.92 (s, OCON(CH$_3$)$_2$), 4.92 (broad s, 3-17-CH); $^{13}$C NMR (CDCl$_3$) δ: 11.4, 12.8, 20.4, 23.1, 26.5, 28.2, 31.5, 32.2, 33.1, 33.2, 35.9, 36.1, 36.2, 38.9, 40.4, 46.9, 50.5, 54.1, 70.5, 73.8, 79.9, 87.7, 156.3; LRMS for C$_{24}$H$_{38}$NO$_3$ [M+H]$^+$: 388.3; HPLC purity: 95.1%.

Tert-butyl 4-[(3β, 5α,17α)-17-hydroxypregn-20-yn-3-yl]piperazine-1-carboxylate (14)

To a solution of compound 13 (27 mg, 0.09 mmol) in MeOH (1.6 mL) and DCM (0.4 mL) under an argon atmosphere was added at 0° C. 1-Boc-piperazine (160 mg, 0.9 mmol), NaBH$_3$CN (14 mg, 0.22 mmol) and acetic acid (3 drops) until reaching a pH of 6. The solution was stirred at room temperature for 21h. The reaction mixture was poured into water, extracted with EtOAc, washed with brine, dried over sodium sulfate, filtered and evaporated under reduced pressure. The crude compound was purified by flash chromatography with hexanes/EtOAc (8:2) as eluent to provide compound 14 as a white solid (21 mg, 51%). IR (KBr) ν: 3433 (OH), 1690 (OCON); $^1$H NMR (CDCl$_3$) δ: 0.77 (s, CH$_3$-19), 0.82 (s, CH$_3$-18), 0.64-1.77 (m, residual CH and CH$_2$), 1.45 (broad s, OC(CH$_3$)$_3$), 1.95 (m, 1H), 2.26 (m, 2H), 2.50 (broad s, 2×CH$_2$N), 2.57 (s, C≡CH), 3.42 (broad s, 2×CH$_2$NCO); $^{13}$C NMR (CDCl$_3$) δ: 12.4, 12.8, 20.8, 23.1, 24.4, 28.4 (3C), 28.8, 31.0, 31.6, 32.7, 35.9, 36.1, 37.8, 38.9, 45.9, 46.9, 49.1, 50.4, 54.0, 63.9, 73.8, 79.4, 79.9, 87.7, 154.7; LRMS for C$_{30}$H$_{49}$N$_2$O$_3$ [M+H]$^+$: 485.7.

{4-[(3β,5α,17α)-17-hydroxypregn-20-yn-3-yl]piperazin-1-yl}[(2S)-1-(quinolin-2-ylcarbonyl)pyrrolidin-2-yl]methanone (15)

A solution of compound 14 (20 mg, 0.04 mmol) in TFA/DCM (95:5) (1 mL) was stirred at room temperature for 4h and then evaporated under reduced pressure to give the corresponding deprotected piperazine derivative. The crude deprotected piperazine derivative (15 mg) was subsequently dissolved in anhydrous DMF (2 mL) and added to a solution of carboxylic acid 9 (30 mg, 0.08 mmol) and HBTU (30 mg, 0.08 mmol) previously stirred in DMF (2 mL) and DIPEA (55 μL, 0.32 mmol) for 10 min. The reaction mixture was poured into water, extracted with DCM, filtered over a phase separator and evaporated under reduced pressure. The crude compound was purified by flash chromatography using DCM/MeOH (95:5 to 9:1) as eluent and triturated with MeOH to provide compound 15 as a white amorphous solid (5 mg, 20%). IR (KBr) ν: 3394 (OH), 1643 (CON); $^1$H NMR (DMSO-d$_6$) δ: 0.67 (s, CH$_3$-19), 0.71 (s, CH$_3$-18), 0.50-2.40 (m, residual CH and CH$_2$), 2.5 (s, C≡CH, under solvent peak), 2.78-3.75 (broad m, 3×CH$_2$NCO), 5.05 (dd, J$_1$=3.3 Hz and J$_2$=8.0 Hz, NCHCO of proline, one of 2 rotamers), 5.65 (dd, J=3.8 Hz, J$_2$=8.3 Hz, NCHCO of proline, one of 2 rotamers), 5.25 (s, OH), 7.65 (t$_{app}$, J=7.5 Hz, CH of quinoline), 7.71 (d, J=8.5 Hz, CH of quinoline), 7.80 (t, J=8.2 Hz, CH of quinoline), 7.84 and 8.06 (2m, CH of quinoline), 8.00 (t, J=8.0 Hz, CH of quinoline), 8.40 and 8.49 (2d, J=8.6 Hz, CH of quinoline); LRMS for C$_{40}$H$_{53}$N$_4$O$_3$ [M+H]$^+$ 637.4; HPLC purity: 93.1%.

With reference to Scheme 12, the preparation of the 2β-side chain of RM-133, in accordance with an embodiment of the present disclosure, is illustrated in the following sections.

(4-methylpiperazin-1-yl)[(2S)-1-(quinolin-2-ylcarbonyl)pyrrolidin-2-yl]methanone (10)

To a solution of compound 9 (2.0 g, 7.40 mmol) in anhydrous DMF (50 mL) was added at room temperature, under an argon atmosphere, O-benzotriazole-N,N,N',N'-tetramethyl-uronium-hexafluoro-phosphate (HBTU) (4.07 g, 10.78 mmol). The solution was stirred for 10 min followed by the addition of N-methylpiperazine (1.08 g, 10.78 mmol) and diisopropylamine (DIPEA) (3.75 mL, 21.5 mmol). The resulting solution was stirred for 3h and then poured into water, extracted with EtOAc, washed with brine, dried over sodium sulfate, filtered, and evaporated under reduced pressure. The crude compound was purified by flash chromatography with DCM/MeOH (95:5 to 90:10) as eluent to provide the desired compound 10 as a white amorphous solid (950 mg, 37%). IR (KBr) ν: 1643 (CON); $^1$H NMR (CDCl$_3$) δ: 1.98 and 2.28 (2s, NCH$_3$), 1.60-2.65 (broad m, 2×CH$_2$ of proline and 2×CH$_2$NCH$_3$ of piperazine), 3.12-3.72 (broad m, 2×CH$_2$NCO of piperazine), 3.80-4.22 (m, CH$_2$NCO of proline), 5.08 and 5.69 (2m, NCHCO of proline, 2 rotamers), 7.52 (m, CH of quinoline), 7.67 (m, CH of quinoline), 7.78 (d, J=7.2 Hz, CH of quinoline), 7.93 (m, CH of quinoline), 7.94 and 8.06 (2d, J=8.4 Hz, CH of quinoline), 8.19 (t$_{app}$, J=8.8 Hz, CH of quinoline); $^{13}$C NMR (CDCl$_3$) δ: 22.3, 25.2, 28.8, 31, 5, 41.5, 42.0, 44.7, 45.5, 45.6, 45.9, 48.1, 49.8, 54.2 (2C), 54.6, 54.9, 57.4, 59.1, 120.9, 121.5, 127.4 (127.5), 127.7, 128.1 (2C), 129.2, 129.6 (129.7), 136.6, 145.8 (146.3), 153.4 (154.1), 166.0 (166.6), 169.9 (170.1); LRMS for C$_{20}$H$_{25}$N$_4$O$_2$ [M+H]$^+$: 354.2; HPLC purity: 100.0%.

While the present disclosure has been described with reference to specific examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Arpicco S, Dosio F, Stella B, Cattel L. Anticancer prodrugs: an overview of major strategies and recent developments. Curr. Top. Med. Chem. 2011; 11:2346-81.
2. Nagelkerke A, Bussink J, Sweep F C, Span P N. The unfolded protein response as a target for cancer therapy. Biochim. Biophys Acta. 2014; 1846:277-84.
3. Wang M, Kaufman R J. The impact of the endoplasmic reticulum protein-folding environment on cancer development. Nat Rev Cancer. 2014; 14:581-97.
4. Konigs M, Lenczyk M, Schwerdt G, Holzinger H, Gekle M, Humpf H U. Cytotoxicity, metabolism and cellular uptake of the mycotoxin deoxynivalenol in human proximal tubule cells and lung fibroblasts in primary culture. Toxicology. 2007; 240:48-59.
5. Jegham H, Maltais R, Roy J, Doillon C, Poirier D. Biological evaluation of a new family of aminosteroids that display a selective toxicity for various malignant cell lines. Anticancer Drugs. 2012; 23:803-14.
6. Bell L C, Wang J. Probe ADME and test hypotheses: a PATH beyond clearance in vitro-in vivo correlations in early drug discovery. Expert Opin Drug Metab. Toxicol. 2012; 8:1131-55.

The invention claimed is:
1. An aminosteroid derivative of Formula I:

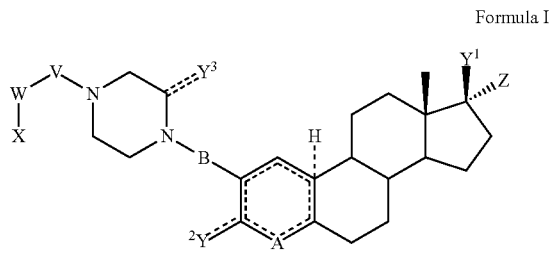

Formula I wherein:
⸺ represents a single or a double bond, provided that two double bonds are not adjacent each other;
A is C, N or NR$^1$;
B is CO, SO, SO$_2$, CH$_2$, C(X$^1$)$_2$, or absent;
Y$^1$ is chosen from OH, halogen, OR$^2$, OCOR$^3$, OCONR$^4$R$^5$ and OSO$_2$NR$^4$R$^5$;
Y$^2$ is chosen from H, halogen, OH, OR$^2$, OMOM (O-methoxymethyl ether), OCOR$^3$, OCONR$^4$R$^5$, OSO$_2$NH$_2$, OPO(OH)$_2$, when Y$^2$⸺C is Y$^2$—C and Y$^2$ is O or S when Y$^2$⸺C is Y$^2$=C,
Y$^3$ is H$_2$ or O;
Z is H, halogen or C≡CR$^6$;
V is an amino acid,

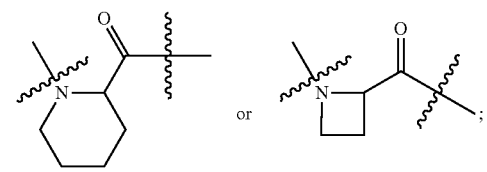

W is CO, SO$_2$, CH$_2$, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;

$X^1$ is halogen;
$R^1$ is H or alkyl;
$R^2$ is alkyl;
$R^3$ is H, alkyl or heterocyclyl;
$R^4$ and $R^5$ are independently chosen from H and alkyl; and
$R^6$ is H or alkyl;

or a pharmaceutically acceptable salt, or an N-oxide thereof.

2. The aminosteroid derivative of claim 1, having the structure:

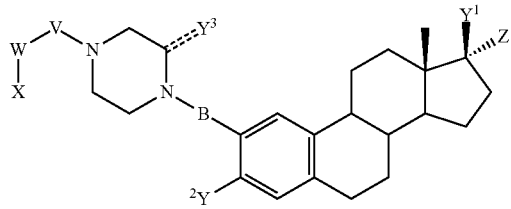

wherein:
B is CO, SO, SO$_2$, CH$_2$, C(X$^1$)$_2$, or absent;
$Y^1$ is chosen from OH, halogen, OR$^2$, OCOR$^3$, OCONR$^4$R$^5$; and OSO$_2$NR$^4$R$^5$;
$Y^2$ is chosen from H, halogen, OH, OR$^2$, OMOM (0-methoxymethyl ether), OCOR$^3$, OCONR$^4$R$^5$, OSO$_2$NH$_2$ and OPO(OH)$_2$;
$Y^3$ is H$_2$ or O;
Z is H, halogen or C≡CR$^6$;
V is an amino acid,

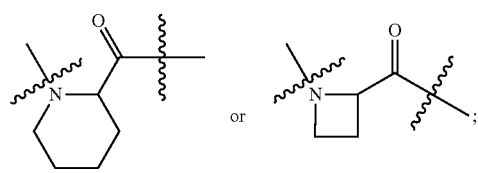

W is CO, SO$_2$, CH$_2$, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;

$X^1$ is halogen;
$R^2$ is alkyl;
$R^3$ is H, alkyl or heterocyclyl;
$R^4$ and $R^5$ are independently chosen from H and alkyl; and
$R^6$ is H or alkyl;

or a pharmaceutically acceptable salt, or an N-oxide thereof.

3. The aminosteroid derivative of claim 1, wherein V is proline and wherein the variables W and X are linked to form the linkage W-X, wherein W-X is chosen from

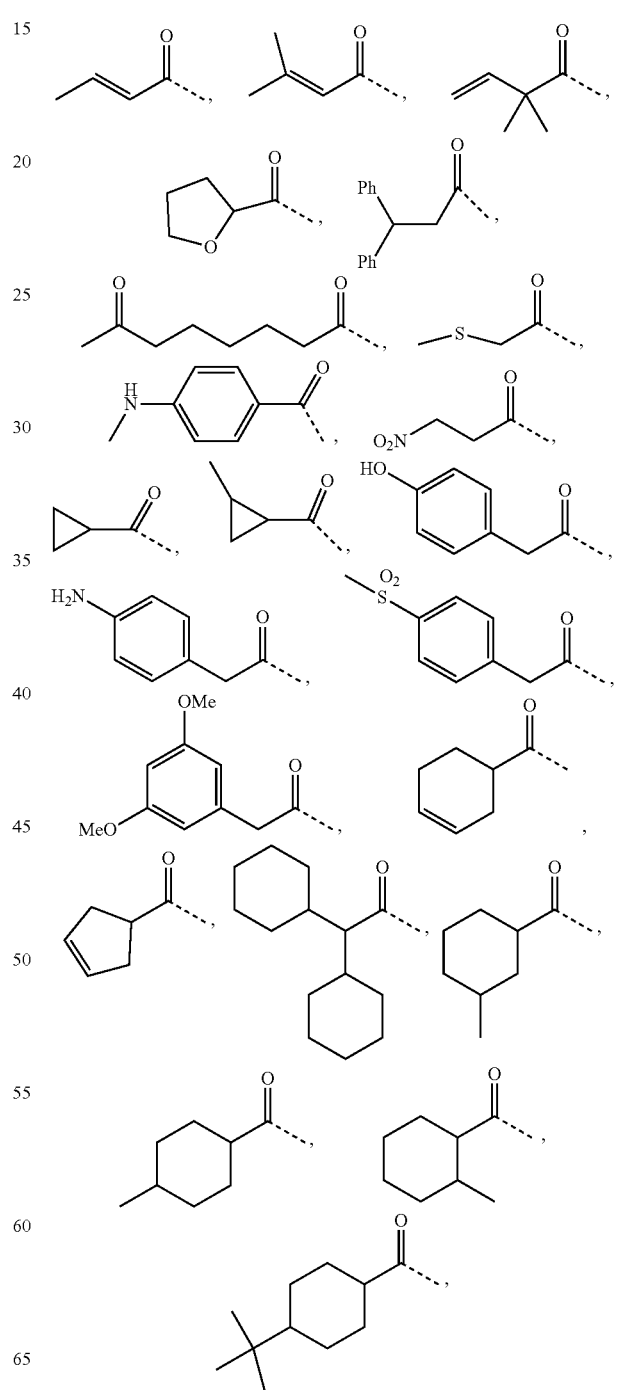

135
-continued
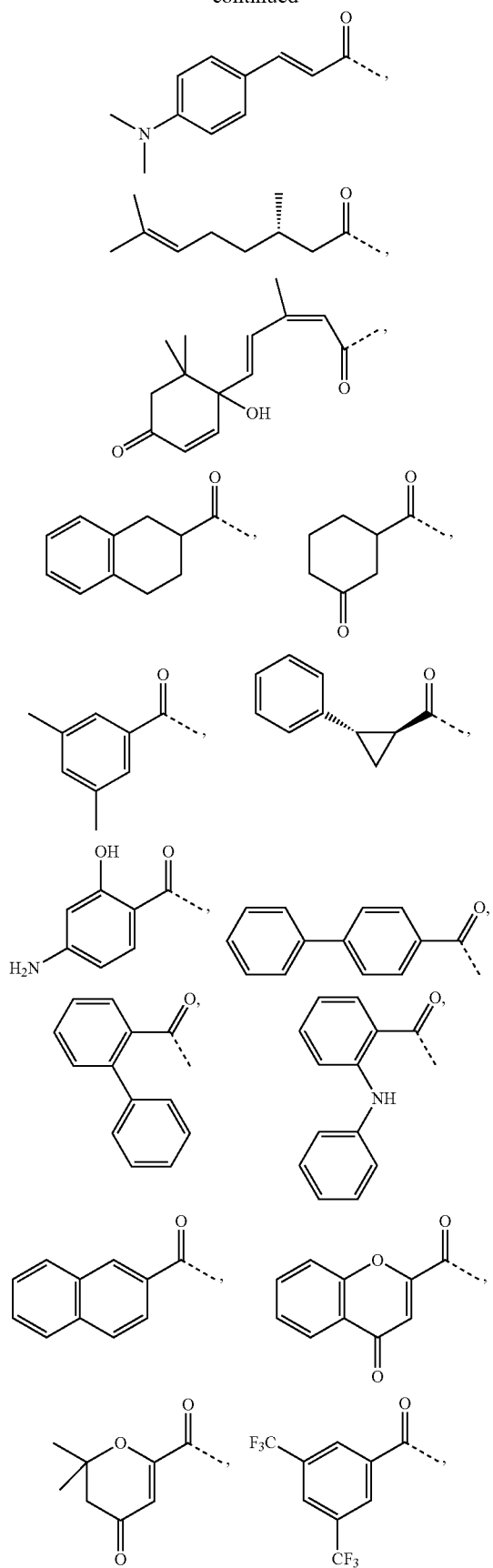
136
-continued
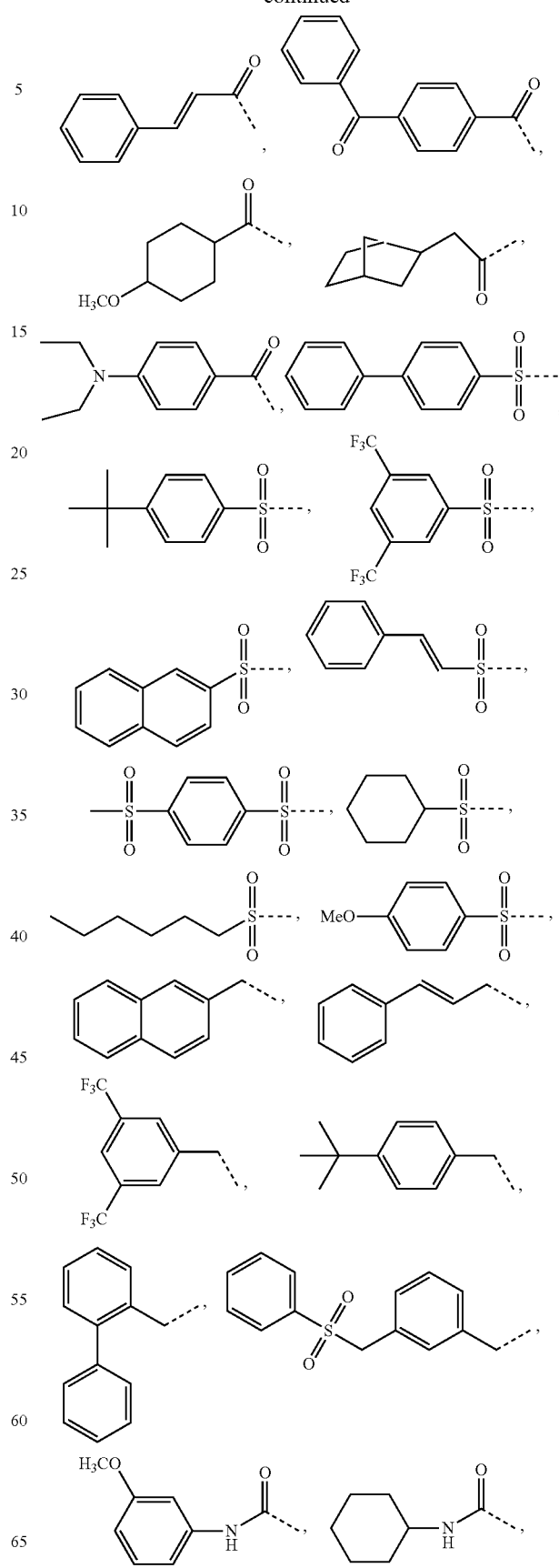

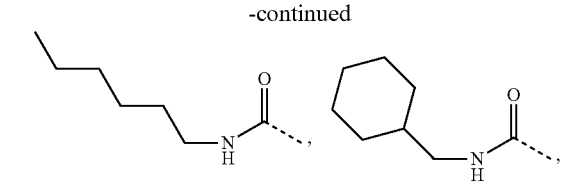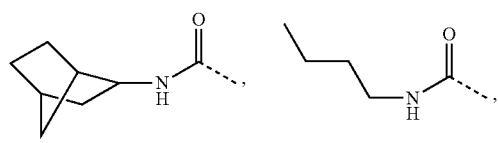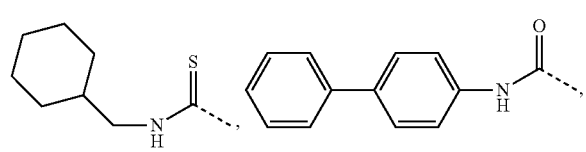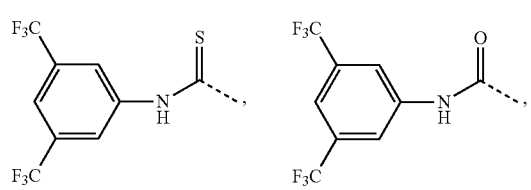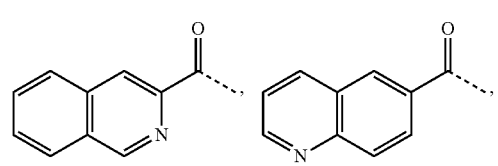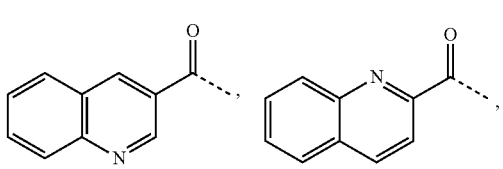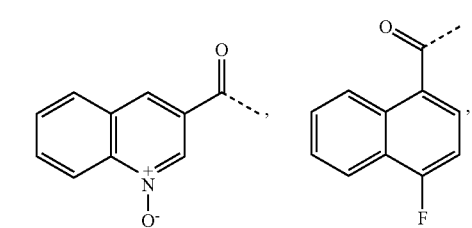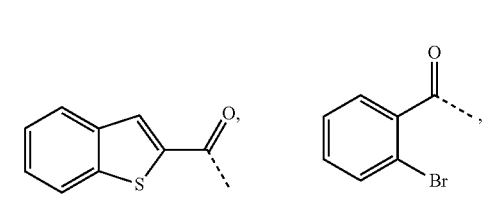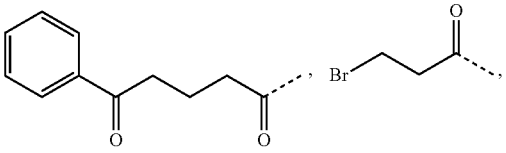
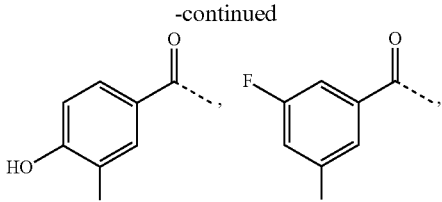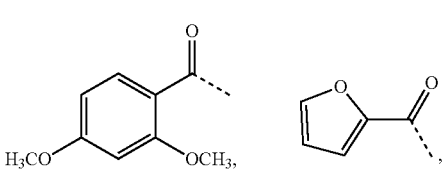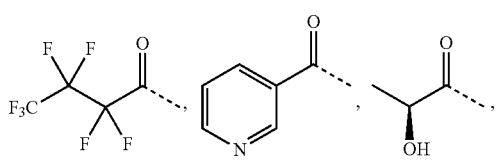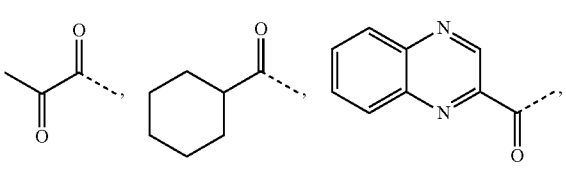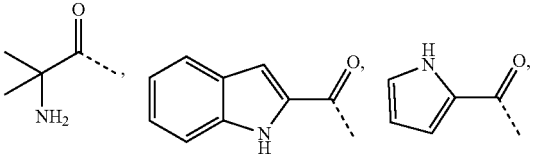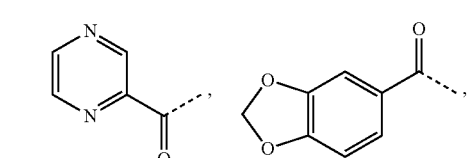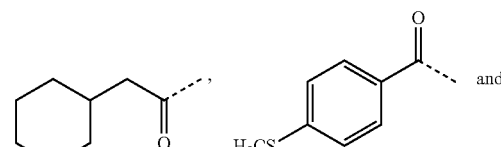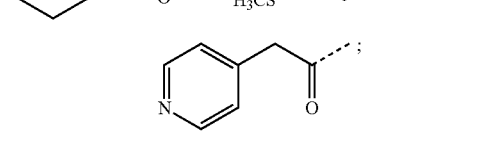
or a pharmaceutically acceptable salt, or an N-oxide thereof.

4. An aminosteroid derivative of having at least one of the following structures:
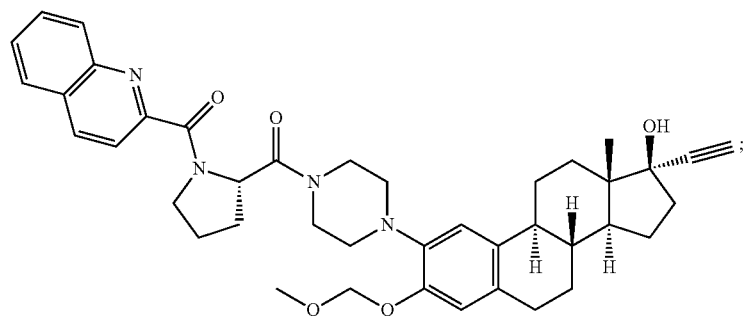
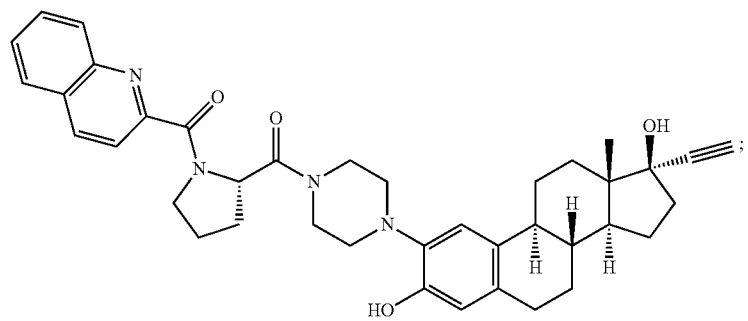
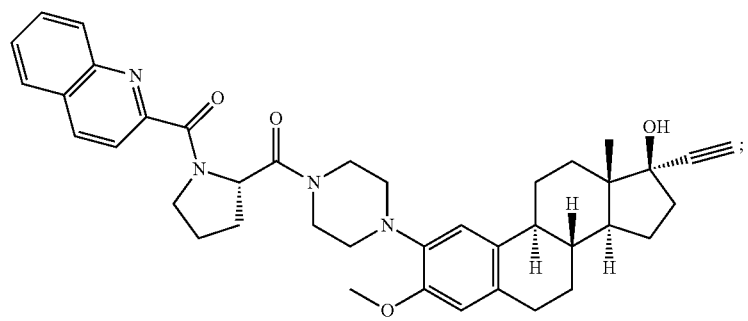
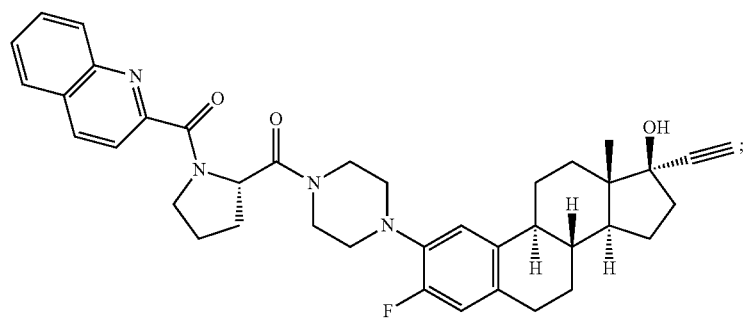
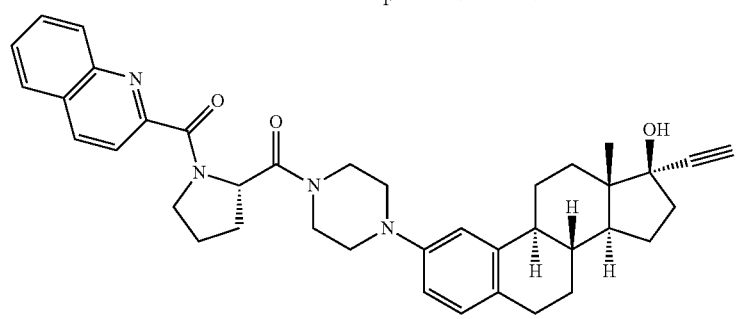

-continued
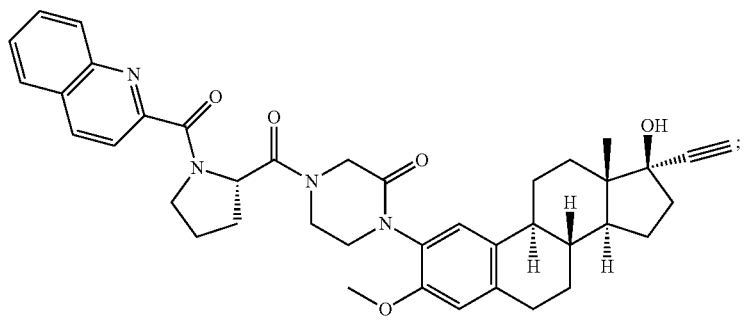
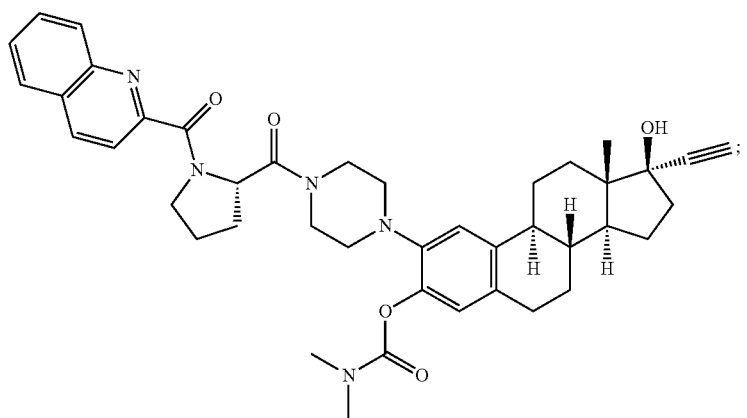
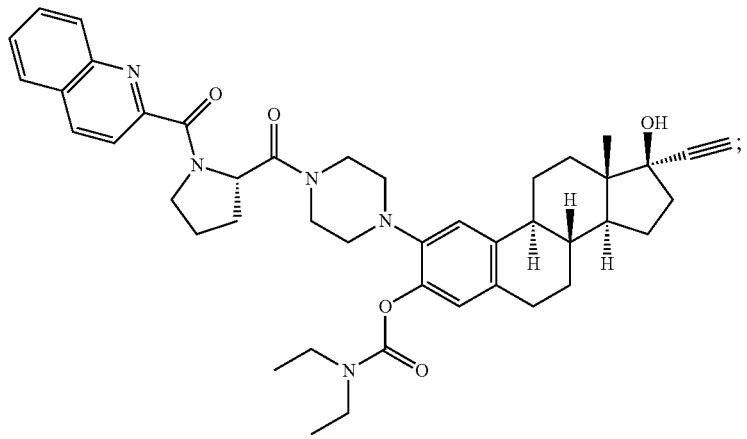
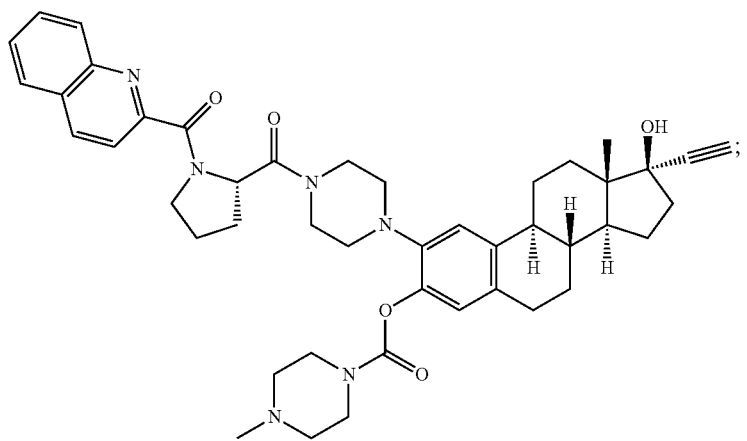

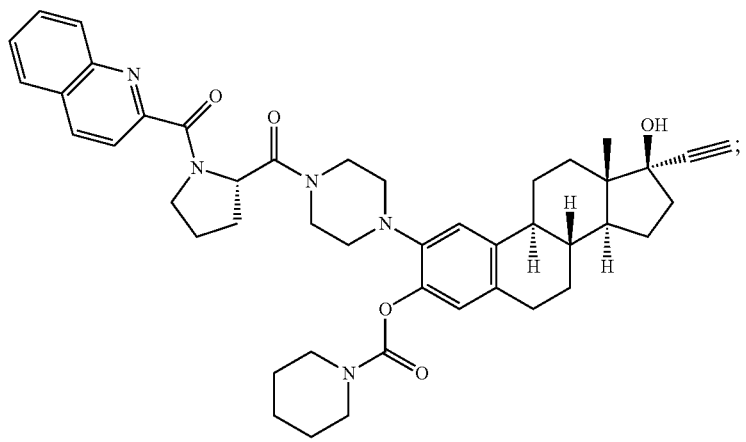
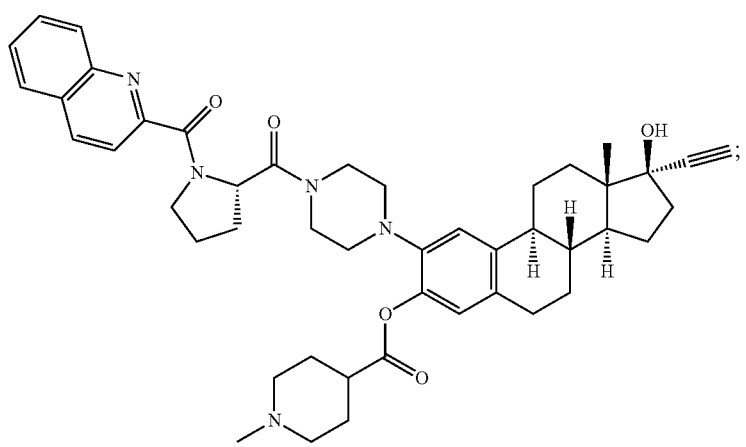
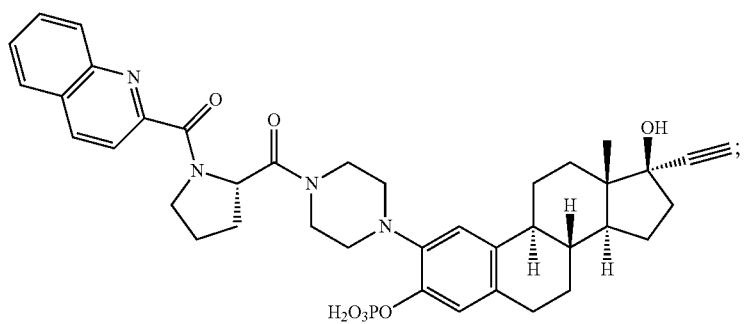
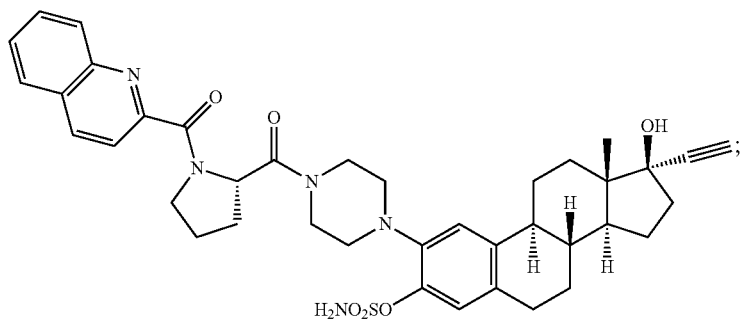

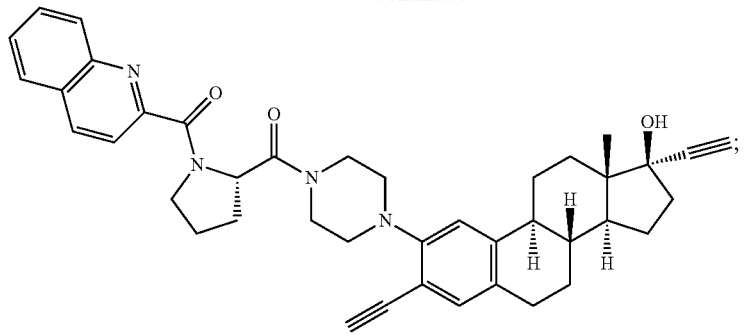
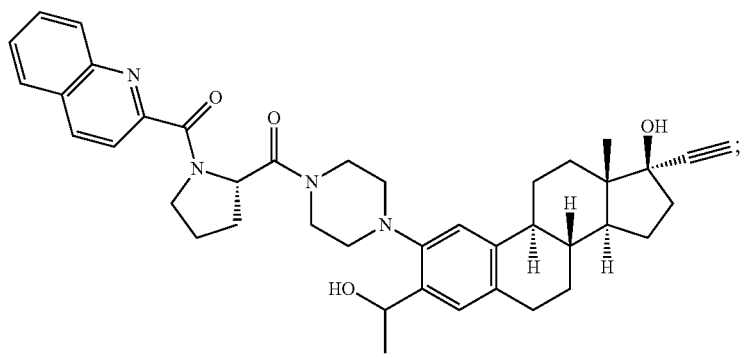
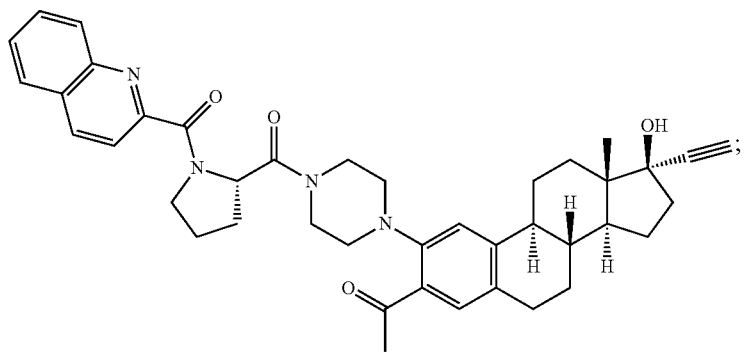
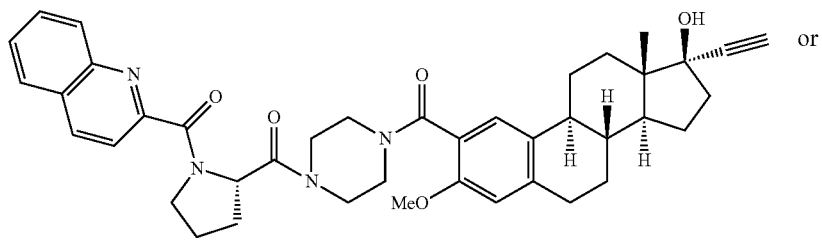
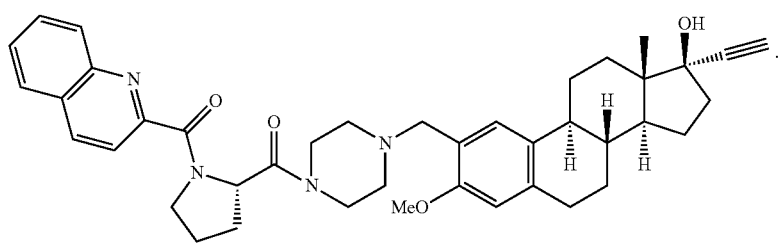

5. An aminosteroid derivative of Formula II:

Formula II wherein:
A is CHR$^1$, NR$^1$, O or S;
B is CO, SO, SO$_2$, CH$_2$, C(X$^1$)$_2$, or absent;
Y$^1$ is chosen from OH, halogen, OR$^2$, OCOR$^3$, OCONR$^4$R$^5$ and OSO$_2$NR$^4$R$^5$;
Y$^2$ is chosen from O and S;
Y$^3$ is H$_2$ or O;
Z is H, halogen or C≡CR$^6$;
V is an amino acid, or ;

W is CO, SO$_2$, CH$_2$, CONH, CSNH, or

;

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
X$^1$ is halogen;
R$^1$ is H or alkyl;
R$^2$ is alkyl;
R$^3$ is H, alkyl or heterocyclyl;
R$^4$ and R$^5$ are independently chosen from H and alkyl; and
R$^6$ is H or alkyl;
or a pharmaceutically acceptable salt, or an N-oxide thereof.

6. The aminosteroid derivative of claim 5, having the structure:

wherein:
B is CO, SO, SO$_2$, CH$_2$, C(X$^1$)$_2$, or absent;
Y$^1$ is chosen from OH, halogen, OR$^2$, OCOR$^3$, OCONR$^4$R$^5$ and OSO$_2$NR$^4$R$^5$;
Y$^2$ is chosen from O and S;
Y$^3$ is H$_2$ or O;
Z is H, halogen or C≡CR$^6$;
V is an amino acid, or ;

W is CO, SO$_2$, CH$_2$, CONH, CSNH, or

;

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
X$^1$ is halogen;
R$^2$ is alkyl;
R$^3$ is H, alkyl or heterocyclyl;
R$^4$ and R$^5$ are independently chosen from H and alkyl; and
R$^6$ is H or alkyl;
or a pharmaceutically acceptable salt, or an N-oxide thereof.

7. The aminosteroid derivative of claim 5, wherein V is proline and wherein the variables W and X are linked to form the linkage W-X, wherein W-X is chosen from -continued
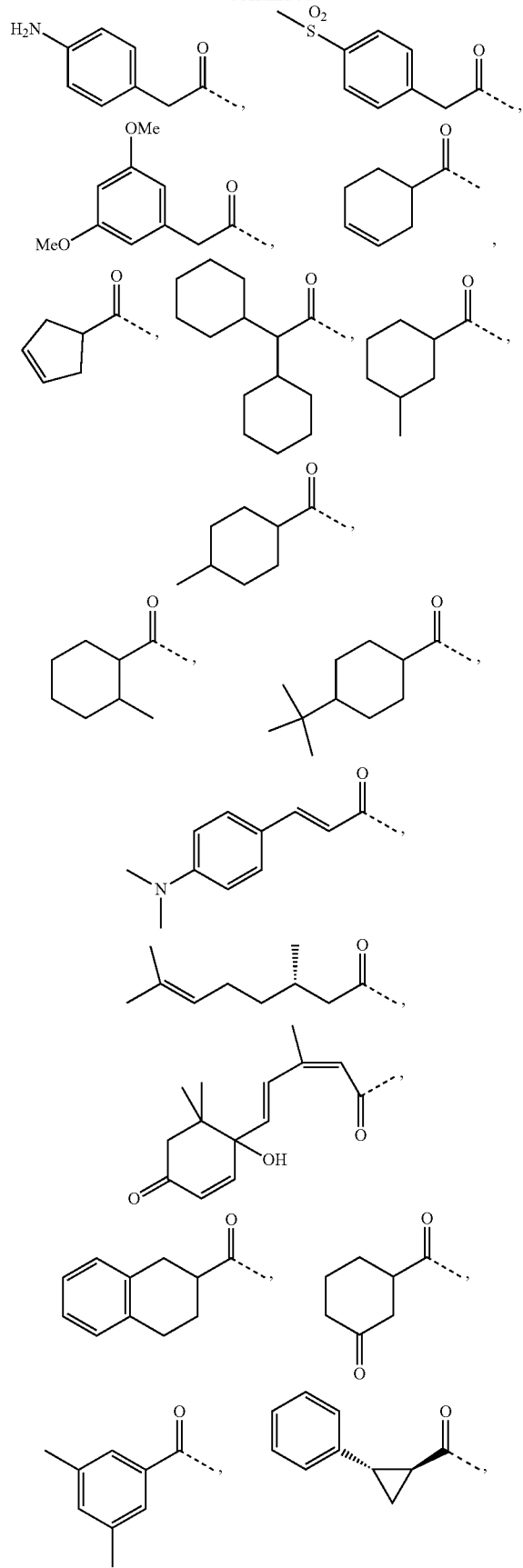
-continued
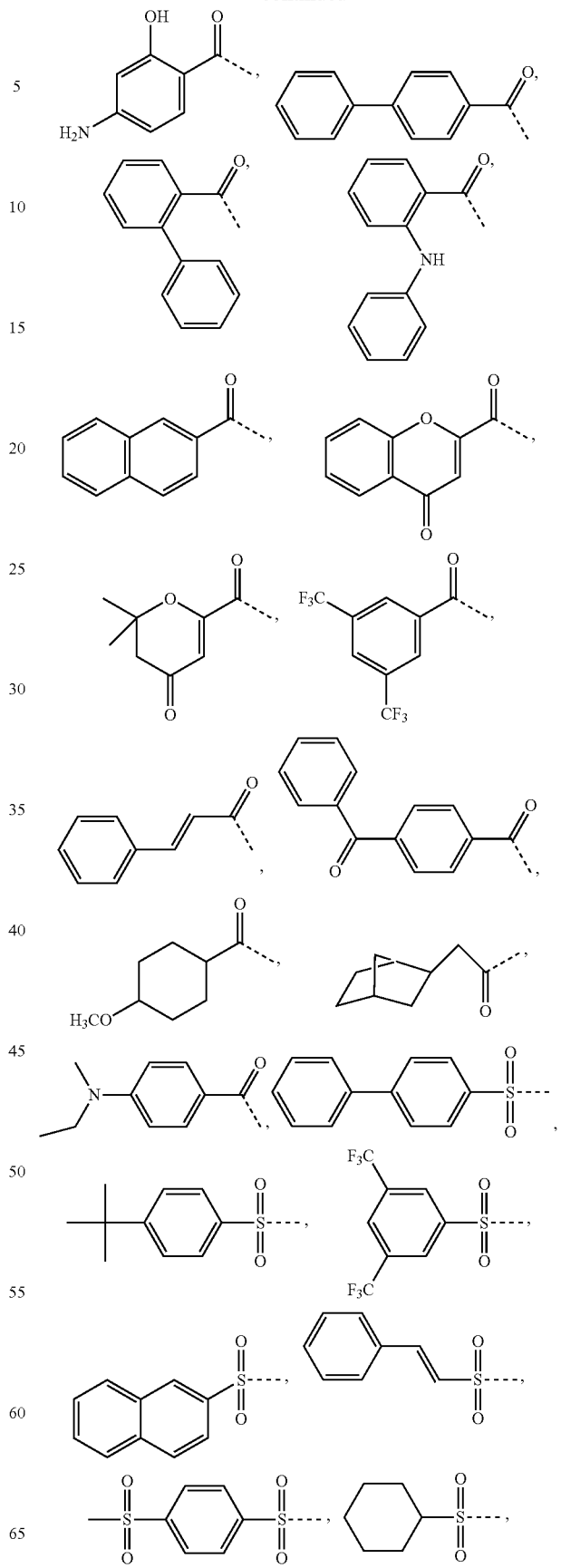

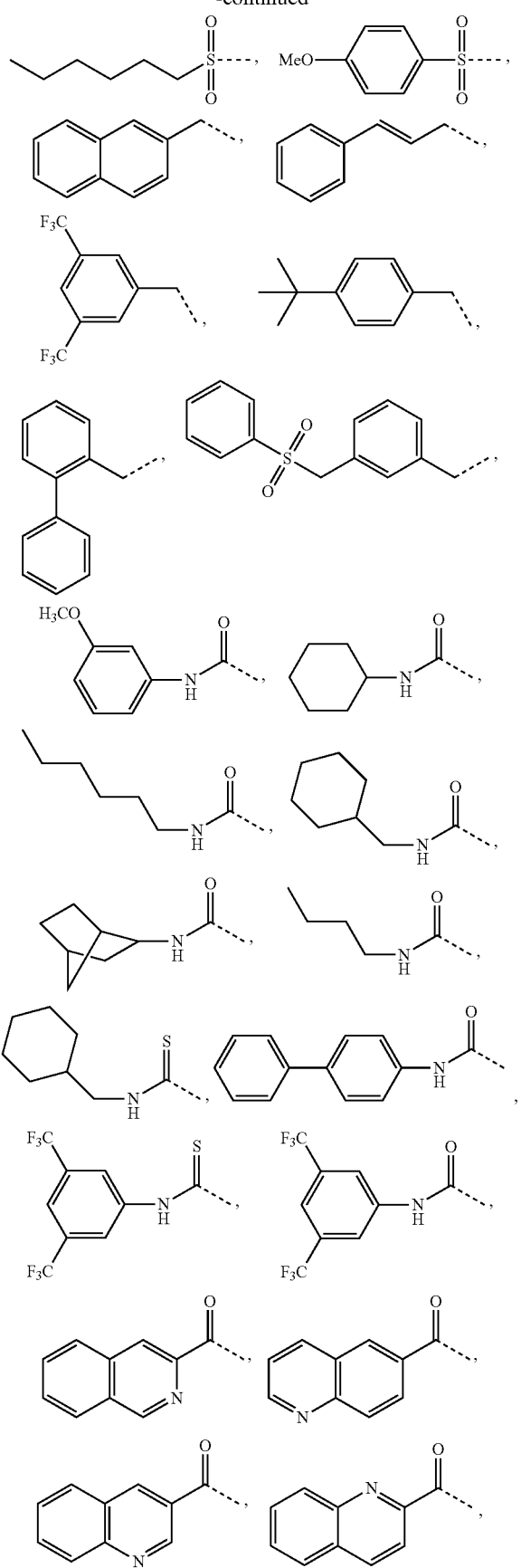
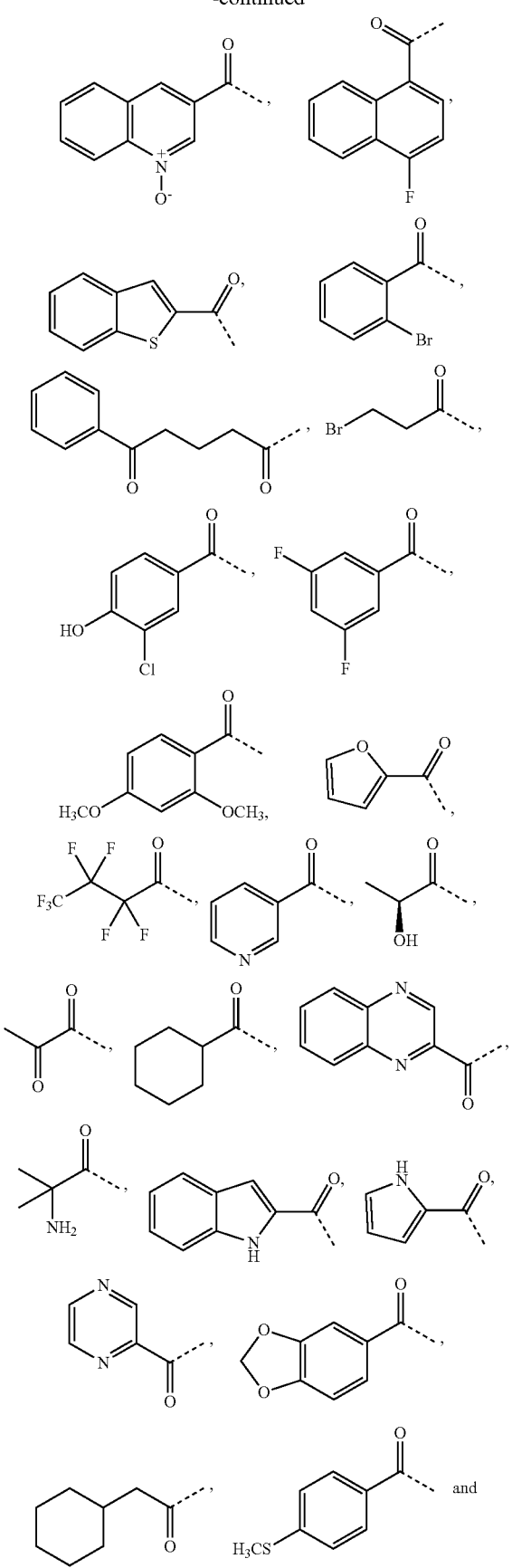

-continued

[structure: pyridin-4-yl-CH2-C(=O)-]

or a pharmaceutically acceptable salt, or an N-oxide thereof.

8. The aminosteroid derivative of claim 5, having at least one of the following structures

[three steroid structures with quinoline-proline-piperazine substituents]

9. An aminosteroid derivative of Formula III:

Formula III

[steroid structure with W-V-piperazine and Y1, Y2, Y3, Z substituents on ring A]

wherein:
A is $CHR^1$, $NR^1$, O or S;
$Y^1$ is chosen from OH, halogen, $OR^2$, $OCOR^3$; $OCONR^4R^5$ and $OSO_2NR^4R^5$;
$Y^2$ is chosen from H, halogen, OH, $OR^2$, OMOM (O-methoxymethyl ether), $OCOR^3$, $OCONR^4R^5$, $OSO_2NH_2$ or $OPO(OH)_2$ when $Y^2$═C is $Y^2$—C and
$Y^2$ is O or S when $Y^2$═C is $Y^2$═C,
$Y^3$ is $H_2$ or O;
Z is H or C≡$CR^6$;
V is an amino acid,

[two structures showing piperidine-C(=O)- and azetidine-C(=O)- linkers] or ;

W is CO, $SO_2$, $CH_2$, CONH, CSNH, or

[acryloyl group CH2=CH-C(=O)-] ;

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
$R^1$ is H or alkyl;
$R^2$ is alkyl;
$R^3$ is H, alkyl or heterocyclyl;
$R^4$ and $R^5$ are independently chosen from H and alkyl; and
$R^6$ is H or alkyl;
or a pharmaceutically acceptable salt, or an N-oxide thereof.

10. The aminosteroid derivative of claim 9, having the structure:

[steroid structure similar to Formula III]

wherein:
$Y^1$ is chosen from OH, halogen, $OR^2$, $OCOR^3$, $OCONR^4R^5$ and $OSO_2NR^4R^5$;
$Y^2$ is chosen from H, halogen, OH, $OR^2$, OMOM (O-methoxymethyl ether), $OCOR^3$, $OCONR^4R^5$, $OSO_2NH_2$ or $OPO(OH)_2$, when $Y^2$═C is $Y^2$—C and
$Y^2$ is O or S when $Y^2$═C is $Y^2$═C,
$Y^3$ is $H_2$ or O;
Z is H or C≡$CR^6$;
V is an amino acid,

[two structures showing piperidine-C(=O)- and azetidine-C(=O)- linkers] or ;

W is CO, SO$_2$, CH$_2$, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;

R$^1$ is H or alkyl;

R$^2$ is alkyl;

R$^3$ is H, alkyl or heterocyclyl;

R$^4$ and R$^5$ are independently chosen from H and alkyl; and

R$^6$ is H or alkyl;

or a pharmaceutically acceptable salt, or an N-oxide thereof.

11. The aminosteroid derivative of claim 9, wherein V is proline and wherein the variables W and X are linked to form the linkage W-X, wherein W-X is chosen from

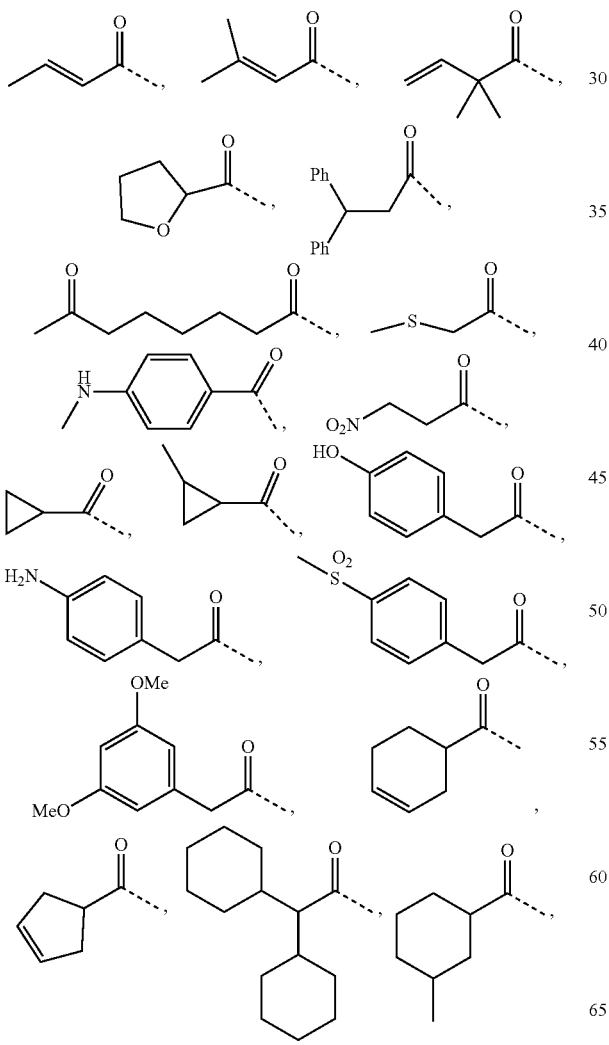

-continued

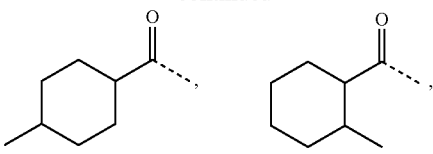

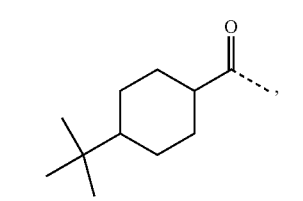

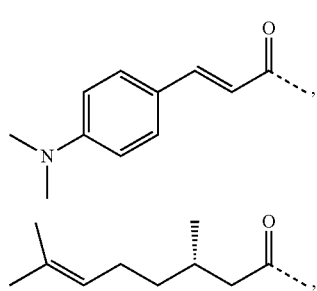

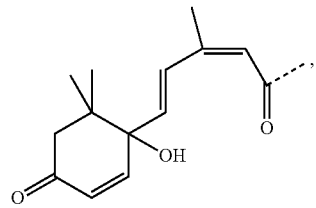

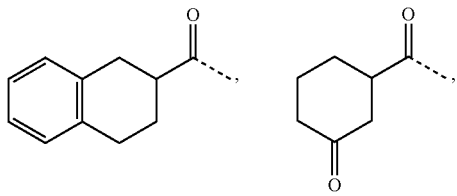

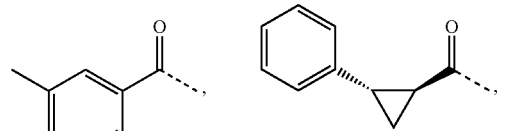

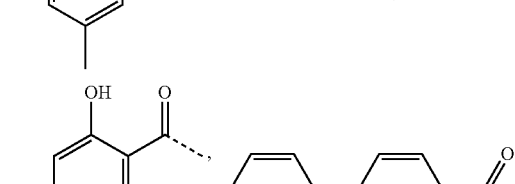

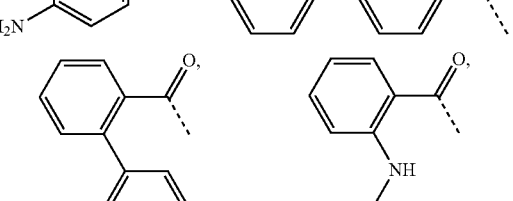

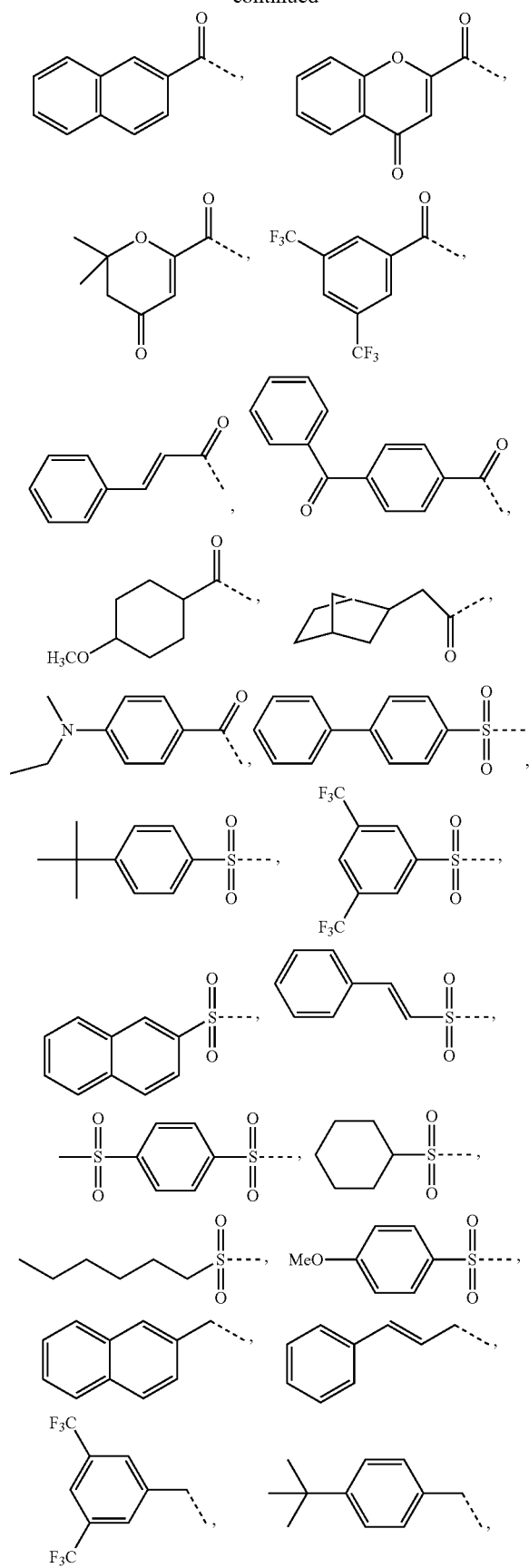
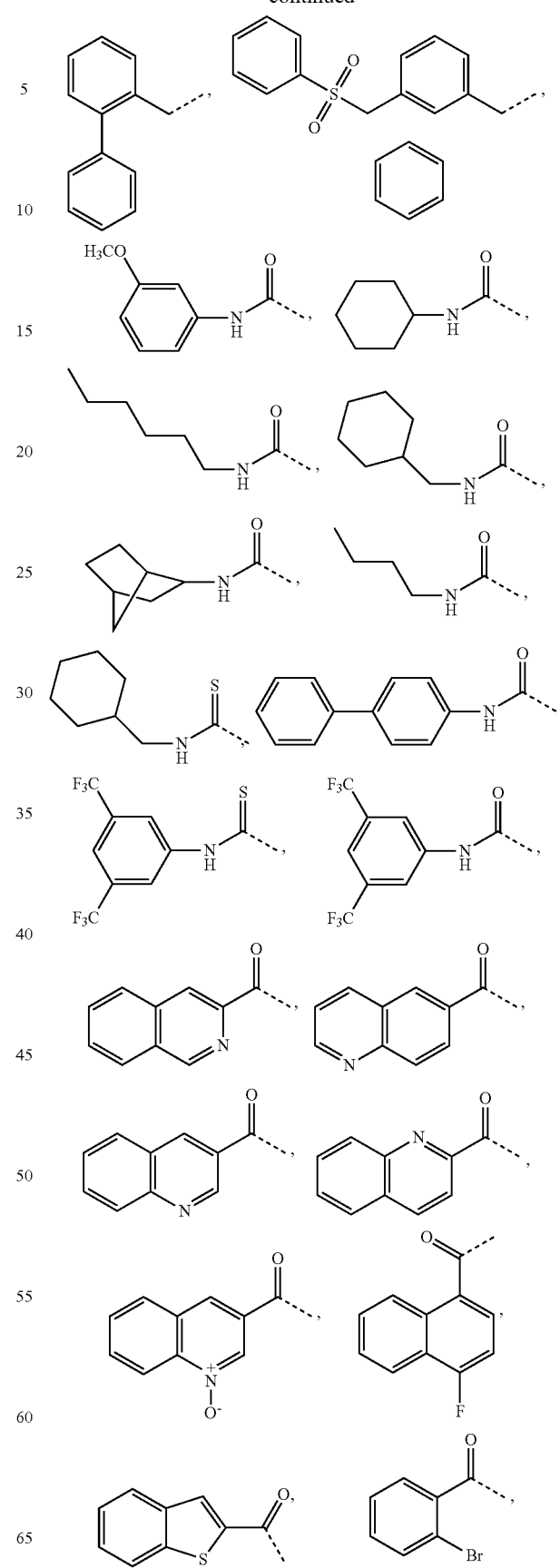

-continued
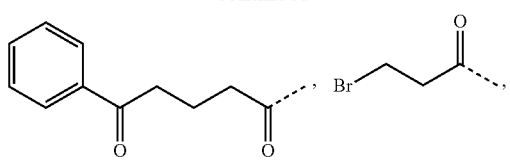
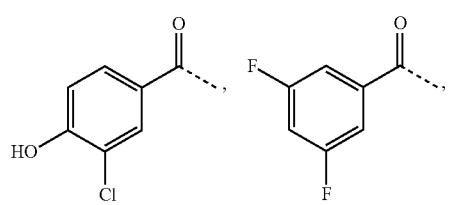
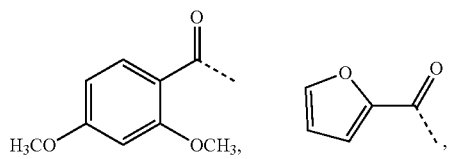
-continued
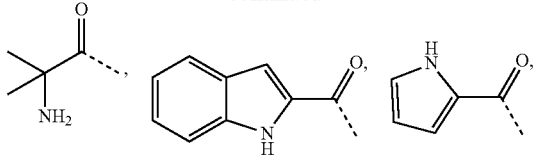
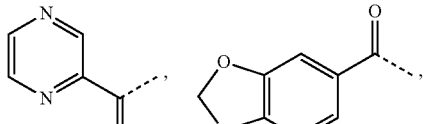
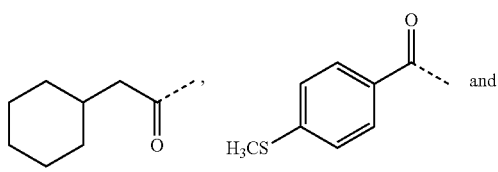
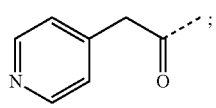
or a pharmaceutically acceptable salt, or an N-oxide thereof.
12. The aminosteroid derivative of claim 9, having the structure:
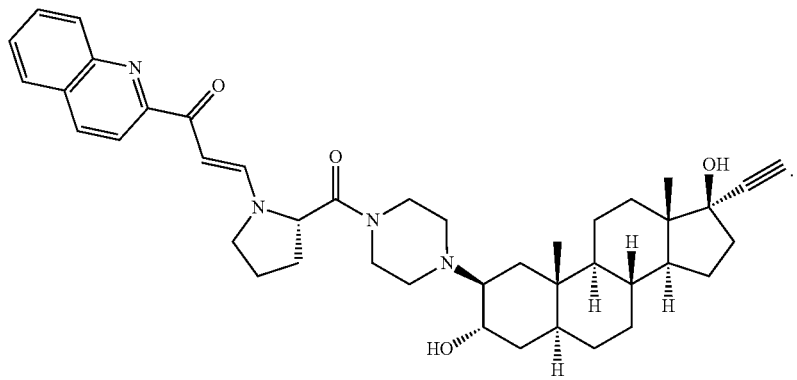
-continued
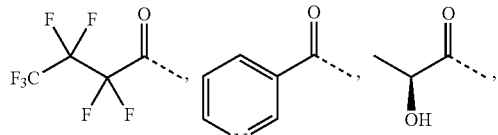
13. An aminosteroid derivative of Formula IV:
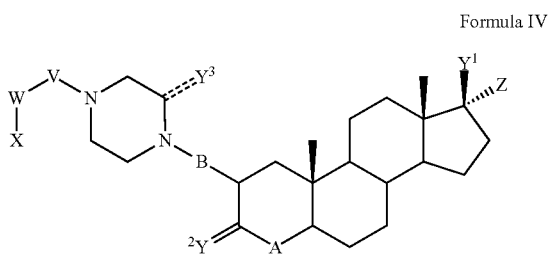
Formula IV
wherein:
A is $CHR^1$, $NR^1$, O or S;
B is CO, $SO_2$, $CH_2$, $C(X^1)_2$, or absent;
$Y^1$ is chosen from OH, halogen, $OR^2$, $OCOR^3$, $OCONR^4R^5$ and $OSO_2NR^4R^5$;
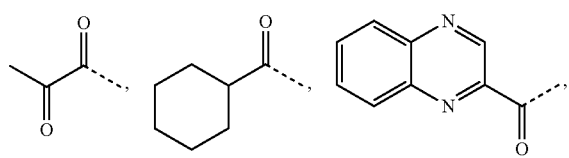

$Y^2$ is O or S;
$Y^3$ is $H_2$ or O;
Z is H or $C\equiv CR^6$;
V is an amino acid,

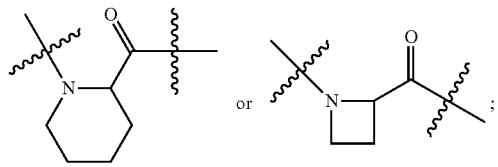

W is CO, $SO_2$, $CH_2$, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
$X^1$ is halogen;
$R^1$ is H or alkyl;
$R^2$ is alkyl;
$R^3$ is H, alkyl or heterocyclyl;
$R^4$ and $R^5$ are independently chosen from H and alkyl; and
$R^6$ is H or alkyl;
or a pharmaceutically acceptable salt, or an N-oxide thereof.

14. The aminosteroid derivative of claim 13, having the structure:

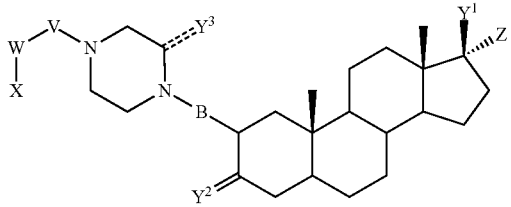

wherein:
B is CO, $SO_2$, $CH_2$, $C(X^1)_2$, or absent;
$Y^1$ is chosen from OH, halogen, $OR^2$, $OCOR^3$, $OCONR^4R^5$ and $OSO_2NR^4R^5$;
$Y^2$ is O or S;
$Y^3$ is $H_2$ or O;
Z is H or $C\equiv CR^6$;
V is an amino acid,

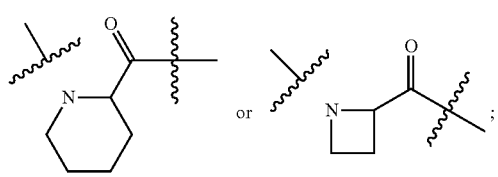

W is CO, $SO_2$, $CH_2$, CONH, CSNH, or

X is chosen from alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy and thioalkoxy;
$X^1$ is halogen;
$R^2$ is alkyl;
$R^3$ is H, alkyl or heterocyclyl;
$R^4$ and $R^5$ are independently chosen from H and alkyl; and
$R^6$ is H or alkyl;
or a pharmaceutically acceptable salt, or an N-oxide thereof.

15. The aminosteroid derivative of claim 13 wherein V is proline and wherein the variables W and X are linked to form the linkage W-X, wherein W-X is chosen from

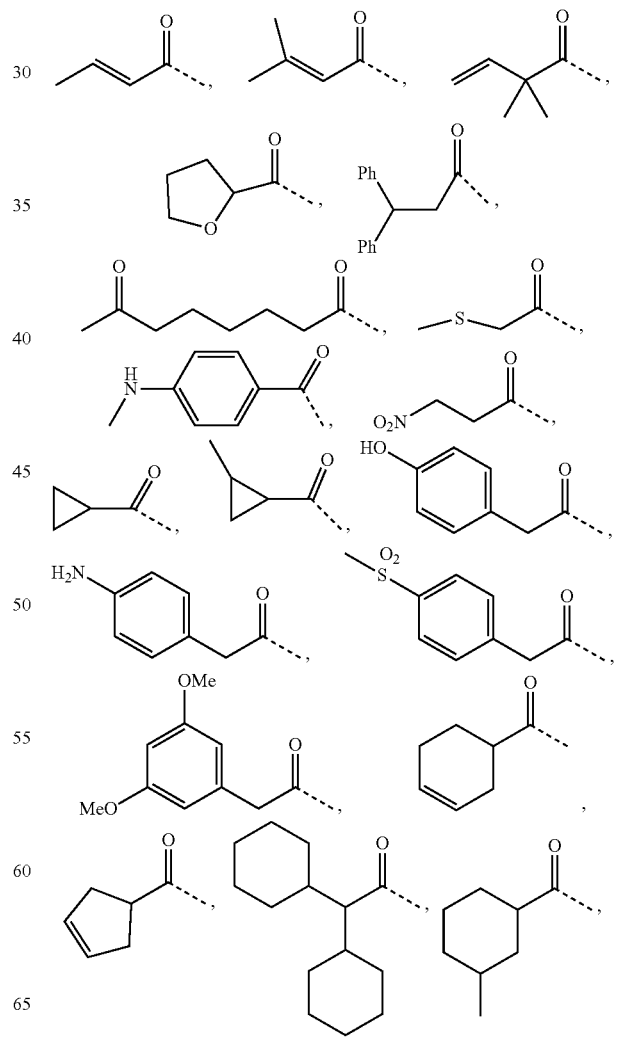

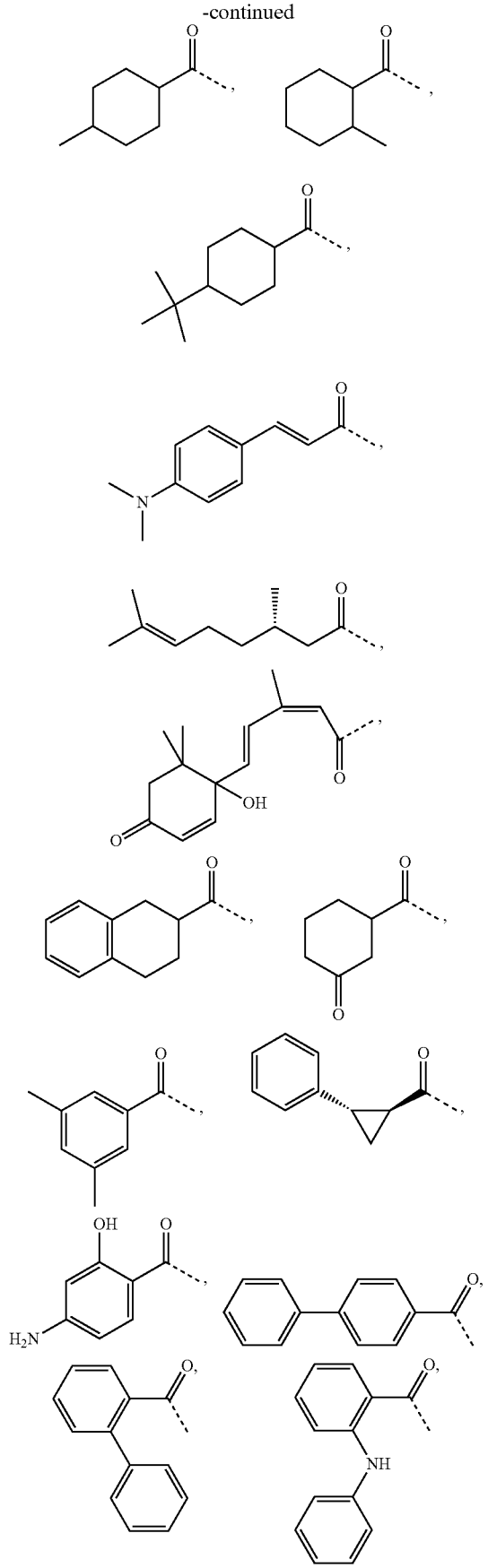
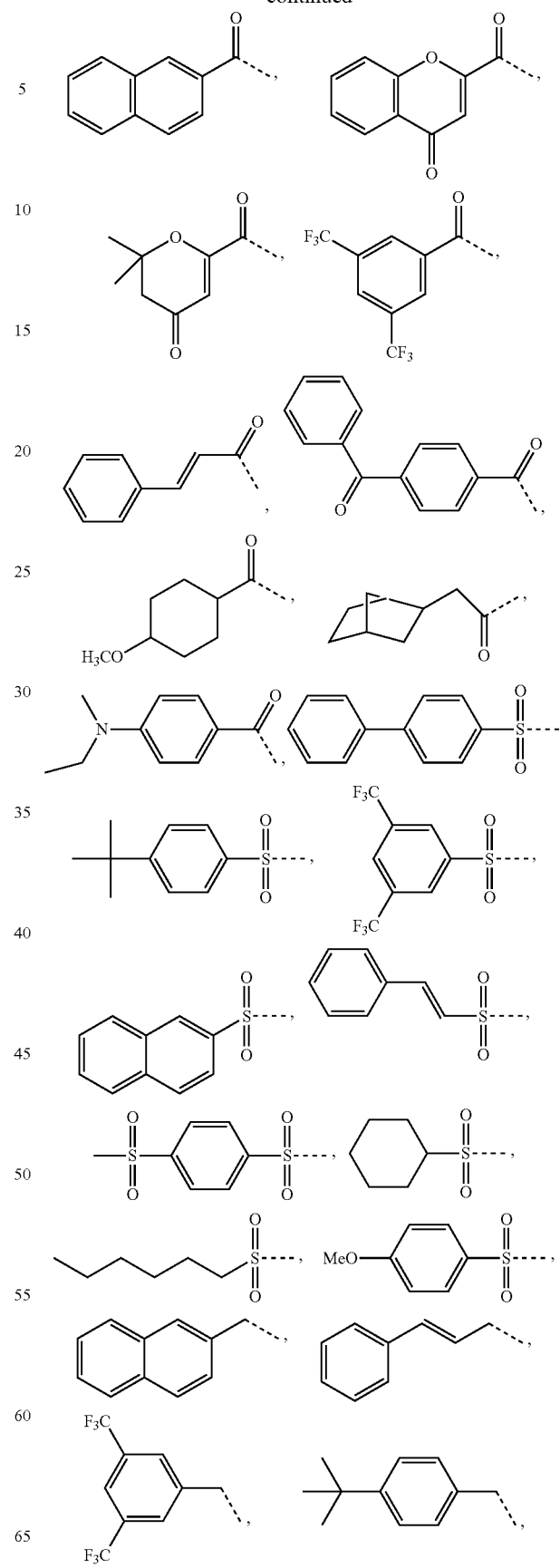

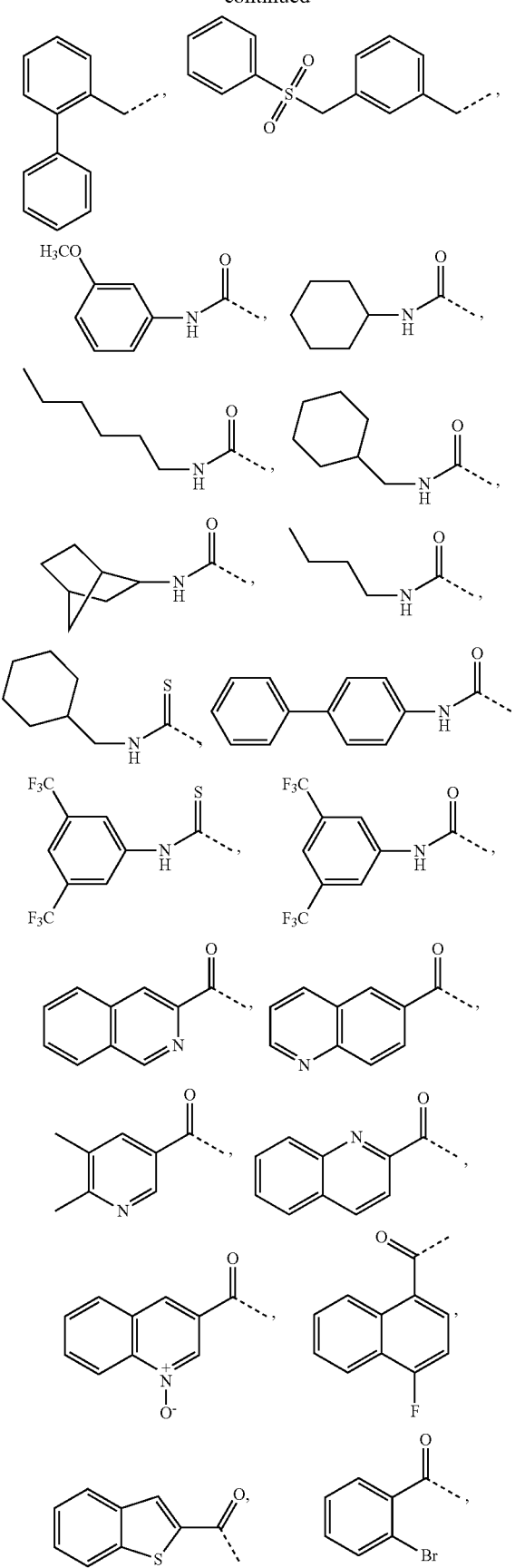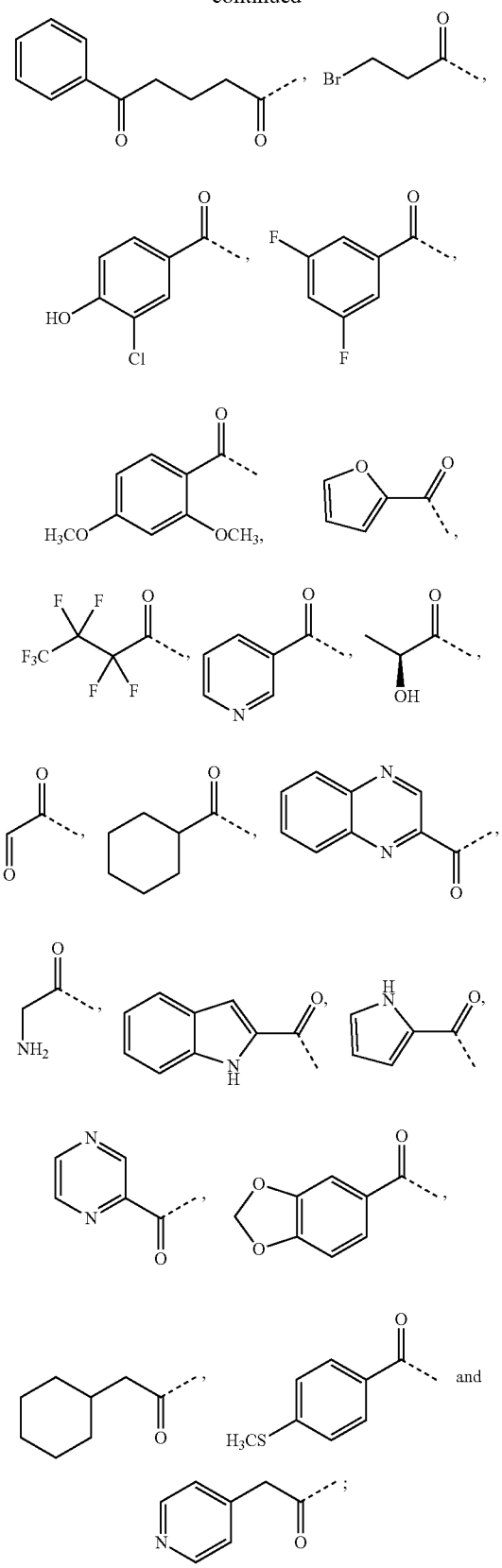
or a pharmaceutically acceptable salt, or an N-oxide thereof.

16. The aminosteroid derivative of claim 13, having the structure:

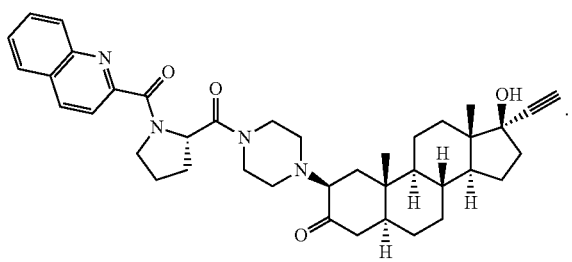

17. A pharmaceutical composition comprising a pharmaceutically acceptable amount of the aminosteroid derivative according to claim 1 and a pharmaceutically acceptable carrier.

18. A pharmaceutical combination comprising an aminosteroid derivative according to claim 1, and one or more agents, wherein the one or more agents are at least one of docetaxel, paclitaxel, taxol, ixabepilone, patupilone, sagopilone; mitoxantrone; predinisolone; dexamethasone; estramustin; vinblastin; vincristin; doxorubicin; adriamycin; idarubicin; daunorubicin; bleomycin; etoposide; cyctophosphamide; ifosfamide; procarbazine; metphalan; 5-fluorouracil; capecitabine; fludarabine; cytarabine; ara-C; 2-chloro-2"-deoxyadenosine, thioguanine, flutamide, cyproterone acetate, bicatutamide, bortezomib, cisplatin, carboplatin; chlorambucil; methotrexate or rituximab.

19. A method of treating ovarian cancer, pancreatic cancer, leukemia, prostate cancer, or breast cancer in a subject comprising administering to the subject an aminosteroid derivative according to claim 1.

20. The method of claim 19, wherein the aminosteroid derivative is administered intravenously, intra-arterially, subcutaneously, topically, or intramuscularly.

21. The method of claim 19, wherein the aminosteroid derivative is administered systemically, regionally to a tumor/disease site, locally to a tumor/disease site, into tumor/tissue vasculature or intratumorally.

22. The method of claim 19, wherein the subject is a human.

23. The method of claim 19, wherein the subject is a non-human animal.

* * * * *